(12) United States Patent
Delhomel

(10) Patent No.: US 8,088,819 B2
(45) Date of Patent: Jan. 3, 2012

(54) DERIVATIVES OF SUBSTITUTED 3-PHENYL-1-(PHENYLTHIENYL)PROPAN-1-ONES AND OF 3-PHENYL-1-(PHENYLFURANYL) PROPAN-1-ONES, PREPARATION AND USE

(76) Inventor: Jean-François Delhomel, Acq (FR)

( * ) Notice: Subject to any disclaimer, the term of this patent is extended or adjusted under 35 U.S.C. 154(b) by 284 days.

(21) Appl. No.: 12/448,668

(22) PCT Filed: Dec. 28, 2007

(86) PCT No.: PCT/FR2007/052634
§ 371 (c)(1),
(2), (4) Date: Jun. 29, 2009

(87) PCT Pub. No.: WO2008/087366
PCT Pub. Date: Jul. 24, 2008

(65) Prior Publication Data
US 2010/0029745 A1      Feb. 4, 2010

(30) Foreign Application Priority Data
Dec. 29, 2006   (FR) .................................... 06 56067

(51) Int. Cl.
*A61K 31/381* (2006.01)
*C07D 333/20* (2006.01)

(52) U.S. Cl. .......................................... 514/438; 549/80
(58) Field of Classification Search .................. 514/438; 549/80
See application file for complete search history.

(56) References Cited

FOREIGN PATENT DOCUMENTS
WO   2004/063184   7/2004
WO   2006/090920   8/2006

OTHER PUBLICATIONS

International Search Report for PCT/FR2007/052634, mailed Sep. 2, 2008.
Fisera, L. et al., "Thiophene Derivatives. IV. .alpha., .beta.-Unsaturated Ketones of the Phenylthiophene Series", CA No. 1979; 137601; ZBornik Prac Chemickotechnologickej Fakulty SVST, Volume Date 1975-1976, 91-6.

*Primary Examiner* — Taofiq A Solola
(74) *Attorney, Agent, or Firm* — Nixon & Vanderhye P.C.

(57) ABSTRACT

The present invention relates to compounds derived from substituted 3-phenyl-1-(thien-2-yl)propan-1-ones, pharmaceutical compositions comprising them as well as their therapeutic applications, notably in the field of human and animal health.

24 Claims, 12 Drawing Sheets

Figure 1:
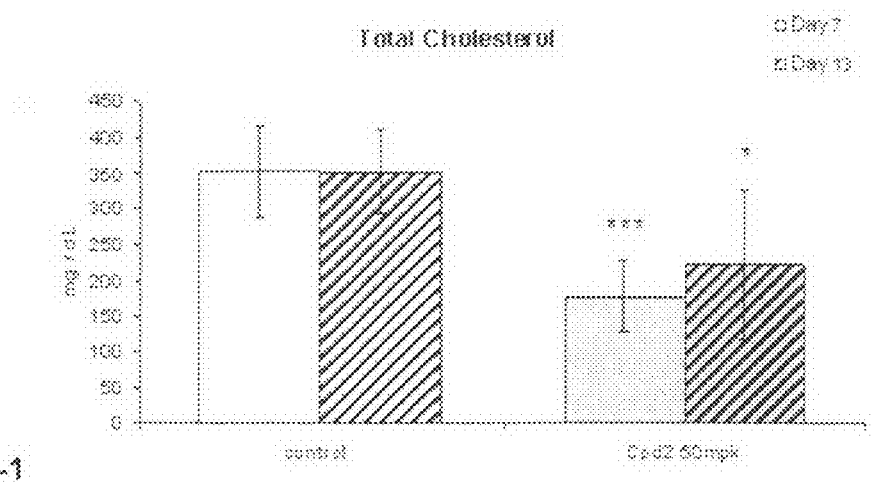

SEQUENCE LISTING

<160> NUMBER OF SEQ ID NOS: 22

<210> SEQ ID NO 1
<211> LENGTH: 21
<212> TYPE: DNA
<213> ORGANISM: Artificial
<220> FEATURE:
<223> OTHER INFORMATION: Sense primer hABCA1

<400> SEQUENCE: 1
ctgaggttgc tgctgtggaa g                                           21

<210> SEQ ID NO 2
<211> LENGTH: 20
<212> TYPE: DNA
<213> ORGANISM: Artificial
<220> FEATURE:
<223> OTHER INFORMATION: Antisense primer hABCA1

<400> SEQUENCE: 2
catctgagaa caggcgagcc                                             20

<210> SEQ ID NO 3
<211> LENGTH: 20
<212> TYPE: DNA
<213> ORGANISM: Artificial
<220> FEATURE:
<223> OTHER INFORMATION: Sense primer mACOX1

<400> SEQUENCE: 3
gaagccagcg ttacgaggtg                                             20

<210> SEQ ID NO 4
<211> LENGTH: 20
<212> TYPE: DNA
<213> ORGANISM: Artificial
<220> FEATURE:
<223> OTHER INFORMATION: Antisense primer mACOX1

<400> SEQUENCE: 4
tggagttctt gggacgggtg                                             20

<210> SEQ ID NO 5
<211> LENGTH: 20
<212> TYPE: DNA
<213> ORGANISM: Artificial
<220> FEATURE:
<223> OTHER INFORMATION: Sense primer mApoCIII

<400> SEQUENCE: 5
ctcttggctc tcctggcatc                                             20

<210> SEQ ID NO 6
<211> LENGTH: 20
<212> TYPE: DNA
<213> ORGANISM: Artificial
<220> FEATURE:
<223> OTHER INFORMATION: Antisense primer mApoCIII

<400> SEQUENCE: 6
gcatcctgga ccgtcttgga                                             20

<210> SEQ ID NO 7
<211> LENGTH: 22
<212> TYPE: DNA

```
<213> ORGANISM: Artificial
<220> FEATURE:
<223> OTHER INFORMATION: Sense primer mCPT1b

<400> SEQUENCE: 7
ggactgagac tgtgcgttcc tg                                          22

<210> SEQ ID NO 8
<211> LENGTH: 20
<212> TYPE: DNA
<213> ORGANISM: Artificial
<220> FEATURE:
<223> OTHER INFORMATION: Antisense primer mCPT1b

<400> SEQUENCE: 8
agtgcttggc ggatgtggtt                                             20

<210> SEQ ID NO 9
<211> LENGTH: 21
<212> TYPE: DNA
<213> ORGANISM: Artificial
<220> FEATURE:
<223> OTHER INFORMATION: Sense primer hMCP1

<400> SEQUENCE: 9
aggaagatct cagtgcagag g                                           21

<210> SEQ ID NO 10
<211> LENGTH: 21
<212> TYPE: DNA
<213> ORGANISM: Artificial
<220> FEATURE:
<223> OTHER INFORMATION: Antisense primer hMCP1

<400> SEQUENCE: 10
agtcttcgga gtttgggttt g                                           21

<210> SEQ ID NO 11
<211> LENGTH: 22
<212> TYPE: DNA
<213> ORGANISM: Artificial
<220> FEATURE:
<223> OTHER INFORMATION: Sense primer mPDK4

<400> SEQUENCE: 11
tactccactg ctccaacacc tg                                          22

<210> SEQ ID NO 12
<211> LENGTH: 20
<212> TYPE: DNA
<213> ORGANISM: Artificial
<220> FEATURE:
<223> OTHER INFORMATION: Antisense primer mPDK4

<400> SEQUENCE: 12
gttcttcggt tccctgcttg                                             20

<210> SEQ ID NO 13
<211> LENGTH: 24
<212> TYPE: DNA
<213> ORGANISM: Artificial
<220> FEATURE:
<223> OTHER INFORMATION: Sense primer mUCP2

<400> SEQUENCE: 13
gtcggagata ccagagcact gtcg                                        24
```

```
<210> SEQ ID NO 14
<211> LENGTH: 20
<212> TYPE: DNA
<213> ORGANISM: Artificial
<220> FEATURE:
<223> OTHER INFORMATION: Antisense primer mUCP2

<400> SEQUENCE: 14
cacatcaaca ggggaggcga                                              20

<210> SEQ ID NO 15
<211> LENGTH: 20
<212> TYPE: DNA
<213> ORGANISM: Artificial
<220> FEATURE:
<223> OTHER INFORMATION: Sense primer mUCP3

<400> SEQUENCE: 15
gcaccgccag atgagttttg                                              20

<210> SEQ ID NO 16
<211> LENGTH: 20
<212> TYPE: DNA
<213> ORGANISM: Artificial
<220> FEATURE:
<223> OTHER INFORMATION: Antisense primer mUCP3

<400> SEQUENCE: 16
gacgctggag tggtccgctc                                              20

<210> SEQ ID NO 17
<211> LENGTH: 20
<212> TYPE: DNA
<213> ORGANISM: Artificial
<220> FEATURE:
<223> OTHER INFORMATION: Sense primer hMMP9

<400> SEQUENCE: 17
tggcaccacc acaacatcac                                              20

<210> SEQ ID NO 18
<211> LENGTH: 20
<212> TYPE: DNA
<213> ORGANISM: Artificial
<220> FEATURE:
<223> OTHER INFORMATION: Antisense primer hMMP9

<400> SEQUENCE: 18
accacaactc gtcatcgtcg                                              20

<210> SEQ ID NO 19
<211> LENGTH: 25
<212> TYPE: DNA
<213> ORGANISM: Artificial
<220> FEATURE:
<223> OTHER INFORMATION: Sense primer 36B4

<400> SEQUENCE: 19
catgctcaac atctcccccct tctcc                                       25

<210> SEQ ID NO 20
<211> LENGTH: 25
<212> TYPE: DNA
<213> ORGANISM: Artificial
<220> FEATURE:
<223> OTHER INFORMATION: Antisense primer 36B4
```

```
<400> SEQUENCE: 20
gggaaggtgt aatccgtctc cacag                                    25

<210> SEQ ID NO 21
<211> LENGTH: 22
<212> TYPE: DNA
<213> ORGANISM: Artificial
<220> FEATURE:
<223> OTHER INFORMATION: Sense primer 18S

<400> SEQUENCE: 21
cggacacgga caggattgac ag                                       22

<210> SEQ ID NO 22
<211> LENGTH: 20
<212> TYPE: DNA
<213> ORGANISM: Artificial
<220> FEATURE:
<223> OTHER INFORMATION: Antisense primer 18S

<400> SEQUENCE: 22
aatctcgggt ggctgaacgc                                          20
```

DERIVATIVES OF SUBSTITUTED 3-PHENYL-1-(PHENYLTHIENYL)PROPAN-1-ONES AND OF 3-PHENYL-1-(PHENYLFURANYL) PROPAN-1-ONES, PREPARATION AND USE

This application is the U.S. national phase of International Application No. PCT/FR2007/052634, filed 28 Dec. 2007 which designated the U.S. and claims priority to French Application No. 0656067, filed 29 Dec. 2006, the entire contents of each of which are hereby incorporated by reference.

The present invention relates to compounds derived from substituted 3-phenyl-1-(phenylthienyl)propan-1-ones and substituted 3-phenyl-1-(phenylfuranyl)propan-1-ones, the pharmaceutical compositions comprising them as well as their therapeutic applications, notably in the areas of human and animal health.

The inventors have demonstrated, surprisingly, that the compounds according to the invention intrinsically possess PPAR (Peroxisome Proliferator-Activated Receptor) agonist properties.

The molecules described in the invention are therefore of particular interest for treating complications associated with metabolic syndrome, atherosclerosis, cardiovascular diseases, insulin resistance, obesity, hypertension, diabetes, dyslipidemias, inflammatory diseases (asthma, etc.), cerebral ischemia, autoimmune diseases, neurodegenerative pathologies (Alzheimer's disease, etc.), cancers, etc., as well as to allow reduction of global cardiovascular risk. Preferably, the compounds according to the invention can be used for the treatment of dyslipidemias and improvement of global cardiovascular risk.

Diabetes, obesity and dyslipidemias (high plasma levels of LDL cholesterol and triglycerides, low plasma levels of HDL cholesterol, etc.) are among the clearly identified cardiovascular risk factors which predispose an individual to develop a cardiovascular pathology (Mensah M, 2004). These risk factors are added to the risk factors connected with lifestyle, such as cigarette smoking, physical inactivity and unbalanced diet. There is a synergistic effect between these various factors: the simultaneous presence of several of them leads to a dramatic aggravation of cardiovascular risk and it is then appropriate to talk of global risk for the cardiovascular diseases. The prevalence of dyslipidemias reached 43.6% of the population in 2004 in the principal developed countries. The prevalence of diabetes, currently showing a net increase, is on the way to becoming more and more significant in the epidemiology of the cardiovascular diseases: the prevalence of diabetes is in fact estimated at 7.6% of the population for 2010 (Fox-Tucker J, 2005).

According to the International Atherosclerosis Society (International Atherosclerosis Society, 2003), cardiovascular diseases represent the primary cause of mortality in industrialized countries and are becoming more and more common in developing countries. These diseases are notably coronary diseases, cerebral ischemia and peripheral arterial diseases.

These data therefore justify the adoption of energetic measures for significantly reducing the morbidity and mortality due to the cardiovascular pathologies, and the need to find effective treatments, complementary to a change to a healthier lifestyle, acting on the risk factors of the cardiovascular diseases and on their consequences is now becoming a global emergency.

Owing to their properties as PPAR agonists, the compounds according to the invention are of particular interest for the treatment of pathologies associated with disturbances of lipid and/or carbohydrate metabolism, such as diabetes, obesity, dyslipidemias or inflammation, as well as for lowering global cardiovascular risk.

Indeed, the PPARs ($\alpha$, $\gamma$ and $\delta$) are known to be involved in pathologies of this type (Kota B P et al., 2005): ligands of these receptors are marketed for treating such pathologies (Lefebvre P et al., 2006) and numerous PPAR modulators, agonists or antagonists, selective or nonselective, are currently at an advanced stage of pharmaceutical development. A PPAR modulator having beneficial effects on insulin resistance, obesity, dyslipidemias, hypertension and/or inflammation could be used in the treatment of metabolic syndrome (or syndrome X) (Liu Y and Miller A, 2005).

The PPAR family comprises three isoforms, designated $\alpha$, $\gamma$ and $\delta$ (also called $\beta$), each encoded by a different gene. These receptors form part of the superfamily of nuclear receptors and transcription factors that are activated by the binding of certain fatty acids and/or of their lipid metabolites. Activated PPARs form heterodimers with the receptors of 9-cis retinoic acid (RXR or Retinoid X Receptor) and attach to specific response elements (PPRE or Peroxisome Proliferator Response Element) at the promoter of their target genes, thus permitting control of transcription.

PPAR$\alpha$ mainly controls lipid metabolism (hepatic and muscular) and glucose homeostasis, by directly controlling the transcription of genes coding for proteins involved in lipid homeostasis. It exerts antiinflammatory and antiproliferative effects and prevents the proatherogenic effects of accumulation of cholesterol in the macrophages by stimulating the efflux of cholesterol (Lefebvre P, Chinetti G, Fruchart J C and Staels B, 2006). Fibrates (fenofibrate, bezafibrate, ciprofibrate, gemfibrozil), through the intermediary of PPAR$\alpha$, thus find clinical application in the treatment of certain dyslipidemias by lowering triglyceride levels and increasing plasma levels of HDL cholesterol (HDL: High Density Lipoprotein).

PPAR$\gamma$ is involved in the lipid metabolism of mature adipocytes (a key regulator of adipogenesis), in glucose homeostasis (notably in insulin resistance), in inflammation, in the accumulation of cholesterol at the macrophage level and in cellular proliferation (Lehrke M and Lazar M A, 2005). PPAR$\gamma$ consequently plays a role in the pathogenesis of obesity, of insulin resistance and of diabetes. The thiazolidinediones (rosiglitazone, troglitazone, etc.) are PPAR$\gamma$ receptor ligands used in the treatment of type 2 diabetes.

There are PPAR$\delta$ ligands currently in clinical development (for example GW501516 (CAS Registry Number 317318-70-0)), but no PPAR$\delta$ ligand is used at present as a medicament. This receptor is an attractive target for the development of medicament for use in the treatment of the risk factors associated with metabolic syndrome and with atherosclerosis such as dyslipidemias, obesity, inflammation and insulin resistance. PPAR$\delta$ is indeed involved in the control of lipid and carbohydrate metabolisms, in the energy balance, in the proliferation and differentiation of neurons, and in the inflammatory response (Gross B et al., 2005).

Beyond to the direct role of PPAR ligands in the regulation of lipid and carbohydrate metabolism, these molecules have a spectrum of pleiotropic action due to the great diversity of target genes of the PPAR target genes. These multiple properties make the PPARs interesting therapeutic targets for the treatment of various pathologies, notably cardio-metabolic pathologies (i.e. cardiovascular and metabolic pathologies) as well as for lowering global cardiovascular risk.

PPAR ligands have a neuroprotective role in Alzheimer's disease, multiple sclerosis, Parkinson's disease and more generally in any pathology involving death or degeneration of neurons, whether they are neurons of the central or peripheral nervous system, death or degeneration of oligodendrocytes, death or degeneration of glial cells, inflammation of glial cells (i.e. astrocytes, microglia or oligodendrocytes) or Schwann cells. Thus, it was recently shown that PPARδ agonists made it possible to preserve learning and memory in rats in which Alzheimer's disease had been induced (de la Monte S M et al., 2006). It has also been shown that the oral administration of PPARδ agonists reduced the clinical symptoms and the activation of astroglial and microglial inflammation in a model of multiple sclerosis (Polak, 2005).

Owing to their PPAR agonist properties, the compounds according to the invention therefore represent an advantageous therapeutic tool for the improvement of pathologies associated with disturbances of lipid and/or carbohydrate metabolism, for lowering global cardiovascular risk as well as for neuroprotection.

Notably, the compounds according to the invention possess PPARδ and PPARα agonist properties and are therefore of interest in the treatment of metabolic pathologies such as metabolic syndrome (the characteristics of which are obesity (in particular abdominal obesity), an abnormal blood lipid concentration (high level of triglycerides and/or low level of HDL cholesterol (dyslipidemia)), raised glycemia and/or insulin resistance and hypertension) and in the treatment of dyslipidemias.

The present invention relates to compounds derived from substituted 3-phenyl-1-(phenylthienyl)propan-1-ones and 3-phenyl-1-(phenylfuranyl)propan-1-ones of the following general formula (I):

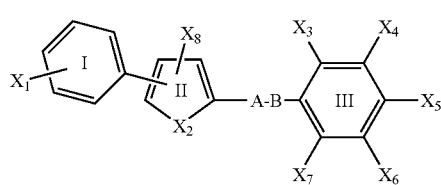

(I)

in which:
X1 represents a halogen, a R1, —SR1 or —OR1 group;
X2 represents a sulfur or oxygen atom;
X3 represents a halogen, a R3, —SR3 or —OR3 group;
X4 represents a halogen, a R4, —SR4 or —OR4 group;
X5 represents a R5, —SR5 or —OR5 group;
X6 represents a halogen, a R6, —SR6 or —OR6 group;
X7 represents a halogen, a R7, —SR7 or —OR7 group;
X8 represents an R8 group;
R1, R3, R4, R6, R7 and R8, which may be identical or different, representing a hydrogen or an alkyl group;
R5 representing an alkyl group substituted with one or more substituent(s) of group 1 or of group 2;
R5 which can, in addition to the substitution or substitutions described above, be substituted with a cycloalkyl, heterocycloalkyl, aryl or heteroaryl group as defined below;
A represents:
  (i) a carbonyl group (CO),
  (ii) an oxime group (C=N—O—H) or oxime ether group (C=N—O—R11),
  (iii) a —CR9R10 group, R9 and R10 being different, representing a hydrogen, an alkyl group or an —OR11 group,
  R11 representing a hydrogen or an aryl, heterocycloalkyl, or heteroaryl group as defined below or an alkyl group, substituted or not with a cycloalkyl, heterocycloalkyl, aryl or heteroaryl group as defined below;

B represents:
  (i) an unsubstituted, saturated alkyl group having two carbon atoms (CH₂—CH₂),
  (ii) an unsubstituted alkene group, having two carbon atoms (CH=CH),
  (iii) an alkyne group having two carbon atoms (C≡C);
the substituents of group 1 are selected from —COOR12 and —CONR12R13.
the substituents of group 2 are selected from —SO₃H and —SO₂NR12R13;
R12 and R13, which may be identical or different, representing a hydrogen or an unsubstituted alkyl radical;
their stereoisomers (diastereoisomers, enantiomers), pure or mixed, racemic mixtures, geometric isomers, tautomers, salts, hydrates, solvates, solid forms and mixtures thereof.

Within the scope of the present invention:
  the term "alkyl" denotes a saturated, linear, branched, halogenated or unhalogenated, hydrocarbon radical having more particularly from 1 to 24 carbon atoms, preferably from 1 to 10, and having more particularly 1, 2, 3, 4, 5, 6, 7, 8, 9 or 10 carbon atoms. We may mention, for example, the methyl, trifluoromethyl, ethyl, n-propyl, isopropyl, n-butyl, isobutyl, tert-butyl, sec-butyl, pentyl, neopentyl or n-hexyl radicals.

In particular, an alkyl or alkenyl radical having 1 to 4 carbon atoms is preferably selected from the group comprising methyl, ethyl, n-propyl, n-butyl, isopropyl, sec-butyl, isobutyl, tert-butyl and their unsaturated derivatives, having at least one double bond (such as notably: CH=CH).

the term "cycloalkyl" denotes an alkyl group as defined above and forming at least one ring. We may mention, as cycloalkyl groups having from 3 to 8 carbon atoms, cyclopropyl, cyclobutyl, cyclopentyl, cyclohexyl, cycloheptyl and cyclooctyl.

the term "heterocycloalkyl" denotes a saturated or unsaturated alkyl group forming at least one ring interrupted by one or more heteroatoms selected from N, O, S or P. We may mention, as heterocycloalkyl groups, aziridine, pyrrolidine, tetrahydrothiophene, imidazoline, piperidine, piperazine and morpholine.

the term "aryl" refers to aromatic groups preferably comprising 5 to 14 carbon atoms, advantageously 6 to 14 carbon atoms (i.e. 6, 7, 8, 9, 10, 11, 12, 13 or 14 carbon atoms). They are generally mono- or bi-cyclic. We may mention for example phenyl, benzyl, α-naphthyl, β-naphthyl, anthracenyl or fluorenyl. Within the scope of the present invention, the aryl groups can be substituted with one or more substituents, which may be identical or different. Among the substituents of the aryl groups, we may mention as examples the halogens, the alkyl groups (as defined above) and alkyloxy groups (defined as an alkyl chain (as defined above) bound to the molecule via an oxygen (ether bond)), the alkylthio groups (defined as an alkyl chain (as defined above) bound to the molecule via a sulfur (thioether bond)) such as methyl, trifluoromethyl, methoxy and trifluoromethoxy, methylthio and trifluoromethylthio, the amines, the nitro groups, the hydroxy groups, the aryl, heteroaryl and heterocyclic groups.

the term "heteroaryl" refers to aromatic groups preferably comprising 3 to 14 carbon atoms, advantageously 3 to 8 carbon atoms (i.e. 3, 4, 6, 7 or 8 carbon atoms), interrupted by one or more heteroatoms selected from N, O, S or P. We may mention, as heteroaryl groups having from 3 to 8 carbon atoms, pyrrole, imidazole, and pyridine.

Among the substituents of the heteroaryl groups, we may mention for example the halogens, the alkyl groups (as defined above) and alkyloxy groups (defined as an alkyl chain (as defined above) bound to the molecule via an oxygen (ether bond)), the alkylthio groups (defined as an alkyl chain (as defined above) bound to the molecule via a sulfur (thioether bond)). Examples of these substituents are methyl, trifluoromethyl, methoxy and trifluoromethoxy, methylthio and trifluoromethylthio, the amines, the nitro groups, the hydroxy groups, the aryl, heteroaryl and heterocyclic groups.

The halogen atoms are selected from the bromine, fluorine, iodine, and chlorine atoms.

Within the scope of the present invention, in general formula (I), the atoms of ring II are numbered starting from the atom $X_2$, which bears the number 1, the other atoms of the ring being numbered starting from the carbon of ring II bound to the group A-B. Thus, the carbon of ring II bound to the group A-B is carbon 2 (or $C_2$), the carbon adjacent to $C_2$ is carbon 3 (or $C_3$), etc.

A particular aspect of the invention relates to compounds of general formula (I) in which A represents a carbonyl group (CO).

Another particular aspect of the invention relates to compounds of general formula (I) in which A represents an oxime group (C=N—O—H) or oxime ether group (C=N—O—R11), R11 representing a branched or linear alkyl group, notably an alkyl group having 1 to 7 carbon atoms, substituted or not with a cycloalkyl, heterocycloalkyl, aryl or heteroaryl group. Preferably, R11 represents a methyl group.

In a particular embodiment, when A represents a C=N—O—R11 group, R11 is an alkyl group having 1 to 7 carbon atoms substituted with an aryl group, notably a phenyl group. More preferably, R11 is a methyl group substituted with a phenyl group, in other words R11 is a benzyl group.

Another particular aspect of the invention relates to compounds of general formula (I) in which A represents a —CR9R10 group, R9 representing a hydrogen and R10 representing a hydroxyl group, an alkyl group or a —OR11 group, R11 representing an alkyl group, substituted or not with a cycloalkyl, heterocycloalkyl, aryl or heteroaryl group. Said alkyl, cycloalkyl, heterocycloalkyl, aryl or heteroaryl groups are optionally halogenated.

In particular, R11 represents a linear or branched alkyl group, having 1 to 7 carbon atoms, preferably 1, 2, 3 or 4 carbon atoms, preferably 1 or 2 carbon atoms, advantageously R11 represents the methyl or ethyl group. For example, R11 can also be an isopropyl.

Advantageously R11 is substituted with a cycloalkyl group, notably cyclohexyl, an aryl group, notably phenyl, a heterocyclic or heteroaryl group, notably pyridinyl, said cycloalkyl, aryl, heterocyclic or heteroaryl group optionally being halogenated. Even more preferably, R11 represents an alkyl group, preferably comprising a carbon atom, substituted with a phenyl, iodophenyl, cyclohexyl, or pyridinyl group.

Another particular aspect of the invention relates to compounds of general formula (I) in which A represents a —CR9R10 group, R9 representing a hydrogen and R10 representing a hydroxyl group.

A particular aspect of the invention relates to compounds of general formula (i) in which B represents an unsubstituted, saturated alkyl group comprising two carbon atoms (CH2-CH2).

Another particular aspect of the invention relates to compounds of general formula (I) in which X5 represents a R5, —OR5 or —SR5 group, R5 representing an alkyl group substituted with a substituent of group 1.

Even more preferably, X5 represents a —OR5 group in which R5 represents an alkyl group substituted with a substituent of group 1. Preferably, the substituent of group 1 is —COOR12.

Preferably, R5 represents an alkyl radical formed from a saturated linear carbon chain having 1 to 4 carbon atoms, said chain being bound by its end opposite to the phenyl group (III), to a substituent of group 1. Said chain can be branched with at least one alkyl or alkenyl group having 1 to 4 carbon atoms, or substituted with a phenyl group.

Preferably, R12 and R13, which may be identical or different, represent a hydrogen or an alkyl radical having 1 to 4 carbon atoms.

Preferably, the substituent of group 1 is of the type —COOR12, R12 being as defined above and preferably representing a hydrogen or an alkyl group comprising 1, 2, 3, 4, 5 or 6 carbon atoms, preferably comprising 1, 2, 3 or 4 carbon atoms, in particular a tert-butyl group.

In a particular aspect of the invention, X5 is selected from the groups: —OC(CH$_3$)$_2$COOR12, —OCH(CH$_2$CH$_3$)COOR12, —O(CH$_2$)$_3$C(CH$_3$)$_2$COOR12, —OCH(C$_6$H$_5$)COOR12 and —OCH$_2$COOR12. Advantageously, R12 can notably be selected from hydrogen and the —CH$_3$, —C(CH$_3$)$_3$ and —CH$_2$CH$_3$ groups.

Even more preferably, X5 represents a —OC(CH$_3$)$_2$COOH, —OC(CH$_3$)$_2$COOC(CH$_3$)$_3$, —OCH(CH$_2$CH$_3$)COOC(CH$_3$)$_3$, —OCH(CH$_2$CH$_3$)COOH, —OCH$_2$COOH, —OCH$_2$COOC(CH$_3$)$_3$, —O(CH$_2$)$_3$C(CH$_3$)$_2$COOH, —O(CH$_2$)$_3$C(CH$_3$)$_2$COOCH$_3$, —OCH(C$_6$H$_5$)COO(C$_2$H$_5$), or —OCH(C$_6$H$_5$)COOH group.

A particular aspect of the invention relates to compounds of general formula (I) in which X8 represents a hydrogen atom.

According to another aspect of the invention, the compounds of general formula (I) have at least one of the X3, X4, X6 and X7 groups representing a halogen atom or an alkyl group having 1 to 4 carbon atoms, preferably a halogen.

Another particular object of the invention relates to compounds of general formula (I) in which X3 and/or X4, which may be identical or different, represent a halogen, preferably chlorine or fluorine.

Preferably, X3 and X4 are identical and represent a halogen, preferably a chlorine or fluorine atom, even more preferably a chlorine atom.

Another particular object of the invention relates to compounds of general formula (I) in which X3 represents a hydrogen atom and X4 represents a bromine or fluorine atom.

According to another aspect of the invention, the compounds of general formula (I) have at least one of the X3, X4, X6 and X7 groups representing a halogen atom or an alkyl group having 1 to 4 carbon atoms and the remaining group(s) (i.e. the unhalogenated or unalkylated group(s) selected from X3, X4, X6 and X7) represent a hydrogen atom or hydrogen atoms.

Another particular object of the invention relates to compounds of formula (I) in which X4 and/or X6 represent an alkyl group, in particular compounds in which X4 and X6 are two methyl groups, and X3 and X7 are hydrogen atoms.

Another particular object of the invention relates to compounds of general formula (I) in which X6 and X7 represent a hydrogen atom.

Preferably, X6 and X7 represent a hydrogen and X3 and/or X4, which may be identical or different, represent a halogen, preferably chlorine or fluorine.

Another preferred aspect relates to compounds of general formula (I) in which X1 represents a group R1 or —OR1, R1 representing a hydrogen or an alkyl group. Preferably, R1 represents an alkyl group having 1, 2 or 3 carbon atoms, even more preferably the alkyl group is halogenated.

Preferably, X1 is selected from a trifluoromethyl group, a bromine atom, a methyloxy group, a methylthio group, a trifluoromethoxy group and a hydrogen atom. Optionally, X1 represents a group —CF$_3$, —OCF$_3$, —SCH$_3$.

Another preferred aspect relates to compounds of general formula (I) in which X1 represents a halogen, preferably bromine.

Another particular object of the invention relates to compounds of general formula (I) in which X2 represents a sulfur atom.

Another particular object of the invention relates to compounds of general formula (I) in which ring II is substituted with ring I in position $C_4$.

Another particular object of the invention relates to compounds of general formula (I) in which ring II is substituted with ring I in position $C_5$.

Another particular object of the invention relates to compounds of general formula (I) in which ring I is substituted with the group X1 in position $C_3$ (or meta relative to ring II)

Another particular object of the invention relates to compounds of general formula (I) in which ring I is substituted with the X1 group in position $C_4$ (or para relative to ring II).

Another particular aspect of the invention relates to compounds of general formula (I) in which R1 represents a hydrogen or an alkyl group having 1 to 4 carbon atoms which can optionally be halogenated, and R3, R4, R6, R7 and R8, which may be identical or different, being selected from a hydrogen or an alkyl group having 1 to 4 carbon atoms.

Even more preferably, the invention relates to compounds of general formula (I) in which at least one of the following conditions, preferably all the conditions, are fulfilled:

X6 and X7, which are identical, represent a hydrogen; and/or

X3 and/or X4, which may be identical or different, represent a halogen, preferably chlorine or fluorine; and/or X2 represents an oxygen or a sulfur, preferably sulfur; and/or X5 represents a R5, —OR5 or —SR5 group, R5 representing an alkyl group substituted with a substituent of group 1; and/or ring II is substituted with ring I in position $C_4$ or in position $C_5$; and/or ring I is substituted with the X1 group in position $C_3$ or in position $C_4$; and/or X1 represents a halogen, a R1, —SR1 or —OR1 group, R1 representing a hydrogen or an alkyl group; and/or A represents:
  (i) a carbonyl group (CO),
  (ii) an oxime group (C=N—O—H) or oxime ether group (C=N—O—R11),
  (iii) a —CR9R10 group, R9 and R10 being different, representing a hydrogen, an alkyl group or a —OR11 group, R11 being as defined below, R11 representing a hydrogen or an aryl, heterocycloalkyl, or heteroaryl group as defined below or an alkyl group, substituted or not with a cycloalkyl, heterocycloalkyl, aryl or heteroaryl group as defined above; and/or B represents an unsubstituted, saturated alkyl group comprising two carbon atoms (CH$_2$—CH$_2$).

In a particularly preferred embodiment, the invention relates to compounds derived from substituted 3-phenyl-1-(phenylthienyl)propan-1-ones and 3-phenyl-1-(phenylfuranyl)propan-1-ones of the following general formula (I):

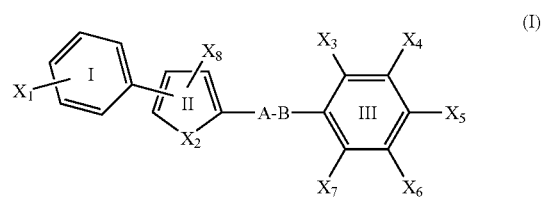

in which:
  X1 represents a halogen, an R1, —SR1 or —OR1 group;
  X2 represents a sulfur or oxygen atom;
  X3 represents a halogen, an R3, —SR3 or —OR3 group;
  X4 represents a halogen, an R4, —SR4 or —OR4 group;
  X5 represents an R5, —SR5 or —OR5 group;
  X6 represents a halogen, an R6, —SR6 or —OR6 group;
  X7 represents a halogen, an R7, —SR7 or —OR7 group;
  X8 represents an R8 group;

R1 representing a hydrogen or an alkyl group having 1 to 4 carbon atoms, said alkyl group being optionally halogenated;

R3, R4, R6, R7 and R8, which may be identical or different, being selected from a hydrogen or an alkyl group having 1 to 4 carbon atoms;

R5 representing an alkyl radical formed from a saturated linear carbon chain, having 1 to 4 carbon atoms, preferably 1 carbon atom, said carbon chain being:
  bound, by its end opposite to the phenyl group (III), to a substituent selected from —COOR12 and —CONR12R13, R12 and R13, which may be identical or different, representing a hydrogen or an alkyl group having 1 to 4 carbon atoms;
  unbranched or branched with at least one alkyl or alkenyl group having 1 to 4 carbon atoms, or substituted with a phenyl group;

A represents:
  (i) a carbonyl group (CO),
  (ii) an oxime group (C=N—O—H) or oxime ether group (C=N—O—R11), with R11 selected from a hydrogen atom, an alkyl group (linear or branched) having 1 to 7 carbon atoms, substituted or not with an aryl group, notably a phenyl group, said alkyl and aryl groups being optionally halogenated, or
  (iii) a —CR9R10 group, R9 representing a hydrogen atom and R10 representing a —OR11 group, R11 being selected from a hydrogen atom, an alkyl group (linear or branched) having 1 to 7 carbon atoms, preferably having 1, 2 or 3 carbon atoms, said alkyl group being unsubstituted or substituted with a cycloalkyl group, notably cyclohexyl, an aryl group, notably phenyl, or a heteroaryl group, notably pyridinyl, said alkyl, cycloalkyl, aryl or heteroaryl groups optionally being halogenated, B represents:
  (i) an unsubstituted, saturated alkyl group having two carbon atoms (CH$_2$—CH$_2$), or
  (ii) an unsubstituted alkene group, having two carbon atoms (CH=CH).

A variant of the particularly preferred embodiment of the invention relates to compounds of general formula (I) in which A represents a carbonyl group (C=O).

Another variant of the particularly preferred embodiment of the invention relates to compounds of general formula (I) in which A represents a —CHOR11 group, R11 preferably being selected from a hydrogen atom, a methyl, ethyl, isopropyl, cyclohexylmethyl, benzyl, iodobenzyl and pyridinylmethoxyl group.

A further variant of the particularly preferred embodiment of the invention relates to compounds of general formula (I) in which A represents an oxime group or oxime ether group (C=N—O—R11), group R11 preferably being selected from a hydrogen atom, a methyl, ethyl, isopropyl, cyclohexylmethyl, benzyl, iodobenzyl, or pyridinylmethyl group, even more preferably from a hydrogen atom and a methyl group.

In another variant, the particularly preferred embodiment of the invention relates to compounds of general formula (I) in which X5 is a —OR5 group, or a bioisomer of the —OR5 group, notably a —SR5 group, with R5 representing an alkyl radical in which said carbon chain is bound to a —COOR12 substituent.

Advantageously, X5 is selected from the groups: —OC(CH$_3$)$_2$COOR12, —OCH(CH$_2$CH$_3$)COOR12, —O(CH$_2$)$_3$C(CH$_3$)$_2$COOR12, —OCH(C$_6$H$_5$)COOR12 and —OCH$_2$COOR12.

Advantageously, R12 is selected from hydrogen and the —CH$_3$, —C(CH$_3$)$_3$ and —CH$_2$CH$_3$ groups.

According to a variant of the particularly preferred embodiment of the invention, X8 represents a hydrogen atom.

A particular object of the invention relates, in the particularly preferred embodiment of the invention, to compounds of general formula (I) in which ring II is substituted with ring I in position C$_4$.

Another particular object of the invention relates, in the particularly preferred embodiment of the invention, to compounds of general formula (I) in which ring II is substituted with ring I in position C$_5$.

The X1 group can be in any position of ring I, i.e. in ortho, meta or para position relative to ring II. In a particular variant of the particularly preferred embodiment of the invention, X1 is in meta or para position, preferably in para position, relative to ring II.

In a particular variant of the particularly preferred embodiment of the invention, X1 is selected from a trifluoromethyl group, a bromine atom, a methyloxy group, a methylthio group, a trifluoromethoxy group and a hydrogen atom.

According to a particular aspect of the invention, in the particularly preferred embodiment of the invention, the compounds according to the invention have at least one of the X3, X4, X6 and X7 groups representing a halogen atom or an alkyl group having 1 to 4 carbon atoms. Preferably, the remaining group(s) (i.e. the unhalogenated or unalkylated group(s) selected from X3, X4, X6 and X7) represent a hydrogen atom or hydrogen atoms.

As an example, they can also be compounds for which X3 and X4 are identical and correspond to halogen atoms (chlorine, fluorine, bromine or iodine), notably chlorine or fluorine.

They can also be compounds for which X4 and/or X6 represent an alkyl group, in particular compounds for which X4 and X6 are two methyl groups, and X3 and X7 are hydrogen atoms.

According to a particular aspect of the invention, in the particularly preferred embodiment of the invention, X4 and/or X6 represent an alkyl group, in particular X4 and X6 are two methyl groups, and X3 and X7 are hydrogen atoms.

Preferably, the compounds according to the invention are selected from:
tert-butyl 2-(2,3-dichloro-4-(3-oxo-3-(5-(4-(trifluoromethyl)phenyl)thien-2-yl)propyl)-phenoxy)-2-methylpropanoate;
2-(2,3-dichloro-4-(3-oxo-3-(5-(4-(trifluoromethyl)phenyl)thien-2-yl)propyl)phenoxy)-2-methylpropanoic acid;
tert-butyl 2-(2,3-dichloro-4-(3-hydroxy-3-(5-(4-(trifluoromethyl)phenyl)thien-2-yl)-propyl)phenoxy)-2-methylpropanoate;
2-(2,3-dichloro-4-(3-hydroxy-3-(5-(4-(trifluoromethyl)phenyl)thien-2-yl)-propyl)phenoxy)-2-methylpropanoic acid;
tert-butyl 2-(4-(3-(4-iodobenzyloxy)-3-(5-(4-(trifluoromethyl)phenyl)thien-2-yl)-propyl)-2,3-dichlorophenoxy)-2-methylpropanoate
2-(4-(3-(4-iodobenzyloxy)-3-(5-(4-(trifluoromethyl)phenyl)thien-2-yl)-propyl)-2,3-dichlorophenoxy)-2-methylpropanoic acid;
2-(4-(3-(benzyloxy)-3-(5-(4-(trifluoromethyl)phenyl)thien-2-yl) propyl)-2,3-dichlorophenoxy)-2-methylpropanoic acid;
tert-butyl 2-(2,3-dichloro-4-(3-oxo-3-(5-(4-(trifluoromethyl)phenyl)thien-2-yl)propyl)-phenoxy)butanoate;
2-(2,3-dichloro-4-(3-oxo-3-(5-(4-(trifluoromethyl)phenyl)thien-2-yl)-propyl)phenoxy)butanoic acid;
tert-butyl 2-(2,3-dichloro-4-(3-oxo-3-(4-(4-(trifluoromethyl)phenyl)thien-2-yl)propyl)-phenoxy)-2-methylpropanoate;
2-(2,3-dichloro-4-(3-oxo-3-(4-(4-(trifluoromethyl)phenyl)thien-2-yl)-propyl)phenoxy)-2-methylpropanoic acid;
methyl 5-(2,3-dichloro-4-(3-oxo-3-(5-(4-(trifluoromethyl)phenyl)thien-2-yl)propyl)-phenoxy)-2,2-dimethylpentanoate;
5-(2,3-dichloro-4-(3-oxo-3-(5-(4-(trifluoromethyl)phenyl)thien-2-yl)-propyl)phenoxy)-2,2-dimethylpentanoic acid;
tert-butyl 2-(2,3-dichloro-4-(3-oxo-3-(5-(4-(trifluoromethyl)phenyl)thien-2-yl)propyl)-phenoxy)acetate;
2-(2,3-dichloro-4-(3-oxo-3-(5-(4-(trifluoromethyl)phenyl)thien-2-yl)-propyl)phenoxy)acetic acid;
ethyl 2-(2,3-dichloro-4-(3-oxo-3-(5-(4-(trifluoromethyl)phenyl)thien-2-yl)propyl)-phenoxy)-2-phenylacetate;
2-(2,3-dichloro-4-(3-oxo-3-(5-(4-(trifluoromethyl)phenyl)thien-2-yl)-propyl)-phenoxy)-2-phenylacetic acid;
tert-butyl 2-(2-chloro-4-(3-oxo-3-(5-(4-(trifluoromethyl)phenyl)thien-2-yl)propyl)-phenoxy)-2-methylpropanoate;
2-(2-chloro-4-(3-oxo-3-(5-(4-(trifluoromethyl)phenyl)thien-2-yl)propyl)phenoxy)-2-methylpropanoic acid;
tert-butyl 2-(3-chloro-4-(3-oxo-3-(5-(4-(trifluoromethyl)phenyl)thien-2-yl)propyl)-phenoxy)-2-methylpropanoate;
2-(3-chloro-4-(3-oxo-3-(5-(4-(trifluoromethyl)phenyl)thien-2-yl)propyl)-phenoxy)-2-methylpropanoic acid;
tert-butyl 2-(2-fluoro-4-(3-oxo-3-(5-(4-(trifluoromethyl)phenyl)thien-2-yl)propyl)-phenoxy)-2-methylpropanoate;
2-(2-fluoro-4-(3-oxo-3-(5-(4-(trifluoromethyl)phenyl)thien-2-yl) propyl)-phenoxy)-2-methylpropanoic acid;
tert-butyl 2-(2-fluoro-4-(3-oxo-3-(5-(4-(trifluoromethyl)phenyl)thien-2-yl)propyl)-phenoxy)acetate;
2-(2-fluoro-4-(3-oxo-3-(5-(4-(trifluoromethyl)phenyl)thien-2-yl)propyl)-phenoxy)acetic acid;
2-(2-fluoro-4-(3-hydroxy-3-(5-(4-(trifluoromethyl)phenyl)thien-2-yl)-propyl)phenoxy)acetic acid;
2-(4-(3-(benzyloxy)-3-(5-(4-(trifluoromethyl)phenyl)thien-2-yl)propyl)-2-fluorophenoxy)acetic acid;
tert-butyl 2-(2-fluoro-4-(3-oxo-3-(5-(4-(trifluoromethyl)phenyl)thien-2-yl)propyl)-phenoxy)butanoate;
2-(2-fluoro-4-(3-oxo-3-(5-(4-(trifluoromethyl)phenyl)thien-2-yl)propyl)-phenoxy)butanoic acid;
2-(2-fluoro-4-(3-hydroxy-3-(5-(4-(trifluoromethyl)phenyl)thien-2-yl)-propyl)phenoxy)butanoic acid;
tert-butyl 2-(2-bromo-4-(3-oxo-3-(5-(4-(trifluoromethyl)phenyl)thien-2-yl)propyl)-phenoxy)butanoate;

2-(2-bromo-4-(3-oxo-3-(5-(4-(trifluoromethyl)phenyl)thien-2-yl)propyl)-phenoxy)butanoic acid;

tert-butyl 2-(2-bromo-4-(3-oxo-3-(5-(4-(trifluoromethyl)phenyl)thien-2-yl)propyl)-phenoxy)acetate;

2-(2-bromo-4-(3-oxo-3-(5-(4-(trifluoromethyl)phenyl)thien-2-yl)propyl)-phenoxy)acetic acid;

tert-butyl 2-(2-bromo-4-(3-oxo-3-(5-(4-(trifluoromethyl)phenyl)thien-2-yl)propyl)-phenoxy)-2-methylpropanoate;

2-(2-bromo-4-(3-oxo-3-(5-(4-(trifluoromethyl)phenyl)thien-2-yl)propyl)-phenoxy)-2-methylpropanoic acid;

tert-butyl 2-(2,3-dichloro-4-(3-oxo-3-(5-(4-(trifluoromethyl)phenyl)fur-2-yl)propyl)-phenoxy)-2-methylpropanoate;

2-(2,3-dichloro-4-(3-oxo-3-(5-(4-(trifluoromethyl)phenyl)fur-2-yl)propyl)-phenoxy)-2-methylpropanoic acid;

2-(2,3-dichloro-4-(3-(pyridin-3-ylmethoxy)-3-(5-(4-(trifluoromethyl)-phenyl)thien-2-yl)propyl)phenoxy)-2-methylpropanoic acid;

2-(2,3-dichloro-4-(3-methoxy-3-(5-(4-(trifluoromethyl)phenyl)thien-2-yl)propyl)phenoxy)-2-methylpropanoic acid;

2-(2,3-dichloro-4-(3-ethoxy-3-(5-(4-(trifluoromethyl)phenyl)thien-2-yl)-propyl)phenoxy)-2-methylpropanoic acid;

2-(2,3-dichloro-4-(3-(cyclohexylmethoxy)-3-(5-(4-(trifluoromethyl)-phenyl)-thien-2-yl)propyl)phenoxy)-2-methylpropanoic acid;

tert-butyl 2-(2,3-dichloro-4-(3-oxo-3-(5-(4-(trifluoromethoxy)phenyl)thien-2-yl)propyl)-phenoxy)-2-methylpropanoate;

2-(2,3-dichloro-4-(3-oxo-3-(5-(4-(trifluoromethoxy)phenyl)thien-2-yl)-propyl)phenoxy)-2-acid;

tert-butyl 2-(2,3-difluoro-4-(3-oxo-3-(5-(4-(trifluoromethyl)phenyl)thien-2-yl)propyl)-phenoxy)-2-methylpropanoate;

2-(2,3-difluoro-4-(3-oxo-3-(5-(4-(trifluoromethyl)phenyl)thien-2-yl)-propyl)phenoxy)-2-methylpropanoic acid;

tert-butyl 2-(2,6-dimethyl-4-(3-oxo-3-(5-(4-(trifluoromethyl)phenyl)thien-2-yl)propyl)-phenoxy)-2-methylpropanoate;

2-(2,6-dimethyl-4-(3-oxo-3-(5-(4-(trifluoromethyl)phenyl)thien-2-yl)-propyl)-phenoxy)-2-methylpropanoic acid;

2-(2,3-dichloro-4-(3-(hydroxyimino)-3-(5-(4-(trifluoromethyl)phenyl)-thien-2-yl)propyl)phenoxy)-2-methylpropanoic acid;

2-(2,3-dichloro-4-(3-(methoxyimino)-3-(5-(4-(trifluoromethyl)phenyl)-thien-2-yl)propyl)phenoxy)-2-methylpropanoic acid;

tert-butyl 2-(4-(3-(5-(4-bromophenyl)thien-2-yl)-3-oxopropyl)-2,3-dichlorophenoxy)-2-methylpropanoate;

2-(4-(3-(5-(4-bromophenyl)thien-2-yl)-3-oxopropyl)-2,3-dichloro-phenoxy)-2-methylpropanoic acid;

tert-butyl 2-(2,3-dichloro-4-(3-(5-(4-(methylthio)phenyl)thien-2-yl)-3-oxopropyl)-phenoxy)-2-methylpropanoate;

2-(2,3-dichloro-4-(3-(5-(4-(methylthio)phenyl)thien-2-yl)-3-oxo-propyl)phenoxy)-2-methylpropanoic acid;

2-(2,3-dichloro-4-(3-isopropoxy-3-(5-(4-(trifluoromethyl)phenyl)thien-2-yl)propyl)phenoxy)-2-methylpropanoic acid;

tert-butyl 2-(2,3-dichloro-4-(3-oxo-3-(5-phenylthiophen-2-yl)propyl)phenoxy)-2-methylpropanoate;

2-(2,3-dichloro-4-(3-oxo-3-(5-phenylthien-2-yl)propyl)phenoxy)-2-methylpropanoic acid;

tert-butyl 2-methyl-2-(2-methyl-4-(3-oxo-3-(5-(4-(trifluoromethyl)phenyl)thiophen-2-yl)-propyl)phenoxy)propanoate;

2-methyl-2-(2-methyl-4-(3-oxo-3-(5-(4-(trifluoromethyl)phenyl)-thiophen-2-yl)propyl)phenoxy)propanoic acid;

2-(2,3-dichloro-4-(3-hydroxy-3-(4-(4-(trifluoromethyl)phenyl)thien-2-yl)-propyl)phenoxy)-2-methylpropanoic acid;

2-(4-(3-(benzyloxy)-3-(4-(4-(trifluoromethyl)phenyl)thien-2-yl)propyl)-2,3-dichlorophenoxy)-2-methylpropanoic acid;

2-(2,3-difluoro-4-(3-hydroxy-3-(5-(4-(trifluoromethyl)phenyl)thien-2-yl)-propyl)phenoxy)-2-methylpropanoic acid;

2-(4-(3-(benzyloxy)-3-(5-(4-(trifluoromethyl)phenyl)thien-2-yl)propyl)-2,3-difluorophenoxy)-2-methylpropanoic acid;

tert-butyl 2-(4-(3-oxo-3-(5-(4-(trifluoromethyl)phenyl)thien-2-yl)propyl)phenoxy)-butanoate;

2-(4-(3-oxo-3-(5-(4-(trifluoromethyl)phenyl)thien-2-yl)propyl)-phenoxy)-butanoic acid;

tert-butyl 2-methyl-2-(4-(3-oxo-3-(5-(4-(trifluoromethyl)phenyl)thien-2-yl)propyl)-phenoxy)propanoate;

2-(4-(3-oxo-3-(5-(4-(trifluoromethyl)phenyl)thien-2-yl)propyl)-phenoxy)-2-methylpropanoic acid;

tert-butyl 2-(4-(3-oxo-3-(5-(4-(trifluoromethyl)phenyl)thien-2-yl)propyl)phenoxy)-acetate;

2-(4-(3-oxo-3-(5-(4-(trifluoromethyl)phenyl)thien-2-yl)propyl)phenoxy)-acetic acid;

2-(4-(3-(benzyloxy)-3-(5-(4-(trifluoromethyl)phenyl)thien-2-yl)propyl)-2-fluorophenoxy)butanoic acid;

2-(2,3-dichloro-4-(3-hydroxy-3-(5-(4-(trifluoromethyl)phenyl)furan-2-yl)-propyl)phenoxy)-2-methylpropanoic acid;

2-(2,3-dichloro-4-(3-methoxy-3-(5-(4-(trifluoromethyl)phenyl)fur-2-yl)-propyl)phenoxy)-2-methylpropanoic acid;

2-(4-(3-hydroxy-3-(5-(4-(trifluoromethyl)phenyl)thien-2-yl)propyl)-2,6-dimethylphenoxy)-2-methylpropanoic acid;

2-(4-(3-methoxy-3-(5-(4-(trifluoromethyl)phenyl)thien-2-yl)propyl)-2,6-dimethylphenoxy)-2-methylpropanoic acid;

ethyl 2-(2,3-dichloro-4-(3-oxo-3-(5-(3-(trifluoromethyl)phenyl)thien-2-yl)propyl)-phenoxy)-2-methylpropanoate;

2-(2,3-dichloro-4-(3-oxo-3-(5-(3-(trifluoromethyl)phenyl)thien-2-yl)-propyl)phenoxy)-2-methylpropanoic acid;

ethyl 2-(2,3-dichloro-4-(3-hydroxy-3-(5-(3-(trifluoromethyl)phenyl)thien-2-yl)-propyl)phenoxy)-2-methylpropanoate;

ethyl 2-(2,3-dichloro-4-(3-methoxy-3-(5-(3-(trifluoromethyl)phenyl)thien-2-yl)-propyl)phenoxy)-2-methylpropanoate;

2-(2,3-dichloro-4-(3-hydroxy-3-(5-(4-(trifluoromethoxy)phenyl)thien-2-yl)propyl)phenoxy)-2-methylpropanoic acid;

2-(2,3-dichloro-4-(3-methoxy-3-(5-(4-(trifluoromethoxy)phenyl)thien-2-yl)propyl)phenoxy)-2-methylpropanoic acid.

The compounds according to the invention can contain one or more asymmetric centers. The present invention includes the stereoisomers (diastereoisomers, enantiomers), pure or mixed, as well as racemic mixtures and geometric isomers. When an enantiomerically pure (or enriched) mixture is desired, it can be obtained either by purifying the final product or chiral intermediates, or by asymmetric synthesis according to methods known by a person skilled in the art (for example using chiral reagents and catalysts). Some compounds according to the invention can have various stable tautomeric forms and all these forms and mixtures thereof are included in the invention.

The present invention also relates to the "pharmaceutically acceptable" salts of the compounds according to the invention. In general, this term denotes the low toxicity or nontoxic salts obtained from bases or from acids, organic or inorganic. These salts can be obtained during the stage of final purification of the compound according to the invention or by incorporating the salt in the compound already purified.

Some compounds according to the invention and their salts could be stable in several solid forms. The present invention includes all the solid forms of the compounds according to the invention, which includes the amorphous, polymorphic, mono- and poly-crystalline forms.

The compounds according to the invention can be in the free form or in a solvated form, for example with pharmaceutically acceptable solvents such as water (hydrates) or ethanol.

Compounds according to the invention labeled with an isotope or with isotopes are also included in the invention: these compounds are structurally identical but differ in that at least one atom of the structure is replaced with an isotope (radioactive or not). Examples of isotopes that can be included in the structure of the compounds according to the invention can be selected from hydrogen, carbon, oxygen, sulfur such as $^2H$, $^3H$, $^{13}C$, $^{14}C$, $^{18}O$, $^{17}O$, $^{35}S$ respectively. The radioactive isotopes $^3H$ and $^{14}C$ are particularly preferred as they are easy to prepare and detect in studies of in vivo bioavailability of the substances. The heavy isotopes (such as $^2H$) are particularly preferred as they are used as internal standards in analytical studies.

The present invention also relates to the method of synthesis of the compounds of general formula (I), which comprises:
1. a stage of contacting, in a basic medium or an acid medium, at least one compound of formula (C) with at least one compound of formula (D)

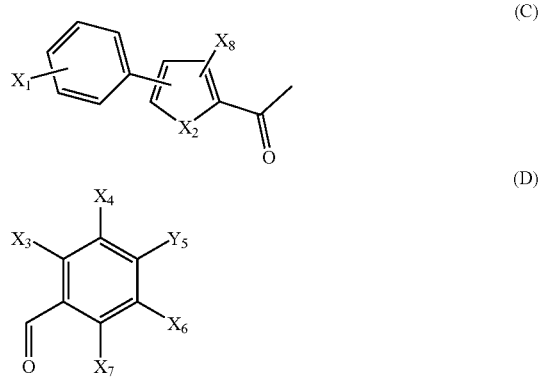

in which X1, X2, X3, X4, X6, X7 and X8 are as defined above,
Y5 represents a R5, —SR5, —OR5, hydroxyl or thiol group, R5 being as defined above;
2. optionally a stage of reduction of the compounds obtained in stage (1),
3. and optionally a stage of insertion of functional groups.

The conditions of implementation of stage (1) in an acid or basic medium and of stage (2) are known by a person skilled in the art and can vary widely. The synthesis protocols can in particular be those presented in the "examples" section of the present invention.

The contacting of these two compounds is advantageously carried out stoichiometrically. It is carried out preferably at a suitable temperature (between about 18° C. and 100° C.) and preferably at atmospheric pressure.

In a basic medium, the reaction is preferably carried out in the presence of a strong base, such as an alkali metal hydroxide, such as sodium hydroxide, or an alkali metal alcoholate such as sodium ethylate.

In an acid medium, the reaction is preferably carried out in the presence of a strong acid, such as hydrochloric acid.

The compounds thus obtained can be isolated by conventional methods known by a person skilled in the art.

The present invention also relates to the compounds as described above, as medicaments.

The present invention also relates to a compound as described above, for the treatment of complications associated with metabolic syndrome, of atherosclerosis, cerebral ischemia, autoimmune diseases, cardiovascular diseases, insulin resistance, obesity, hypertension, diabetes, dyslipidemias, inflammatory diseases (such as asthma), neurodegenerative pathologies (in particular multiple sclerosis, Parkinson's disease, Alzheimer's disease, tauopathies (frontotemporal dementias, Pick's disease, cortical basal degeneration, progressive supranuclear paralysis), cortical dementias, spinal amyotrophies, mild cognitive impairment (MCI), synucleopathies, pathologies with Lewy bodies, Huntington's chorea, epilepsies, amyotrophic lateral sclerosis, prion diseases (Creutzfeldt-Jacob disease), Down syndrome, Friedreich ataxia, spinocerebellar ataxias, Charcot-Marie-Tooth disease, neurological complications associated with AIDS, chronic pains, cerebellar degeneration, cerebellar hypoxia, neuropathies associated with diabetes), cancers, etc., as well as for lowering general cardiovascular risk.

Preferably, the invention relates to a compound as described above, for treating the cardiovascular risk factors connected with disturbances of lipid and/or carbohydrate metabolism, notably hyperlipidemias and obesity, and in particular diabetes (type II diabetes).

Even more preferably, the invention relates to a compound as described above, for the treatment of dyslipidemias.

The present invention also relates to a pharmaceutical composition comprising, in a pharmaceutically acceptable carrier, at least one compound as described above, optionally in combination with one or more other therapeutic and/or cosmetic active principles.

Advantageously it is a pharmaceutical composition for treating the complications associated with metabolic syndrome, atherosclerosis, cerebral ischemia, autoimmune diseases, cardiovascular diseases, insulin resistance, obesity, hypertension, diabetes, dyslipidemias, inflammatory diseases (such as asthma), neurodegenerative pathologies (in particular multiple sclerosis, Parkinson's disease, Alzheimer's disease, tauopathies (frontotemporal dementias, Pick's disease, cortical basal degeneration, progressive supranuclear paralysis), cortical dementias, spinal amyotrophies, mild cognitive impairment (MCI), synucleopathies, pathologies with Lewy bodies, Huntington's chorea, epilepsies, amyotrophic lateral sclerosis, prion diseases (Creutzfeldt-Jacob disease), Down syndrome, Friedreich ataxia, spinocerebellar ataxias, Charcot-Marie-Tooth disease, neurological complications associated with AIDS, chronic pains, cerebellar degeneration, cerebellar hypoxia, neuropathies associated with diabetes), cancers, etc., as well as for lowering general cardiovascular risk.

Preferably it relates to a pharmaceutical composition for treating the cardiovascular risk factors connected with disturbances of lipid and/or carbohydrate metabolism, notably hyperlipidemias and obesity, and in particular diabetes (type II diabetes).

Even more preferably, the pharmaceutical composition according to the invention is intended for the treatment of dyslipidemias.

Another object of the invention relates to a nutritional composition comprising at least one compound as described above.

The present invention also relates to the compounds as described above, as cosmetic products.

Another object of the invention relates to the use of at least one compound as described above for the preparation of pharmaceutical compositions intended for the treatment of various pathologies as defined above, notably connected with disorders of lipid and/or carbohydrate metabolism, among which we may mention the dyslipidemias. More generally, the invention relates to the use of at least one compound as described above for the preparation of pharmaceutical compositions intended for treating the risk factors for cardiovascular diseases connected with disturbances of the metabolism of lipids and/or of carbohydrates and intended for thus lowering the general cardiovascular risk.

As a nonlimiting example, the compounds according to the invention can advantageously be administered in combination with one or more other therapeutic and/or cosmetic agents, marketed or under development, such as:

antidiabetic agents: insulin secretors (sulfonylureas (glibenclamide, glimepiride, glyclazide, etc.) and glinides (repaglinide, nateglinide, etc.)), inhibitors of alpha-glucosidase, PPARγ agonists (thiazolidinediones such as rosiglitazone, pioglitazone), mixed PPARα/PPARγ agonists (tesaglitazar, muraglitazar), pan-PPARs (compounds activating the 3 PPAR isoforms simultaneously), biguanides (metformin), inhibitors of dipeptidyl peptidase IV (sitagliptin, vildagliptin), glucagon-like peptide-1 (GLP-1) agonists (exenatide), etc.

insulin antilipemic and/or cholesterol-lowering agents: fibrates (fenofibrate, gemfibrozil), inhibitors of HMG CoA reductase or hydroxymethylglutaryl coenzyme A reductase (statins such as atorvastatin, simvastatin, fluvastatin), inhibitors of cholesterol absorption (ezetimibe, phytosterols), cholesterol ester transfer protein (CETP) inhibitors (torcetrapib), Acyl-Coenzyme A cholesterol acyltransferase (ACAT) inhibitors (avasimibe, eflucimibe), microsomal triglyceride transfer protein (MTP) inhibitors, bile acid sequestering agents (cholestyramine), vitamin E, polyunsaturated fatty acids, omega 3 fatty acids, derivatives of the nicotinic acid type (niacin), etc.

antihypertensive agents and hypotensive agents: angiotensin-converting enzyme (ACE) inhibitors (captopril, enalapril, ramipril or quinapril), angiotensin II receptor antagonists (losartan, valsartan, telmisartan, eposartan, irbesartan, etc.), beta-blockers (atenolol, metoprolol, labetalol, propranolol), thiazide and nonthiazide diuretics (furosemide, indapamide, hydrochlorothiazide, antialdosterone), vasodilators, calcium channel blockers (nifedipine, felodipine or amlodipine, diltiazem or verapamil), etc.

antiplatelet drugs: aspirin, ticlopidine, dipyridamole, clopidogrel, flurbiprofen, etc.

antiobesity agents: sibutramine, lipase inhibitors (orlistat), PPARδ agonists and antagonists, cannabinoid CB1 receptor antagonists (rimonabant), etc.

antiinflammatory agents: for example, corticoids (prednisone, betamethasone, dexamethasone, prednisolone, methylprednisolone, hydrocortisone, etc.), nonsteroidal antiinflammatory drugs (NSAIDs) derived from indole (indomethacin, sulindac), NSAIDS of the arylcarboxylic group (tiaprofenic acid, diclofenac, etodolac, flurbiprofen, ibuprofen, ketoprofen, naproxen, nabumetone, alminoprofen), NSAIDS derived from oxicam (meloxicam, piroxicam, tenoxicam), NSAIDS of the fenamate group, selective COX-2 inhibitors (celecoxib, rofecoxib), etc.

antioxidants: for example probucol, etc.

agents used in the treatment of heart failure: the thiazide or nonthiazide diuretics (furosemide, indapamide, hydrochlorothiazide, antialdosterone), ACE inhibitors (captopril, enalapril, ramipril or quinapril), digitalis drugs (digoxin, digitoxin), beta-blockers (atenolol, metoprolol, labetalol, propranolol), phosphodiesterase inhibitors (enoximone, milrinone), etc.

agents used for the treatment of coronary insufficiency: beta-blockers (atenolol, metoprolol, labetalol, propranolol), calcium channel blockers (nifedipine, felodipine or amlodipine, bepridil, diltiazem or verapamil), NO donors (trinitrin, isosorbide dinitrate, molsidomine), amiodarone, etc.

anticancer drugs: cytotoxic agents (agents interacting with DNA, alkylating agents, cisplatin and derivatives), cytostatic agents (gonadotropin-releasing hormone (GnRH) analogs, somatostatin analogs, progestogens, antiestrogens, aromatase inhibitors, etc.), modulators of immune response (interferons, IL2, etc.), etc.

antiasthmatics such as bronchodilators (beta 2 receptor agonists), corticoids, cromoglycate, leukotriene receptor antagonists (montelukast), etc.

corticoids used in the treatment of skin diseases such as psoriasis and dermatides vasodilators and/or antiischemic agents (buflomedil, extracts of Ginkgo biloba, naftidrofuryl, pentoxifylline, piribedil), etc.

The invention also relates to a method of treatment of various pathologies as defined above, notably connected with disorders of lipid and/or carbohydrate metabolism comprising the administration to a subject, notably human, of an effective amount of a compound or of a pharmaceutical composition as defined above.

In the sense of the invention, the term "an effective amount" refers to an amount of the compound sufficient to produce the desired biological result.

The term "subject" denotes a mammal and more particularly a human.

The term "treatment" denotes curative, symptomatic and/or preventive treatment. The compounds of the present invention can thus be used in subjects (such as mammals, in particular humans) who have a declared disease. The compounds of the present invention can also be used for delaying or slowing the progression or preventing further progression of the disease, thus improving the condition of the subjects. The compounds of the present invention can finally be administered to subjects who are not ill, but who could normally develop the disease or who have a considerable risk of developing the disease.

The pharmaceutical compositions according to the invention advantageously include one or more pharmaceutically acceptable excipients or vehicles. We may mention for example saline, physiological, isotonic, buffered, etc. solutions, compatible with pharmaceutical use and known by a person skilled in the art. The compositions can contain one or more agents or vehicles selected from the dispersants, solubilizers, stabilizers, preservatives, etc. Agents or vehicles that can be used in formulations (liquid and/or injectable and/or solid) are notably methylcellulose, hydroxymethyl cellulose, carboxymethylcellulose, polysorbate 80, mannitol, gelatin, lactose, vegetable oils, acacia, liposomes, etc. The compositions can be formulated in the form of injectable suspensions, gels, oils, tablets, suppositories, powders, hard gelatin capsules, capsules, aerosols, etc., optionally by means of galenical forms or devices that provide prolonged and/or delayed release. For this type of formulation, it is advantageous to use an agent such as cellulose, carbonates or starches.

The compounds or compositions according to the invention can be administered in various ways and in various forms. Thus, they can for example be administered systemically, by the oral or parenteral route, by inhalation or by injection, for example by the intravenous, intramuscular, subcutaneous, transdermal, intraarterial route, etc. For injections, the compounds are generally packaged in the form of liquid suspensions, which can be injected by means of syringes or as infusions, for example.

It is understood that the flow rate and/or the dose injected can be adjusted by a person skilled in the art depending on the patient, the pathology, the method of administration, etc. Typically, the compounds are administered at doses that can vary between 1 µg and 2 g per administration, preferably from 0.01 mg to 1 g per administration. The administrations can be daily or can be repeated several times a day, if necessary. Furthermore, the compositions according to the invention can also include other agents or active principles.

LEGENDS TO THE FIGURES

Abbreviations Used in the Figures and in the Tables:
Cpd=compounds;
HDL-cholesterol: High-Density-Lipoprotein cholesterol
LDL-cholesterol: Low-Density-Lipoprotein cholesterol
VLDL-cholesterol: Very-Low-Density-Lipoprotein cholesterol
mpk=mg/kg/day.

FIGS. 1-1 to 1-9: In Vivo Evaluation, in the E2/E2 Mouse, of the Antilipemic Properties and HDL-Cholesterol Synthesis Stimulating Properties of the Compounds According to the Invention by Lipid Assays and Measurement of the Expression of Genes Involved in Lipid and Carbohydrate Metabolism and Dissipation of Energy The antilipemic effect of the compounds according to the invention was evaluated in vivo in the E2/E2 mouse (humanized for the E2 isoform of apolipoprotein E) by analyzing the distribution of cholesterol and of the triglycerides in the various plasma lipoprotein fractions and by measuring the total cholesterol and HDL-cholesterol plasma levels after 7 and 13 days of treatment by the oral route; these levels are compared with those obtained with control animals (not treated with the compounds according to the invention). The measured difference provides evidence of the antilipemic effect of the compounds according to the invention.

Figures 1, 2:
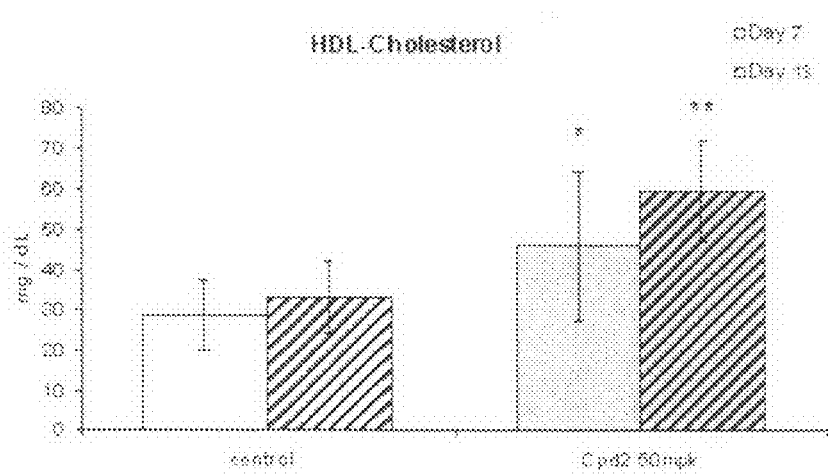
Figures 1, 2, 3:
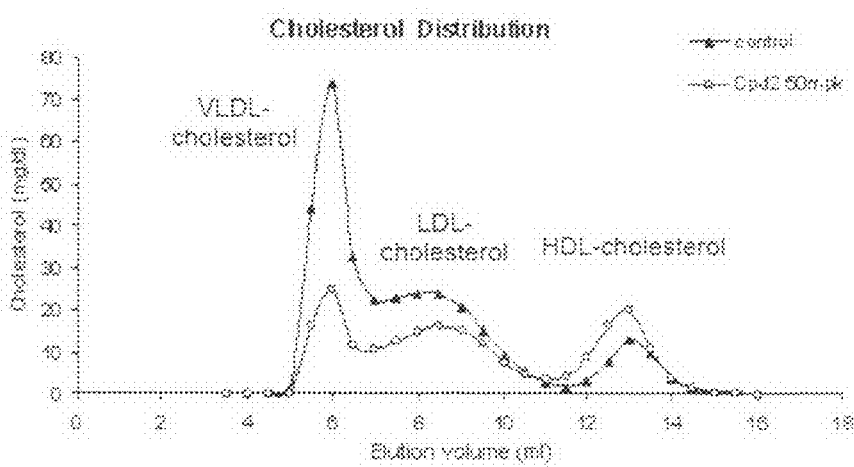

FIG. 1-1: plasma total cholesterol level after 7 and 13 days of treatment with compound 2, administered at 50 mpk;

FIG. 1-2: plasma HDL-cholesterol level after 7 and 13 days of treatment with compound 2, administered at 50 mpk;

FIG. 1-3: distribution of cholesterol in the various plasma lipoprotein fractions after 13 days of treatment with compound 2, administered at 50 mpk;

FIG. 1-4: distribution of triglycerides in the various plasma lipoprotein fractions after 13 days of treatment with compound 2, administered at 50 mpk.

The efficacy of the compounds according to the invention was also evaluated by measuring, in the hepatic and (skeletal) muscle tissues, the expression of genes involved in lipid and carbohydrate metabolism and the dissipation of energy. The levels of expression of each gene were normalized relative to the level of expression of the reference genes 36B4 in the hepatic tissue or 18S in the gastrocnemius skeletal muscle. The induction factor, i.e. the ratio of the relative signal (induced by the compound according to the invention) to the mean of the relative values of the control group was then calculated. The higher this factor, the greater the gene expression activating character of the compound. The final result is represented as the mean of the induction values in each experimental group.

FIG. 1-5: expression of PDK4 (pyruvate dehydrogenase kinase, isoform 4) in the hepatic tissue, in the E2/E2 mouse, after 13 days of treatment with compound 2 (50 mpk);

FIG. 1-6: expression of AcoX1 in the hepatic tissue, in the E2/E2 mouse, after 13 days of treatment with compound 2 (50 mpk);

FIG. 1-7: expression of ApoCIII in the hepatic tissue, in the E2/E2 mouse, after 13 days of treatment with compound 2 (50 mpk);

FIG. 1-8: expression of PDK4 (pyruvate dehydrogenase kinase, isoform 4) in skeletal muscle, in the E2/E2 mouse, after 13 days of treatment with compound 2 (50 mpk);

FIG. 1-9: expression of UCP2 (uncoupling protein 2) in skeletal muscle, in the E2/E2 mouse, after 13 days of treatment with compound 2 (50 mpk).

FIGS. 2-1 to 2-6: In Vivo Evaluation, in the C57Bl6 Mouse, of the Antilipemic Properties and HDL-Cholesterol Synthesis Stimulating Properties of the Compounds According to the Invention by Lipid Assays and Measurement of the Expression of Genes Involved in Lipid and Carbohydrate Metabolism and the Dissipation of Energy.

The effect of compound 2 according to the invention, administered at dose effect, was evaluated in vivo in the C57Bl6 mouse after 14 days of treatment by the oral route. At the end of the treatment, the antilipemic effect of compound 2 according to the invention was evaluated by measuring the plasma levels of total cholesterol, HDL-cholesterol, triglycerides and free fatty acids.

Figures 1, 2, 3, 4:
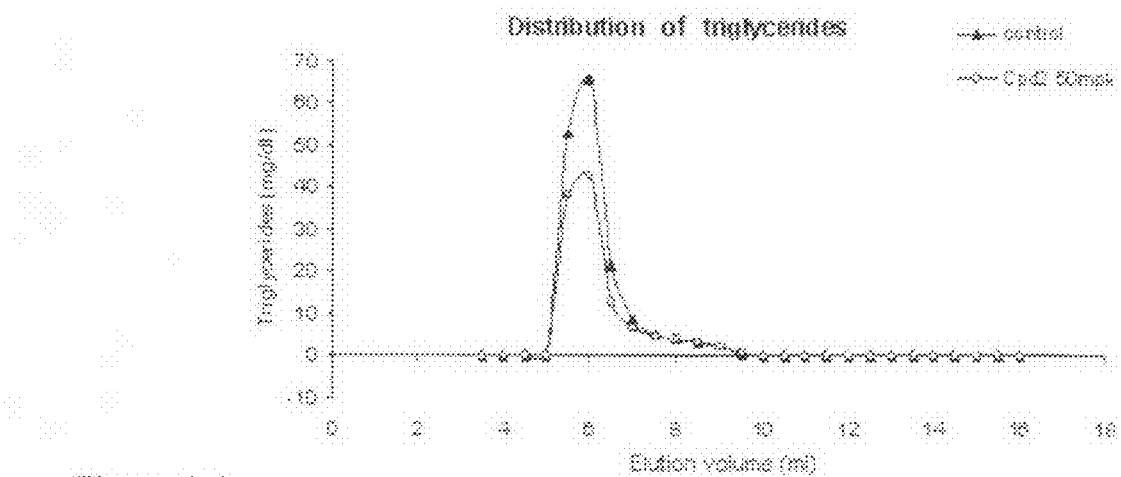

FIG. 2-1: plasma total cholesterol level after 14 days of treatment with compound 2 according to the invention, administered at 1, 5, 10 and 50 mpk, in the C57Bl6 mouse;

FIG. 2-2: plasma HDL-cholesterol level after 14 days of treatment with compound 2 according to the invention, administered at 1, 5, 10 and 50 mpk, in the C57Bl6 mouse;

FIG. 2-3: plasma level of triglycerides after 14 days of treatment with compound 2 according to the invention, administered at 1, 5, 10 and 50 mpk, in the C57Bl6 mouse;

FIG. 2-4: plasma level of free fatty acids after 14 days of treatment with compound 2 according to the invention, administered at 1, 5, 10 and 50 mpk, in the C57Bl6 mouse.

The efficacy of the compounds according to the invention was also evaluated by measuring, in the (skeletal) muscle tissue, the expression of genes involved in carbohydrate metabolism and the dissipation of energy. The levels of expression of each gene were normalized relative to the level of expression of the reference gene 18S. The induction factor was then calculated. The higher this factor, the greater the gene expression activating character of the compounds. The final result is represented as the mean of the induction values in each experimental group.

FIG. 2-5: expression of PDK4 in skeletal muscle, in the C57Bl6 mouse, after 14 days of treatment by the oral route with compound 2 (50 mpk);

FIG. 2-6: expression of UCP2 in skeletal muscle, in the C57Bl6 mouse, after 14 days of treatment by the oral route with compound 2 (50 mpk).

FIGS. 3-1 to 3-7: In Vivo Evaluation, in the C57Bl6 Mouse, of the HDL-Cholesterol Synthesis Stimulating Properties of the Compounds According to the Invention by Lipid Assays and Measurement of the Expression of Genes Involved in Lipid and Carbohydrate Metabolism and the Dissipation of Energy The effect of the compounds according to the invention was evaluated in vivo in the C57Bl6 mouse after 14 days of treatment by the oral route. At the end of the treatment, the distribution of cholesterol in the various plasma lipoprotein fractions was determined. It was compared with the profile obtained for the control animals (not treated with the compounds according to the invention). The effect of the compounds according to the invention was also evaluated in vivo in the C57Bl6 mouse by measuring the plasma levels of total cholesterol and of HDL-cholesterol after 14 days of treatment by the oral route. These levels were compared with those obtained for control animals (not treated with the compounds according to the invention). The measured difference provides evidence of the antilipemic effect of the compounds according to the invention.

FIG. 3-1: plasma total cholesterol level after 14 days of treatment with compounds 4 and 7 according to the invention, administered at 50 mpk;

FIG. 3-2: plasma HDL cholesterol level after 14 days of treatment with compounds 4 and 7 according to the invention, administered at 50 mpk;

FIG. 3-3: distribution of cholesterol in the various plasma lipoprotein fractions after 14 days of treatment with compounds 4 and 7 according to the invention, administered at 50 mpk.

The efficacy of the compounds according to the invention was also evaluated by measuring, in the (skeletal) muscle tissue, the expression of genes involved in lipid and carbohydrate metabolism and the dissipation of energy. The levels of expression of each gene were normalized relative to the level of expression of the reference gene 18S. The induction factor was then calculated. The higher this factor, the greater the gene expression activating character of the compounds. The final result is represented as the mean of the induction values in each experimental group.

Figures 1, 2, 3, 4, 5:
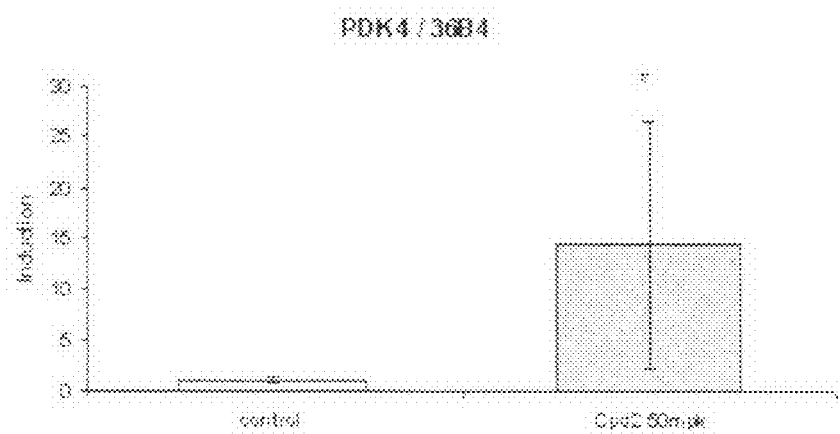

FIG. 3-4: expression of PDK4 in muscle tissue, in the C57Bl6 mouse, after 14 days of treatment with compound 7 (50 mpk);

FIG. 3-5: expression of CPT1b in muscle tissue, in the C57Bl6 mouse, after 14 days of treatment with compounds 4 and 7 (50 mpk);

FIG. 3-6: expression of UCP2 in muscle tissue, in the C57Bl6 mouse, after 14 days of treatment with compounds 4 and 7 (50 mpk);

FIG. 3-7: expression of UCP3 in muscle tissue, in the C57Bl6 mouse, after 14 days of treatment with compounds 4 and 7 (50 mpk).

FIGS. 4-1 to 4-7: In Vivo Evaluation, in the db/db Mouse, of the Antilipemic and Antidiabetic Properties and PPAR-Activating Properties of the Compounds According to the Invention The effect of the compounds according to the invention was evaluated in vivo in the db/db mouse by measuring the plasma triglycerides and insulinemia after 28 days of treatment with compound 2 by the oral route. These levels were compared with those obtained with control animals (not treated with the compound according to the invention). The measured difference provides evidence of the antilipemic effect and effect on insulin resistance of the compound according to the invention.

FIG. 4-1: plasma level of triglycerides after 28 days of treatment with compound 2, administered at 50 mpk in the db/db mouse;

FIG. 4-2: plasma insulin level after 28 days of treatment with compound 2, administered at 50 mpk in the db/db mouse.

The efficacy of compound 2 was also evaluated by measuring, in the hepatic and muscle tissues, the expression of genes involved in carbohydrate and lipid metabolism, and the dissipation of energy. The levels of expression of each gene were normalized relative to the level of expression of the reference genes 36B4 in the liver and 18S in the skeletal muscle. The induction factor, i.e. the ratio of the relative signal (induced by the compound according to the invention) to the mean of the relative values of the control group, was then calculated. The higher this factor, the greater the gene expression activating character of the compound. The final result is represented as the mean of the induction values in each experimental group.

Figures 1, 2, 3, 4, 5, 6:
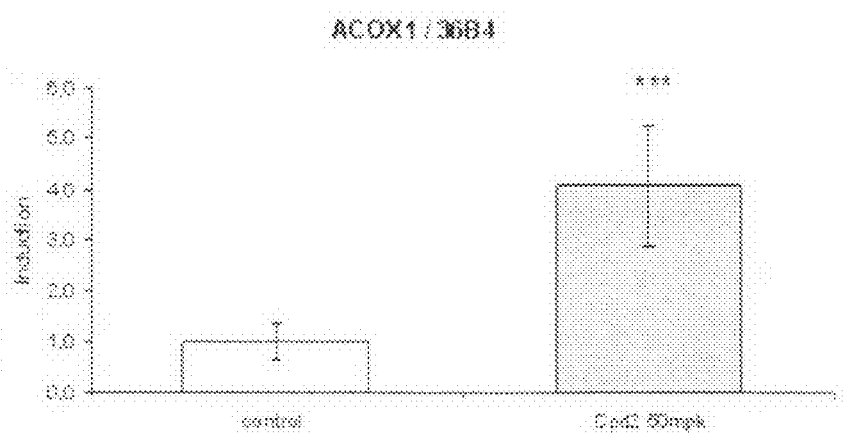

FIG. 4-3: expression of PDK4 in the hepatic tissue, in the db/db mouse, after 28 days of treatment with compound 2, administered at 50 mpk;

FIG. 4-4: expression of ACOX1 in the hepatic tissue, in the db/db mouse, after 28 days of treatment with compound 2, administered at 50 mpk;

FIG. 4-5: expression of CPT1b in the hepatic tissue, in the db/db mouse, after 28 days of treatment with compound 2, administered at 50 mpk;

FIG. 4-6: expression of PDK4 in muscle tissue, in the db/db mouse, after 28 days of treatment with compound 2, administered at 50 mpk;

FIG. 4-7: expression of UCP3 in muscle tissue, in the db/db mouse, after 28 days of treatment with compound 2, administered at 50 mpk.

FIG. 5: In Vitro Evaluation of the Metabolic Properties of the Compounds According to the Invention by Measuring the β-Oxidation of Fatty Acids in Murine Myocytes The stimulating effects of the compounds according to the invention were evaluated by measuring the β-oxidation of fatty acids in murine myocytes pretreated with the compounds according to the invention for 24 hours. The more the induction of the β-oxidation of fatty acids is increased, the greater the stimulating effects of the compounds according to the invention on the degradation of fatty acids in the muscle cells.

FIGS. 6-1 and 6-2: In Vitro Evaluation of the Properties of the Compounds According to the Invention as Activators of Reverse Cholesterol Transport, by Measuring the Expression of the ABCA1 Gene in Macrophages The effect of the compounds according to the invention on reverse cholesterol transport was evaluated by measuring the expression of the ABCA1 gene (ATP-binding cassette, subfamily A, member 1; membrane transporter involved in cholesterol efflux) in human macrophages. The more the expression of ABCA1 is increased, the greater the stimulating action of the compound according to the invention on reverse cholesterol transport.

FIG. 6-1: expression of ABCA1 in human macrophages, after 24 hours of treatment with compound 2, at 1 µM;

FIG. 6-2: expression of ABCA1 in human macrophages, after 24 hours of treatment with compounds 4 and 7 according to the invention, at 1 µM and 300 nM, respectively.

Figures 1, 2, 3, 4, 5, 6, 7:
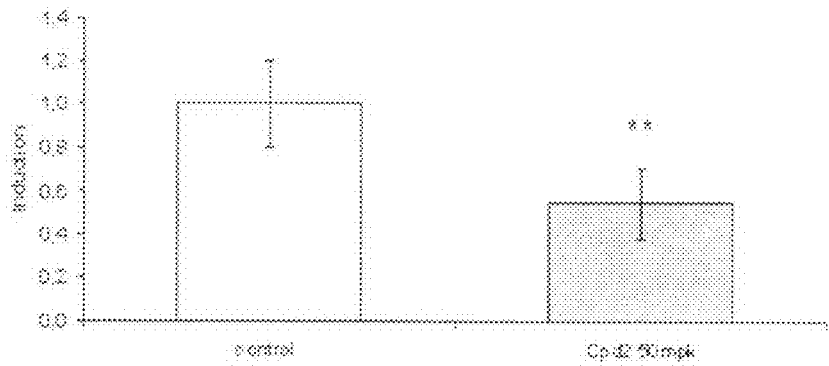
Figures 1, 2, 3, 4, 5, 6, 7, 8:
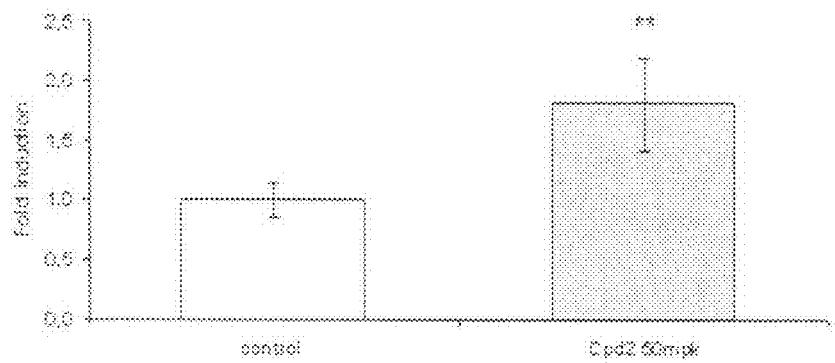
Figures 1, 2, 3, 4, 5, 6, 7, 8, 9:
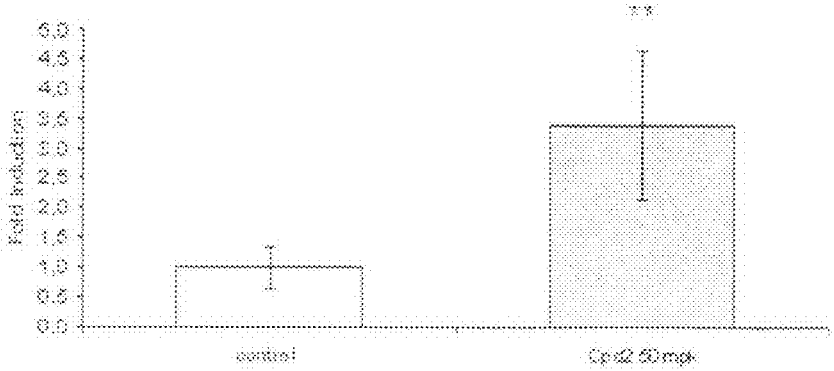
Figures 1, 2:
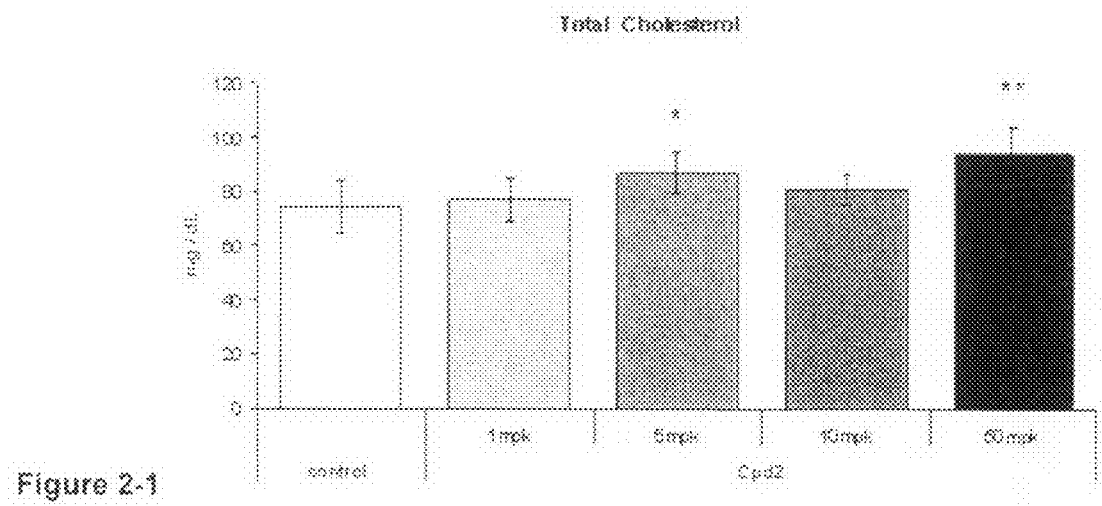
Figure 2:
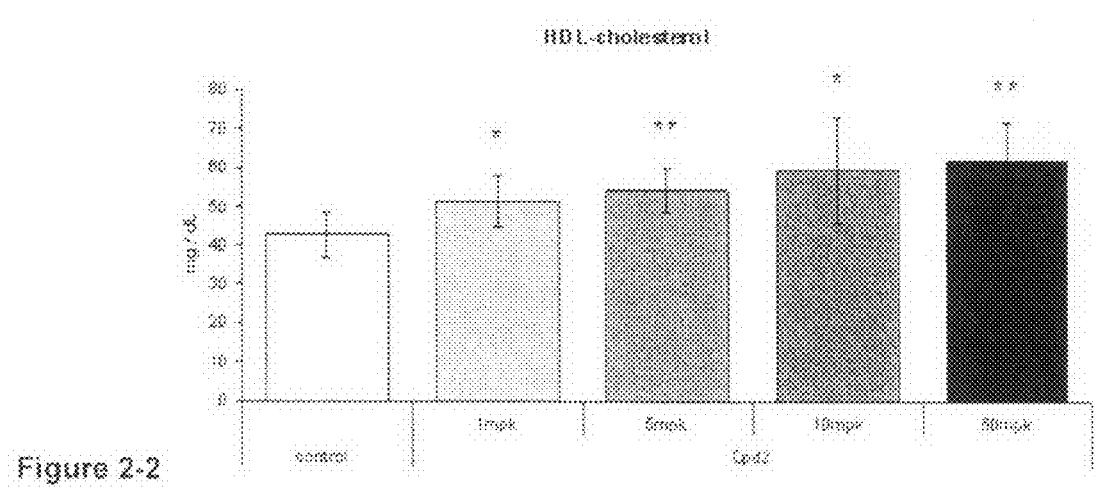
Figures 2, 3:
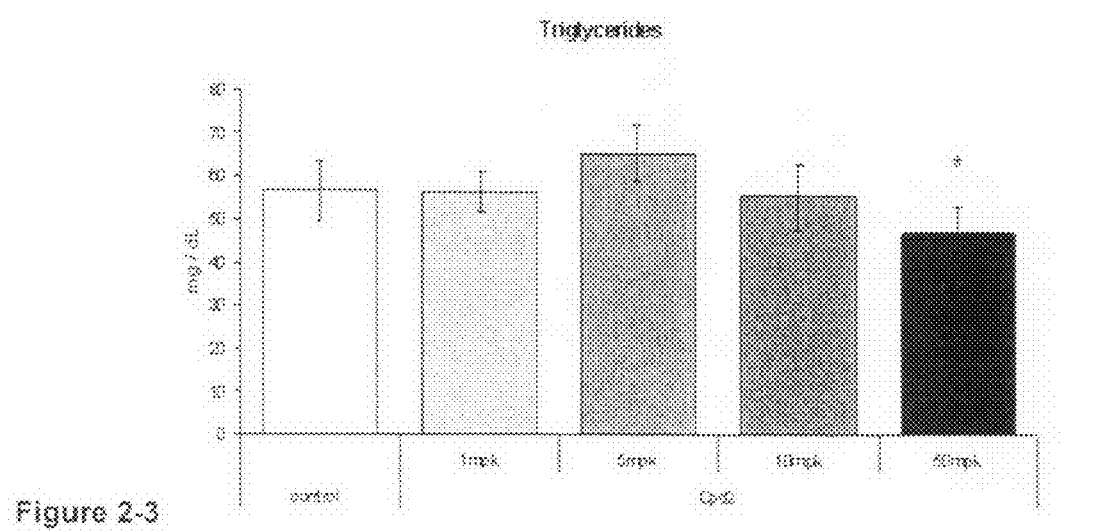
Figures 2, 3, 4:
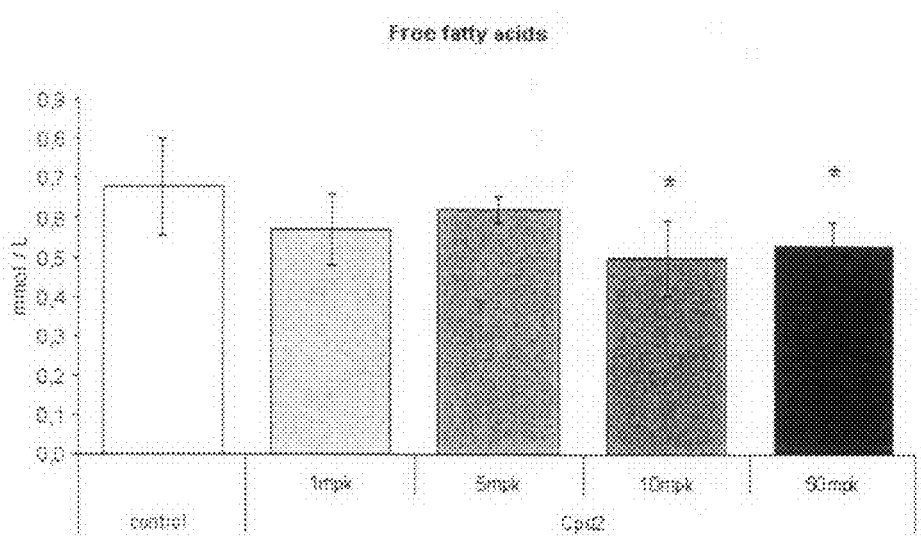
Figures 2, 3, 4, 5:
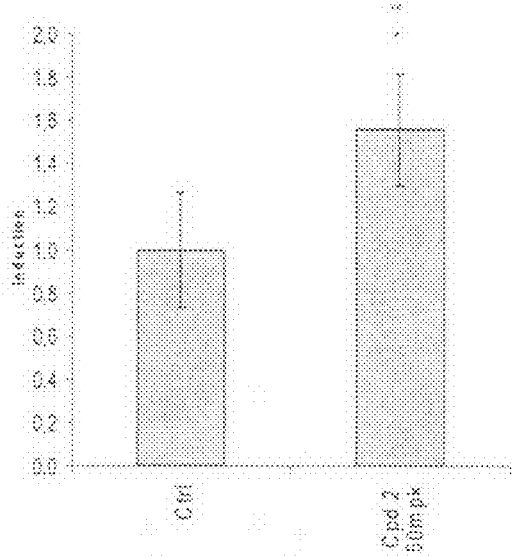
Figures 2, 3, 4, 5, 6:
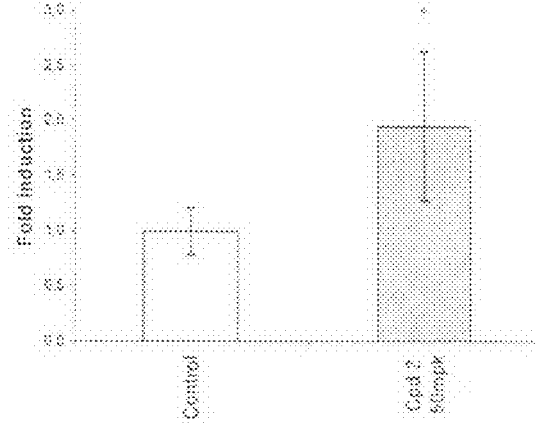
Figures 1, 3:
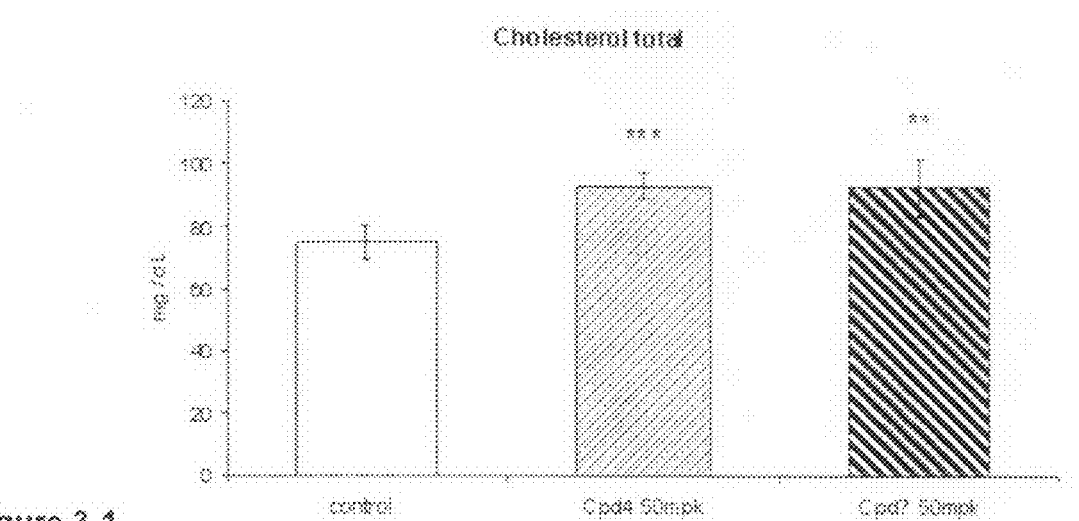
Figures 2, 3:
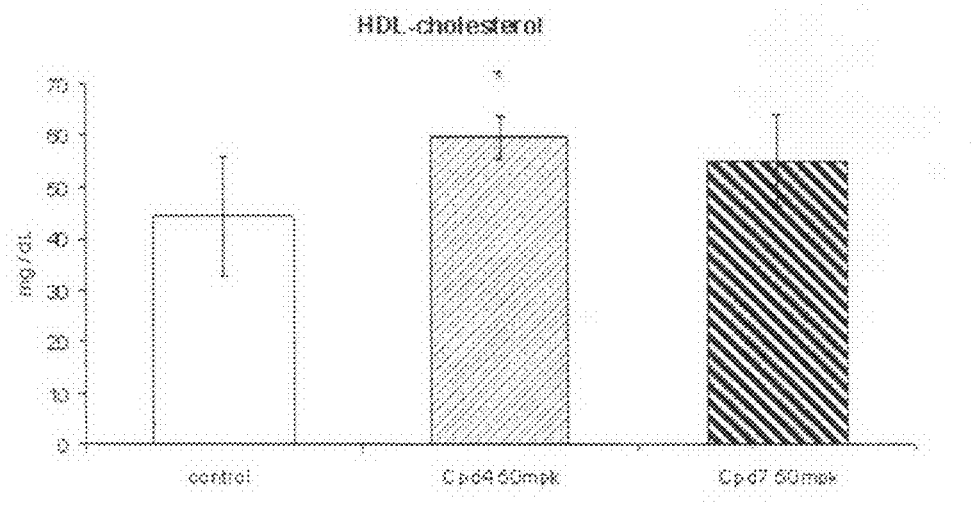
Figure 3:
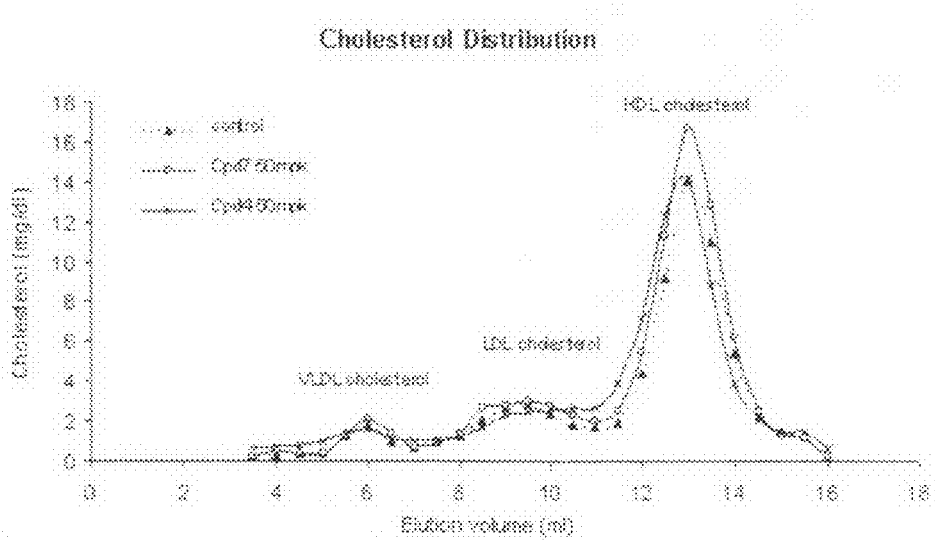
Figures 3, 4:
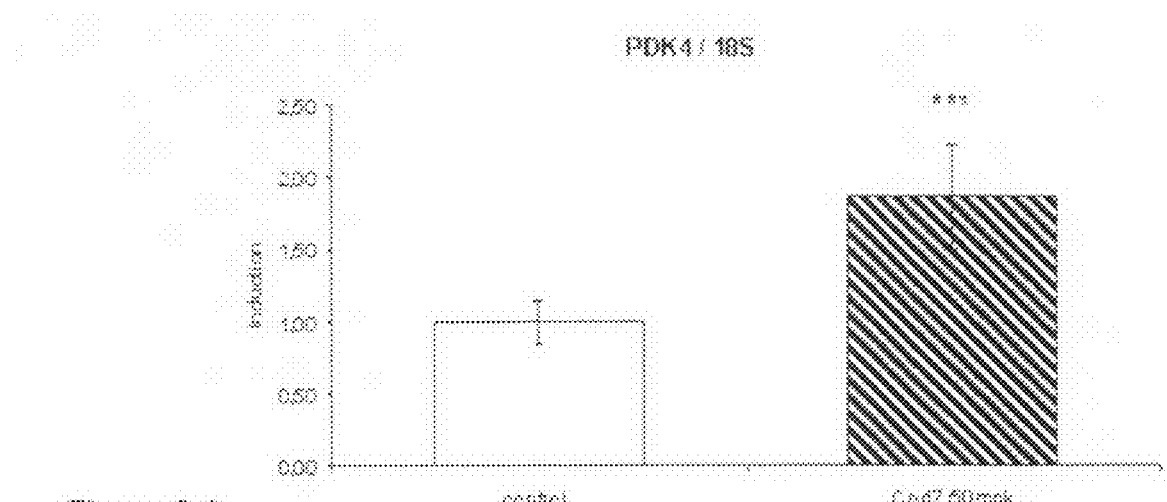
Figures 3, 4, 5:
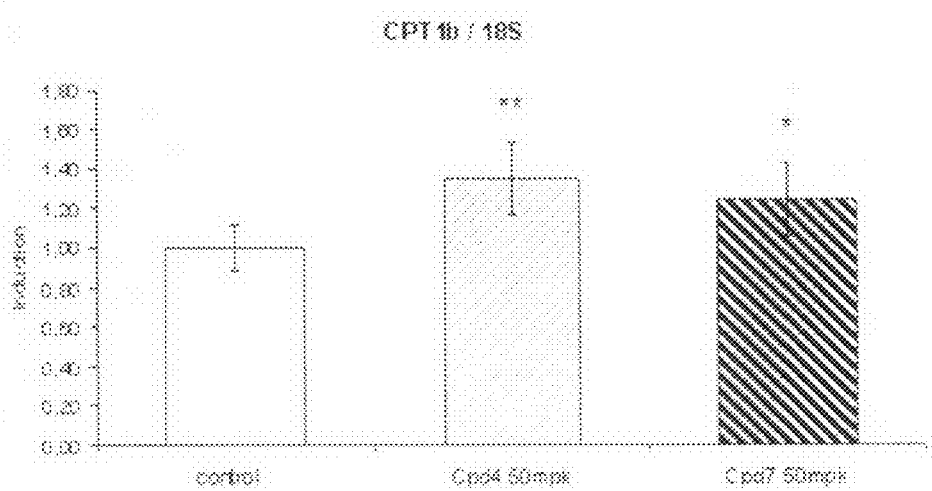
Figures 3, 4, 5, 6:
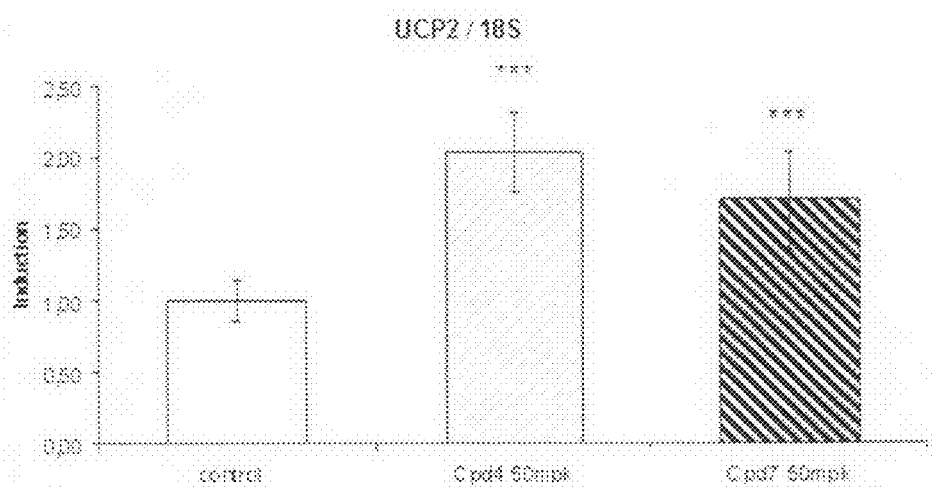
Figures 3, 4, 5, 6, 7:
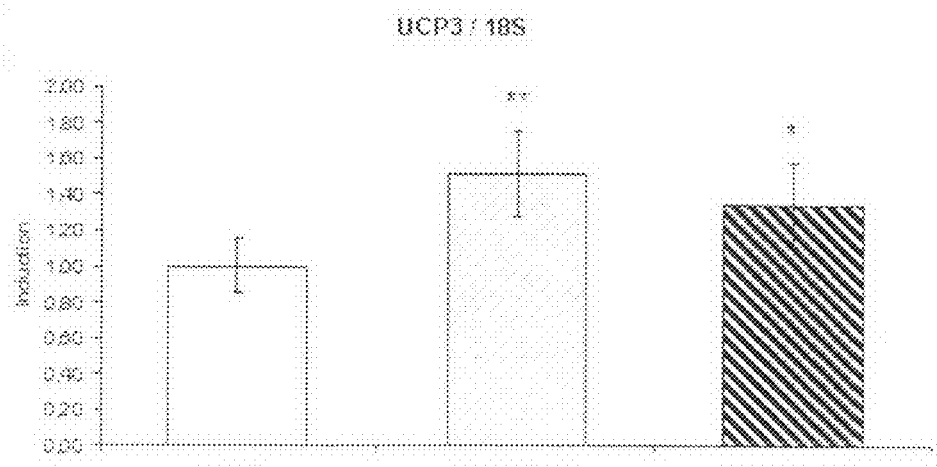
Figures 1, 4:
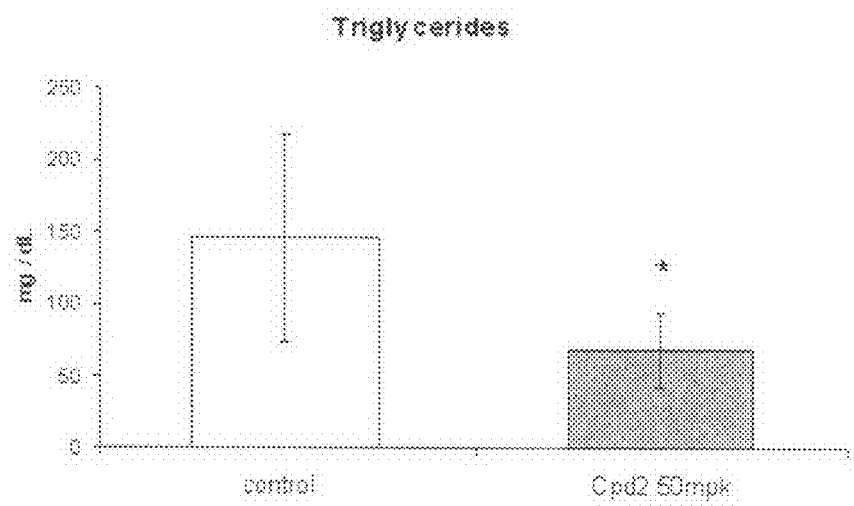
Figures 2, 4:
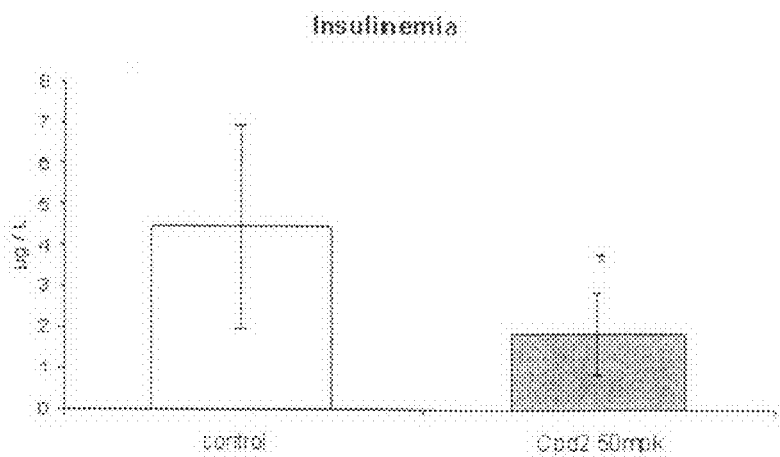
Figures 3, 4:
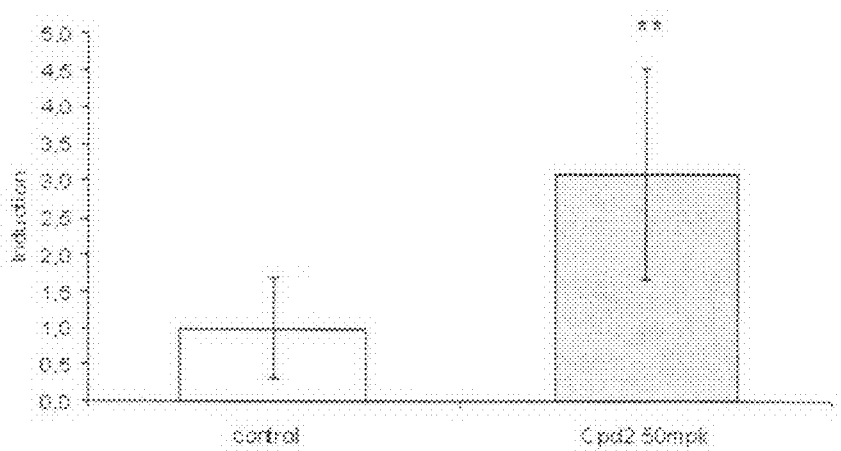
Figure 4:
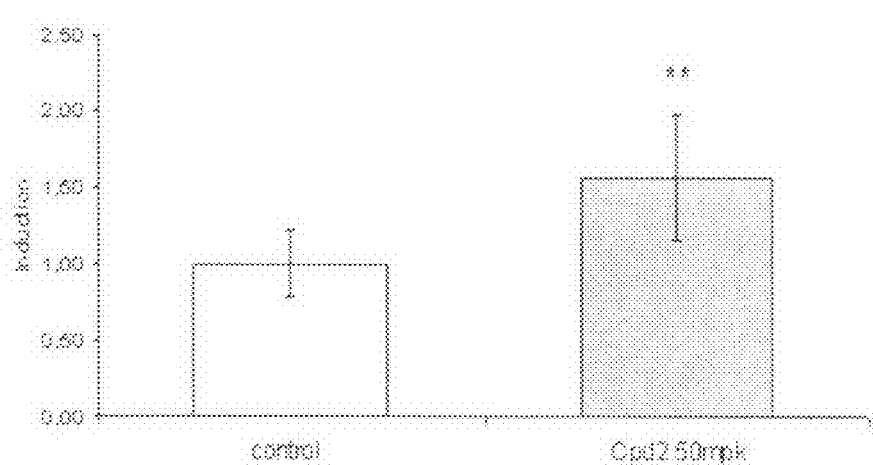
Figures 4, 5:
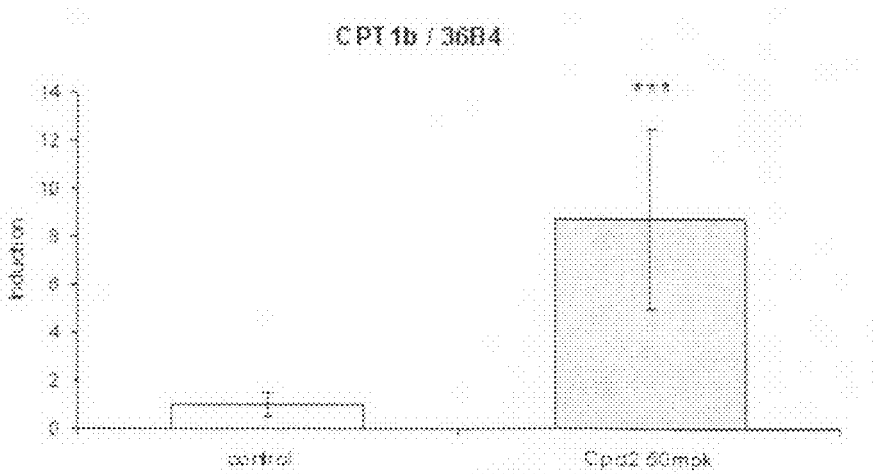
Figures 4, 5, 6:
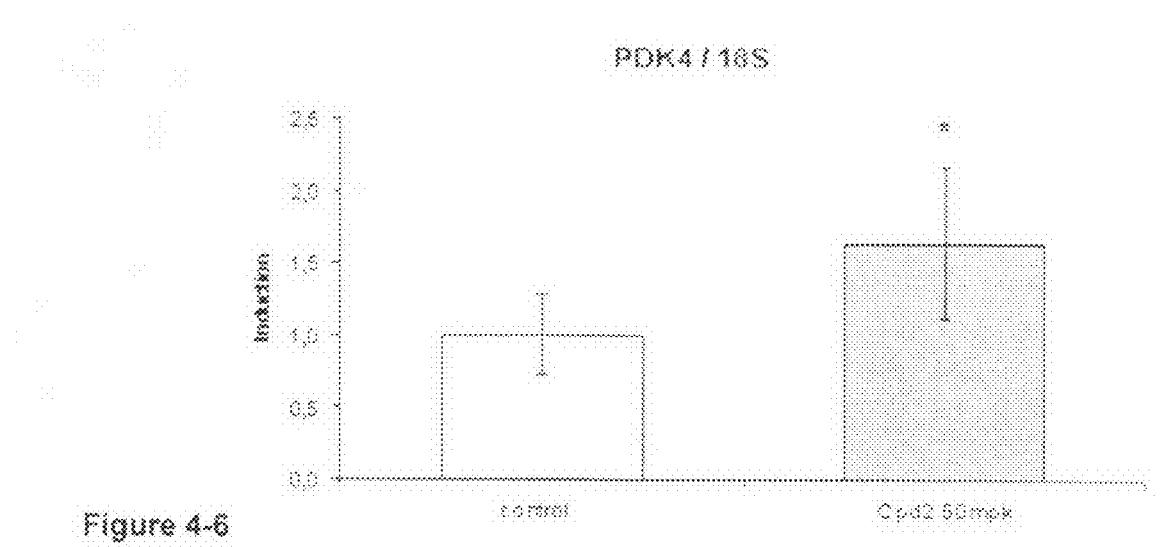
Figures 4, 5, 6, 7:
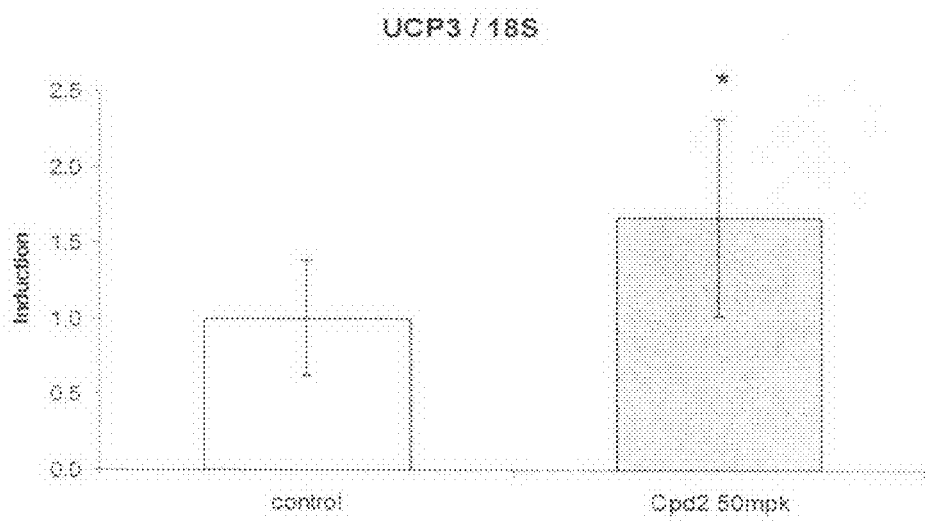
Figure 5:
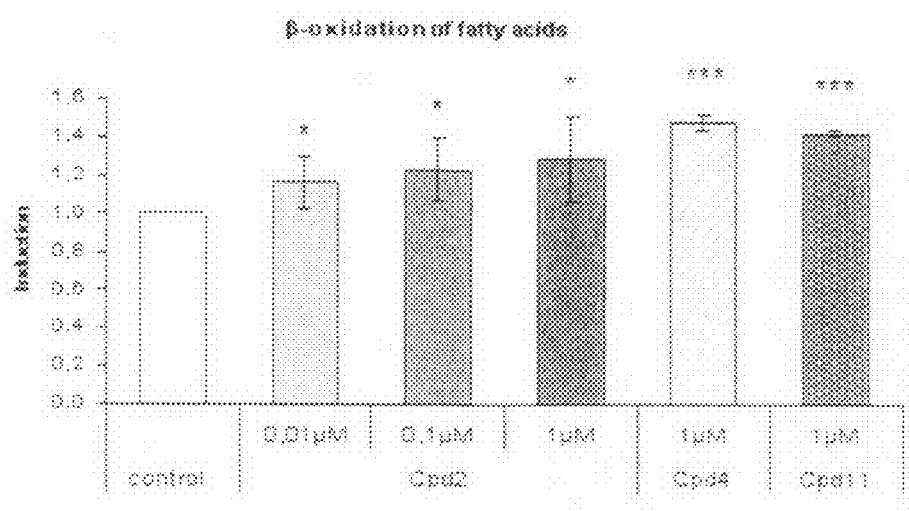
Figures 1, 6:
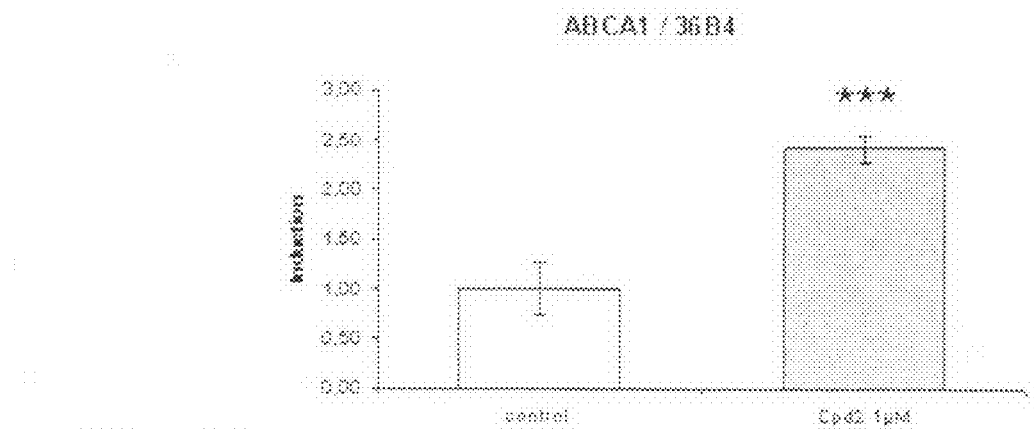
Figures 2, 6:
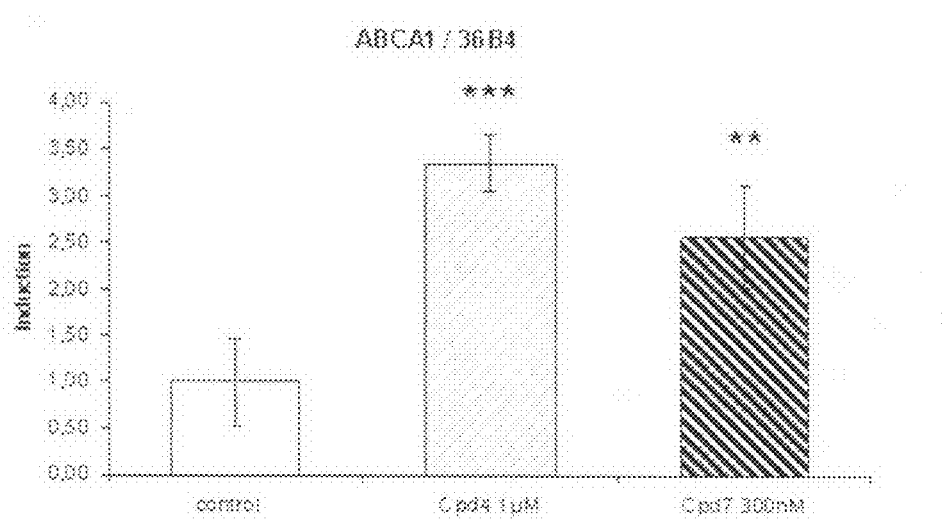
Figures 1, 7:
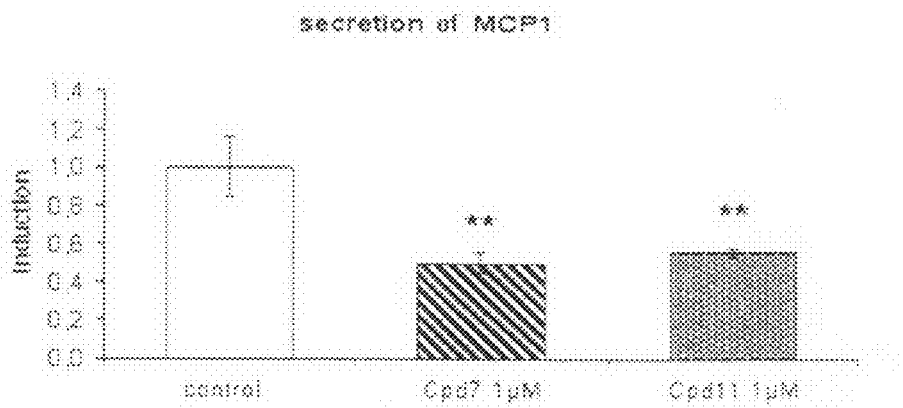
Figures 2, 7:
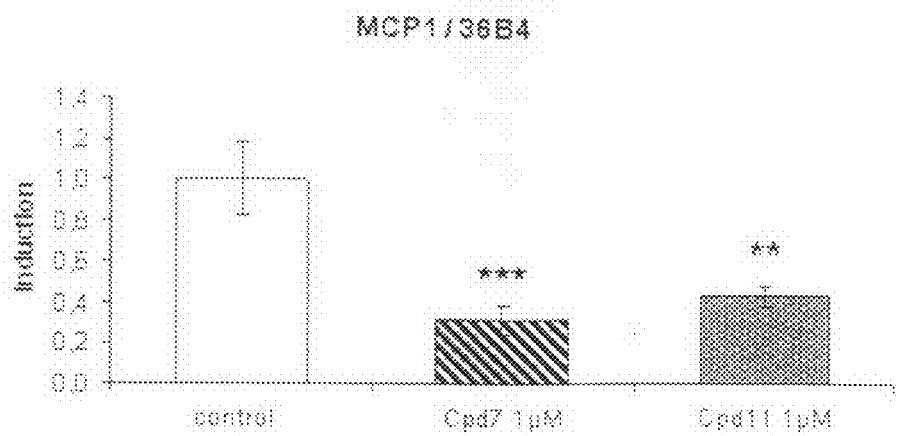
Figures 3, 7:
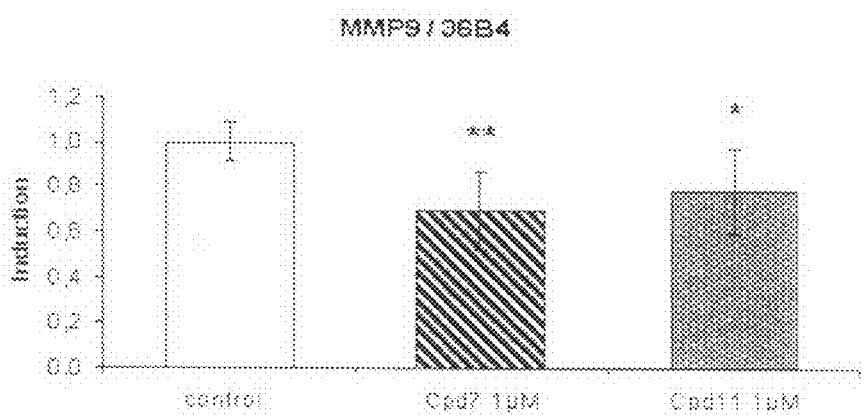
Figures 4, 7:
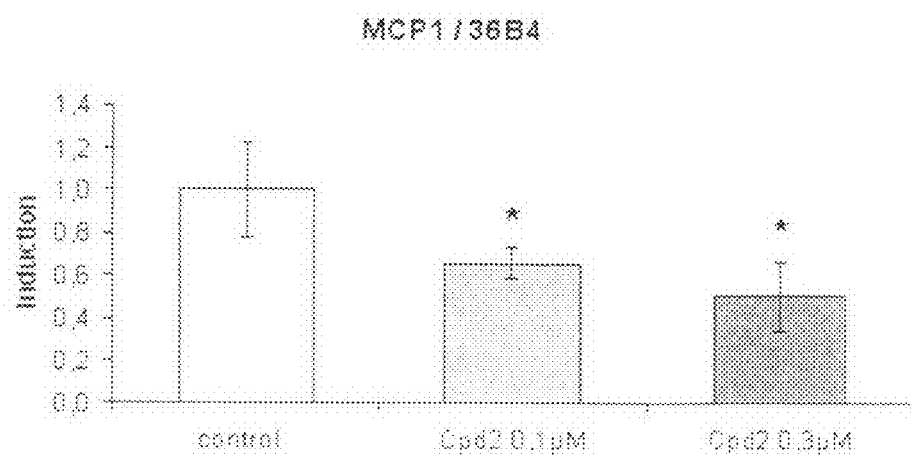

FIGS. 7-1 to 7-4: In Vitro Evaluation of the Antiinflammatory Properties of the Compounds According to the Invention by Measuring the Secretion and Expression of MCP1 and MMP9 by Human Monocytes Treated with the Compounds According to the Invention and Stimulated with PMA The antiinflammatory effects of the compounds according to the invention were evaluated by measuring the secretion and expression of Monocyte Chemoattractant Protein-1 (MCP1) as well as by measuring the expression of matrix metalloproteinase 9 (MMP9) by human monocytes treated with the compounds according to the invention for 24 hours and stimulated with PMA (phorbol 12-myristate 13-acetate, which causes an inflammatory response of the cells). The more the amount of MCP1 secreted is diminished, the greater the inhibitory effect of the compound according to the invention on the inflammatory response. Similarly, the more the expression of the MCP1 and MMP9 genes is inhibited, the more the compound according to the invention is antiinflammatory.

FIG. 7-1: secretion of MCP1 (Monocyte Chemoattractant Protein-1) in human monocytes, treated with compounds 7 and 11 according to the invention at 1 µM;

FIG. 7-2: expression of MCP1 (Monocyte Chemoattractant Protein-1) in human monocytes, treated with compounds 7 and 11 according to the invention at 1 µM;

FIG. 7-3: expression of MMP9 (matrix metalloproteinase 9) in human monocytes, treated with compounds 7 and 11 according to the invention at 1 µM;

FIG. 7-4: expression of MCP1 (Monocyte Chemoattractant Protein-1) in human monocytes, treated with compound 2 at 0.1 and 0.3 µM.

Other advantages and aspects of the invention will become clear on reading the examples given below, which are to be regarded as illustrative and nonlimiting.

Statistical Analysis

The statistical analysis performed consist of a Student t-test and/or a single-factor univariate Analysis of Variance (ANOVA), followed by a Tukey test. The results are compared relative to the control group according to the value of the parameter p:

*: $p<0.05$; : $p<0.01$; *: $p<0.001$.

EXAMPLES

The usual reagents and catalysts are commercially available (Aldrich, Alfa Aesar, Acros, Fluka or Lancaster as required).

In these examples, various analyses are performed for identifying the compounds.

The melting points (m.p.) are given in degrees Celsius.

The purity of the products is verified by thin-layer chromatography (TLC) and/or by HPLC (high-performance liquid chromatography).

The mass spectra are obtained by ESI-MS (Electrospray Ionization-Mass Spectroscopy), Q-TOF (Quadrupole-Time of Flight) or MALDI-TOF (Matrix Assisted Laser Desorption/Ionization-Time of Flight).

The Proton Nuclear Magnetic Resonance ($^1$H-NMR) spectra were recorded on a Bruker AC300P spectrometer. The chemical shifts are expressed in ppm (parts per million) and are recorded at 300 MHz in a deuterated solvent that is specified for each analysis: DMSO-$d_6$, MeOD or CDCl$_3$.

The following abbreviations are used for interpreting the spectra: s for singlet, bs for broad singlet, d for doublet, dd for doublet of doublets, ddd for doublet of doublet of doublets, t for triplet, dt for doublet of triplets, q for quadruplet, quint for quintuplet, sext for sextuplet, m for multiplet.

Example 1

Description of the General Synthesis Protocols According to the Invention

General Procedure A:

The brominated derivative (0.5 to 75 g, 0.05 to 0.5 mol/mL), potassium carbonate (3 eq.) and water (11 eq.) are dissolved in N,N-dimethylformamide under an inert atmosphere. Palladium acetate (0.1 eq.) is added, then solution of boronic acid in N,N-dimethylformamide (1.5 eq., 0.25 g/mL) is added dropwise. The mixture is stirred, under inert atmosphere at room temperature.

General Procedure B:

The ketone (1 eq.) and the aldehyde (1 eq.) are dissolved in a saturated ethanolic solution of gaseous hydrochloric acid (0.2 g to 38 g, 0.2 to 0.5 mol/L). After stirring for 16 hours at room temperature the solvent is removed by evaporation under reduced pressure.

General Procedure C:

The propenone is dissolved in a chloroform/methanol 2:1 mixture (0.2 to 14 g, 0.01 to 0.2 mol/L), then a catalytic amount of palladium on charcoal is added. The whole is placed under a hydrogen atmosphere at atmospheric pressure.

General Procedure D:

Phenol or thiophenol is dissolved in N,N-dimethylformamide (0.3 to 12 g, 0.06 to 0.2 mol/L), then the halogenated derivative (5 eq.) and potassium carbonate (5 eq.) are added. The reaction mixture is stirred vigorously at 70° C.

General Procedure E:

The tert-butyl ester is dissolved in dichloromethane (0.2 to 15 g, 0.1 to 1 mol/L), then trifluoroacetic acid (10 to 17 eq.) is added. It is stirred at room temperature.

General Procedure F:

The ester is dissolved in ethanol (0.2 to 0.4 g, 0.1 to 0.2 mol/L), then a 2N sodium hydroxide solution is added.

General Procedure G:

The propanone is dissolved in ethanol (0.2 to 4 g, 0.1 to 0.5 mol/L). Sodium borohydride (3 eq.) is added. The whole is stirred at room temperature for 3 hours. The solvent is removed by evaporation under reduced pressure, the evaporation residue is taken up in a dilute aqueous hydrochloric acid solution and extracted with dichloromethane.

General Procedure H:

The alcohol is dissolved in N,N-dimethylformamide (0.2 to 3 g, 0.1 to 0.5 mol/L), the solution is cooled to 0° C. then sodium hydride is added. After stirring for 20 minutes, the appropriate alkyl halide is added. The mixture is stirred at room temperature for 4 hours. The solvents are removed by evaporation under reduced pressure.

General Procedure I:

The propanone is dissolved in pyridine (0.3 g, 0.1 mol/L). O-Alkylhydroxylamine hydrochloride (5 to 10 equivalents) is added. After 18 h of reflux, the mixture is evaporated under reduced pressure, taken up in ethyl acetate and washed with dilute hydrochloric acid solution. The organic phase is concentrated under reduced pressure. The evaporation residue is purified by silica-gel flash chromatography.

Example 2

Synthesis of the Raw Materials Used in the Synthesis of the Compounds According to the Invention 2,3-dichloro-4-hydroxybenzaldehyde

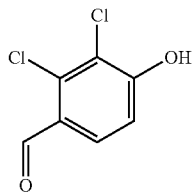

Sodium carbonate (3.5 eq.), calcium hydroxide (4.5 eq.) and 2,3-dichlorophenol (0.15 g/L) are added to the water, and the suspension is heated at 70° C. for 4 hours. Chloroform (2 eq.) is added dropwise and the whole is stirred at 70° C. for 16 hours.

The reaction mixture is cooled to 0° C., and acidified (pH=2) with concentrated hydrochloric acid solution. The whole is extracted with ethyl acetate; the organic phases are washed with water, dried over magnesium sulfate and concentrated under reduced pressure. The evaporation residue is purified by silica-gel flash chromatography. The solid obtained is recrystallized from isopropanol.

Elution: cyclohexane/ethyl acetate: gradient 9/1 to 7/3. Silica 40-63 µm.

$^1$H NMR (300 MHz, DMSO-$d_6$, δ in ppm): 7.20 (d, 1H, J=8.8 Hz); 7.70 (d, 1H, J=8.8 Hz); 10.13 (s, 1H).

4-hydroxy-3,5-dimethylbenzaldehyde

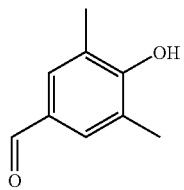

2,6-Dimethylphenol (0.34 g/mL) and hexamethylenetetramine (2 eq.) are dissolved in 2:1 acetic acid/water mixture. The whole is heated at 100° C. for 4 hours. The reaction mixture is cooled to room temperature and poured into a water/ice mixture. The precipitate is drained.

$^1$H NMR (300 MHz, CDCl$_3$, δ in ppm): 2.33 (s, 6H); 5.90 (s, 1H); 7.55 (s, 2H); 9.81 (s, 1H).

1-(5-(4-(trifluoromethyl)phenyl)thien-2-yl)ethanone

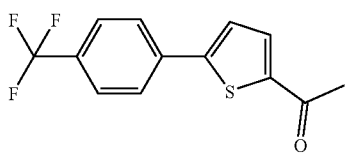

1-(5-(4-(Trifluoromethyl)phenyl)thien-2-yl)ethanone is prepared from 5-acetyl-2-thiopheneboronic acid and 4-bromobenzotrifluoride according to general procedure A.

After stirring for 2 hours, the solvents are removed by evaporation under reduced pressure and the evaporation residue is purified by silica-gel chromatography.

Elution: cyclohexane/ethyl acetate: 8/2. Silica 40-63 µm.

$^1$H NMR (300 MHz, CDCl$_3$, δ in ppm): 2.60 (s, 3H); 7.40 (d, 1H, J=3.8 Hz); 7.66-7.70 (m, 3H); 7.76 (d, 2H, J=8.2 Hz).

1-(4-(4-(trifluoromethyl)phenyl)thien-2-yl)ethanone

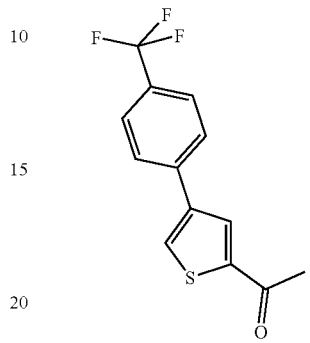

1-(4-(4-(Trifluoromethyl)phenyl)thien-2-yl)ethanone is prepared from (4-bromothien-2-yl)ethanone and 4-trifluoromethylphenylboronic acid according to general procedure A.

After stirring for 18 hours, the solvents are removed by evaporation under reduced pressure and the evaporation residue is purified by silica-gel chromatography.

Elution: cyclohexane/ethyl acetate: 9/1. Silica 40-63 µm.

$^1$H NMR (300 MHz, CDCl$_3$, δ in ppm): 2.63 (s, 3H); 7.70 (m, 4H); 7.82 (d, 1H, J=1.5 Hz); 7.97 (d, 1H, J=1.5 Hz).

1-(5-(4-(trifluoromethoxy)phenyl)thien-2-yl)ethanone

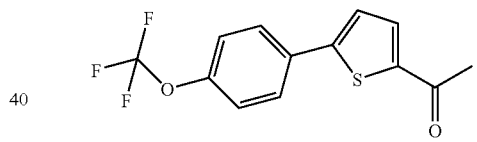

1-(5-(4-(Trifluoromethoxy)phenyl)thien-2-yl)ethanone is prepared from 5-acetyl-2-thiopheneboronic acid and 1-bromo-4-(trifluoromethoxy)benzene according to general procedure A.

After stirring for 1 hour, the reaction mixture is diluted with water, filtered on Celite and then extracted with ethyl acetate. The organic phase is dried over magnesium sulfate, filtered and then concentrated under reduced pressure. The evaporation residue is recrystallized from cyclohexane.

$^1$H NMR (300 MHz, DMSO-$d_6$, δ in ppm): 2.56 (s, 3H); 7.47 (d, 2H, J=8.4 Hz); 7.71 (d, 1H, J=3.9 Hz); 7.91 (d, 2H, J=8.4 Hz); 7.98 (d, 1H, J=3.9 Hz).

1-(5-(4-bromophenyl)thien-2-yl)ethanone

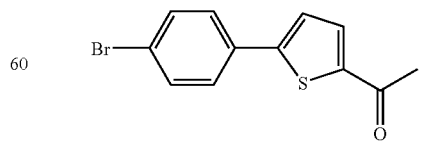

1-(5-(4-Bromophenyl)thien-2-yl)ethanone is prepared from 5-acetyl-2-thiopheneboronic acid and 1-bromo-4-iodobenzene according to general procedure A.

After stirring for 12 hours, the reaction mixture is diluted with water, filtered on Celite and then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 9/1 to 8/2. Silica 40-63 µm.

¹H NMR (300 MHz, CDCl₃, δ in ppm): 2.57 (s, 3H); 7.31 (d, 1H, J=3.9 Hz); 7.51 (d, 2H, J=9.0 Hz); 7.55 (d, 2H, J=9.0 Hz); 7.65 (d, 1H, J=3.9 Hz).

5-bromo-2-acetylfuran

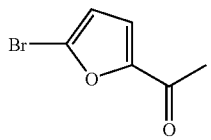

2-Acetylfuran is dissolved in N,N-dimethylformamide (5 g, 1.1 mol/L), and N-bromosuccinimide (1 eq.) is added.

After stirring for 5 hours at room temperature, the reaction mixture is poured into ice water and the precipitate formed is drained.

¹H NMR (300 MHz, CDCl₃, δ in ppm): 2.47 (s, 3H); 6.49 (d, 1H, J=3.6 Hz); 7.12 (d, 1H, J=3.6 Hz).

1-(5-(4-(trifluoromethyl)phenyl)fur-2-yl)ethanone

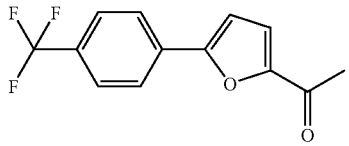

1-(5-(4-(Trifluoromethyl)phenyl)fur-2-yl)ethanone is prepared from 4-trifluoromethylbenzeneboronic acid and 5-bromo-2-acetylfuran according to general procedure A.

After stirring for 18 hours, the reaction mixture is diluted with water and then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 95/5 to 8/2. Silica 40-63 µm.

¹H NMR (300 MHz, CDCl₃, δ in ppm): 2.55 (s, 3H); 6.89 (d, 1H, J=3.7 Hz); 7.28 (d, 1H, J=3.7 Hz); 7.68 (d, 1H, J=8.1 Hz); 7.89 (d, 1H, J=8.1 Hz).

1-(5-(4-(methylthio)phenyl)thien-2-yl)ethanone

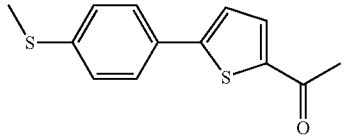

1-(5-(4-(Methylthio)phenyl)thien-2-yl)ethanone is prepared from 5-acetyl-2-thiopheneboronic acid and 1-bromo-4-(methylthio)benzene according to general procedure A.

After stirring for 18 hours at 100° C., the reaction mixture is diluted with water, filtered on Celite and then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 9/1 to 8/2. Silica 40-63 µm.

¹H NMR (300 MHz, DMSO-d₆, δ in ppm): 2.54 (s, 3H); 7.34 (d, 2H, J=8.7 Hz); 7.63 (d, 1H, J=3.9 Hz); 7.75 (d, 2H, J=8.7 Hz); 7.94 (d, 1H, J=3.9 Hz).

1-(5-(3-(trifluoromethyl)phenyl)thien-2-yl)ethanone

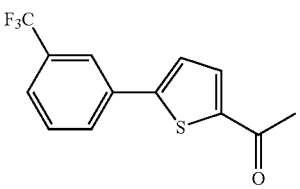

1-(5-(3-(Trifluoromethyl)phenyl)thien-2-yl)ethanone is prepared from 2-acetyl-5-bromothiophene acid and 3-trifluoromethylbenzeneboronic acid according to general procedure A.

After stirring for 4 hours, the solvents are removed by evaporation under reduced pressure and the evaporation residue is purified by silica-gel chromatography.

Elution: cyclohexane/ethyl acetate: 8/2. Silica 40-63 µm.

¹H NMR (300 MHz, CDCl₃, δ in ppm): 2.59 (s, 3H); 7.39 (d, 1H, J=3.9 Hz); 7.53-7.65 (m, 2H); 7.69 (d, 1H, J=3.9 Hz); 7.83 (d, 1H, J=7.6 Hz); 7.90 (s, 1H).

Example 3

Synthesis of the Intermediates Used in the Synthesis of the Compounds According to the Invention Intermediate 1

3-(2,3-dichloro-4-hydroxyphenyl)-1-(5-(4-(trifluoromethyl)-phenyl)thien-2-yl)prop-2-en-1-one

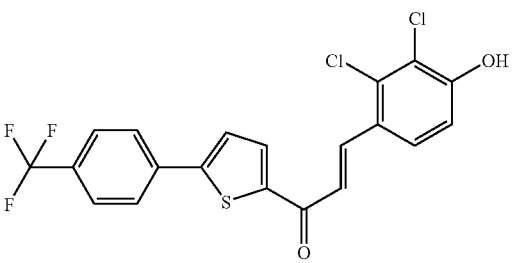

3-(2,3-Dichloro-4-hydroxyphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 2,3-dichloro-4-hydroxybenzaldehyde according to general procedure B. The evaporation residue is crystallized from acetonitrile.

¹H NMR (300 MHz, CDCl₃, δ in ppm): 6.02 (bs, 1H); 7.06 (d, 1H, J=8.8 Hz); 7.34 (d, 1H, J=15.5 Hz); 7.48 (d, 1H, J=3.8

Hz); 7.67-7.72 (m, 3H); 7.81 (d, 2H, J=8.2 Hz); 7.86 (d, 1H, J=3.8 Hz); 8.22 (d, 1H, J=15.5 Hz).

Intermediate 2

3-(2,3-dichloro-4-hydroxyphenyl)-1-(5-(4-(trifluoromethyl)-phenyl)thien-2-yl)propan-1-one

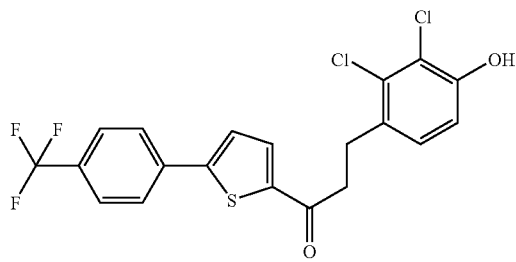

3-(2,3-Dichloro-4-hydroxyphenyl)-1-(5-(4-(trifluoromethyl)phenyl)thien-2-yl)propan-1-one is prepared from 3-(2,3-dichloro-4-hydroxyphenyl)-1-(5-(4-(trifluoromethyl)phenyl)thien-2-yl)prop-2-en-1-one according to general procedure C.

After stirring for 1 hour 30 min at 42° C., the catalyst is removed by filtration and the solvent is removed by evaporation under reduced pressure. The evaporation residue is purified by silica-gel chromatography.

Elution: cyclohexane/ethyl acetate: 7/3. Silica 40-63 μm.

$^1$H NMR (300 MHz, CDCl$_3$, δ in ppm): 3.14-3.27 (m, 4H); 5.64 (bs, 1H); 6.92 (d, 1H, J=8.5 Hz); 7.18 (d, 1H, J=8.5 Hz); 7.39 (d, 1H, J=3.8 Hz); 7.67-7.71 (m, 3H); 7.77 (d, 2H, J=8.2 Hz).

Intermediate 3

3-(2,3-dichloro-4-hydroxyphenyl)-1-(4-(4-(trifluoromethyl)-phenyl)thien-2-yl)prop-2-en-1-one

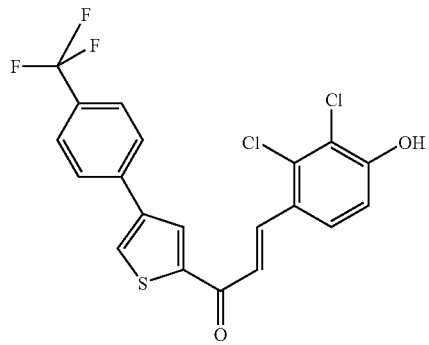

3-(2,3-Dichloro-4-hydroxyphenyl)-1-(4-(4-(trifluoromethyl)phenyl)thien-2-yl)prop-2-en-1-one is prepared from 1-(4-(4-(trifluoromethyl)phenyl)thien-2-yl)ethanone and 2,3-dichloro-4-hydroxybenzaldehyde according to general procedure B. The evaporation residue is purified by silica-gel chromatography.

Elution: cyclohexane/ethyl acetate: 8/2. Silica 40-63 μm.

$^1$H NMR (300 MHz, DMSO-d$_6$, δ in ppm): 7.08 (d, 1H, J=8.8 Hz); 7.82-8.10 (m, 7H); 8.58 (s, 1H); 8.86 (s, 1H).

Intermediate 4

3-(2,3-dichloro-4-hydroxyphenyl)-1-(4-(4-(trifluoromethyl)-phenyl)thien-2-yl)propan-1-one

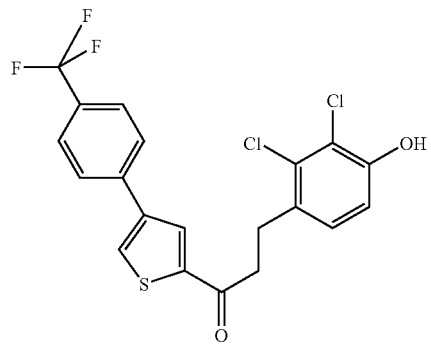

3-(2,3-Dichloro-4-hydroxyphenyl)-1-(4-(4-(trifluoromethyl)phenyl)thien-2-yl)propan-1-one is prepared from 3-(2,3-dichloro-4-hydroxyphenyl)-1-(4-(4-(trifluoromethyl)phenyl)thien-2-yl)prop-2-en-1-one according to general procedure C.

After 6 hours at room temperature, the catalyst is removed by filtration and the solvent is removed by evaporation under reduced pressure. The evaporation residue is purified by silica-gel chromatography.

Elution: cyclohexane/ethyl acetate: 8/2. Silica 40-63 μm.

$^1$H NMR (300 MHz, CDCl$_3$, δ in ppm): 3.15-3.21 (m, 2H); 3.25-3.30 (m, 2H); 5.60 (s, 1H); 6.91 (d, 1H, J=8.5 Hz); 7.17 (d, 1H, J=8.5 Hz); 7.67 (m, 4H); 7.81 (d, 1H, J=1.3 Hz); 7.95 (d, 1H, J=1.3 Hz).

Intermediate 5

3-(3-chloro-4-hydroxyphenyl)-1-(5-(4-(trifluoromethyl)-phenyl)thien-2-yl)prop-2-en-1-one

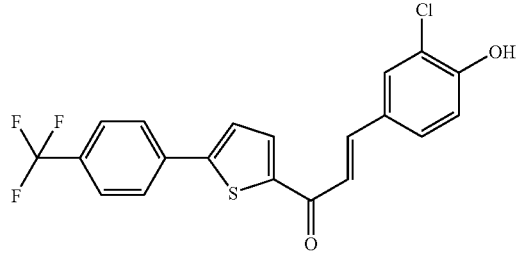

3-(3-Chloro-4-hydroxyphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 3-chloro-4-hydroxybenzaldehyde according to general procedure B. The evaporation residue is purified by silica-gel chromatography.

Elution: cyclohexane/ethyl acetate: 6/4. Silica 40-63 μm.

¹H NMR (300 MHz, DMSO-d₆, δ in ppm): 7.03 (d, 1H, J=8.5 Hz); 7.62-7.67 (m, 2H); 7.77-7.84 (m, 3H); 7.9 (d, 1H, J=4.1 Hz); 8.03 (m, 3H); 8.39 (d, 1H, J=4.1 Hz).

3H); 7.90 (d, 1H, J=4.1 Hz); 7.97-8.05 (m, 3H); 8.12 (d, 1H, J=8.8 Hz); 8.37 (d, 1H, J=4.1 Hz).

Intermediate 6

3-(3-chloro-4-hydroxyphenyl)-1-(5-(4-(trifluoromethyl)-phenyl)thien-2-yl)propan-1-one Intermediate 8

3-(2-chloro-4-hydroxyphenyl)-1-(5-(4-(trifluoromethyl)-phenyl)thien-2-yl)propan-1-one

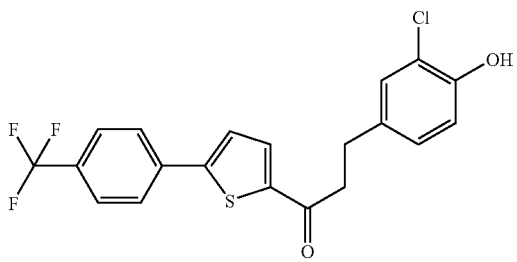

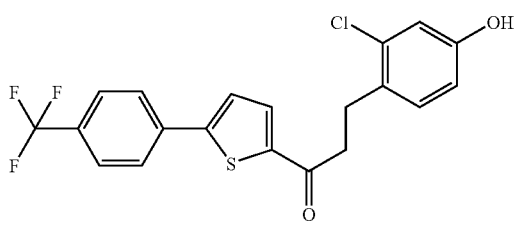

3-(3-Chloro-4-hydroxyphenyl)-1-(5-(4-(trifluoromethyl)phenyl)thien-2-yl)propan-1-one is prepared from 3-(3-chloro-4-hydroxyphenyl)-1-(5-(4-(trifluoromethyl)phenyl)thien-2-yl)prop-2-en-1-one according to general procedure C.

After stirring for 3 hours at room temperature, the catalyst is removed by filtration and the solvent is removed by evaporation under reduced pressure. The evaporation residue is purified by silica-gel chromatography.

Elution: methylene chloride. Silica 40-63 μm.

¹H NMR (300 MHz, CDCl₃, δ in ppm): 3.01 (t, 2H, J=7.7 Hz); 3.21 (t, 2H, J=7.7 Hz); 5.58 (s, 1H); 6.95 (d, 1H, J=8.2 Hz); 7.07 (dd, 1H, J=2.1 Hz, J=8.2 Hz); 7.22 (d, 1H, J=2.1 Hz); 7.38 (d, 1H, J=4.2 Hz); 7.63-7.68 (m, 3H); 7.75 (d, 2H, J=8.2 Hz).

3-(2-Chloro-4-hydroxyphenyl)-1-(5-(4-(trifluoromethyl)phenyl)thien-2-yl)propan-1-one is prepared from 3-(2-chloro-4-hydroxyphenyl)-1-(5-(4-(trifluoromethyl)phenyl)thien-2-yl)prop-2-en-1-one according to general procedure C.

After stirring for 3 hours at room temperature, the catalyst is removed by filtration and the solvent is removed by evaporation under reduced pressure. The evaporation residue is purified by silica-gel chromatography.

Elution: methylene chloride. Silica 40-63 μm.

¹H NMR (300 MHz, CDCl₃, δ in ppm): 3.09-3.15 (m, 2H); 3.19-3.25 (m, 2H); 6.69 (dd, 1, J=2.5 Hz, J=8.2 Hz); 6.9 (d, 1H, J=2.5 Hz); 7.16 (d, 1H); 7.38 (d, 1H, J=3.8 Hz); 7.66-7.71 (m, 3H); 7.76 (d, 1H, J=8.5 Hz).

Intermediate 7

3-(2-chloro-4-hydroxyphenyl)-1-(5-(4-(trifluoromethyl)-phenyl)thien-2-yl)prop-2-en-1-one Intermediate 9

3-(3-fluoro-4-hydroxyphenyl)-1-(5-(4-(trifluoromethyl)-phenyl)thien-2-yl)prop-2-en-1-one

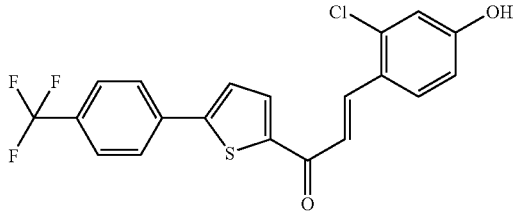

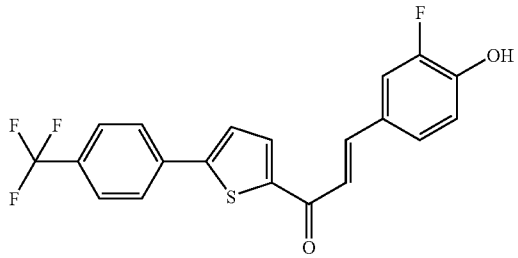

3-(2-Chloro-4-hydroxyphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 2-chloro-4-hydroxybenzaldehyde according to general procedure B. The evaporation residue is purified by silica-gel chromatography.

Elution: cyclohexane/ethyl acetate: 6/4. Silica 40-63 μm.

¹H NMR (300 MHz, DMSO-d₆, δ in ppm): 6.86 (dd, 1H, J=2.3 Hz, J=8.5 Hz); 6.94 (d, 1H, J=2.3 Hz); 7.78-7.84 (m, 3-(3-Fluoro-4-hydroxyphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 3-fluoro-4-hydroxybenzaldehyde according to general procedure B. The residue is crystallized from acetonitrile.

¹H NMR (300 MHz, CDCl₃, δ in ppm): 5.51 (s, 1H); 7.08 (d, 1H, J=8.5 Hz); 7.33-7.48 (m, 3H); 7.71 (m, 1H); 7.77-7.82 (m, 3H); 7.86 (d, 2H, J=8.5 Hz).

Intermediate 10

3-(3-fluoro-4-hydroxyphenyl)-1-(5-(4-(trifluoromethyl)-phenyl)thien-2-yl)propan-1-one

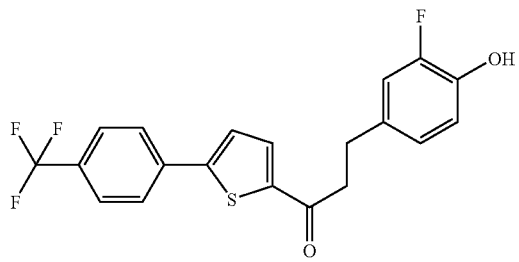

3-(3-Fluoro-4-hydroxyphenyl)-1-(5-(4-(trifluoromethyl) phenyl)thien-2-yl)propan-1-one is prepared from 3-(3-fluoro-4-hydroxyphenyl)-1-(5-(4-(trifluoromethyl)phenyl) thien-2-yl)prop-2-en-1-one according to general procedure C.

After 2 hours 30 min at 42° C., the catalyst is removed by filtration and the solvent is removed by evaporation under reduced pressure. The evaporation residue is purified by silica-gel chromatography.

Elution: cyclohexane/ethyl acetate: 7/3. Silica 40-63 μm.

$^1$H NMR (300 MHz, CDCl$_3$, δ in ppm): 3.02 (t, 2, J=7.5 Hz); 3.21 (t, 2, J=7.5 Hz); 5.01 (d, 1H, J=3.8 Hz); 6.97 (m, 3H); 7.39 (d, 1H, J=3.9 Hz); 7.68 (m, 3H); 7.75 (d, 2H, J=8.2 Hz).

Intermediate 11

3-(3-bromo-4-hydroxyphenyl)-1-(5-(4-(trifluoromethyl)-phenyl)thien-2-yl)prop-2-en-1-one

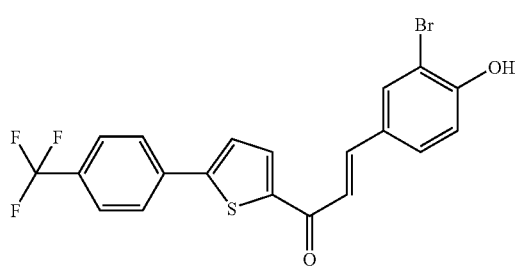

3-(3-Bromo-4-hydroxyphenyl)-1-(5-(4-(trifluoromethyl) phenyl)thien-2-yl)prop-2-en-1-one is prepared from 1-(5-(4-(trifluoromethyl)phenyl)thien-2-yl)ethanone and 3-bromo-4-hydroxybenzaldehyde according to general procedure B. The evaporation residue is crystallized from ethanol.

$^1$H NMR (300 MHz, DMSO-d$_6$, δ in ppm): 7.01 (d, 1H, J=8.2 Hz); 7.65 (d, 1H, J=15.5 Hz); 7.71 (dd, 1H, J=1.9 Hz, J=8.6 Hz); 7.77-7.84 (m, 3H); 7.89 (d, 1H, J=4.1 Hz); 8.03 (d, 2H, J=8.2 Hz); 8.19 (d, 1H, J=1.7 Hz); 8.40 (d, 1H, J=4.1 Hz).

Intermediate 12

3-(3-bromo-4-hydroxyphenyl)-1-(5-(4-(trifluoromethyl)-phenyl)thien-2-yl)propan-1-one

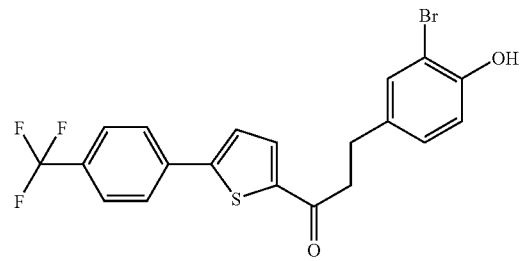

3-(3-Bromo-4-hydroxyphenyl)-1-(5-(4-(trifluoromethyl) phenyl)thien-2-yl)propan-1-one is prepared from 3-(3-bromo-4-hydroxyphenyl)-1-(5-(4-(trifluoromethyl)-phenyl) thien-2-yl)prop-2-en-1-one according to general procedure C.

After stirring for 4 hours at room temperature, the catalyst is removed by filtration, the solvent is removed by evaporation under reduced pressure, and the evaporation residue is purified by silica-gel chromatography.

Elution: cyclohexane/ethyl acetate: 85/15. Silica 40-63 μm.

$^1$H NMR (300 MHz, CDCl$_3$, δ in ppm): 2.99-3.05 (m, 2H); 3.18-3.23 (m, 2H); 6.96 (d, 1H, J=8.2 Hz); 7.10-7.14 (m, 1H); 7.36-7.41 (m, 2H); 7.66-7.69 (m, 3H); 7.75 (d, 2H, J=8.2 Hz).

Intermediate 13

3-(2,3-dichloro-4-hydroxyphenyl)-1-(5-(4-(trifluoromethyl)phenyl)fur-2-yl)prop-2-en-1-one

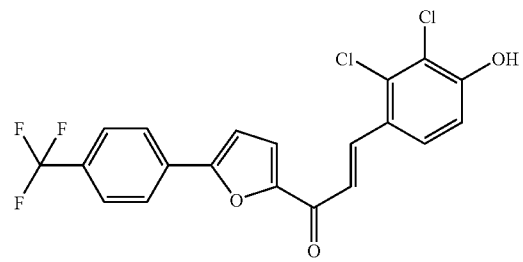

3-(2,3-Dichloro-4-hydroxyphenyl)-1-(5-(4-(trifluoromethyl)phenyl)fur-2-yl)prop-2-en-1-one is prepared from 1-(5-(4-(trifluoromethyl)phenyl)fur-2-yl)ethanone and 2,3-dichloro-4-hydroxybenzaldehyde according to general procedure B. The evaporation residue is washed with dichloromethane.

$^1$H NMR (300 MHz, DMSO-d$_6$, δ in ppm): 7.07 (d, 1H, J=8.8 Hz); 7.51 (d, 1H, J=3.8 Hz); 7.71 (d, 1H, J=15.5 Hz); 7.88 (d, 2H, J=8.3 Hz); 7.93 (d, 1H, J=3.8 Hz); 8.03 (d, 1H, J=15.5 Hz); 8.06 (d, 1H, J=8.8 Hz); 8.14 (d, 2H, J=8.3 Hz).

Intermediate 14

3-(2,3-dichloro-4-hydroxyphenyl)-1-(5-(4-(trifluoromethyl)phenyl)fur-2-yl)propan-1-one

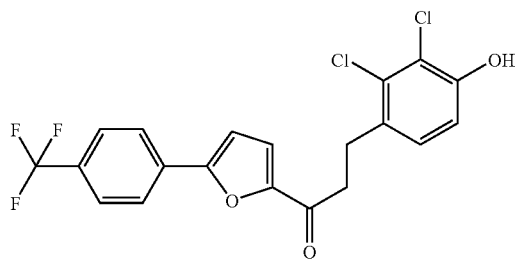

3-(2,3-Dichloro-4-hydroxyphenyl)-1-(5-(4-(trifluoromethyl)phenyl)fur-2-yl)propan-1-one is prepared from 3-(2,3-dichloro-4-hydroxyphenyl)-1-(5-(4-(trifluoromethyl)phenyl)fur-2-yl)prop-2-en-1-one according to general procedure C.

After stirring for 24 hours at 40° C. under 5 bar hydrogen pressure, the catalyst is removed by filtration and the solvents are removed by evaporation under reduced pressure. The evaporation residue is purified by silica-gel chromatography.

Elution: cyclohexane/ethyl acetate: 8/2. Silica 40-63 μm.

$^1$H NMR (300 MHz, CDCl$_3$, δ in ppm): 3.19 (m, 4H); 6.88 (d, 1H, J=4.1 Hz); 6.90 (d, 1H, J=8.9 Hz); 7.17 (d, 1H, J=8.9 Hz); 7.29 (d, 1H, J=4.1 Hz); 7.69 (d, 2H, J=8.2 Hz); 7.88 (d, 2H, J=8.2 Hz).

Intermediate 15

3-(2,3-dichloro-4-hydroxyphenyl)-1-(5-(4-(trifluoromethoxy)phenyl)thien-2-yl)prop-2-en-1-one

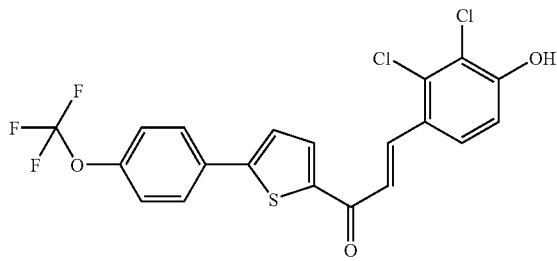

3-(2,3-Dichloro-4-hydroxyphenyl)-1-(5-(4-(trifluoromethoxy)phenyl)thien-2-yl)prop-2-en-1-one is prepared from 1-(5-(4-(trifluoromethoxy)phenyl)thien-2-yl)-ethanone and 2,3-dichloro-4-hydroxybenzaldehyde according to general procedure B. The evaporation residue is crystallized from acetonitrile.

$^1$H NMR (300 MHz, DMSO-d$_6$, δ in ppm): 7.07 (d, 1H, J=9.0 Hz); 7.49 (d, 2H, J=8.4 Hz); 7.80-7.86 (m, 3H); 7.93-7.98 (m, 2H); 8.09 (d, 1H, J=9.0 Hz); 8.36 (d, 1H, J=4.2 Hz).

Intermediate 16

3-(2,3-dichloro-4-hydroxyphenyl)-1-(5-(4-(trifluoromethoxy)phenyl)thien-2-yl)propan-1-one

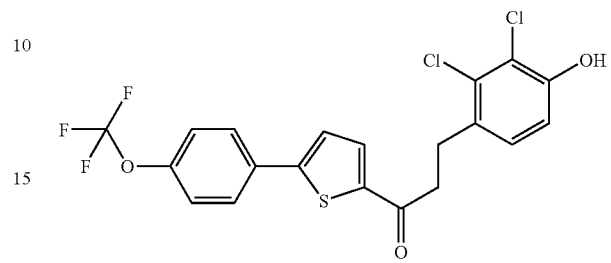

3-(2,3-Dichloro-4-hydroxyphenyl)-1-(5-(4-(trifluoromethoxy)phenyl)thien-2-yl)-propan-1-one is prepared from 3-(2,3-dichloro-4-hydroxyphenyl)-1-(5-(4-(trifluoromethoxy)phenyl)thien-2-yl)prop-2-en-1-one according to general procedure C.

After stirring for 24 hours at room temperature under 10 bar hydrogen pressure, the catalyst is removed by filtration and the solvents are removed by evaporation under reduced pressure. The evaporation residue is purified by silica-gel chromatography.

Elution: cyclohexane/ethyl acetate: 8/2. Silica 40-63 μm.

$^1$H NMR (300 MHz, CDCl$_3$, δ in ppm): 3.13-3.23 (m, 4H); 5.61 (s, 1H); 6.90 (d, 1H, J=8.6 Hz); 7.16 (d, 1H, J=8.6 Hz); 7.25-7.29 (m, 3H); 7.64-7.69 (m, 3H).

Intermediate 17

3-(2,3-difluoro-4-hydroxyphenyl)-1-(5-(4-(trifluoromethyl)-phenyl)thien-2-yl)prop-2-en-1-one

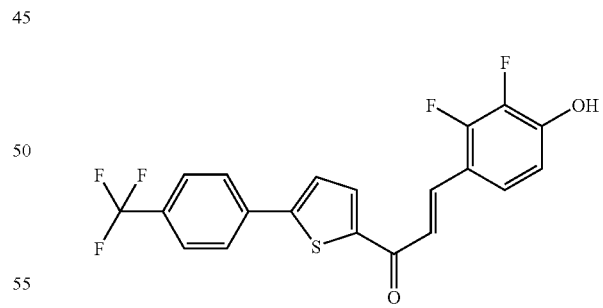

3-(2,3-Difluoro-4-hydroxyphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 2,3-difluoro-4-hydroxybenzaldehyde according to general procedure B. The evaporation residue is crystallized from acetonitrile.

$^1$H NMR (300 MHz, DMSO-d$_6$, δ in ppm): 6.88 (t, 1H, J=8.3 Hz); 7.79 (m, 5H); 7.88 (d, 1H, J=3.5 Hz); 8.04 (d, 2H, J=7.9 Hz); 8.31 (d, 1H, J=3.5 Hz).

Intermediate 18

3-(2,3-difluoro-4-hydroxyphenyl)-1-(5-(4-(trifluoromethyl)-phenyl)thien-2-yl)propan-1-one

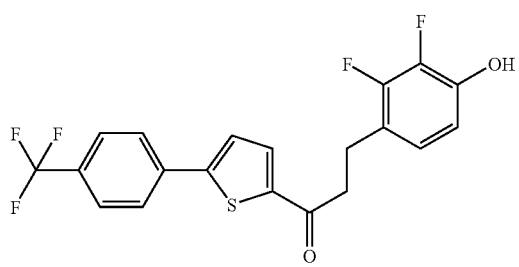

3-(2,3-Difluoro-4-hydroxyphenyl)-1-(5-(4-(trifluoromethyl)phenyl)thien-2-yl)propan-1-one is prepared from 3-(2,3-difluoro-4-hydroxyphenyl)-1-(5-(4-(trifluoromethyl)phenyl)thien-2-yl)prop-2-en-1-one according to general procedure C.

After stirring for 1 hour at 45° C., the catalyst is removed by filtration and the solvents are removed by evaporation under reduced pressure. The evaporation residue is purified by silica-gel chromatography.

Elution: cyclohexane/ethyl acetate: 7/3. Silica 40-63 μm.

$^1$H NMR (300 MHz, DMSO-$d_6$, δ in ppm): 2.89 (t, 2H, J=7.3 Hz); 3.27 (t, 2H, J=7.3 Hz); 6.69 (t, 1H, J=8.5 Hz); 6.93 (t, 1H, J=8.5 Hz); 7.80 (m, 3H); 8.01 (m, 3H).

Intermediate 19

3-(4-hydroxy-3,5-dimethylphenyl)-1-(5-(4-(trifluoromethyl)phenyl)thien-2-yl)prop-2-en-1-one

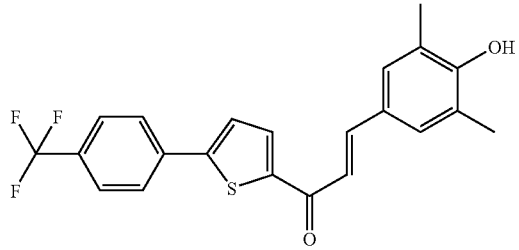

3-(4-Hydroxy-3,5-dimethylphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 4-hydroxy-3,5-dimethylbenzaldehyde according to general procedure B. The evaporation residue is washed with dichloromethane.

$^1$H NMR (300 MHz, CDCl$_3$, δ in ppm): 2.22 (s, 6H); 7.52 (s, 2H); 7.62 (d, 1H, J=15.5 Hz); 7.71 (d, 1H, J=15.5 Hz); 7.83 (d, 2H, J=8.3 Hz); 7.90 (d, 1H, J=4.1 Hz); 8.03 (d, 2H, J=8.3 Hz); 8.36 (d, 1H, J=4.1 Hz); 9.01 (s, 1H).

Intermediate 20

3-(4-hydroxy-3,5-dimethylphenyl)-1-(5-(4-(trifluoromethyl)phenyl)thien-2-yl)propan-1-one

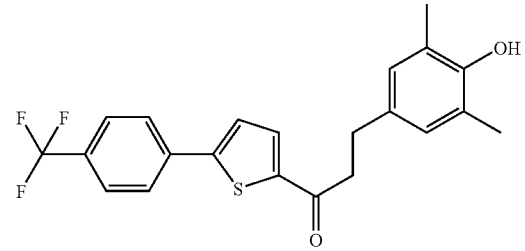

3-(4-Hydroxy-3,5-dimethylphenyl)-1-(5-(4-(trifluoromethyl)phenyl)thien-2-yl)-propan-1-one is prepared from 3-(4-hydroxy-3,5-dimethylphenyl)-1-(5-(4-(trifluoromethyl)phenyl)thien-2-yl)prop-2-en-1-one according to general procedure C.

After stirring for 24 hours at room temperature under 5 bar hydrogen pressure, the catalyst is removed by filtration and the solvents are removed by evaporation under reduced pressure. The evaporation residue is used "as is" for carrying out the next stage.

$^1$H NMR (300 MHz, DMSO-$d_6$, δ in ppm): 2.11 (s, 6H); 2.71-2.87 (m, 2H); 3.18-3.27 (m, 2H); 6.80 (s, 2H); 7.75-8.12 (m, 6H).

Intermediate 21

1-(5-(4-bromophenyl)thien-2-yl)-3-(2,3-dichloro-4-hydroxyphenyl)prop-2-en-1-one

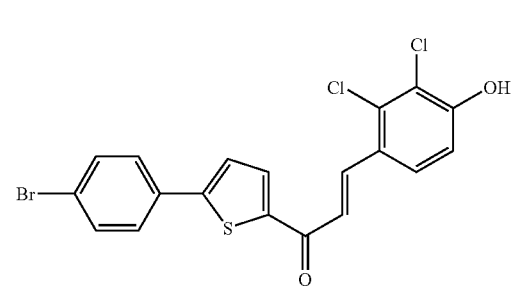

1-(5-(4-Bromophenyl)thien-2-yl)-3-(2,3-dichloro-4-hydroxyphenyl)prop-2-en-1-one is prepared from 1-(5-(4-bromophenyl)thien-2-yl)ethanone and 2,3-dichloro-4-hydroxybenzaldehyde according to general procedure B. The evaporation residue is washed with dichloromethane.

$^1$H NMR (300 MHz, DMSO-$d_6$, δ in ppm): 7.08 (d, 1H, J=8.7 Hz); 7.68 (d, 2H, J=8.7 Hz); 7.77-7.82 (m, 4H); 7.99 (d, 1H, J=15.5 Hz); 8.09 (d, 1H, J=9.0 Hz); 8.35 (d, 1H, J=4.2 Hz); 11.42 (s, 1H).

Intermediate 22

1-(5-(4-bromophenyl)thien-2-yl)-3-(2,3-dichloro-4-hydroxyphenyl)propan-1-one

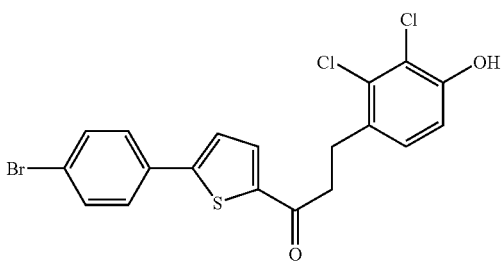

1-(5-(4-Bromophenyl)thien-2-yl)-3-(2,3-dichloro-4-hydroxyphenyl)prop-2-en-1-one is dissolved in dichloromethane (0.7 g, 1.5 mol/L). Triethylsilane (2.1 eq.) and trifluoroacetic acid (8 eq.) are successively added dropwise. After stirring for 16 hours at room temperature, the reaction mixture is washed with water and then the dichloromethane is removed by evaporation under reduced pressure. The evaporation residue is purified by silica-gel chromatography Elution: cyclohexane/ethyl acetate: 9/1 to 8/2. Silica 40-63 μm.

$^1$H NMR (300 MHz, CDCl$_3$, δ in ppm): 3.15-3.20 (m, 4H); 6.90 (d, 1H, J=8.6 Hz); 7.16 (d, 1H, J=8.6 Hz); 7.29 (d, 1H, J=4.2 Hz); 7.50 (d, 2H, J=9.0 Hz); 7.55 (d, 2H, J=9.0 Hz); 7.65 (d, 1H, J=4.2 Hz).

Intermediate 23

3-(2,3-dichloro-4-hydroxyphenyl)-1-(5-(4-(methylthio)-phenyl)thien-2-yl)prop-2-en-1-one

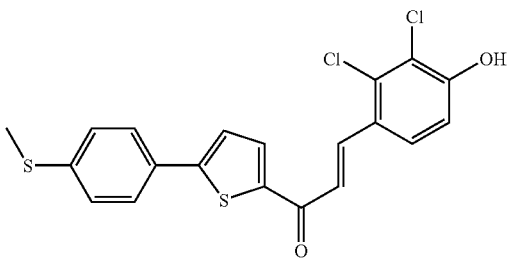

3-(2,3-Dichloro-4-hydroxyphenyl)-1-(5-(4-(methylthio)phenyl)thien-2-yl)prop-2-en-1-one is prepared from 1-(5-(4-(methylthio)phenyl)thien-2-yl)ethanone and 2,3-dichloro-4-hydroxybenzaldehyde according to general procedure B. The evaporation residue is used "as is" for carrying out the next stage.

$^1$H NMR (300 MHz, DMSO-d$_6$, δ in ppm): 2.53 (s, 3H); 7.07 (d, 1H, J=8.8 Hz); 7.35 (d, 2H, J=8.7 Hz); 7.32-7.78 (m, 3H); 7.83 (d, 1H, J=15.3 Hz); 7.99 (d, 1H, J=15.3 Hz); 8.09 (d, 1H, J=8.8 Hz); 8.33 (d, 1H, J=3.9 Hz).

Intermediate 24

3-(2,3-dichloro-4-hydroxyphenyl)-1-(5-(4-(methylthio)-phenyl)thien-2-yl)propan-1-one

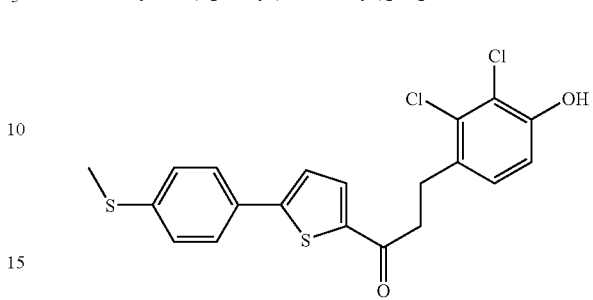

3-(2,3-Dichloro-4-hydroxyphenyl)-1-(5-(4-(methylthio)phenyl)thien-2-yl)propan-1-one is prepared from 3-(2,3-dichloro-4-hydroxyphenyl)-1-(5-(4-(methylthio)phenyl)thien-2-yl)prop-2-en-1-one according to general procedure C in solution in tetrahydrofuran.

After stirring for 24 hours at 50° C. under 10 bar hydrogen pressure, the catalyst is removed by filtration and the solvent is removed by evaporation under reduced pressure. The evaporation residue is purified by silica-gel chromatography.

Elution: cyclohexane/ethyl acetate: 8/2. Silica 40-63 μm.

$^1$H NMR (300 MHz, CDCl$_3$, δ in ppm): 2.52 (s, 3H); 3.11-3.24 (m, 4H); 5.61 (bs, 1H); 6.91 (d, 1H, J=8.6 Hz); 7.17 (d, 1H, J=8.6 Hz); 7.23-7.29 (m, 3H); 7.56 (d, 2H, J=8.5 Hz); 7.64 (d, 1H, J=4.1 Hz).

Intermediate 25

3-(2,3-dichloro-4-hydroxyphenyl)-1-(5-phenylthien-2-yl)-propan-1-one

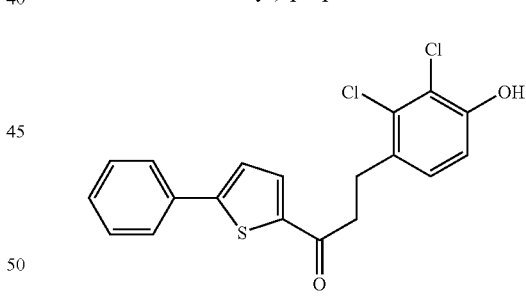

3-(2,3-Dichloro-4-hydroxyphenyl)-1-(5-phenylthien-2-yl)propan-1-one is prepared from 1-(5-(4-bromophenyl)thien-2-yl)-3-(2,3-dichloro-4-hydroxyphenyl)prop-2-en-1-one according to general procedure C.

After stirring for 24 hours at 40° C. under 10 bar hydrogen pressure, the catalyst is removed by filtration and the solvent is removed by evaporation under reduced pressure. The evaporation residue is purified by silica-gel chromatography.

Elution: cyclohexane/ethyl acetate: 9/1 to 8/2. Silica 40-63 μm.

$^1$H NMR (300 MHz, CDCl$_3$, δ in ppm): 3.16-3.21 (m, 4H); 6.91 (d, 1H, J=8.6 Hz); 7.17 (d, 1H, J=8.6 Hz); 7.31 (d, 1H, J=3.9 Hz); 7.39-7.42 (m, 3H); 7.64-7.67 (m, 3H).

Intermediate 26

3-(4-hydroxy-3-methylphenyl)-1-(5-(4-(trifluoromethyl)-phenyl)thien-2-yl)prop-2-en-1-one

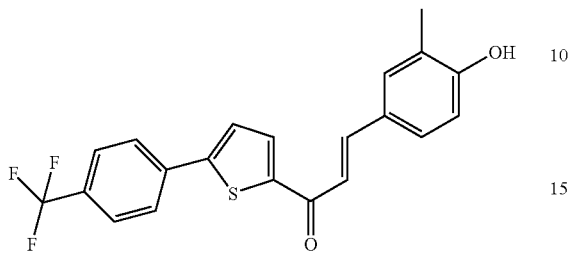

3-(4-Hydroxy-3-methylphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 4-hydroxy-3-methylbenzaldehyde according to general procedure B. The evaporation residue is washed with dichloromethane.

$^1$H NMR (300 MHz, DMSO-$d_6$, δ in ppm): 2.18 (s, 3H); 6.86 (d, 1H, J=8.3 Hz); 7.55 (dd, 1H, J=2.4 Hz, J=8.3 Hz); 7.65 (d, 1H, J=15.6 Hz); 7.71 (d, 1H, J=15.6 Hz); 7.72 (d, 1H, J=2.4 Hz); 7.84 (d, 2H, J=8.2 Hz); 7.91 (d, 1H, J=4.1 Hz); 8.04 (d, 2H, J=8.2 Hz); 8.35 (d, 1H, J=4.1 Hz); 10.10 (bs, 1H).

Intermediate 27

3-(4-hydroxy-3-methylphenyl)-1-(5-(4-(trifluoromethyl)-phenyl)thien-2-yl)propan-1-one

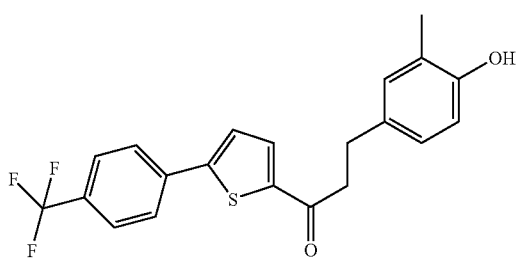

3-(4-Hydroxy-3-methylphenyl)-1-(5-(4-(trifluoromethyl)phenyl)thien-2-yl)propan-1-one is prepared from 3-(4-hydroxy-3-methylphenyl)-1-(5-(4-(trifluoromethyl)-phenyl)thien-2-yl)prop-2-en-1-one according to general procedure C.

After stirring for 40 hours at 40° C. under 5 bar hydrogen pressure, the catalyst is removed by filtration and the solvents are removed by evaporation under reduced pressure. The evaporation residue is purified by silica-gel chromatography.

Elution: cyclohexane/ethyl acetate: 9/1 to 8/2. Silica 40-63 μm.

$^1$H NMR (300 MHz, CDCl$_3$, δ in ppm): 2.24 (s, 3H); 2.96-3.01 (m, 2H); 3.17-3.22 (m, 2H); 4.68 (s, 1H); 6.71 (d, 1H, J=8.1 Hz); 6.96 (dd, 1H, J=2.3 Hz, J=8.1 Hz); 7.01 (d, 1H, J=2.3 Hz); 7.38 (d, 1H, J=3.9 Hz); 7.66-7.68 (m, 3H); 7.75 (d, 2H, J=8.4 Hz).

Intermediate 28

3-(4-hydroxyphenyl)-1-(5-(4-(trifluoromethyl)phenyl)-thien-2-yl)prop-2-en-1-one

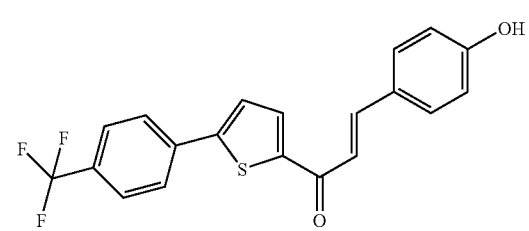

3-(4-Hydroxyphenyl)-1-(5-(4-(trifluoromethyl)phenyl)thien-2-yl)prop-2-en-1-one is prepared from 1-(5-(4-(trifluoromethyl)phenyl)thien-2-yl)ethanone and 4-hydroxybenzaldehyde according to general procedure B. The evaporation residue is purified by silica-gel chromatography.

Elution: cyclohexane/ethyl acetate: 6/4. Silica 40-63 μm.

$^1$H NMR (300 MHz, CDCl$_3$, δ in ppm): 6.91 (d, 1H, J=8.4 Hz); 7.32 (d, 1H, J=15.4 Hz); 7.46 (d, 1H, J=4.1 Hz); 7.59 (d, 2H, J=8.4 Hz); 7.79-7.88 (m, 4H).

Intermediate 29

3-(4-hydroxyphenyl)-1-(5-(4-(trifluoromethyl)phenyl)-thien-2-yl)propan-1-one

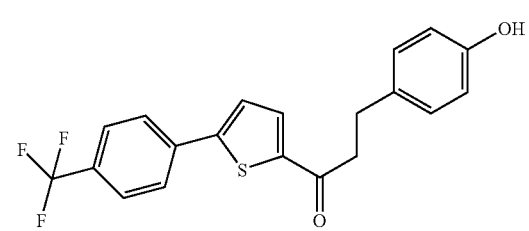

3-(4-Hydroxyphenyl)-1-(5-(4-(trifluoromethyl)phenyl)thien-2-yl)propan-1-one is prepared from 3-(4-hydroxyphenyl)-1-(5-(4-(trifluoromethyl)phenyl)thien-2-yl)prop-2-en-1-one according to general procedure C.

After stirring for 1.5 hours at room temperature, the catalyst is removed by filtration and the solvents are removed by evaporation under reduced pressure. The evaporation residue is purified by silica-gel chromatography.

Elution: cyclohexane/ethyl acetate: 8/2. Silica 40-63 μm.

$^1$H NMR (300 MHz, CDCl$_3$, δ in ppm): 3.01-3.06 (m, 2H); 3.19-3.24 (m, 2H); 4.72 (bs, 1H); 6.78 (d, 2H, J=8.5 Hz); 7.13 (d, 2H, J=8.5 Hz); 7.38 (d, 1H, J=4.1 Hz); 7.67-7.68 (m, 3H); 7.76 (d, 2H, J=8.2 Hz).

Intermediate 30

3-(2,3-dichloro-4-hydroxyphenyl)-1-(5-(3-(trifluoromethyl)phenyl)thien-2-yl)prop-2-en-1-one

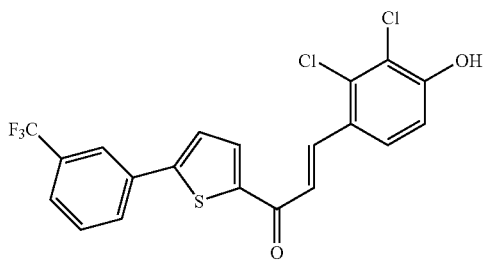

3-(2,3-Dichloro-4-hydroxyphenyl)-1-(5-(3-(trifluoromethyl)phenyl)thien-2-yl)prop-2-en-1-one is prepared from 1-(5-(3-(trifluoromethyl)phenyl)thien-2-yl)ethanone and 2,3-dichloro-4-hydroxybenzaldehyde according to general procedure B, at 50° C. for 30 hours. The evaporation residue is purified by silica-gel chromatography.

Elution: cyclohexane/ethyl acetate: 7/3. Silica 40-63 µm.

$^1$H NMR (300 MHz, CDCl$_3$, δ in ppm): 5.95 (s, 1H); 7.06 (d, 1H, J=8.8 Hz); 7.33 (d, 1H, J=15.5 Hz); 7.46 (d, 1H, J=4.1 Hz); 7.55-7.70 (m, 3H); 7.85 (d, 1H, J=4.1 Hz); 7.88-7.93 (m, 2H); 8.21 (d, 1H, J=15.5 Hz).

Intermediate 31

3-(2,3-dichloro-4-hydroxyphenyl)-1-(5-(3-(trifluoromethyl)phenyl)thien-2-yl)propan-1-one

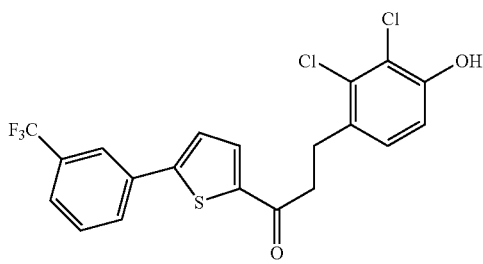

3-(2,3-dichloro-4-hydroxyphenyl)-1-(5-(3-(trifluoromethyl)phenyl)thien-2-yl)propan-1-one is prepared from 3-(2,3-dichloro-4-hydroxyphenyl)-1-(5-(3-(trifluoromethyl)phenyl)thien-2-yl)prop-2-en-1-one according to general procedure C.

After stirring for 3 hours at 40° C., the catalyst is removed by filtration and the solvents are removed by evaporation under reduced pressure. The evaporation residue is purified by silica-gel chromatography.

Elution: cyclohexane/ethyl acetate: 8/2. Silica 40-63 µm.

$^1$H NMR (300 MHz, CDCl$_3$, δ in ppm): 3.15-3.25 (m, 4H); 5.57 (s, 1H); 6.92 (d, 1H, J=8.4 Hz); 7.17 (d, 1H, J=8.4 Hz); 7.38 (d, 1H, J=4.1 Hz); 7.56 (m, 1H); 7.63 (d, 1H, J=7.9 Hz); 7.69 (d, 1H, J=4.1 Hz); 7.82 (d, 1H, J=7.9 Hz); 7.89 (s, 1H).

Example 4

Synthesis of the Compounds According to the Invention

Compound 1 tert-butyl 2-(2,3-dichloro-4-(3-oxo-3-(5-(4-(trifluoromethyl)phenyl)thien-2-yl)-propyl)phenoxy)-2-methylpropanoate

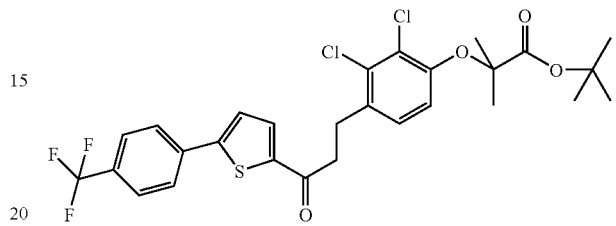

Tert-butyl 2-(2,3-dichloro-4-(3-oxo-3-(5-(4-(trifluoromethyl)phenyl)thien-2-yl)propyl)phenoxy)-2-methylpropanoate is prepared from 3-(2,3-dichloro-4-hydroxyphenyl)-1-(5-(4-(trifluoromethyl)phenyl)thien-2-yl)propan-1-one and tert-butyl bromoisobutyrate according to general procedure D.

After stirring for 16 hours, the solvent is removed by evaporation under reduced pressure and the evaporation residue is purified by silica-gel chromatography.

Elution: cyclohexane/ethyl acetate: 95/5. Silica 40-63 µm.

$^1$H NMR (300 MHz, CDCl$_3$, δ in ppm): 1.46 (s, 9H); 1.61 (s, 6H); 3.16-3.26 (m, 4H); 6.81 (d, 1H, J=8.5 Hz); 7.11 (d, 1H, J=8.5 Hz); 7.39 (d, 1H, J=3.8 Hz); 7.66-7.69 (m, 3H); 7.77 (d, 2H, J=8.2 Hz).

Compound 2

2-(2,3-dichloro-4-(3-oxo-3-(5-(4-(trifluoromethyl)phenyl)thien-2-yl)propyl)phenoxy)-2-methylpropanoic acid

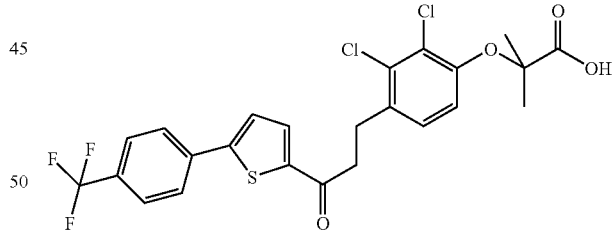

2-(2,3-Dichloro-4-(3-oxo-3-(5-(4-(trifluoromethyl)phenyl)thien-2-yl)propyl)-phenoxy)-2-methylpropanoic acid is prepared from tert-butyl 2-(2,3-dichloro-4-(3-oxo-3-(5-(4-(trifluoromethyl)phenyl)thien-2-yl)propyl)phenoxy)-2-methylpropanoate according to general procedure E using 10 equivalents of trifluoroacetic acid.

After 16 hours at room temperature, the reaction mixture is washed with water and then the dichloromethane is removed by evaporation under reduced pressure. The evaporation residue is recrystallized from methylene chloride.

$^1$H NMR (300 MHz, CDCl$_3$, δ in ppm): 1.64 (s, 6H); 3.19-3.28 (m, 4H); 6.96 (d, 1H, J=8.5 Hz); 7.21 (d, 1H, J=8.5 Hz); 7.39 (d, 1H, J=4.1 Hz); 7.67-7.69 (m, 3H); 7.76 (d, 2H, J=8.5 Hz).

Mass (ES⁺): 531/533 (M+1).
M.p.=153-154° C.

Compound 3 tert-butyl 2-(2,3-dichloro-4-(3-hydroxy-3-(5-(4-(trifluoromethyl)phenyl)thien-2-yl)-propyl)phenoxy)-2-methylpropanoate

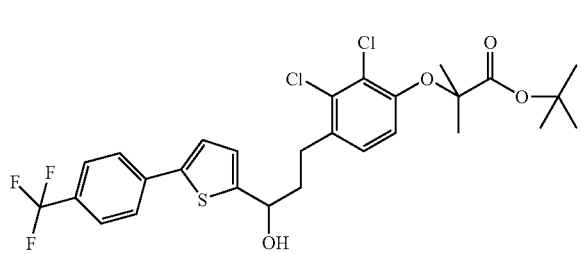

Tert-butyl 2-(2,3-dichloro-4-(3-hydroxy-3-(5-(4-(trifluoromethyl)phenyl)thien-2-yl)propyl)-phenoxy)-2-methylpropanoate is prepared from tert-butyl 2-(2,3-dichloro-4-(3-oxo-3-(5-(4-(trifluoromethyl)phenyl)thien-2-yl)propyl)phenoxy)-2-methylpropanoate according to general procedure G.

¹H NMR (300 MHz, CDCl₃, δ in ppm): 1.46 (s, 9H); 1.60 (s, 6H); 2.15-2.22 (m, 2H); 2.79-3.01 (m, 2H); 4.95 (t, 1H, J=6.6 Hz); 6.83 (d, 1H, J=8.5 Hz); 7.01 (d, 1H, J=3.8 Hz); 7.05 (d, 1H, J=8.5 Hz); 7.28 (m, 1H); 7.63 (d, 2H, J=8.5 Hz); 7.69 (d, 2H, J=8.5 Hz).

Compound 4

2-(2,3-dichloro-4-(3-hydroxy-3-(5-(4-(trifluoromethyl)phenyl)thien-2-yl)propyl)phenoxy)-2-methylpropanoic acid

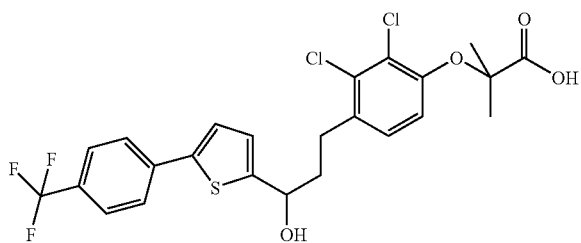

2-(2,3-Dichloro-4-(3-hydroxy-3-(5-(4-(trifluoromethyl)phenyl)thien-2-yl)propyl)-phenoxy)-2-methylpropanoic acid is prepared from 2-(2,3-dichloro-4-(3-oxo-3-(5-(4-(trifluoromethyl)phenyl)thien-2-yl)propyl)phenoxy)-2-methylpropanoic acid according to general procedure G.

The evaporation residue is purified by silica-gel chromatography.

Elution: dichloromethane/methanol: 95/5. Silica 40-63 μm.

¹H NMR (300 MHz, CDCl₃, δ in ppm): 1.65 (s, 6H); 2.17-2.24 (m, 2H); 2.82-3.04 (m, 2H); 4.98 (t, 1H, J=6.6 Hz); 6.97 (d, 1H, J=8.5 Hz); 7.02 (d, 1H, J=3.8 Hz); 7.14 (d, 1H, J=8.5 Hz); 7.28 (m, 1H); 7.64 (d, 2H, J=8.3 Hz); 7.69 (d, 2H, J=8.3 Hz).

Mass (ES⁺): 515/517 (M−OH); 550 (M+NH₄)⁺; 555/557 (M+Na)⁺.

M.p.=54-56° C.

Compound 5 tert-butyl 2-(4-(3-(4-iodobenzyloxy)-3-(5-(4-(trifluoromethyl)phenyl)thien-2-yl)-propyl)-2,3-dichlorophenoxy)-2-methylpropanoate

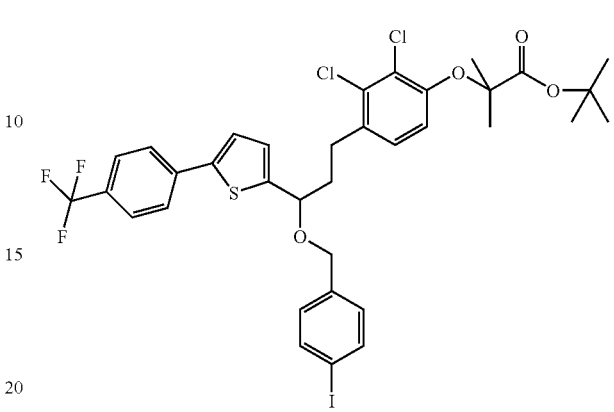

Tert-butyl 2-(4-(3-(4-iodobenzyloxy)-3-(5-(4-(trifluoromethyl)phenyl)thien-2-yl)propyl)-2,3-dichlorophenoxy)-2-methylpropanoate is prepared from tert-butyl 2-(2,3-dichloro-4-(3-hydroxy-3-(5-(4-(trifluoromethyl)phenyl)thien-2-yl)propyl)phenoxy)-2-methylpropanoate using 1.1 equivalents of sodium hydride and 1.1 equivalents of 4-iodobenzyl bromide according to general procedure H.

The evaporation residue is purified by silica-gel chromatography.

Elution: cyclohexane/ethyl acetate: 95/5. Silica 40-63 μm.

¹H NMR (300 MHz, CDCl₃, δ in ppm): 1.46 (s, 9H); 1.58 (s, 6H); 2.05-2.31 (m, 2H); 2.71-2.97 (m, 2H); 4.33 (d, 1H, J=11.7 Hz); 4.53-4.59 (m, 2H); 6.79 (d, 1H, J=8.6 Hz); 6.95 (d, 1H, J=8.6 Hz); 6.99 (d, 1H, J=3.5 Hz); 7.11 (d, 2H, J=7.9 Hz); 7.28 (m, 1H); 7.64 (d, 2H, J=8.5 Hz); 7.70 (m, 4H).

Compound 6

2-(4-(3-(4-iodobenzyloxy)-3-(5-(4-(trifluoromethyl)phenyl)thien-2-yl)propyl)-2,3-dichlorophenoxy)-2-methylpropanoic acid

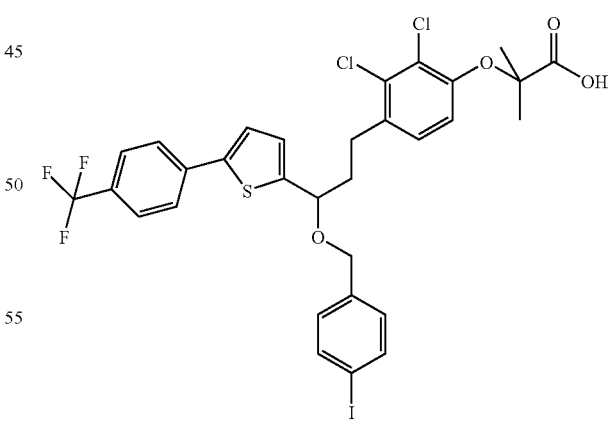

2-(4-(3-(4-Iodobenzyloxy)-3-(5-(4-(trifluoromethyl)phenyl)thien-2-yl)propyl)-2,3-dichlorophenoxy)-2-methylpropanoic acid is prepared from tert-butyl 2-(4-(3-(4-iodobenzyloxy)-3-(5-(4-(trifluoromethyl) phenyl)thien-2-yl)propyl)-2,3-dichlorophenoxy)-2-methylpropanoate according to general procedure E using 10 equivalents of trifluoroacetic acid.

After stirring for 16 hours at room temperature, the reaction mixture is washed with water and then the dichloromethane is removed by evaporation under reduced pressure. The evaporation residue is purified by silica-gel chromatography.

Elution: methylene chloride/methanol: 9/1. Silica 40-63 μm.

$^1$H NMR (300 MHz, CDCl$_3$, δ in ppm): 1.61 (s, 6H); 2.02-2.25 (m, 2H); 2.70-2.95 (m, 2H); 4.32 (d, 1H, J=11.9 Hz); 4.52-4.58 (m, 2H); 6.91 (d, 1H, J=8.6 Hz); 6.87 (d, 1H, J=8.6 Hz); 6.98 (d, 1H, J=3.5 Hz); 7.09 (d, 2H, J=8.2 Hz); 7.27 (m, 1H); 7.61-7.72 (m, 6H).

Mass (ES$^-$): 747/748/749 (M−1).

Appearance: viscous oil

Compound 7

2-(4-(3-(benzyloxy)-3-(5-(4-(trifluoromethyl)phenyl)thien-2-yl)propyl)-2,3-dichlorophenoxy)-2-methyl-propanoic acid

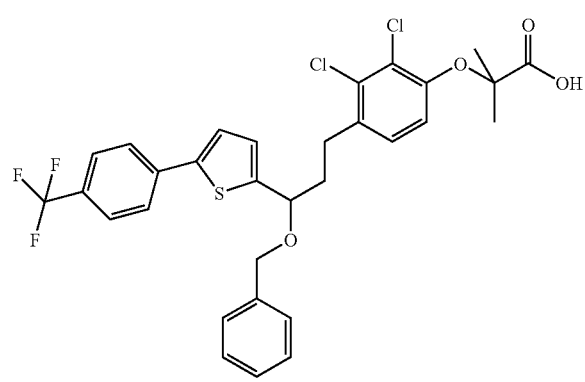

2-(4-(3-(Benzyloxy)-3-(5-(4-(trifluoromethyl)phenyl)thien-2-yl)propyl)-2,3-di-chlorophenoxy)-2-methylpropanoic acid is prepared from 2-(2,3-dichloro-4-(3-hydroxy-3-(5-(4-(trifluoromethyl)phenyl)thien-2-yl)propyl)phenoxy)-2-methylpropanoic acid using 2.2 equivalents of sodium hydride and 2.2 equivalents of benzyl bromide according to general procedure H.

The evaporation residue is dissolved in ethanol in the presence of 2N sodium hydroxide (20 eq.). After stirring for 16 hours, the solvents are removed by evaporation under reduced pressure. The evaporation residue is acidified using dilute solution of hydrochloric acid and is then extracted with dichloromethane. The organic phase is dried over magnesium sulfate, filtered and then concentrated under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 22/78 to 0/100.

$^1$H NMR (300 MHz, CDCl$_3$, δ in ppm): 1.64 (s, 6H); 2.31-2.08 (m, 2H); 3.01-2.74 (m, 2H); 4.39 (d, 1H, J=11.7 Hz); 4.57-4.66 (m, 2H); 6.91 (d, 1H, J=8.5 Hz); 6.99 (d, 1H, J=8.5 Hz); 7.01 (d, 1H, J=3.5 Hz); 7.27-7.38 (m, 6H); 7.63 (d, 2H, J=8.5 Hz); 7.70 (d, 2H, J=8.5 Hz).

Mass (ES$^+$): 640/642 (M+NH$_4$)$^+$, 645/647 (M+Na)$^+$.

M.p.=46-48° C.

Compound 7a and 7b

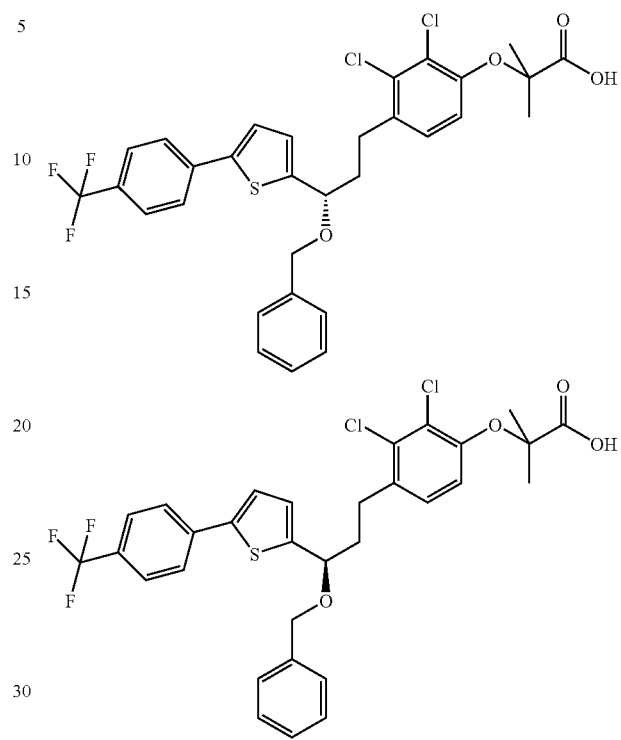

The two enantiomers of compound 7 are separated by chiral-column semi-preparative HPLC Chiralpak®AD-H (250*20 mm, 5 μm, Chiral Technologies Europe) at room temperature. Elution is carried out isocratically with n-heptane-ethanol (95-5) mobile phase with 0.1% of trifluoroacetic acid added, at a flow rate of 18 ml/min.

The enantiomeric purity of each of the two enantiomers thus obtained is checked by analytical HPLC: column Chiralpak®AD-H (250*46 mm, 5 μm, Daicel Chemical Industries, Ltd.) at 30° C.; isocratic elution with n-heptane-ethanol (92-8) mobile phase with 0.1% of trifluoroacetic acid added; flow rate 1 ml/min; UV detection at 298 nm.

Compound 7a: tR=11.85 min, ee=100%
Compound 7b: tR=16.28 min, ee=99.6%

Compound 8 tert-butyl 2-(2,3-dichloro-4-(3-oxo-3-(5-(4-(trifluoromethyl)phenyl)thien-2-yl)-propyl)phenoxy)butanoate

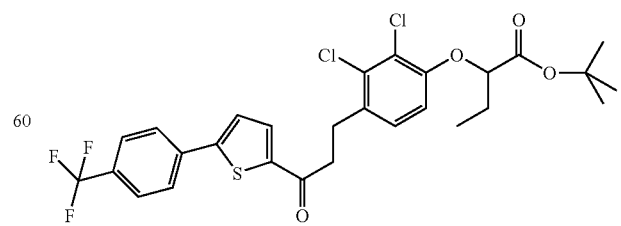

Tert-butyl 2-(2,3-dichloro-4-(3-oxo-3-(5-(4-(trifluoromethyl)phenyl)thien-2-yl)propyl)phenoxy)-butanoate is prepared from 3-(2,3-dichloro-4-hydroxyphenyl)-1-(5-(4-(trifluoromethyl)phenyl)thien-2-yl)propan-1-one and tert-butyl 2-bromobutanoate according to general procedure D.

After stirring for 2 hours, the mixture is acidified using dilute solution of hydrochloric acid and is then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 9/1. Silica 40-63 µm.

$^1$H NMR (300 MHz, CDCl$_3$, δ in ppm): 1.11 (t, 3H, J=7.6 Hz); 1.43 (s, 9H); 1.97-2.07 (m, 2H); 3.14-3.26 (m, 4H); 4.45 (t, 1H, J=5.8 Hz); 6.66 (d, 1H, J=8.8 Hz); 7.13 (d, 1H, J=8.8 Hz); 7.38 (d, 1H, J=4.1 Hz); 7.66-7.69 (m, 3H); 7.75 (d, 2H, J=8.2 Hz).

Compound 9

2-(2,3-dichloro-4-(3-oxo-3-(5-(4-(trifluoromethyl)phenyl)thien-2-yl)propyl)phenoxy)butanoic acid

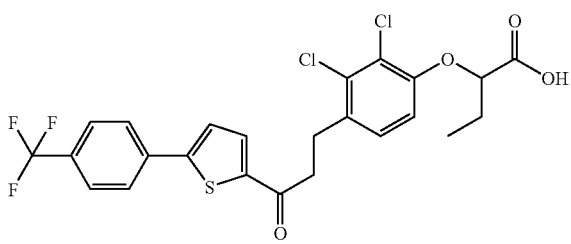

2-(2,3-Dichloro-4-(3-oxo-3-(5-(4-(trifluoromethyl)phenyl)thien-2-yl)propyl)-phenoxy)butanoic acid is prepared from tert-butyl 2-(2,3-dichloro-4-(3-oxo-3-(5-(4-(trifluoromethyl)phenyl)thien-2-yl)propyl)phenoxy)butanoate according to general procedure E using 17 equivalents of trifluoroacetic acid.

After stirring for 4 hours at room temperature, the reaction mixture is washed with water and then the dichloromethane is removed by evaporation under reduced pressure. The evaporation residue is purified by silica-gel chromatography (preparative HPLC, lichrospher (Merck) RP18 12 µm 100 A, column: 25*250 mm).

Elution: gradient of water, methanol+0.1% trifluoroacetic acid: 30/70 to 10/90.

$^1$H NMR (300 MHz, DMSO-d$_6$, δ in ppm): 1.01 (t, 3H, J=7.3 Hz); 1.84-1.98 (m, 2H); 3.03 (t, 2H, J=7.5 Hz); 3.31 (t, 2H, J=7.5 Hz); 4.82 (t, 1H, J=6.4 Hz); 6.92 (d, 1H, J=8.8 Hz); 7.32 (d, 1H, J=8.8 Hz); 7.79-7.83 (m, 3H); 7.99 (d, 2H, J=8.2 Hz); 8.05 (d, 1H, J=4.2 Hz); 13.15 (s, 1H).

Mass (ES$^+$): 531 (M+1).

M.p.=169-171° C.

Compound 10 tert-butyl 2-(2,3-dichloro-4-(3-oxo-3-(4-(4-(trifluoromethyl)phenyl)thien-2-yl)-propyl)phenoxy)-2-methylpropanoate

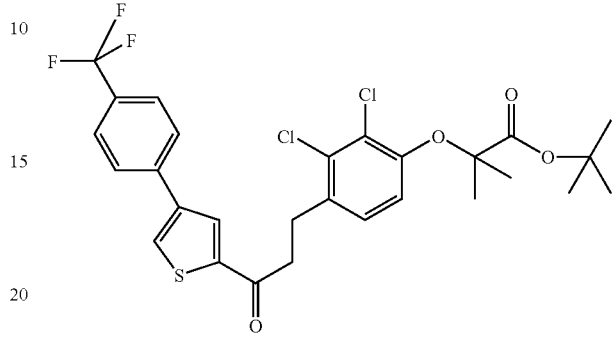

Tert-butyl 2-(2,3-dichloro-4-(3-oxo-3-(4-(4-(trifluoromethyl)phenyl)thien-2-yl)propyl)phenoxy)-2-methylpropanoate is prepared from 3-(2,3-dichloro-4-hydroxyphenyl)-1-(4-(4-(trifluoromethyl)phenyl)thien-2-yl)propan-1-one and tert-butyl bromoisobutyrate according to general procedure D.

After stirring for 18 hours, the mixture is acidified using dilute solution of hydrochloric acid and is then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 9/1. Silica 40-63 µm.

$^1$H NMR (300 MHz, CDCl$_3$, δ in ppm): 1.45 (s, 9H); 1.57 (s, 6H); 3.16-3.21 (m, 2H); 3.25-3.30 (m, 2H); 6.79 (d, 1H, J=8.5 Hz); 7.09 (d, 1H, J=8.5 Hz); 7.68 (m, 4H); 7.8 (d, 1H, J=1.5); 7.95 (d, 1H, J=1.5 Hz).

Compound 11

2-(2,3-dichloro-4-(3-oxo-3-(4-(4-(trifluoromethyl)phenyl)thien-2-yl)propyl)phenoxy)-2-methylpropanoic acid

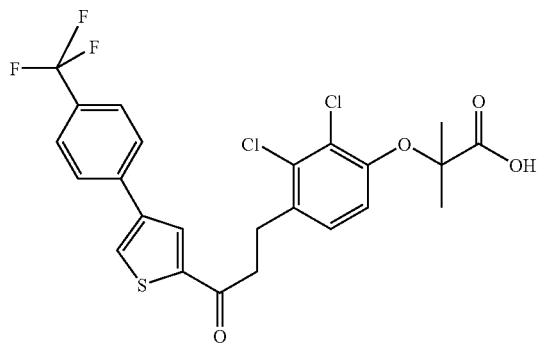

2-(2,3-Dichloro-4-(3-oxo-3-(4-(4-(trifluoromethyl)phenyl)thien-2-yl)propyl)-phenoxy)-2-methylpropanoic acid is prepared from tert-butyl 2-(2,3-dichloro-4-(3-oxo-3-(4-(4-(trifluoromethyl)phenyl)thien-2-yl)propyl)phenoxy)-2-methylpropanoate according to general procedure E using 17 equivalents of trifluoroacetic acid.

After stirring for 4 hours at room temperature, the reaction mixture is washed with water and then the dichloromethane is removed by evaporation under reduced pressure. The evaporation residue is purified by silica-gel chromatography.

Elution: methylene chloride/methanol: 9/1. Silica 40-63 μm.

$^1$H NMR (300 MHz, DMSO-d$_6$, δ in ppm): 1.52 (s, 6H); 3.03 (t, 2H, J=7.9 Hz); 3.38 (t, 2H, J=7.9 Hz); 6.88 (d, 1H, J=8.6 Hz); 7.32 (d, 1H, J=8.6 Hz); 7.78 (d, 2H, J=8.3 Hz); 8.03 (d, 2H, J=8.3 Hz); 8.51 (s, 1H); 8.57 (s, 1H).

Mass (ES$^-$): 529 (M−1).

M.p.=99-101° C.

Compound 12 methyl 5-(2,3-dichloro-4-(3-oxo-3-(5-(4-(trifluoromethyl)phenyl)thien-2-yl)-propyl)phenoxy)-2,2-dimethylpentanoate

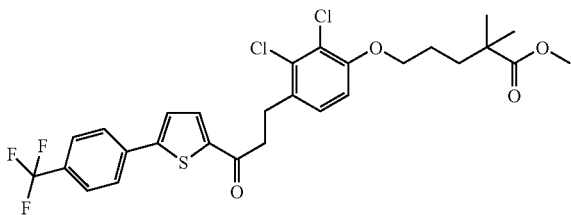

Methyl 5-(2,3-dichloro-4-(3-oxo-3-(5-(4-(trifluoromethyl)phenyl)thien-2-yl)propyl)phenoxy)-2,2-dimethylpentanoate is prepared from 3-(2,3-dichloro-4-hydroxyphenyl)-1-(5-(4-(trifluoromethyl)phenyl)thien-2-yl)propan-1-one and methyl 5-iodo-2,2-dimethylpentanoate according to general procedure D.

After stirring for 2 hours, the mixture is acidified using dilute solution of hydrochloric acid and is then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 8/2. Silica 40-63 μm.

$^1$H NMR (300 MHz, CDCl$_3$, δ in ppm): 1.22 (s, 6H); 1.72-1.81 (m, 6H); 3.16-3.25 (m, 4H); 3.67 (s, 3H); 6.76 (d, 1H, J=8.5 Hz); 7.18 (d, 1H, J=8.5 Hz); 7.39 (d, 1H, J=4.1 Hz); 7.66-7.69 (m, 3H); 7.75 (d, 2H, J=8.5 Hz).

Compound 13

5-(2,3-dichloro-4-(3-oxo-3-(5-(4-(trifluoromethyl)phenyl)thien-2-yl)propyl)phenoxy)-2,2-dimethylpentanoic acid

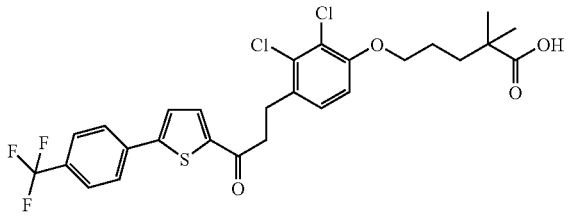

5-(2,3-Dichloro-4-(3-oxo-3-(5-(4-(trifluoromethyl)phenyl)thien-2-yl)propyl)-phenoxy)-2,2-dimethylpentanoic acid is prepared from methyl 5-(2,3-dichloro-4-(3-oxo-3-(5-(4-(trifluoromethyl)phenyl)thien-2-yl)propyl)phenoxy)-2,2-dimethylpentanoate according to general procedure F using 10 equivalents of 2N sodium hydroxide solution.

After stirring for 18 hours at 50° C., the solvents are removed by evaporation under reduced pressure. The evaporation residue is taken up in dilute hydrochloric acid solution and is then extracted with methylene chloride. The organic phase is dried over magnesium sulfate, filtered and then concentrated under reduced pressure. The evaporation residue is purified by silica-gel chromatography.

Elution: methylene chloride/methanol: 95/5. Silica 40-63 μm.

$^1$H NMR (300 MHz, DMSO-d$_6$, δ in ppm): 1.10 (s, 6H); 1.58-1.70 (m, 4H); 3.03 (t, 2H, J=7.6 Hz); 3.31 (t, 2H, J=5.9 Hz); 4.03 (t, 2H, J=5.6 Hz); 7.08 (d, 1H, J=8.8 Hz); 7.33 (d, 1H, J=8.8 Hz); 7.79-7.82 (m, 3H); 7.99 (d, 2H, J=8.2 Hz); 8.04 (d, 1H, J=4.1 Hz); 12.12 (s, 1H).

Mass (ES$^-$): 571 (M−1).

M.p.=167-169° C.

Compound 14 tert-butyl 2-(2,3-dichloro-4-(3-oxo-3-(5-(4-(trifluoromethyl)phenyl)thien-2-yl)propyl)phenoxy)acetate

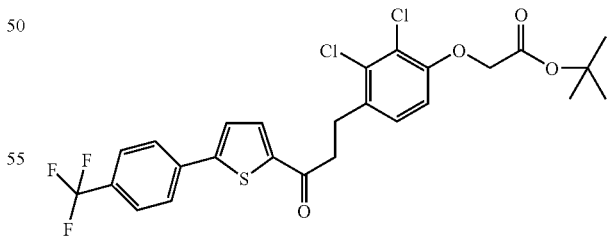

Tert-butyl 2-(2,3-dichloro-4-(3-oxo-3-(5-(4-(trifluoromethyl)phenyl)thien-2-yl)propyl)phenoxy)-acetate is prepared from 3-(2,3-dichloro-4-hydroxyphenyl)-1-(5-(4-(trifluoromethyl)phenyl)thien-2-yl)propan-1-one and tert-butyl bromoacetate according to general procedure D.

After stirring for 2 hours, the mixture is acidified using dilute solution of hydrochloric acid and is then extracted with ethyl acetate. The combined organic phase is dried over magnesium sulfate, filtered and then concentrated under reduced pressure. The evaporation residue is purified by silica-gel chromatography.

Elution: cyclohexane/ethyl acetate: 9/1. Silica 40-63 μm.

$^1$H NMR (300 MHz, CDCl$_3$, δ in ppm): 1.45 (s, 9H); 3.16-3.26 (m, 4H); 4.60 (s, 2H); 6.68 (d, 1H, J=8.4 Hz); 7.18 (d, 1H, J=8.4 Hz); 7.39 (d, 1H, J=3.8 Hz); 7.66-7.69 (m, 3H); 7.76 (d, 2H, J=8.2 Hz).

Compound 15

2-(2,3-dichloro-4-(3-oxo-3-(5-(4-(trifluoromethyl) phenyl)thien-2-yl)propyl)phenoxy)acetic acid

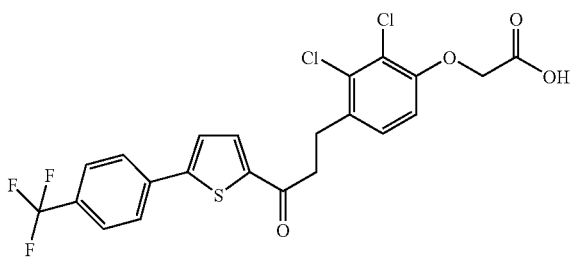

2-(2,3-Dichloro-4-(3-oxo-3-(5-(4-(trifluoromethyl)phenyl)thien-2-yl)propyl)-phenoxy)acetic acid is prepared from tert-butyl 2-(2,3-dichloro-4-(3-oxo-3-(5-(4-(trifluoromethyl)phenyl)thien-2-yl)propyl)phenoxy)acetate according to general procedure E using 17 equivalents of trifluoroacetic acid.

After stirring for 4 hours at room temperature, the reaction mixture is washed with water and then the dichloromethane is removed by evaporation under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 14/86 to 10/90.

$^1$H NMR (300 MHz, DMSO-d$_6$, δ in ppm): 3.04 (t, 2H, J=7.5 Hz); 3.31 (t, 2H, J=7.5 Hz); 4.83 (s, 2H); 7.01 (d, 1H, J=8.6 Hz); 7.33 (d, 1H, J=8.6 Hz); 7.79-7.93 (m, 3H); 7.99 (d, 2H, J=8.2 Hz); 8.06 (d, 1H, J=4.1 Hz); 13.13 (s, 1H).

Mass (ES$^-$): 501 (M−1).

M.p.=217-219° C.

Compound 16 ethyl 2-(2,3-dichloro-4-(3-oxo-3-(5-(4-(trifluoromethyl)phenyl)thien-2-yl)-propyl)phenoxy)-2-phenyl-ethyl acetate

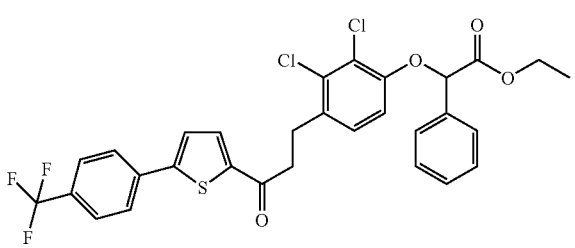

Ethyl 2-(2,3-dichloro-4-(3-oxo-3-(5-(4-(trifluoromethyl) phenyl)thien-2-yl)propyl)phenoxy)-2-phenylethyl acetate is prepared from 3-(2,3-dichloro-4-hydroxyphenyl)-1-(5-(4-(trifluoromethyl)phenyl)thien-2-yl)propan-1-one and 2-bromophenylethyl acetate according to general procedure D.

After stirring for 16 hours, the mixture is acidified using dilute solution of hydrochloric acid and is then extracted with ethyl acetate. The organic phase is dried over magnesium sulfate, filtered and then concentrated under reduced pressure. The evaporation residue is purified by silica-gel chromatography.

Elution: cyclohexane/ethyl acetate: 9/1. Silica 40-63 μm.

$^1$H NMR (300 MHz, CDCl$_3$, δ in ppm): 1.24 (t, 3H, J=7.6 Hz); 3.17-3.22 (m, 4H); 4.15 (q, 2H, J=7.6 Hz); 5.64 (s, 1H); 6.75 (d, 1H, J=8.7 Hz); 7.13 (d, 1H, J=8.7 Hz); 7.32-7.46 (m, 6H); 7.62-7.67 (m, 3H); 7.72-7.77 (m, 2H).

Compound 17

2-(2,3-dichloro-4-(3-oxo-3-(5-(4-(trifluoromethyl) phenyl)thien-2-yl)propyl)phenoxy)-2-phenylacetic acid

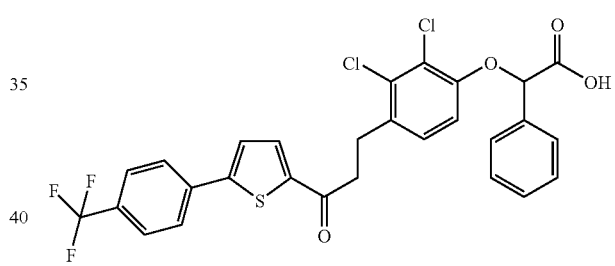

2-(2,3-Dichloro-4-(3-oxo-3-(5-(4-(trifluoromethyl)phenyl)thien-2-yl)propyl)-phenoxy)-2-phenylacetic acid is prepared from ethyl 2-(2,3-dichloro-4-(3-oxo-3-(5-(4-(trifluoromethyl)phenyl)thien-2-yl)propyl) phenoxy)-2-phenylacetate according to general procedure F using 20 equivalents of 2N sodium hydroxide solution.

After 16 hours at 40° C., the mixture is acidified using dilute solution of hydrochloric acid and is then extracted with ethyl acetate. The organic phase is dried over magnesium sulfate, filtered and then concentrated under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 14/86 to 10/90.

$^1$H NMR (300 MHz, DMSO-d$_6$, δ in ppm): 3.03 (t, 2H, J=7.6 Hz); 3.31 (t, 2H, J=7.6 Hz); 6.02 (s, 1H); 7.07 (d, 1H, J=8.8 Hz); 7.35 (d, 1H, J=8.8 Hz); 7.38-7.47 (m, 3H); 7.58 (d, 2H, J=6.5 Hz); 7.79-7.82 (m, 3H); 7.99 (d, 2H, J=8.2 Hz); 8.06 (d, 1H, J=4.1 Hz); 13.35 (s, 1H).

Mass (ES$^-$): 577 (M−1).

M.p.=189-191° C.

Compound 18 tert-butyl 2-(2-chloro-4-(3-oxo-3-(5-(4-(trifluoromethyl)phenyl)thien-2-yl)propyl)-phenoxy)-2-methyl propanoate

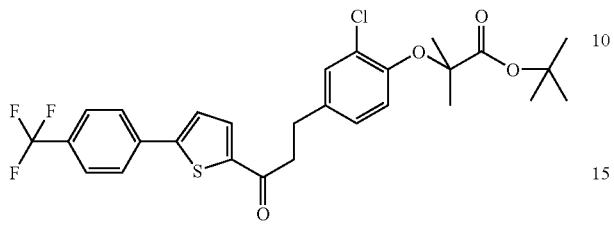

Tert-butyl 2-(2-chloro-4-(3-oxo-3-(5-(4-(trifluoromethyl)phenyl)thien-2-yl)propyl)phenoxy)-2-methylpropanoate is prepared from 3-(3-chloro-4-hydroxyphenyl)-1-(5-(4-(trifluoromethyl)phenyl)thien-2-yl)propan-1-one and tert-butyl bromoisobutyrate according to general procedure D.

After stirring for 2 hours, the mixture is acidified using 1N dilute solution of citric acid and is then extracted with ethyl acetate. The organic phase is dried over magnesium sulfate, filtered and then concentrated under reduced pressure. The evaporation residue is purified by silica-gel flash chromatography.

Elution: cyclohexane/dichloromethane: 5/5. Silica 40-63 μm.

$^1$H NMR (300 MHz, CDCl$_3$, δ in ppm): 1.46 (s, 9H); 1.57 (s, 6H); 3.01 (t, 2H, J=7.3 Hz); 3.2 (t, 2H, J=7.3 Hz); 6.88 (d, 1H, J=8.5 Hz); 7.01 (dd, 1H, J=2.1 Hz, J=8.5 Hz); 7.26 (m, 1H); 7.39 (d, 1H, J=3.8 Hz); 7.66-7.69 (m, 3H); 7.76 (d, 2H, J=8.2 Hz).

Compound 19

2-(2-chloro-4-(3-oxo-3-(5-(4-(trifluoromethyl)phenyl)thien-2-yl)-propyl)phenoxy)-2-methylpropanoic acid

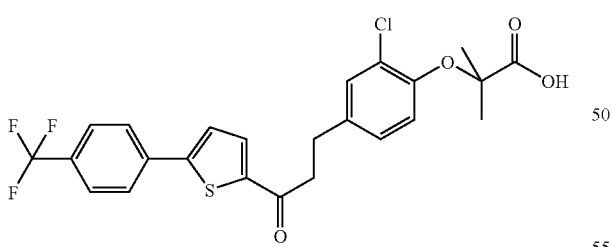

2-(2-Dichloro-4-(3-oxo-3-(5-(4-(trifluoromethyl)phenyl)thien-2-yl)propyl)-phenoxy)-2-methylpropanoic acid is prepared from tert-butyl 2-(2-chloro-4-(3-oxo-3-(5-(4-(trifluoromethyl)phenyl)thien-2-yl)propyl)phenoxy)-2-methylpropanoate according to general procedure E using 17 equivalents of trifluoroacetic acid.

After 1 hour at room temperature, the reaction mixture is washed with water and then the dichloromethane is removed by evaporation under reduced pressure.

The evaporation residue is crystallized from a methylene chloride/heptane mixture: 5/5.

$^1$H NMR (300 MHz, DMSO-d$_6$, δ in ppm): 1.49 (s, 6H); 2.87 (t, 2H, J=7.7 Hz); 3.32 (t, 2H, J=7.7 Hz); 6.84 (d, 1H, J=8.3 Hz); 7.15 (dd, 1H, J=2.3 Hz, J=8.3 Hz); 7.39 (d, 1H, J=2.3 Hz); 7.79-7.82 (m, 3H); 7.99 (d, 2H, J=8.2 Hz); 8.05 (d, 1H, J=4.1 Hz).

Mass (ES$^-$): 495 (M−1).

M.p.=136-137° C.

Compound 20 tert-butyl 2-(3-chloro-4-(3-oxo-3-(5-(4-(trifluoromethyl)phenyl)thien-2-yl)propyl)-phenoxy)-2-methyl-propanoate

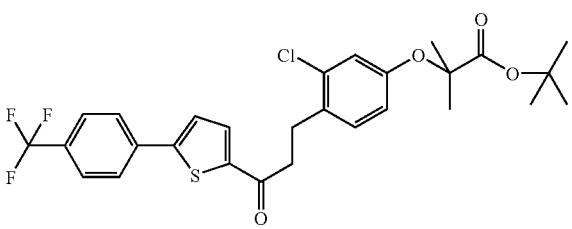

Tert-butyl 2-(3-chloro-4-(3-oxo-3-(5-(4-(trifluoromethyl)phenyl)thien-2-yl)propyl)phenoxy)-2-methylpropanoate is prepared from 3-(2-chloro-4-hydroxyphenyl)-1-(5-(4-(trifluoromethyl)phenyl)thien-2-yl)propan-1-one and tert-butyl bromoisobutyrate according to general procedure D.

After stirring for 2 hours, the mixture is acidified using 1N dilute solution of citric acid and is then extracted with ethyl acetate. The organic phase is dried over magnesium sulfate, filtered and then concentrated under reduced pressure. The evaporation residue is purified by silica-gel flash chromatography.

Elution: cyclohexane/dichloromethane: 5/5. Silica 40-63 μm.

$^1$H NMR (300 MHz, CDCl$_3$, δ in ppm): 1.50 (s, 9H); 1.55 (s, 6H); 3.09-3.14 (m, 2H); 3.18-3.24 (m, 2H); 6.7 (dd, 1, J=2.4 Hz, J=8.5 Hz); 6.91 (d, 1H, J=2.6 Hz); 7.15 (d, 1H, J=8.5 Hz); 7.38 (d, 1H, J=3.8 Hz); 7.66-7.69 (m, 3H); 7.75 (d, 2H, J=8.2 Hz).

Compound 21

2-(3-chloro-4-(3-oxo-3-(5-(4-(trifluoromethyl)phenyl)thien-2-yl)-propyl)phenoxy)-2-methylpropanoic acid

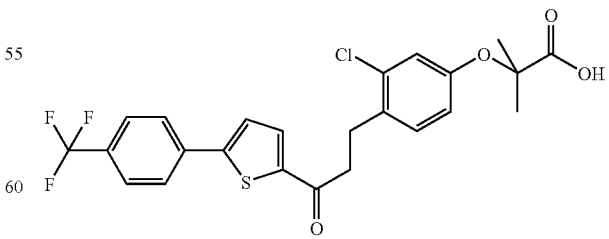

2-(3-Dichloro-4-(3-oxo-3-(5-(4-(trifluoromethyl)phenyl)thien-2-yl)propyl)-phenoxy)-2-methylpropanoic acid is prepared from tert-butyl 2-(3-chloro-4-(3-oxo-3-(5-(4-(trifluoromethyl)phenyl)thien-2-yl)propyl)phenoxy)-2- methylpropanoate according to general procedure E using 17 equivalents of trifluoroacetic acid.

After 1 hour at room temperature, the reaction mixture is washed with water and then the dichloromethane is removed by evaporation under reduced pressure.

The evaporation residue is crystallized from a methylene chloride/heptane mixture: 5/5.

$^1$H NMR (300 MHz, DMSO-d$_6$, δ in ppm): 1.49 (s, 6H); 2.97 (t, 2H, J=8.2 Hz); 3.28 (t, 2H, J=8.2 Hz); 6.76 (dd, 1, J=2.6 Hz, J=8.6 Hz); 6.88 (d, 1H, J=2.6 Hz); 7.32 (d, 1H, J=8.6 Hz); 7.79-7.83 (m, 3H); 7.99 (d, 2H, J=8.2 Hz); 8.04 (d, 1H, J=4.1 Hz).

Mass (ES$^-$): 495 (M−1).

M.p.=104-106° C.

Compound 22 tert-butyl 2-(2-fluoro-4-(3-oxo-3-(5-(4-(trifluoromethyl)phenyl)thien-2-yl)propyl)-phenoxy)-2-methylpropanoate

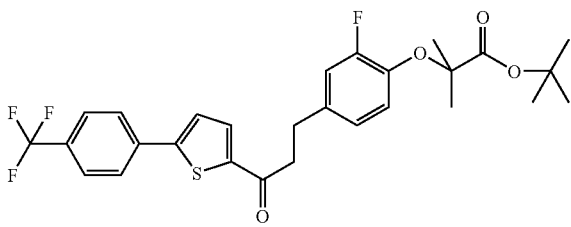

Tert-butyl 2-(2-fluoro-4-(3-oxo-3-(5-(4-(trifluoromethyl)phenyl)thien-2-yl)propyl)phenoxy)-2-methylpropanoate is prepared from 3-(3-fluoro-4-hydroxyphenyl)-1-(5-(4-(trifluoromethyl)phenyl)thien-2-yl)propan-1-one and tert-butyl bromoisobutyrate according to general procedure D.

After stirring for 16 hours, the solvent is removed by evaporation under reduced pressure and the evaporation residue is taken up in dichloromethane. The organic phase is washed with a saturated solution of ammonium chloride, dried over magnesium sulfate, filtered and then concentrated under reduced pressure. The evaporation residue is purified by silica-gel chromatography.

Elution: cyclohexane/ethyl acetate: gradient 97/3 to 9/1. Silica 40-63 μm.

$^1$H NMR (300 MHz, CDCl$_3$, δ in ppm): 1.46 (s, 9H); 1.54 (s, 6H); 3.02 (m, 2H); 3.21 (m, 2H); 6.9 (m, 3H); 7.36 (d, 1H, J=4.1 Hz); 7.67 (m, 3H); 7.76 (d, 2H J=8.1 Hz).

Compound 23

2-(2-fluoro-4-(3-oxo-3-(5-(4-(trifluoromethyl)phenyl)thien-2-yl)propyl)phenoxy)-2-methylpropanoic acid

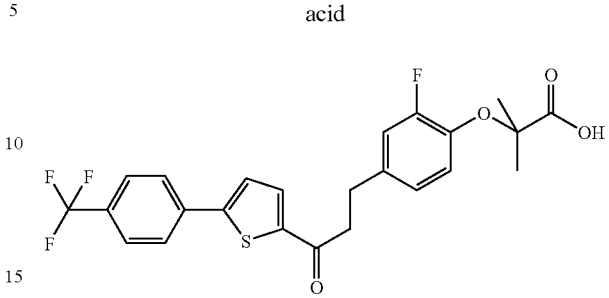

2-(2-Fluoro-4-(3-oxo-3-(5-(4-(trifluoromethyl)phenyl)thien-2-yl)propyl)-phenoxy)-2-methylpropanoic acid is prepared from tert-butyl 2-(2-fluoro-4-(3-oxo-3-(5-(4-(trifluoromethyl)phenyl)thien-2-yl)propyl)phenoxy)-2-methylpropanoate according to general procedure E using 17 equivalents of trifluoroacetic acid.

After stirring for 4 hours at room temperature, the reaction mixture is washed with water and then the dichloromethane is removed by evaporation under reduced pressure. The evaporation residue is purified by silica-gel chromatography.

Elution: methylene chloride/methanol: 95/5. Silica 40-63 μm.

$^1$H NMR (300 MHz, CDCl$_3$, δ in ppm): 1.57 (s, 6H); 3.07 (m, 2H); 3.24 (m, 2H); 6.99 (m, 3H); 7.39 (d, 1H, J=4.1 Hz); 7.68 (m, 3H); 7.76 (d, 2H, J=8.2 Hz).

Mass (ES$^+$): 481 (M+1); 498 (M+NH$_4$)$^+$; 503 (M+Na)$^+$.

M.p.=150-151° C.

Compound 24 tert-butyl 2-(2-fluoro-4-(3-oxo-3-(5-(4-(trifluoromethyl)phenyl)thien-2-yl)propyl)-phenoxy)acetate

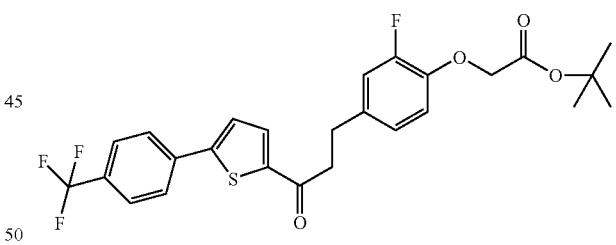

Tert-butyl 2-(2-fluoro-4-(3-oxo-3-(5-(4-(trifluoromethyl)phenyl)thien-2-yl)propyl)phenoxy)-acetate is prepared from 3-(3-fluoro-4-hydroxyphenyl)-1-(5-(4-(trifluoromethyl)phenyl)thien-2-yl)propan-1-one and tert-butyl bromoacetate according to general procedure D.

After stirring for 18 hours, the solvent is removed by evaporation under reduced pressure and the evaporation residue is taken up in ethyl acetate. The organic phase is washed with a saturated solution of ammonium chloride, dried over magnesium sulfate, filtered and then concentrated under reduced pressure. The evaporation residue is purified by silica-gel chromatography.

Elution: cyclohexane/ethyl acetate: 95/5. Silica 40-63 μm.

$^1$H NMR (300 MHz, CDCl$_3$, δ in ppm): 1.46 (s, 9H); 3.01-3.06 (m, 2H); 3.21 (m, 2H); 4.56 (s, 2H); 6.79-6.98 (m, 3H); 7.39 (d, 1H, J=4.1 Hz); 7.65-7.69 (m, 3H); 7.75 (m, 2H).

Compound 25

2-(2-fluoro-4-(3-oxo-3-(5-(4-(trifluoromethyl)phenyl)thien-2-yl)-propyl)phenoxy)acetic acid

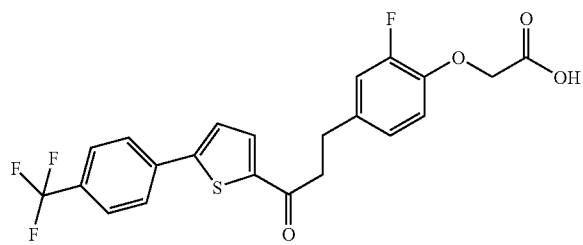

2-(2-Fluoro-4-(3-oxo-3-(5-(4-(trifluoromethyl)phenyl)thien-2-yl)propyl)-phenoxy)acetic acid is prepared from tert-butyl 2-(2-fluoro-4-(3-oxo-3-(5-(4-(trifluoromethyl)phenyl)thien-2-yl)propyl)phenoxy)acetate according to general procedure E using 10 equivalents of trifluoroacetic acid.

After stirring for 18 hours at room temperature, the reaction mixture is washed with water and then the dichloromethane is removed by evaporation under reduced pressure. The evaporation residue is purified by silica-gel chromatography.

Elution: methylene chloride/methanol: gradient 95/5 to 9/1. Silica 40-63 μm.

$^1$H NMR (300 MHz, CDCl$_3$, δ in ppm): 3.04 (t, 2H, J=4.5 Hz); 3.22 (t, 2H, J=4.5 Hz); 4.72 (s, 2H); 6.89-7.06 (m, 3H); 7.39 (d, 1H, J=3.8 Hz); 7.69 (m, 3H); 7.76 (d, 2H, J=8.2 Hz).

Mass (ES$^+$): 453 (M+1); 470 (M+NH$_4$)$^+$; 475 (M+Na)$^+$.

M.p.=170-171° C.

Compound 26

2-(2-fluoro-4-(3-hydroxy-3-(5-(4-(trifluoromethyl)phenyl)thien-2-yl)propyl)phenoxy)acetic acid

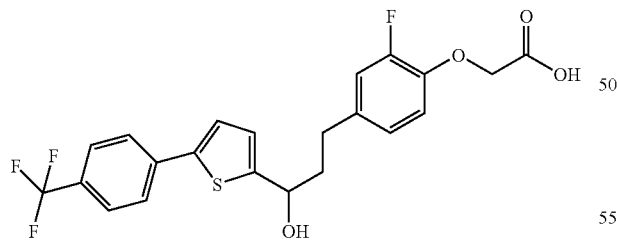

2-(2-Fluoro-4-(3-hydroxy-3-(5-(4-(trifluoromethyl)phenyl)thien-2-yl)propyl)-phenoxy)acetic acid is prepared from 2-(2-fluoro-4-(3-oxo-3-(5-(4-(trifluoromethyl)phenyl)thien-2-yl)propyl)phenoxy)acetic acid according to general procedure G.

$^1$H NMR (300 MHz, CDCl$_3$, δ in ppm): 2.11-2.22 (m, 2H); 2.67-2.76 (m, 2H); 4.69 (s, 2H); 4.91 (m, 1H); 6.86-6.99 (m, 4H); 7.25 (d, 1H, J=3.8 Hz); 7.62 (d, 2H, J=8.5 Hz); 7.68 (d, 2H, J=8.5 Hz).

Compound 27

2-(4-(3-(benzyloxy)-3-(5-(4-(trifluoromethyl)phenyl)thien-2-yl)-propyl)-2-fluorophenoxy)acetic acid

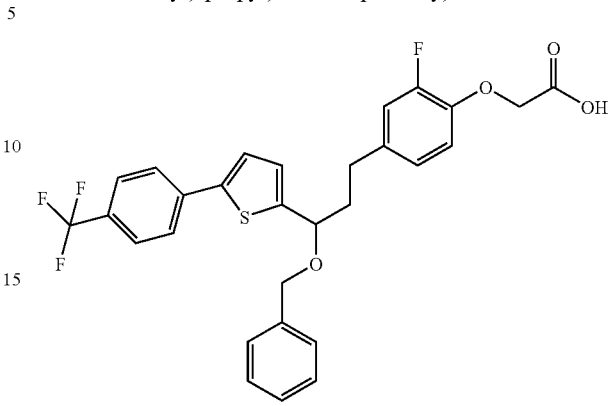

2-(4-(3-(Benzyloxy)-3-(5-(4-(trifluoromethyl)phenyl)thien-2-yl)propyl)-2-fluoro-phenoxy)acetic acid is prepared from 2-(2-fluoro-4-(3-hydroxy-3-(5-(4-(trifluoromethyl)phenyl)thien-2-yl)propyl)phenoxy)acetic acid using 2.2 equivalents of sodium hydride and 2.2 equivalents of benzyl bromide according to general procedure H.

The evaporation residue is dissolved in ethanol in the presence of 2N sodium hydroxide (20 eq.). After stirring for 16 hours, the solvents are removed by evaporation under reduced pressure. The evaporation residue is acidified using dilute solution of hydrochloric acid and is then extracted with methylene chloride.

The organic phase is dried over magnesium sulfate, filtered and then concentrated under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 22/78 to 10/90.

$^1$H NMR (300 MHz, CDCl$_3$, δ in ppm): 1.99-2.11 (m, 1H); 2.23-2.35 (m, 1H); 2.58-2.80 (m, 2H); 4.35 (d, 1H, J=11.4 Hz); 4.53 (m, 1H); 4.61 (d, 1H, J=11.4 Hz); 4.71 (s, 2H); 6.82-6.93 (m, 3H); 6.97 (d, 1H, J=3.5 Hz); 7.27-7.39 (m, 6H); 7.63 (d, 2H, J=8.5 Hz); 7.71 (d, 2H, J=8.5 Hz).

Mass (MALDI-TOF): 566 (M+Na)$^+$.

Compound 28 tert-butyl 2-(2-fluoro-4-(3-oxo-3-(5-(4-(trifluoromethyl)phenyl)thien-2-yl)propyl)-phenoxy)butanoate

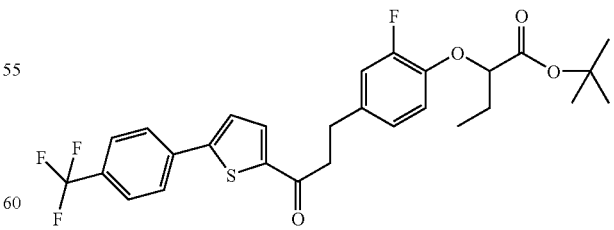

Tert-butyl 2-(2-fluoro-4-(3-oxo-3-(5-(4-(trifluoromethyl)phenyl)thien-2-yl)propyl)phenoxy)-butanoate is prepared from 3-(3-fluoro-4-hydroxyphenyl)-1-(5-(4-(trifluoromethyl)phenyl)thien-2-yl)propan-1-one and tert-butyl 2-bromobutanoate according to general procedure D.

After stirring for 16 hours, the solvent is removed by evaporation under reduced pressure. The evaporation residue is taken up in ethyl acetate. The organic phase is washed with a saturated solution of ammonium chloride, dried over magnesium sulfate, filtered and then concentrated under reduced pressure. The evaporation residue is purified by silica-gel chromatography.

Elution: cyclohexane/ethyl acetate: gradient 95/5 to 9/1. Silica 40-63 μm.

$^1$H NMR (300 MHz, CDCl$_3$, δ in ppm): 1.09 (t, 3H, J=7.3 Hz); 1.43 (s, 9H); 1.98 (m, 2H); 3.02 (t, 2H, J=4.5 Hz); 3.23 (t, 2H, J=4.5 Hz); 4.42 (t, 1H, J=6.1 Hz); 6.81-7.01 (m, 3H); 7.38 (d, 1H, J=4.1 Hz); 7.66-7.69 (m, 3H); 7.76 (d, 2H, J=8.2 Hz).

Compound 29

2-(2-fluoro-4-(3-oxo-3-(5-(4-(trifluoromethyl)phenyl)thien-2-yl)-propyl)phenoxy)butanoic acid

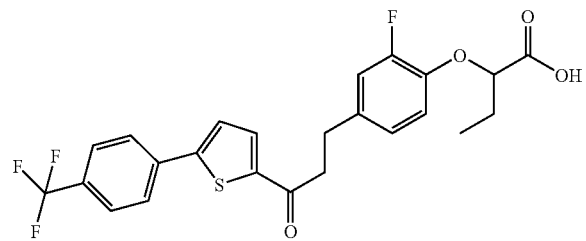

2-(2-Fluoro-4-(3-oxo-3-(5-(4-(trifluoromethyl)phenyl)thien-2-yl)propyl)-phenoxy)butanoic acid is prepared from tert-butyl 2-(2-fluoro-4-(3-oxo-3-(5-(4-(trifluoromethyl)phenyl)thien-2-yl)propyl)phenoxy)butanoate according to general procedure E using 17 equivalents of trifluoroacetic acid.

After stirring for 6 hours at room temperature, the reaction mixture is washed with water and then the dichloromethane is removed by evaporation under reduced pressure. The evaporation residue is purified by silica-gel chromatography. The oil obtained is crystallized from dichloromethane.

Elution: methylene chloride/methanol: 9/1. Silica 40-63 μm.

$^1$H NMR (300 MHz, CDCl$_3$, δ in ppm): 1.11 (t, 3H, J=7.3 Hz); 2.03 (m, 2H); 3.01 (t, 2H, J=7.4 Hz); 3.19 (t, 2H, J=7.4 Hz); 4.58 (t, 1H, J=5.7 Hz); 6.86-7.01 (m, 3H); 7.37 (d, 1H, J=3.8 Hz); 7.66 (m, 3H); 7.76 (d, 2H, J=7.9 Hz).

Mass (MALDI-TOF): 481 (M+1).

M.p.=119-120° C.

Compound 30

2-(2-fluoro-4-(3-hydroxy-3-(5-(4-(trifluoromethyl)phenyl)thien-2-yl)propyl)phenoxy)butanoic acid

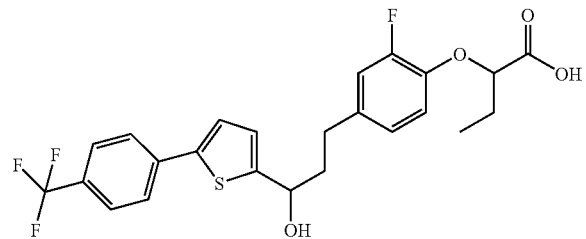

2-(2-Fluoro-4-(3-hydroxy-3-(5-(4-(trifluoromethyl)phenyl)thien-2-yl)propyl)-phenoxy)butanoic acid is prepared from 2-(2-fluoro-4-(3-oxo-3-(5-(4-(trifluoromethyl)phenyl)thien-2-yl)propyl)phenoxy)butanoic acid according to general procedure G.

The evaporation residue is purified by silica-gel chromatography.

Elution: methylene chloride/methanol: 95/5. Silica 40-63 μm.

$^1$H NMR (300 MHz, CDCl$_3$, δ in ppm): 1.12 (t, 3H, J=7.6 Hz); 1.98-2.25 (m, 4H); 2.69 (m, 2H); 4.59 (t, 1H, J=6.6 Hz); 4.9 (t, 1H, J=5.8 Hz); 6.83-6.96 (m, 4H); 7.23 (d, 1H, J=3.8 Hz); 7.61 (d, 2H, J=8.7 Hz); 7.66 (d, 2H, J=8.7 Hz).

Mass (ES$^+$): 483 (M+1).

Appearance: colorless viscous oil.

Compound 31 tert-butyl 2-(2-bromo-4-(3-oxo-3-(5-(4-(trifluoromethyl)phenyl)thien-2-yl)propyl)-phenoxy)butanoate

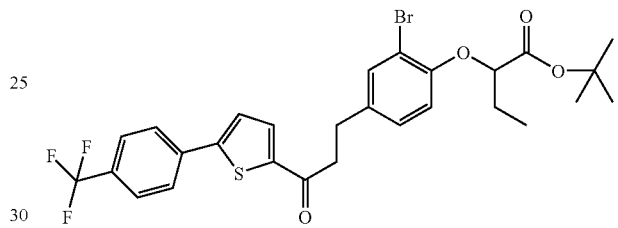

Tert-butyl 2-(2-bromo-4-(3-oxo-3-(5-(4-(trifluoromethyl)phenyl)thien-2-yl)propyl)phenoxy)-butanoate is prepared from 3-(3-bromo-4-hydroxyphenyl)-1-(5-(4-(trifluoromethyl)phenyl)thien-2-yl)propan-1-one and tert-butyl 2-bromobutanoate according to general procedure D.

After stirring for 2 hours, the mixture is acidified using 1N dilute solution of citric acid and is then extracted with ethyl acetate. The organic phase is dried over magnesium sulfate, filtered and then concentrated under reduced pressure. The evaporation residue is purified by silica-gel flash chromatography.

Elution: cyclohexane/ethyl acetate: 8/2. Silica 40-63 μm.

$^1$H NMR (300 MHz, CDCl$_3$, δ in ppm): 0.95-1.25 (m, 3H); 1.45 (s, 9H); 1.84-2.06 (m, 2H); 3.01 (m, 2H); 3.2 (t, 2H, J=7.3 Hz); 4.45 (t, 1H, J=6.1 Hz); 6.69 (d, 1H, J=8.5 Hz); 7.09 (dd, 1H, J=2.1 Hz, J=8.5 Hz); 7.37-7.39 (m, 1H); 7.45 (d, 1H, J=2.1 Hz); 7.65-7.69 (m, 3H); 7.76 (d, 2H, J=8.5 Hz).

Compound 32

2-(2-bromo-4-(3-oxo-3-(5-(4-(trifluoromethyl)phenyl)thien-2-yl)propyl)phenoxy)butanoic acid

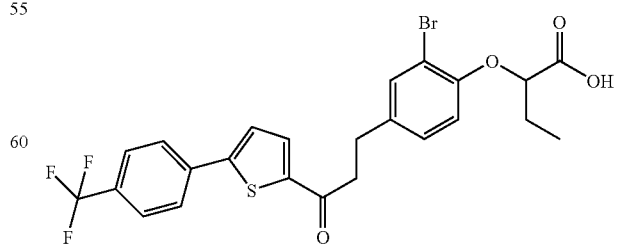

2-(2-Bromo-4-(3-oxo-3-(5-(4-(trifluoromethyl)phenyl)thien-2-yl)propyl)-phenoxy)butanoic acid is prepared from tert-butyl 2-(2-bromo-4-(3-oxo-3-(5-(4-(trifluoromethyl)phenyl)thien-2-yl)propyl)phenoxy)butanoate according to general procedure E using 17 equivalents of trifluoroacetic acid.

After 1 hour at room temperature, the reaction mixture is washed with water and then the dichloromethane is removed by evaporation under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 30/70 to 0/100.

$^1$H NMR (300 MHz, CDCl$_3$, δ in ppm): 1.13 (t, 3H, J=7.3 Hz); 2.11 (m, 2H); 3.02 (t, 2H, J=7.4 Hz); 3.21 (t, 2H, J=7.4 Hz); 4.68 (t, 1H, J=5.6 Hz); 6.78 (d, 1H, J=8.5 Hz); 7.14 (dd, 1H, J=2.1 Hz, J=8.5 Hz); 7.39 (d, 1H, J=4.1 Hz); 7.48 (d, 1H, J=2.1 Hz); 7.67-7.69 (m, 3H); 7.76 (d, 2H, J=8.5 Hz).

Mass (ES$^+$): 541/543 (M+1).

M.p.=126-128° C.

Compound 33 tert-butyl 2-(2-bromo-4-(3-oxo-3-(5-(4-(trifluoromethyl)phenyl)thien-2-yl)propyl)phenoxy)acetate

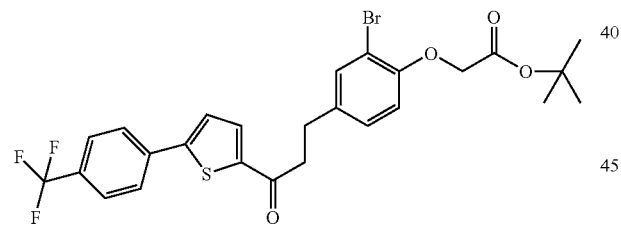

Tert-butyl 2-(2-bromo-4-(3-oxo-3-(5-(4-(trifluoromethyl)phenyl)thien-2-yl)propyl)phenoxy)-acetate is prepared from 3-(3-bromo-4-hydroxyphenyl)-1-(5-(4-(trifluoromethyl)phenyl)thien-2-yl)propan-1-one and tert-butyl bromoacetate according to general procedure D.

After stirring for 12 hours, the mixture is acidified using 1N dilute solution of citric acid and is then extracted with ethyl acetate. The organic phase is dried over magnesium sulfate, filtered and then concentrated under reduced pressure. The evaporation residue is purified by silica-gel flash chromatography.

Elution: cyclohexane/ethyl acetate: 85/15. Silica 40-63 μm.

$^1$H NMR (300 MHz, CDCl$_3$, δ in ppm): 1.48 (s, 9H); 2.98-3.05 (m, 2H); 3.2 (t, 2H, J=7.1 Hz); 4.57 (s, 2H); 6.72 (d, Compound 34

2-(2-bromo-4-(3-oxo-3-(5-(4-(trifluoromethyl)phenyl)thien-2-yl)propyl)phenoxy)acetic acid

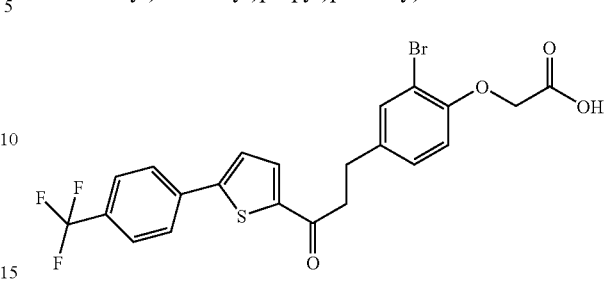

2-(2-Bromo-4-(3-oxo-3-(5-(4-(trifluoromethyl)phenyl)thien-2-yl)propyl)-phenoxy)acetic acid is prepared from tert-butyl 2-(2-bromo-4-(3-oxo-3-(5-(4-(trifluoromethyl)phenyl)thien-2-yl)propyl)phenoxy)acetate according to general procedure E using 17 equivalents of trifluoroacetic acid.

After 1 hour at room temperature, the reaction mixture is washed with water and then the dichloromethane is removed by evaporation under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 30/70 to 0/100.

$^1$H NMR (300 MHz, CDCl$_3$, δ in ppm): 3.04 (t, 2H, J=7.6 Hz); 3.22 (t, 2H, J=7.6 Hz); 4.7 (s, 2H); 6.82 (d, 1H, J=8.2 Hz); 7.19 (dd, 1, J=2.1 Hz, J=8.2 Hz); 7.39 (d, 1H, J=4.1 Hz); 7.49 (d, 1H, J=2.1 Hz); 7.67-7.70 (m, 3H); 7.76 (d, 2H, J=8.5 Hz).

Mass (ES$^+$): 513/515 (M+1).

M.p.=180-182° C.

Compound 35 tert-butyl 2-(2-bromo-4-(3-oxo-3-(5-(4-(trifluoromethyl)phenyl)thien-2-yl)propyl)-phenoxy)-2-methylpropanoate

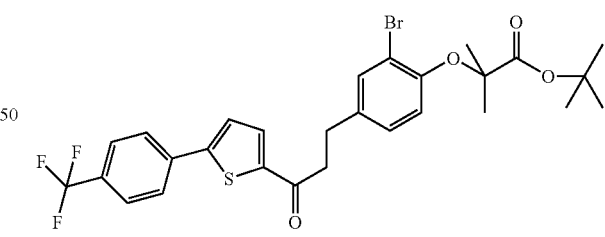

Tert-butyl 2-(2-bromo-4-(3-oxo-3-(5-(4-(trifluoromethyl)phenyl)thien-2-yl)propyl)phenoxy)-2-methylpropanoate is prepared from 3-(3-bromo-4-hydroxyphenyl)-1-(5-(4-(trifluoromethyl)phenyl)thien-2-yl)propan-1-one and tert-butyl bromoisobutyrate according to general procedure D.

After stirring for 2 hours, the mixture is acidified using 1N dilute solution of citric acid and is then extracted with ethyl acetate. The organic phase is dried over magnesium sulfate, filtered and then concentrated under reduced pressure. The evaporation residue is purified by silica-gel flash chromatography.

Elution: cyclohexane/ethyl acetate: 9/1. Silica 40-63 μm.

$^1$H NMR (300 MHz, CDCl$_3$, δ in ppm): 1.46 (s, 9H); 1.58 (s, 6H); 2.98-3.05 (m, 2H); 3.2 (t, 2H, J=7.1 Hz); 6.86 (d, 1H, J=8.5 Hz); 7.05 (dd, 1H, J=2.1 Hz, J=8.5 Hz); 7.39 (d, 1H, J=4.1 Hz); 7.44 (d, 1H, J=2.1 Hz); 7.65-7.69 (m, 3H); 7.76 (d, 2H, J=8.2 Hz).

Compound 36

2-(2-bromo-4-(3-oxo-3-(5-(4-(trifluoromethyl)phenyl)thien-2-yl)propyl)phenoxy)-2-methylpropanoic acid

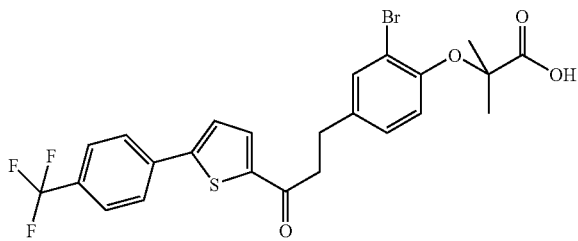

2-(2-Bromo-4-(3-oxo-3-(5-(4-(trifluoromethyl)phenyl)thien-2-yl)propyl)-phenoxy)-2-methylpropanoic acid is prepared from tert-butyl 2-(2-bromo-4-(3-oxo-3-(5-(4-(trifluoromethyl)phenyl)thien-2-yl)propyl)phenoxy)-2-methylpropanoate according to general procedure E using 17 equivalents of trifluoroacetic acid.

After stirring for 1 hour at room temperature, the reaction mixture is washed with water and then the dichloromethane is removed by evaporation under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 30/70 to 0/100.

$^1$H NMR (300 MHz, CDCl$_3$, δ in ppm): 1.64 (s, 6H); 3.05 (t, 2H, J=7.6 Hz); 3.23 (t, 2H, J=7.6 Hz); 7.01 (d, 1H, J=8.3 Hz); 7.15 (dd, 1H, J=2.1 Hz, J=8.3 Hz); 7.39 (d, 1H, J=4.1 Hz); 7.5 (d, 1H, J=2.1 Hz); 7.67-7.70 (m, 3H); 7.76 (d, 2H, J=8.5 Hz).

Mass (ES$^+$): 541/543 (M+1).

M.p.=102-104° C.

Compound 37 tert-butyl 2-(2,3-dichloro-4-(3-oxo-3-(5-(4-(trifluoromethyl)phenyl)fur-2-yl)propyl)-phenoxy)-2-methyl propanoate

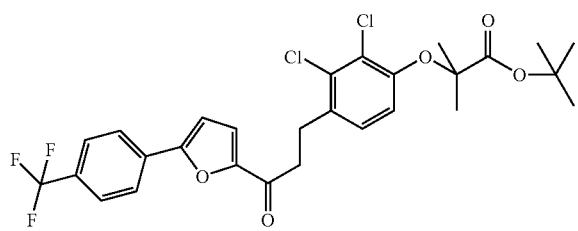

Tert-butyl 2-(2,3-dichloro-4-(3-oxo-3-(5-(4-(trifluoromethyl)phenyl)fur-2-yl)propyl)phenoxy)-2-methylpropanoate is prepared from 3-(2,3-dichloro-4-hydroxyphenyl)-1-(5-(4-(trifluoromethyl)phenyl)fur-2-yl)propan-1-one and tert-butyl bromoisobutyrate according to general procedure D.

After stirring for 16 hours, the solvent is removed by evaporation under reduced pressure. The evaporation residue is taken up in ethyl acetate. The organic phase is washed with a saturated solution of ammonium chloride, dried over magnesium sulfate, filtered and then concentrated under reduced pressure. The evaporation residue is purified by silica-gel chromatography.

Elution: cyclohexane/ethyl acetate: gradient 95/5 to 8/2. Silica 40-63 μm.

$^1$H NMR (300 MHz, CDCl$_3$, δ in ppm): 1.45 (s, 9H); 1.57 (s, 6H); 3.19 (m, 4H); 6.79 (d, 1H, J=8.6 Hz); 6.87 (d, 1H, J=3.7 Hz); 7.10 (d, 1H, J=8.6 Hz); 7.27 (d, 1H, J=3.7 Hz); 7.69 (d, 2H, J=8.5 Hz); 7.88 (d, 2H, J=8.5 Hz).

Compound 38

2-(2,3-dichloro-4-(3-oxo-3-(5-(4-(trifluoromethyl)phenyl)fur-2-yl)-propyl)phenoxy)-2-methylpropanoic acid

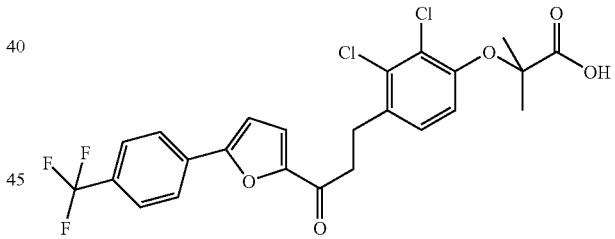

2-(2,3-Dichloro-4-(3-oxo-3-(5-(4-(trifluoromethyl)phenyl)fur-2-yl)propyl)-phenoxy)-2-methylpropanoic acid is prepared from tert-butyl 2-(2,3-dichloro-4-(3-oxo-3-(5-(4-(trifluoromethyl)phenyl)fur-2-yl)propyl)phenoxy)-2-methylpropanoate according to general procedure E using 10 equivalents of trifluoroacetic acid.

After stirring for 2 hours at room temperature, the reaction mixture is washed with water and then the dichloromethane is removed by evaporation under reduced pressure. The evaporation residue is purified by silica-gel chromatography.

Elution: dichloromethane/methanol: 9/1. Silica 40-63 μm.

$^1$H NMR (300 MHz, CDCl$_3$, δ in ppm): 1.63 (s, 6H); 3.19 (m, 4H); 6.86 (d, 1H, J=3.7 Hz); 6.92 (d, 1H, J=8.5 Hz); 7.13 (d, 1H, J=8.5 Hz); 7.29 (d, 1H, J=3.7 Hz); 7.65 (d, 2H, J=8.5 Hz); 7.84 (d, 2H, J=8.5 Hz); 11.07 (s, 1H).

Mass (ES$^-$): 513/515 (M−1)

M.p.=85° C. .

Compound 39

2-(2,3-dichloro-4-(3-(pyridin-3-ylmethoxy)-3-(5-(4-(trifluoromethyl)phenyl)thien-2-yl)propyl)phenoxy)-2-methylpropanoic acid

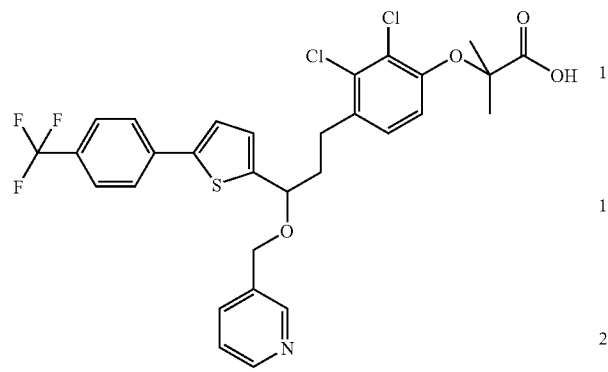

2-(2,3-Dichloro-4-(3-(pyridin-3-ylmethoxy)-3-(5-(4-(trifluoromethyl)phenyl)-thien-2-yl)propyl)phenoxy)-2-methylpropanoic acid is prepared from 2-(2,3-dichloro-4-(3-hydroxy-3-(5-(4-(trifluoromethyl)phenyl)thien-2-yl)propyl)phenoxy)-2-methylpropanoic acid using 8 equivalents of sodium hydride and 2.1 equivalents of 3-(bromomethyl)pyriine hydrobromide according to general procedure H. After stirring for 12 hours at 70° C., the reaction mixture is diluted with water, acidified with 1N hydrochloric acid solution, and extracted with ethyl acetate. The organic phase is concentrated under reduced pressure, treated with 2N sodium hydroxide solution, and extracted with dichloromethane. After acidification with 1N citric acid solution, the dichloromethane is removed by evaporation under reduced pressure and the evaporation residue is purified by silica-gel flash chromatography.

Elution: dichloromethane/methanol: 100/0 to 95/5. Silica 40-63 μm.

$^1$H NMR (300 MHz, CDCl$_3$, δ in ppm): 1.73 (s, 6H); 2.22-2.35 (m, 2H); 2.85-2.97 (m, 2H); 4.35 (d, 1H, J=12.5 Hz); 4.55 (d, 1H, J=12.5 Hz); 4.59-4.67 (m, 1H); 6.86 (d, 1H, J=7.6 Hz); 6.96 (d, 1H, J=3.5 Hz); 7.01 (d, 1H, J=7.6 Hz); 7.27-7.36 (m, 1H); 7.61-7.64 (m, 3H); 7.68 (d, 2H, J=8.4 Hz); 8.06 (bs, 1H); 8.52 (d, 2H, J=4.1 Hz).

Mass (ES$^-$): 622/624/623 (M−1).

M.p.=75-77° C.

Compound 39a and 39b

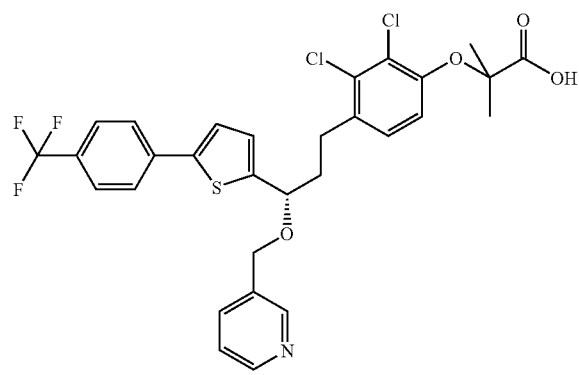

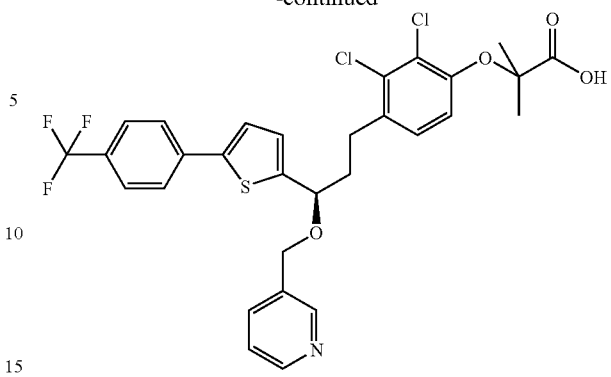

The two enantiomers of compound 39 are separated by chiral-column semi-preparative HPLC Chiralpak® AD-H (250*20 mm, 5 μm, Chiral Technologies Europe) at room temperature. Elution is carried out isocratically with n-heptane-ethanol (87-13) mobile phase at a flow rate of 12 ml/min.

The enantiomeric purity of each of the two enantiomers thus obtained is checked by analytical HPLC: column Chiralpak® AD-H (250*46 mm, 5 μm, Daicel Chemical Industries, Ltd.) at 30° C.; isocratic elution with n-heptane-isopropanol (87-13) mobile phase; flow rate 1 ml/min; UV detection at 205 nm.

Compound 39a: tR=16.2 min, ee=96%
Compound 39b: tR=19.3 min, ee=99.1%

Compound 40

2-(2,3-dichloro-4-(3-methoxy-3-(5-(4-(trifluoromethyl)phenyl)-thien-2-yl)propyl)phenoxy)-2-methylpropanoic acid

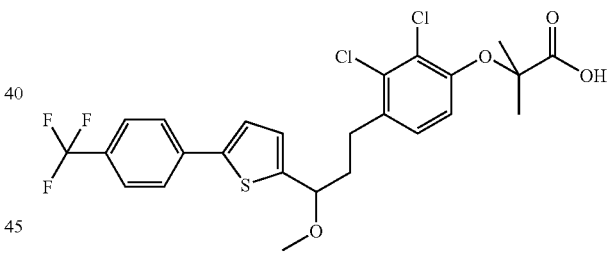

2-(2,3-Dichloro-4-(3-methoxy-3-(5-(4-(trifluoromethyl)phenyl)thien-2-yl)-propyl)phenoxy)-2-methylpropanoic acid is prepared from 2-(2,3-dichloro-4-(3-hydroxy-3-(5-(4-(trifluoromethyl)phenyl)thien-2-yl)propyl)phenoxy)-2-methylpropanoic acid using 2.2 equivalents of sodium hydride and 2.2 equivalents of iodomethane according to general procedure H.

The evaporation residue is purified by silica-gel chromatography (elution: cyclohexane/ethyl acetate: 9/1. Silica 40-63 μm.). The oil isolated is dissolved in ethanol in the presence of 2N sodium hydroxide (20 eq.). After stirring for 16 hours, the solvents are removed by evaporation under reduced pressure. The evaporation residue is acidified using dilute solution of hydrochloric acid and is then extracted with dichloromethane. The organic phase is dried over magnesium sulfate, filtered and then concentrated under reduced pressure.

$^1$H NMR (300 MHz, CDCl$_3$, δ in ppm): 1.65 (s, 6H); 2.03-2.29 (m, 2H); 2.75-2.97 (m, 2H); 3.34 (s, 3H); 4.38 (dd, 1H, J=5.7 Hz J=7.7 Hz); 6.95 (d, 1H, J=8.6 Hz); 6.99 (d, 1H, J=3.6 Hz); 7.07 (d, 1H, J=8.6 Hz); 7.27 (d, 1H, J=3.6 Hz); 7.62 (d, 2H, J=8.5 Hz); 7.68 (d, 2H, J=8.5 Hz).

Mass (ES$^+$): 564/566 (M+NH$_4$)$^+$, 569/571 (M+Na)$^+$, 585/587 (M+K)$^+$.

M.p.=46-48° C.

Compound 40a and 40b

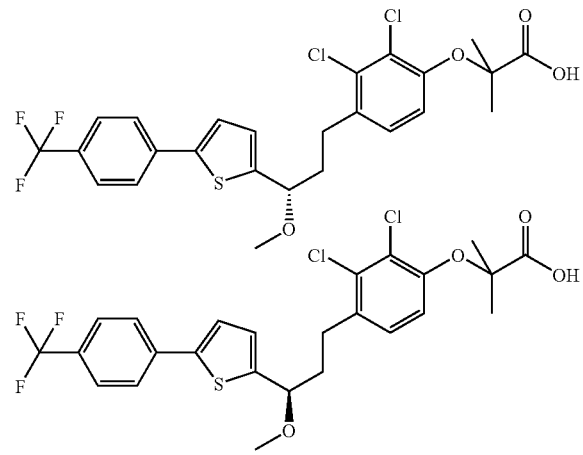

The two enantiomers of compound 40 are separated by chiral-column semi-preparative HPLC Chiralpak® AD-H (250*20 mm, 5 μm, Chiral Technologies Europe) at room temperature. Elution is carried out isocratically with n-heptane-ethanol (93-7) mobile phase with 0.1% of trifluoroacetic acid added, at a flow rate of 16 to 18 ml/min.

The enantiomeric purity of each of the two enantiomers thus obtained is checked by analytical HPLC: column Chiralpak® AD-H (250*46 mm, 5 μm, Daicel Chemical Industries, Ltd.) at 30° C.; isocratic elution with n-heptane-ethanol (93-7) mobile phase with 0.1% of trifluoroacetic acid added; flow rate 1 ml/min; UV detection at 292 nm.

Compound 40a: tR=13.4 min, ee=100%
Compound 40b: tR=18.3 min, ee=99.4%

Compound 41

2-(2,3-dichloro-4-(3-ethoxy-3-(5-(4-(trifluoromethyl)phenyl)thien-2-yl)propyl)phenoxy)-2-methylpropanoic acid

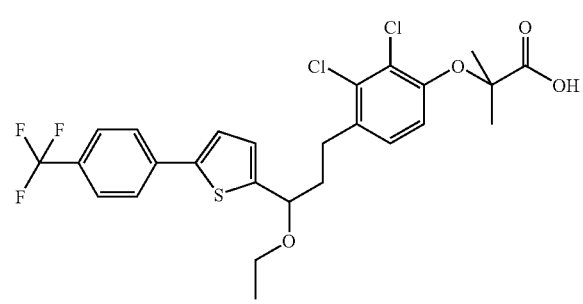

2-(2,3-Dichloro-4-(3-ethoxy-3-(5-(4-(trifluoromethyl)phenyl)thien-2-yl)propyl)-phenoxy)-2-methylpropanoic acid is prepared from 2-(2,3-dichloro-4-(3-hydroxy-3-(5-(4-(trifluoromethyl)phenyl)thien-2-yl)propyl)phenoxy)-2-methylpropanoic acid using 8 equivalents of sodium hydride and 2.1 equivalents of iodoethane according to general procedure H.

After stirring for 20 minutes at 70° C., the reaction mixture brought back to room temperature, treated with 2N sodium hydroxide solution, then acidified with 1N hydrochloric acid solution and extracted with ethyl acetate. The organic phase is concentrated under reduced pressure and the evaporation residue is purified by silica-gel flash chromatography.

Elution: dichloromethane/methanol: 100/0 to 95/5. Silica 40-63 μm.

$^1$H NMR (300 MHz, CDCl$_3$, δ in ppm): 1.24 (t, 3H, J=7.0 Hz); 1.64 (s, 6H); 2.03-2.28 (m, 2H); 2.78-2.99 (m, 2H); 3.37-3.47 (m, 1H); 3.53-3.63 (m, 1H); 4.48 (dd, 1H, J=5.5 Hz, J=7.6 Hz); 6.92-6.97 (m, 2H); 7.10 (d, 1H, J=8.5 Hz); 7.25 (d, 1H, J=3.9 Hz); 7.27 (d, 1H, J=3.8 Hz); 7.62 (d, 2H, J=8.3 Hz); 7.69 (d, 2H, J=8.3 Hz).

Mass (ES$^-$): 559/561 (M−1).

Appearance: viscous yellow oil.

Compound 42

2-(2,3-dichloro-4-(3-(cyclohexylmethoxy)-3-(5-(4-(trifluoromethyl)phenyl)thien-2-yl)propyl)phenoxy)-2-methylpropanoic acid

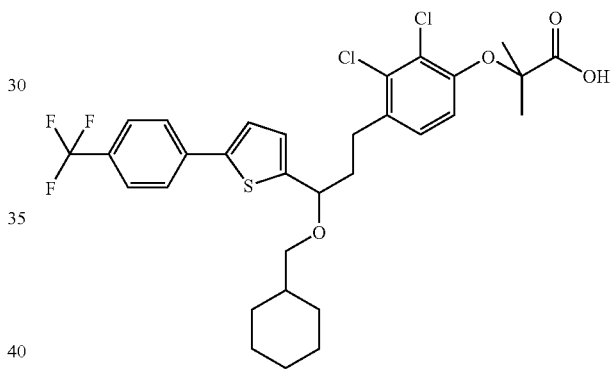

2-(2,3-Dichloro-4-(3-(cyclohexylmethoxy)-3-(5-(4-(trifluoromethyl)phenyl)thien-2-yl)propyl)phenoxy)-2-methylpropanoic acid is prepared from 2-(2,3-dichloro-4-(3-hydroxy-3-(5-(4-(trifluoromethyl)phenyl)thien-2-yl)propyl)phenoxy)-2-methylpropanoic acid using 8 equivalents of sodium hydride and 2.5 equivalents of bromomethylcyclohexane according to general procedure H.

After stirring for 18 hours at 70° C., the reaction mixture is acidified with 1N hydrochloric acid solution and extracted with ethyl acetate. The organic phase is concentrated under reduced pressure and the evaporation residue is purified by silica-gel flash chromatography.

Elution: dichloromethane/methanol: 100/0 to 9/1. Silica 40-63 μm.

$^1$H NMR (300 MHz, CDCl$_3$, δ in ppm): 0.89-0.99 (m, 3H); 1.14-1.28 (m, 4H); 1.55-1.84 (m, 10H); 2.03-2.27 (m. 2H); 2.78-3.01 (m, 2H); 3.14 (dd, 1H, J=6.4 Hz, J=9.0 Hz); 3.22 (dd, 1H, J=6.7 Hz, J=8.7 Hz); 4.43 (dd, 1H, J=4.9 Hz, J=7.8 Hz); 6.94-6.97 (m, 2H); 7.11 (d, 1H, J=8.4 Hz); 7.25 (d, 1H, J=3.9 Hz); 7.27 (d, 1H, J=3.8 Hz); 7.62 (d, 2H, J=8.3 Hz); 7.69 (d, 2H, J=8.3 Hz).

Mass (ES$^-$): 627/629 (M−1).

Appearance: viscous yellow oil.

Compound 43 tert-butyl 2-(2,3-dichloro-4-(3-oxo-3-(5-(4-(trifluoromethoxy)phenyl)thien-2-yl)-propyl)phenoxy)-2-methylpropanoate

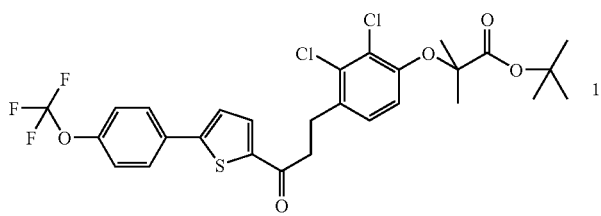

Tert-butyl 2-(2,3-dichloro-4-(3-oxo-3-(5-(4-(trifluoromethoxy)phenyl)thien-2-yl)propyl)-phenoxy)-2-methylpropanoate is prepared from 3-(2,3-dichloro-4-hydroxyphenyl)-1-(5-(4-(trifluoromethoxy)phenyl)thien-2-yl)propan-1-one and tert-butyl bromoisobutyrate according to general procedure D.

After stirring for 6 hours, the mixture is diluted with a saturated solution of ammonium chloride and is then extracted with ethyl acetate. The organic phase is dried over magnesium sulfate, filtered and then concentrated under reduced pressure. The evaporation residue is purified by silica-gel flash chromatography.

Elution: cyclohexane/ethyl acetate: 9/1. Silica 40-63 µm.
$^1$H NMR (300 MHz, CDCl$_3$, δ in ppm): 1.44 (s, 9H); 1.58 (s, 6H); 3.14-3.24 (m, 4H); 6.79 (d, 1H, J=8.6 Hz); 7.09 (d, 1H, J=8.6 Hz); 7.25-7.29 (m, 3H); 7.64-7.68 (m, 3H).

Compound 44

2-(2,3-dichloro-4-(3-oxo-3-(5-(4-(trifluoromethoxy)phenyl)thien-2-yl)propyl)phenoxy)-2-methylpropanoic acid

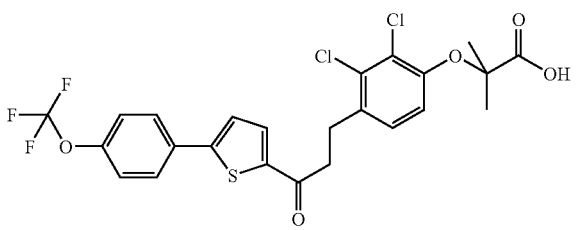

2-(2,3-Dichloro-4-(3-oxo-3-(5-(4-(trifluoromethoxy)phenyl)thien-2-yl)propyl)-phenoxy)-2-methylpropanoic acid is prepared from tert-butyl 2-(2,3-dichloro-4-(3-oxo-3-(5-(4-(trifluoromethoxy)phenyl)thien-2-yl)propyl)phenoxy)-2-methylpropanoate according to general procedure E using 10 equivalents of trifluoroacetic acid.

After stirring for 48 hours at room temperature, the solvents are removed by evaporation under reduced pressure. The evaporation residue is purified by silica-gel chromatography.

Elution: cyclohexane/ethyl acetate: 9/1 to 0/100. Silica 40-63 µm.
$^1$H NMR (300 MHz, CDCl$_3$, δ in ppm): 1.63 (s, 6H); 3.17-3.26 (m, 4H); 6.93 (d, 1H, J=8.4 Hz); 7.18 (d, 1H, J=8.4 Hz); 7.17-7.29 (m, 3H); 7.64-7.68 (m, 3H).
Mass (ES$^-$): 545/547 (M−1).
M.p.=135-136° C.

Compound 45 tert-butyl 2-(2,3-difluoro-4-(3-oxo-3-(5-(4-(trifluoromethyl)phenyl)thien-2-yl)-propyl)phenoxy)-2-methylpropanoate

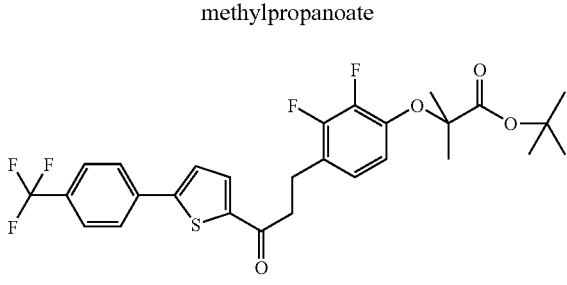

Tert-butyl 2-(2,3-difluoro-4-(3-oxo-3-(5-(4-(trifluoromethyl)phenyl)thien-2-yl)propyl)phenoxy)-2-methylpropanoate is prepared from 3-(2,3-difluoro-4-hydroxyphenyl)-1-(5-(4-(trifluoromethyl)phenyl)thien-2-yl)propan-1-one and tert-butyl bromoisobutyrate according to general procedure D.

After stirring for 4 hours, the mixture is acidified using 1N dilute solution of citric acid and is then extracted with dichloromethane. The organic phase is dried over magnesium sulfate, filtered and then concentrated under reduced pressure. The evaporation residue is purified by silica-gel flash chromatography.

Elution: cyclohexane/ethyl acetate: 92/8. Silica 40-63 µm.
$^1$H NMR (300 MHz, CDCl$_3$, δ in ppm): 1.46 (s, 9H); 1.56 (s, 6H); 3.08 (t, 2H, J=7.0 Hz); 3.22 (t, 2H, J=7.0 Hz); 6.70 (m, 1H); 6.86 (m, 1H); 7.38 (d, 1H, J=4.1 Hz); 7.67 (m, 3H); 7.75 (d, 2H, J=8.2 Hz).

Compound 46

2-(2,3-difluoro-4-(3-oxo-3-(5-(4-(trifluoromethyl)phenyl)thien-2-yl)propyl)phenoxy)-2-methylpropanoic acid

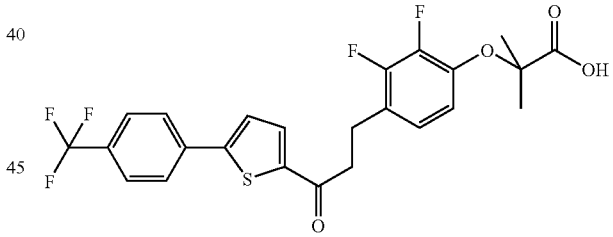

2-(2,3-Difluoro-4-(3-oxo-3-(5-(4-(trifluoromethyl)phenyl)thien-2-yl)propyl)-phenoxy)-2-methylpropanoic acid is prepared from tert-butyl 2-(2,3-difluoro-4-(3-oxo-3-(5-(4-(trifluoromethyl)phenyl)thien-2-yl)propyl)phenoxy)-2-methylpropanoate according to general procedure E using 15 equivalents of trifluoroacetic acid.

After stirring for 18 hours at room temperature, the reaction mixture is washed with water and then the dichloromethane is removed by evaporation under reduced pressure. The evaporation residue is purified by silica-gel chromatography.

Elution: dichloromethane/methanol: 9/1. Silica 40-63 µm.
$^1$H NMR (300 MHz, CDCl$_3$, δ in ppm): 1.59 (s, 6H); 3.11 (t, 2H, J=7.6 Hz); 3.25 (t, 2H, J=7.6 Hz); 6.80 (t, 1H, J=8.2 Hz); 6.96 (t, 1H, J=8.2 Hz); 7.39 (d, 1H, J=3.8 Hz); 7.68 (m, 3H); 7.76 (d, 2H, J=8.2 Hz).
Mass (MALDI-TOF): 499 (M+1), 516 (M+NH4$^+$), 521 (M+Na$^+$).
M.p.=165-166° C.

Compound 47 tert-butyl 2-(2,6-dimethyl-4-(3-oxo-3-(5-(4-(trifluoromethyl)phenyl)thien-2-yl)-propyl)phenoxy)-2-methylpropanoate

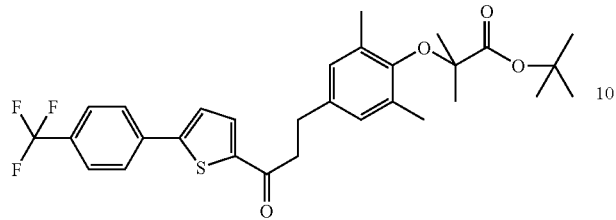

Tert-butyl 2-(2,6-dimethyl-4-(3-oxo-3-(5-(4-(trifluoromethyl)phenyl)thien-2-yl)propyl)-phenoxy)-2-methylpropanoate is prepared from 3-(4-hydroxy-3,5-dimethylphenyl)-1-(5-(4-(trifluoromethyl)phenyl)thien-2-yl)propan-1-one according to general procedure D, using 15 equivalents of tert-butyl bromoisobutyrate and 15 equivalents of potassium carbonate added in portions of 3 equivalents in the course of the reaction.

After stirring for 4 days at 100° C., the solvents are removed by evaporation under reduced pressure. The evaporation residue is taken up in ethyl acetate and washed with a saturated solution of ammonium chloride. The evaporation residue is purified by silica-gel flash chromatography.

Elution: cyclohexane/ethyl acetate: 95/5 to 9/1. Silica 40-63 μm.

$^1$H NMR (300 MHz, CDCl$_3$, δ in ppm): 1.41 (s, 9H); 1.51 (s, 6H); 2.20 (s, 6H); 2.92-2.97 (m, 2H); 3.15-3.21 (m, 2H); 6.83 (s, 2H); 7.37 (d, 1H, J=3.9 Hz); 7.65 (d, 1H, J=3.9 Hz); 7.67 (d, 2H, J=8.4 Hz); 7.75 (d, 2H, J=8.4 Hz).

Compound 48

2-(2,6-dimethyl-4-(3-oxo-3-(5-(4-(trifluoromethyl)phenyl)thien-2-yl)propyl)phenoxy)-2-methylpropanoic acid

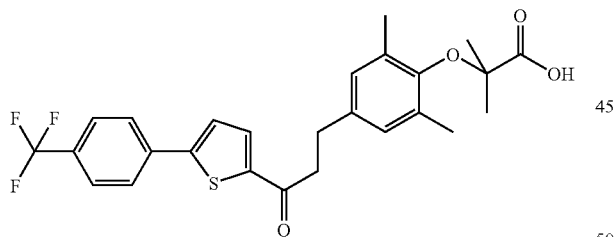

2-(2,6-Dimethyl-4-(3-oxo-3-(5-(4-(trifluoromethyl)phenyl)thien-2-yl)propyl)-phenoxy)-2-methylpropanoic acid is prepared from tert-butyl-(2,6-dimethyl-4-(3-oxo-3-(5-(4-(trifluoromethyl)phenyl)thien-2-yl)propyl)phenoxy)-2-methylpropanoate according to general procedure E using 10 equivalents of trifluoroacetic acid.

After stirring for 48 hours at room temperature, the solvents are removed by evaporation under reduced pressure. The evaporation residue is purified by silica-gel chromatography.

Elution: dichloromethane/methanol: 97/3 to 0/100. Silica 40-63 μm.

$^1$H NMR (300 MHz, CDCl$_3$, δ in ppm): 1.51 (s, 6H); 2.22 (s, 6H); 2.96 (t, 2H, J=7.5 Hz); 3.19 (t, 2H, J=7.5 Hz); 6.88 (s, 2H); 7.37 (d, 1H, J=3.9 Hz); 7.65-7.67 (m, 3H); 7.74 (d, 2H, J=8.4 Hz).

Mass (ES$^-$): 489 (M−1).
M.p.=157-158° C.

Compound 49

2-(2,3-dichloro-4-(3-(hydroxyimino)-3-(5-(4-(trifluoromethyl)-phenyl)thien-2-yl)propyl)phenoxy)-2-methylpropanoic acid

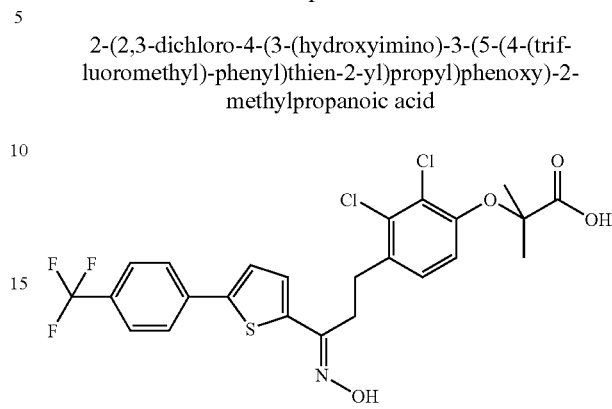

2-(2,3-Dichloro-4-(3-(hydroxyimino)-3-(5-(4-(trifluoromethyl)phenyl)thien-2-yl)propyl)phenoxy)-2-methylpropanoic acid is prepared from 2-(2,3-dichloro-4-(3-oxo-3-(5-(4-(trifluoromethyl)phenyl)thien-2-yl)propyl)phenoxy)-2-methyl propanoic acid and hydroxylamine hydrochloride according to general procedure I.

Elution: dichloromethane/methanol: 98/2 to 95/5. Silica 40-63 μm.

Main Conformation:
$^1$H NMR (300 MHz, MeOD, δ in ppm): 1.39 (s, 6H); 2.92-2.97 (m, 4H); 6.7 (d, 1H, J=8.4 Hz); 6.99 (d, 1H, J=8.4 Hz); 7.03 (d, 1H, J=3.9 Hz); 7.28 (d, 1H, J=3.9 Hz); 7.57 (d, 2H, J=8.4 Hz); 7.69 (d, 2H, J=8.4 Hz).

Minor Conformation:
$^1$H NMR (300 MHz, MeOD, δ in ppm): 1.47 (s, 6H); 2.82-3.01 (m, 4H); 6.81 (d, 1H, J=8.4 Hz); 7.03 (d, 1H, J=8.4 Hz); 7.43 (d, 1H, J=4.2 Hz); 7.48 (d, 1H, J=4.2 Hz); 7.60 (d, 2H, J=8.2 Hz); 7.78 (d, 2H, J=8.2 Hz).

Mass (ES$^-$): 544/546 (M−1).
M.p.=135-136° C.

Compound 50

2-(2,3-dichloro-4-(3-(methoxyimino)-3-(5-(4-(trifluoromethyl)-phenyl)thien-2-yl)propyl)phenoxy)-2-methylpropanoic acid

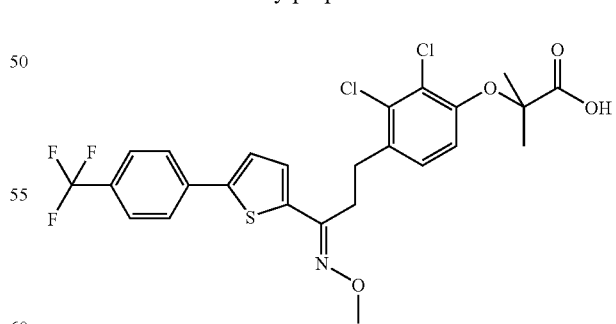

2-(2,3-Dichloro-4-(3-(methoxyimino)-3-(5-(4-(trifluoromethyl)phenyl)thien-2-yl)propyl)phenoxy)-2-methylpropanoic acid is prepared from 2-(2,3-dichloro-4-(3-oxo-3-(5-(4-(trifluoromethyl)phenyl)thien-2-yl)propyl)phenoxy)-2-methyl propanoic acid and O-methylhydroxylamine hydrochloride according to general procedure I.

Elution: dichloromethane/methanol: 98/2. Silica 40-63 μm.

Main Conformation:
$^1$H NMR (300 MHz, MeOD, δ in ppm): 1.58 (s, 6H); 2.91-3.17 (m, 4H); 3.96 (s, 3H); 6.91 (d, 1H, J=8.4 Hz); 7.11 (d, 1H, J=8.4 Hz); 7.12 (d, 1H, J=3.9 Hz); 7.24 (d, 1H, J=3.9 Hz); 7.61 (d, 2H, J=8.4 Hz); 7.67 (d, 2H, J=8.4 Hz).

Minor Conformation:
$^1$H NMR (300 MHz, MeOD, δ in ppm): 1.64 (s, 6H); 2.95-3.15 (m, 4H); 4.07 (s, 3H); 6.94 (d, 1H, J=8.4 Hz); 7.05 (d, 1H, J=8.4 Hz); 7.36 (d, 1H, J=4.2 Hz); 7.51 (d, 1H, J=4.2 Hz); 7.64 (d, 2H, J=8.2 Hz); 7.76 (d, 2H, J=8.2 Hz).

Mass (ES$^-$): 558/560 (M−1).

M.p.=68-69° C.

Compound 51 tert-butyl 2-(4-(3-(5-(4-bromophenyl)thien-2-yl)-3-oxopropyl)-2,3-dichloro-phenoxy)-2-methylpropanoate

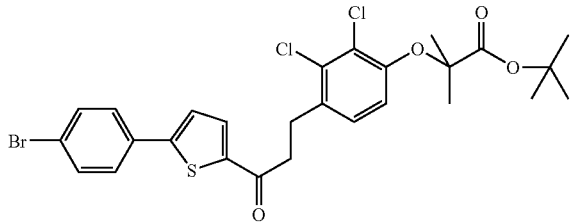

Tert-butyl 2-(4-(3-(5-(4-bromophenyl)thien-2-yl)-3-oxopropyl)-2,3-dichlorophenoxy)-2-methylpropanoate is prepared from 1-(5-(4-bromophenyl)thien-2-yl)-3-(2,3-dichloro-4-hydroxyphenyl)propan-1-one according to general procedure D, using 4 equivalents of tert-butyl bromoisobutyrate and 5 equivalents of potassium carbonate.

After stirring for 16 hours at 80° C., the mixture is diluted with a saturated solution of ammonium chloride and is extracted with ethyl acetate. The organic phase is dried over magnesium sulfate, filtered and then concentrated under reduced pressure. The evaporation residue is purified by silica-gel flash chromatography.

Elution: cyclohexane/ethyl acetate: 95/5. Silica 40-63 μm.
$^1$H NMR (300 MHz, CDCl$_3$, δ in ppm): 1.44 (s, 9H); 1.58 (s, 6H); 3.12-3.25 (m, 4H); 6.79 (d, 1H, J=8.6 Hz); 7.08 (d, 1H, J=8.6 Hz); 7.28 (d, 1H, J=4.1 Hz); 7.49 (d, 2H, J=9.1 Hz); 7.54 (d, 2H, J=9.1 Hz); 7.64 (d, 1H, J=4.2 Hz).

Compound 52

2-(4-(3-(5-(4-bromophenyl)thien-2-yl)-3-oxopropyl)-2,3-dichloro-phenoxy)-2-methylpropanoic acid

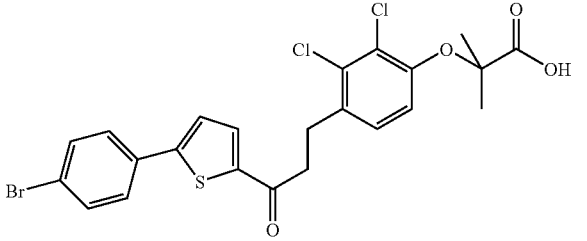

2-(4-(3-(5-(4-Bromophenyl)thien-2-yl)-3-oxopropyl)-2,3-dichlorophenoxy)-2-methylpropanoic acid is prepared from tert-butyl 2-(4-(3-(5-(4-bromophenyl)thien-2-yl)-3-oxopropyl)-2,3-dichlorophenoxy)-2-methylpropanoate according to general procedure E using 38 equivalents of trifluoroacetic acid.

After stirring for 1 hour at room temperature, the solvents are removed by evaporation under reduced pressure. The evaporation residue is purified by silica-gel chromatography.

Elution: dichloromethane/methanol: 97/3 to 0/100. Silica 40-63 μm.
$^1$H NMR (300 MHz, MeOD, δ in ppm): 1.58 (s, 6H); 3.11-3.19 (m, 2H); 3.23-3.30 (m, 2H); 6.93 (d, 1H, J=8.7 Hz); 7.21 (d, 1H, J=8.7 Hz); 7.49 (d, 1H, J=4.1 Hz); 7.61 (d, 2H, J=8.7 Hz); 7.66 (d, 2H, J=8.7 Hz); 7.81 (d, 1H, J=4.1 Hz).

Mass (ES$^-$): 539/541/542/543 (M−1).

M.p.=155-157° C.

Compound 53 tert-butyl 2-(2,3-dichloro-4-(3-(5-(4-(methylthio)phenyl)thien-2-yl)-3-oxopropyl)-phenoxy)-2-methylpropanoate

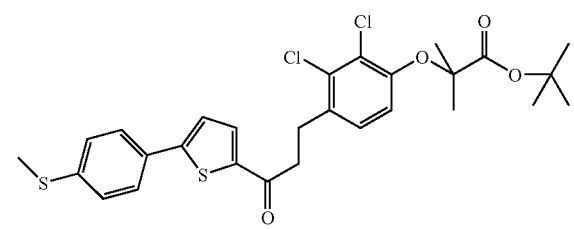

Tert-butyl 2-(2,3-dichloro-4-(3-(5-(4-(methylthio)phenyl)thien-2-yl)-3-oxopropyl)-phenoxy)-2-methylpropanoate is prepared from 3-(2,3-dichloro-4-hydroxyphenyl)-1-(5-(4-(methylthio)phenyl)thien-2-yl)propan-1-one dissolved in tetrahydrofuran, according to general procedure D.

After stirring for 20 hours at 70° C., the mixture is diluted with a saturated solution of ammonium chloride and extracted with ethyl acetate. The organic phase is dried over magnesium sulfate, filtered and then concentrated under reduced pressure. The evaporation residue is purified by silica-gel flash chromatography.

Elution: cyclohexane/ethyl acetate: 9/1. Silica 40-63 μm.
$^1$H NMR (300 MHz, CDCl$_3$, δ in ppm): 1.44 (s, 9H); 1.59 (s, 6H); 2.52 (s, 3H); 3.16-3.23 (m, 4H); 6.95 (d, 1H, J=8.5 Hz); 7.21 (d, 1H, J=8.5 Hz); 7.27-7.30 (m, 3H); 7.56 (d, 2H, J=8.5 Hz); 7.66 (d, 1H, J=4.1 Hz).

Compound 54

2-(2,3-dichloro-4-(3-(5-(4-(methylthio)phenyl)thien-2-yl)-3-oxo-propyl)phenoxy)-2-methylpropanoic acid

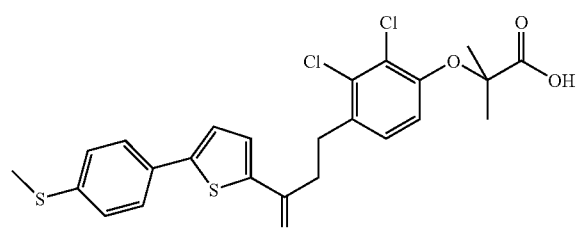

2-(2,3-Dichloro-4-(3-(5-(4-(methylthio)phenyl)thien-2-yl)-3-oxopropyl)-phenoxy)-2-methylpropanoic acid is prepared from 2-(2,3-dichloro-4-(3-(5-(4-(methylthio)phenyl)thien-2-yl)-3-oxopropyl)phenoxy)-2-methylpropanoate according to general procedure E using 10 equivalents of trifluoroacetic acid. After stirring for 18 hours at room temperature, the reaction mixture is washed with water and then the dichloromethane is removed by evaporation under reduced pressure. The evaporation residue is purified by silica-gel chromatography.

Elution: dichloromethane/methanol: 9/1. Silica 40-63 μm.

$^1$H NMR (300 MHz, CDCl$_3$, δ in ppm): 1.63 (s, 6H); 2.53 (s, 3H); 3.18-3.25 (m, 4H); 6.95 (d, 1H, J=8.5 Hz); 7.20 (d, 1H, J=8.5 Hz); 7.26-7.29 (m, 3H); 7.57 (d, 2H, J=8.5 Hz); 7.65 (d, 1H, J=4.1 Hz).

Mass (ES$^-$): 507/508 (M−1).

M.p.=171-172° C.

Compound 55

2-(2,3-dichloro-4-(3-isopropoxy-3-(5-(4-(trifluoromethyl)-phenyl)thien-2-yl)propyl)phenoxy)-2-methyl-propanoic acid

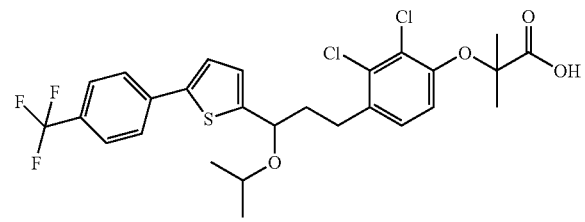

2-(2,3-Dichloro-4-(3-isopropoxy-3-(5-(4-(trifluoromethyl)phenyl)thien-2-yl)propyl)phenoxy)-2-methylpropanoic acid is prepared from 2-(2,3-dichloro-4-(3-hydroxy-3-(5-(4-(trifluoromethyl)phenyl)thien-2-yl)propyl)phenoxy)-2-methylpropanoic acid using 5 equivalents of sodium hydride and 4 equivalents of 2-bromopropane according to general procedure H.

After stirring for 12 hours at 70° C., the reaction mixture is diluted with water, acidified with 0.5N hydrochloric acid solution, and extracted with ethyl acetate. The organic phase is concentrated under reduced pressure. The evaporation residue is purified by silica-gel flash chromatography.

Elution: cyclohexane/ethyl acetate: 8/2. Silica 40-63 μm.

$^1$H NMR (300 MHz, CDCl$_3$, δ in ppm): 1.24 (d, 6H, J=6.3 Hz); 1.59 (s, 6H); 2.12-2.23 (m, 2H); 2.76-2.97 (m, 2H); 4.91-4.95 (m, 1H); 5.09 (sep, 1H, J=6.3); 6.78 (d, 1H, J=8.6 Hz); 6.98 (d, 1H, J=3.7 Hz); 7.02 (d, 1H, J=8.6 Hz); 7.24 (d, 1H, J=3.7 Hz); 7.61 (d, 2H, J=8.6 Hz); 7.66 (d, 2H, J=8.6 Hz).

Mass (ES$^+$): 557/559 (M+1), 592/594 (NH$_4$)$^+$, 597/599 (M+Na)$^+$.

M.p.=88-90° C.

Compound 56 tert-butyl 2-(2,3-dichloro-4-(3-oxo-3-(5-phenylthien-2-yl)propyl)phenoxy)-2-methylpropanoate

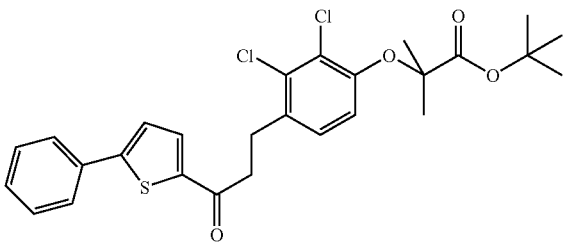

Tert-butyl 2-(2,3-dichloro-4-(3-oxo-3-(5-phenylthien-2-yl)propyl)phenoxy)-2-methylpropanoate is prepared from 3-(2,3-dichloro-4-hydroxyphenyl)-1-(5-phenylthien-2-yl)propan-1-one dissolved in tetrahydrofuran, according to general procedure D.

After stirring for 12 hours at 80° C., the mixture is diluted with a saturated solution of ammonium chloride and extracted with ethyl acetate. The organic phase is concentrated under reduced pressure. The evaporation residue is washed with cyclohexane.

$^1$H NMR (300 MHz, CDCl$_3$, δ in ppm): 1.44 (s, 9H); 1.57 (s, 6H); 3.11-3.25 (m, 4H); 6.79 (d, 1H, J=8.4 Hz); 7.09 (d, 1H, J=8.4 Hz); 7.31 (d, 1H, J=3.9 Hz); 7.34-7.44 (m, 3H); 7.63-7.66 (m, 3H).

Compound 57

2-(2,3-dichloro-4-(3-oxo-3-(5-phenylthien-2-yl)propyl)phenoxy)-2-methylpropanoic acid

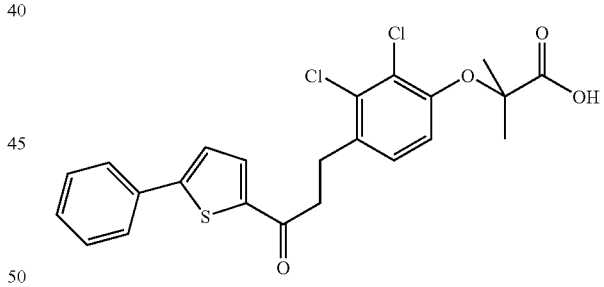

2-(2,3-Dichloro-4-(3-oxo-3-(5-phenylthien-2-yl)propyl)phenoxy)-2-methylpropanoic acid is prepared from tert-butyl 2-(2,3-dichloro-4-(3-oxo-3-(5-phenylthien-2-yl)propyl)phenoxy)-2-methylpropanoate according to general procedure E using 12 equivalents of trifluoroacetic acid. After stirring for 12 hours at room temperature, the reaction mixture is washed with water and then the dichloromethane is removed by evaporation under reduced pressure.

$^1$H NMR (300 MHz, CDCl$_3$, δ in ppm): 1.63 (s, 6H); 3.13-3.28 (m, 4H); 6.94 (d, 1H, J=8.6 Hz); 7.18 (d, 1H, J=8.6 Hz); 7.31 (d, 1H, J=4.2 Hz); 7.35-7.46 (m, 3H); 7.61-7.67 (m, 3H).

Mass (ES$^-$): 461/463 (M−1).

M.p.=179-180° C.

Compound 58 tert-butyl 2-methyl-2-(2-methyl-4-(3-oxo-3-(5-(4-(trifluoromethyl)phenyl)thien-2-yl)propyl)phenoxy)propanoate

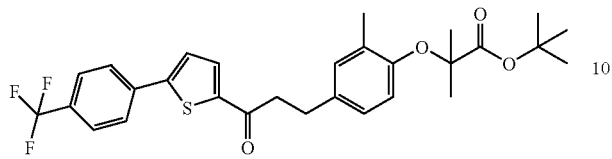

Tert-butyl 2-methyl-2-(2-methyl-4-(3-oxo-3-(5-(4-(trifluoromethyl)phenyl)thien-2-yl)propyl)-phenoxy)propanoate is prepared from 3-(4-hydroxy-3-methylphenyl)-1-(5-(4-(trifluoromethyl)phenyl)thien-2-yl)propan-1-one dissolved in tetrahydrofuran, according to general procedure D.

After stirring for 12 hours at 70° C., the mixture is diluted with a saturated solution of ammonium chloride and extracted with ethyl acetate. The organic phase is concentrated under reduced pressure. The evaporation residue is purified by silica-gel flash chromatography.

Elution: cyclohexane/ethyl acetate: 8/2. Silica 40-63 μm.

$^1$H NMR (300 MHz, CDCl$_3$, δ in ppm): 1.45 (s, 9H); 1.55 (s, 6H); 2.23 (s, 3H); 2.93-2.98 (m, 2H); 3.17-3.22 (m, 2H); 6.79 (d, 1H, J=8.4 Hz); 6.98-7.01 (m, 1H); 7.08 (m, 1H); 7.39 (d, 1H, J=3.9 Hz); 7.66-7.72 (m, 3H); 7.75 (d, 2H, J=8.4 Hz).

Compound 59

2-methyl-2-(2-methyl-4-(3-oxo-3-(5-(4-(trifluoromethyl)phenyl)-thien-2-yl)propyl)phenoxy)propanoic acid

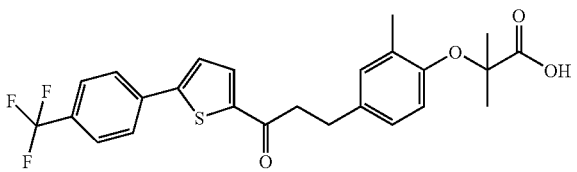

2-Methyl-2-(2-methyl-4-(3-oxo-3-(5-(4-(trifluoromethyl)phenyl)-thien-2-yl)-propyl)phenoxy)propanoic acid is prepared from tert-butyl 2-methyl-2-(2-methyl-4-(3-oxo-3-(5-(4-(trifluoromethyl)phenyl)thien-2-yl)propyl)phenoxy)propanoate according to general procedure E using 10 equivalents of trifluoroacetic acid. After stirring for 25 hours at room temperature, the reaction mixture is washed with water and then the dichloromethane is removed by evaporation under reduced pressure. The evaporation residue is purified by silica-gel chromatography.

Elution: dichloromethane/methanol: 9/1. Silica 40-63 μm.

$^1$H NMR (300 MHz, CDCl$_3$, δ in ppm): 1.60 (s, 6H); 2.24 (s, 3H); 3.02 (t, 2H, J=8.2 Hz); 3.21 (t, 2H, J=8.2 Hz); 6.79 (d, 1H, J=8.4 Hz); 6.98-7.01 (m, 1H); 7.08 (s, 1H); 7.39 (d, 1H, J=4.0 Hz); 7.67-7.70 (m, 3H); 7.76 (d, 2H, J=8.4 Hz).

Mass (ES$^-$): 475 (M−1).

M.p.=130-131° C.

Compound 60

2-(2,3-dichloro-4-(3-hydroxy-3-(4-(4-(trifluoromethyl)phenyl)-thien-2-yl)propyl)phenoxy)-2-methylpropanoic acid

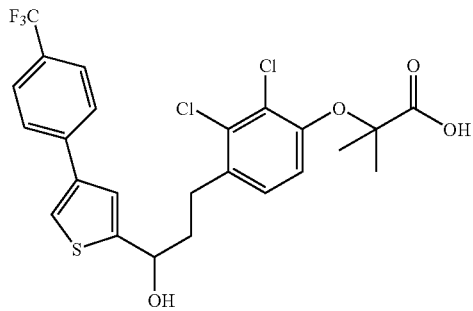

2-(2,3-Dichloro-4-(3-hydroxy-3-(4-(4-(trifluoromethyl)phenyl)thien-2-yl)propyl)-phenoxy)-2-methylpropanoic acid is prepared from 2-(2,3-dichloro-4-(3-oxo-3-(4-(4-(trifluoromethyl)phenyl)thien-2-yl)propyl)phenoxy)-2-methylpropanoic acid according to general procedure G. The evaporation residue is used "as is" for carrying out the next stage.

$^1$H NMR (300 MHz, CDCl$_3$, δ in ppm): 1.64 (s, 6H); 2.14-2.22 (m, 2H); 3.01-2.78 (m, 2H); 4.99 (t, 1H, J=6.5 Hz); 6.92 (d, 1H, J=8.6 Hz); 7.07 (d, 1H, J=8.6 Hz); 7.29 (d, 1H, J=1.2 Hz); 7.45 (d, 1H, J=1.2 Hz); 7.61-7.67 (m, 4H).

Compound 61

2-(4-(3-(benzyloxy)-3-(4-(4-(trifluoromethyl)phenyl)thien-2-yl)propyl)-2,3-dichlorophenoxy)-2-methylpropanoic acid

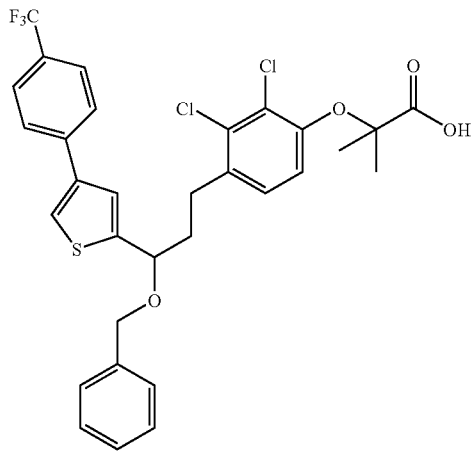

2-(4-(3-(Benzyloxy)-3-(4-(4-(trifluoromethyl)phenyl)thien-2-yl)propyl)-2,3-dichlorophenoxy)-2-methylpropanoic acid is prepared from 2-(2,3-dichloro-4-(3-hydroxy-3-(4-(4-(trifluoromethyl)phenyl)thien-2-yl)propyl)phenoxy)-2-methylpropanoic acid using 2.2 equivalents of sodium hydride and 2.2 equivalents of benzyl bromide according to general procedure H.

The evaporation residue is dissolved in ethanol in the presence of 2N sodium hydroxide (20 eq.). After stirring for 16 hours, the solvents are removed by evaporation under reduced pressure. The evaporation residue is acidified using dilute solution of hydrochloric acid and is then extracted with dichloromethane. The organic phase is dried over magnesium sulfate, filtered and then concentrated under reduced pressure. The evaporation residue is purified by silica-gel chromatography.

Elution: cyclohexane/ethyl acetate 7/3 then dichloromethane/methanol: 9/1. Silica 40-63 µm.

$^1$H NMR (300 MHz, CDCl$_3$, δ in ppm): 1.62 (s, 6H); 2.08-2.18 (m, 1H); 2.21-2.29 (m, 1H); 2.75-2.85 (m, 1H); 3.01-2.92 (m, 1H); 4.40 (t, 1H, J=11.7 Hz); 4.62-4.65 (m, 2H); 6.90 (d, 1H, J=8.5 Hz); 7.01 (d, 1H, J=8.5 Hz); 7.29-7.37 (m, 6H); 7.51 (d, 1H, J=1.2 Hz); 7.67-7.70 (m, 4H).

Mass (ES$^-$): 621/623 (M−1).

M.p.=58-59° C.

Compound 62

2-(2,3-difluoro-4-(3-hydroxy-3-(5-(4-(trifluoromethyl)phenyl)-thien-2-yl)propyl)phenoxy)-2-methylpropanoic acid

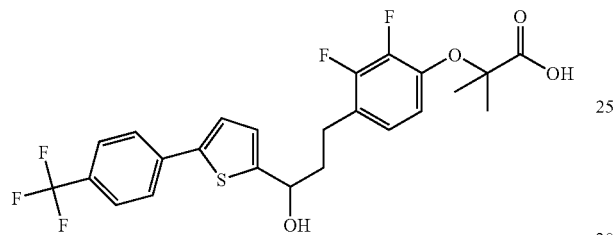

2-(2,3-Difluoro-4-(3-hydroxy-3-(5-(4-(trifluoromethyl)phenyl)thien-2-yl)propyl)-phenoxy)-2-methylpropanoic acid is prepared from 2-(2,3-difluoro-4-(3-oxo-3-(5-(4-(trifluoromethyl)phenyl)thien-2-yl)propyl)phenoxy)-2-methylpropanoic acid according to general procedure G. The evaporation residue is used "as is" for carrying out the next stage.

$^1$H NMR (300 MHz, CDCl$_3$, δ in ppm): 1.56 (s, 6H); 2.14-2.23 (m, 2H); 2.74-2.87 (m, 2H); 4.95 (t, 1H, J=7.4 Hz); 6.79 (m, 2H); 6.99 (d, 1H, J=3.8 Hz); 7.25 (d, 1H, J=3.7 Hz); 7.62 (d, 2H, J=8.6 Hz); 7.64 (d, 2H, J=8.6 Hz).

Compound 63

2-(4-(3-(benzyloxy)-3-(5-(4-(trifluoromethyl)phenyl)thien-2-yl)-propyl)-2,3-difluorophenoxy)-2-methylpropanoic acid

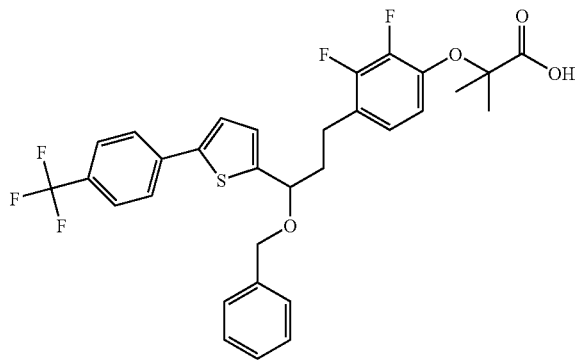

2-(4-(3-(Benzyloxy)-3-(5-(4-(trifluoromethyl)phenyl)thien-2-yl)propyl)-2,3-difluorophenoxy)-2-methylpropanoic acid is prepared from 2-(4-(3-(benzyloxy)-3-(5-(4-(trifluoromethyl)phenyl)thien-2-yl)propyl)-2,3-difluorophenoxy)-2-methylpropanoic acid using 2.2 equivalents of sodium hydride and 2.2 equivalents of benzyl bromide according to general procedure H.

The evaporation residue is purified by silica-gel chromatography (elution: cyclohexane/ethyl acetate: 9/1. Silica 40-63 µm.). The oil isolated is dissolved in ethanol in the presence of 2N sodium hydroxide (20 eq.). After stirring for 16 hours, the solvents are removed by evaporation under reduced pressure. The evaporation residue is acidified using dilute solution of hydrochloric acid and is then extracted with dichloromethane. The organic phase is concentrated under reduced pressure. The evaporation residue is purified by silica-gel chromatography.

Elution: cyclohexane/ethyl acetate 7/3 then dichloromethane/methanol: 9/1. Silica 40-63 µm.

$^1$H NMR (300 MHz, CDCl$_3$, δ in ppm): 1.59 (s, 6H); 2.03-2.33 (m, 2H); 2.63-2.82 (m, 2H); 4.37 (d, 1H, J=11.7 Hz); 4.58 (m, 2H); 6.77 (m, 2H); 6.98 (d, 1H, J=3.5 Hz); 7.30 (m, 6H); 7.63 (d, 2H, J=8.5 Hz); 7.70 (d, 2H, J=8.5 Hz).

Mass (ES$^-$): 589 (M−1).

Appearance: viscous oil.

Compound 64 tert-butyl 2-(4-(3-oxo-3-(5-(4-(trifluoromethyl)phenyl)thien-2-yl)propyl)phenoxy)-butanoate

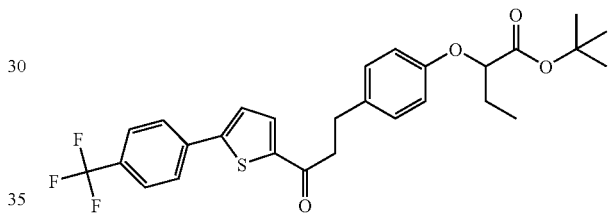

Tert-butyl 2-(4-(3-oxo-3-(5-(4-(trifluoromethyl)phenyl)thien-2-yl)propyl)-phenoxy)butanoate is prepared from 3-(4-hydroxyphenyl)-1-(5-(4-(trifluoromethyl)-phenyl)thien-2-yl)propan-1-one and tert-butyl 2-bromobutanoate according to general procedure D.

After stirring for 16 hours, the solvent is removed by evaporation under reduced pressure. The evaporation residue is taken up in ethyl acetate. The organic phase is washed with a saturated solution of ammonium chloride, dried over magnesium sulfate, filtered and then concentrated under reduced pressure. The evaporation residue is used "as is" for carrying out the next stage.

Compound 65

2-(4-(3-oxo-3-(5-(4-(trifluoromethyl)phenyl)thien-2-yl)propyl)-phenoxy)butanoic acid

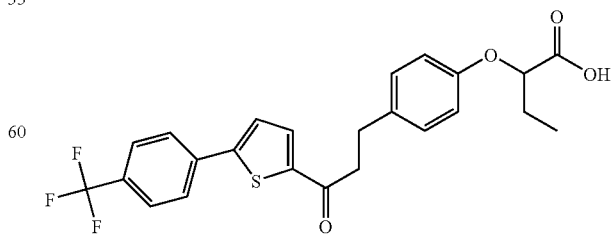

2-(4-(3-Oxo-3-(5-(4-(trifluoromethyl)phenyl)thien-2-yl)propyl)phenoxy)-butanoic acid is prepared from tert-butyl 2-(4-(3-oxo-3-(5-(4-(trifluoromethyl)phenyl)thien-2-yl)propyl)phenoxy)butanoate according to general procedure E using 10 equivalents of trifluoroacetic acid.

After stirring for 12 hours at room temperature, the reaction mixture is washed with water and then the dichloromethane is removed by evaporation under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 30/70 to 0/100.

Elution: dichloromethane/methanol: 9/1. Silica 40-63 μm.

$^1$H NMR (300 MHz, CDCl$_3$, δ in ppm): 1.10 (t, 3H, J=7.3 Hz); 1.98-2.08 (m, 2H); 3.03 (t, 2H, J=7.5 Hz); 3.18-3.24 (m, 2H); 4.61 (t, 1H, J=6.0 Hz); 6.86 (d, 2H, J=8.8 Hz); 7.18 (d, 2H, J=8.8 Hz); 7.38 (d, 1H, J=3.8 Hz); 7.65-7.69 (m, 3H); 7.76 (d, 2H, J=8.5 Hz).

Mass (ES$^+$): 461 (M+1).

M.p.=116-117° C.

Compound 66 tert-butyl 2-methyl-2-(4-(3-oxo-3-(5-(4-(trifluoromethyl)phenyl)thien-2-yl)propyl)-phenoxy)propanoate

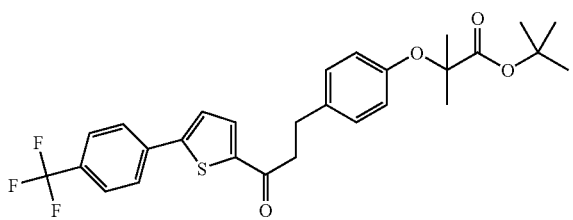

Tert-butyl 2-methyl-2-(4-(3-oxo-3-(5-(4-(trifluoromethyl)phenyl)thien-2-yl)propyl)-phenoxy)propanoate is prepared from 3-(4-hydroxyphenyl)-1-(5-(4-(trifluoromethyl)phenyl)thien-2-yl)propan-1-one and 2-tert-butyl bromoisobutyrate according to general procedure D.

After stirring for 16 hours, the solvent is removed by evaporation under reduced pressure. The evaporation residue is taken up in ethyl acetate. The organic phase is washed with a saturated solution of ammonium chloride, dried over magnesium sulfate, filtered and then concentrated under reduced pressure. The evaporation residue is used "as is" for carrying out the next stage.

Compound 67

2-(4-(3-oxo-3-(5-(4-(trifluoromethyl)phenyl)thien-2-yl)propyl)-phenoxy)-2-methylpropanoic acid

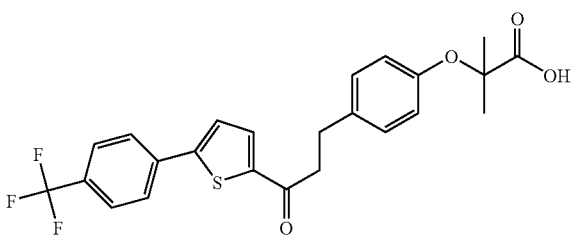

2-(4-(3-Oxo-3-(5-(4-(trifluoromethyl)phenyl)thien-2-yl)propyl)phenoxy)-2-methylpropanoic acid is prepared from tert-butyl 2-methyl-2-(4-(3-oxo-3-(5-(4-(trifluoromethyl)

phenyl)thien-2-yl)propyl)phenoxy)propanoate according to general procedure E using 10 equivalents of trifluoroacetic acid.

After stirring for 12 hours at room temperature, the reaction mixture is washed with water and then the dichloromethane is removed by evaporation under reduced pressure. The evaporation residue is purified by silica-gel chromatography (preparative HPLC, lichrospher (Merck) RP18 12 μm 100 A, column: 25*250 mm).

Elution: gradient of water, methanol+0.1% trifluoroacetic acid: 30/70 to 0/100.

$^1$H NMR (300 MHz, CDCl$_3$, δ in ppm): 1.57 (s, 6H); 3.06 (t, 2H, J=7.9 Hz); 3.23 (t, 2H, J=6.7 Hz); 6.89 (d, 2H, J=8.5 Hz); 7.18 (d, 2H, J=8.5 Hz); 7.38 (d, 1H, J=4.1 Hz); 7.66-7.69 (m, 3H); 7.75 (d, 2H, J=8.2 Hz).

Mass (ES$^+$): 463 (M+1).

M.p.=154-155° C.

Compound 68 tert-butyl 2-(4-(3-oxo-3-(5-(4-(trifluoromethyl)phenyl)thien-2-yl)propyl)phenoxy)-acetate

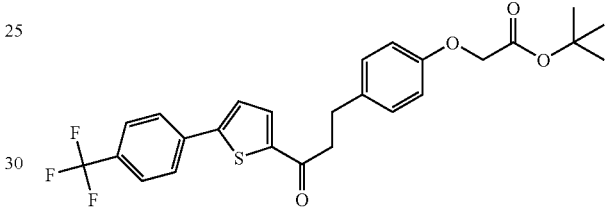

Tert-butyl 2-methyl-2-(4-(3-oxo-3-(5-(4-(trifluoromethyl)phenyl)thien-2-yl)propyl)phenoxy)-propanoate is prepared from 3-(4-hydroxyphenyl)-1-(5-(4-(trifluoromethyl)phenyl)thien-2-yl)propan-1-one and tert-butyl bromoacetate according to general procedure D.

After stirring for 18 hours, the mixture is acidified with citric acid solution and extracted with ethyl acetate. The organic phase is washed with a saturated solution of ammonium chloride, dried over magnesium sulfate, filtered and then concentrated under reduced pressure. The evaporation residue is purified by silica-gel chromatography.

Elution: cyclohexane/ethyl acetate: 85/15.

$^1$H NMR (300 MHz, CDCl$_3$, δ in ppm): 1.49 (s, 9H); 3.01-3.06 (m, 2H); 3.18-3.23 (m, 2H); 4.50 (s, 2H); 6.85 (d, 2H, J=8.5 Hz); 7.17 (d, 2H, J=8.5 Hz); 7.39 (d, 1H, J=4.1 Hz); 7.65-7.69 (m, 3H); 7.76 (d, 2H, J=8.4 Hz).

Compound 69

2-(4-(3-oxo-3-(5-(4-(trifluoromethyl)phenyl)thien-2-yl)propyl)-phenoxy)acetic acid

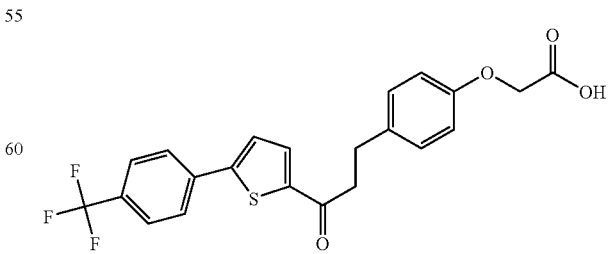

2-(4-(3-Oxo-3-(5-(4-(trifluoromethyl)phenyl)thien-2-yl)propyl)phenoxy)acetic acid is prepared from tert-butyl 2-(4-

(3-oxo-3-(5-(4-(trifluoromethyl)phenyl)thien-2-yl)propyl) phenoxy)acetate according to general procedure E using 10 equivalents of trifluoroacetic acid.

After stirring for 12 hours at room temperature, the reaction mixture is washed with water and then the dichloromethane is removed by evaporation under reduced pressure. The evaporation residue is purified by silica-gel chromatography.

Elution: dichloromethane/methanol: 9/1. Silica 40-63 μm.

$^1$H NMR (300 MHz, CDCl$_3$, δ in ppm): 3.03-3.08 (m, 2H); 3.19-3.24 (m, 2H); 4.66 (s, 2H); 6.89 (d, 2H, J=8.8 Hz); 7.22 (d, 2H, J=8.8 Hz); 7.38 (d, 1H J=4.1 Hz); 7.66-7.69 (m, 3H); 7.76 (d, 2H, J=8.5 Hz).

Mass (ES$^+$): 435 (M+1).

M.p.=182-183° C.

Compound 70

2-(4-(3-(benzyloxy)-3-(5-(4-(trifluoromethyl)phenyl) thien-2-yl)propyl)-2-fluorophenoxy)butanoic acid

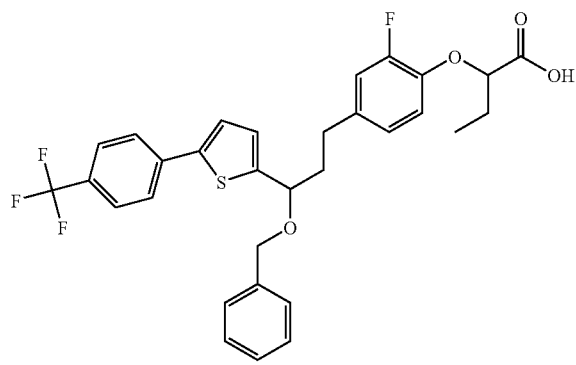

2-(4-(3-(Benzyloxy)-3-(5-(4-(trifluoromethyl)phenyl) thien-2-yl)propyl)-2-fluoro-phenoxy)butanoic acid is prepared from 2-(2-fluoro-4-(3-hydroxy-3-(5-(4-(trifluoromethyl)phenyl)thien-2-yl)propyl)phenoxy)butanoic acid using 2.1 equivalents of sodium hydride and 2.1 equivalents of benzyl bromide according to general procedure H.

The evaporation residue is purified by silica-gel chromatography (elution: cyclohexane/ethyl acetate: 95/5 to 8/2. Silica 40-63 μm.). The oil isolated is dissolved in ethanol in the presence of 2N sodium hydroxide (20 eq.). After stirring for 18 hours, the solvents are removed by evaporation under reduced pressure. The evaporation residue is acidified using dilute solution of hydrochloric acid and is then extracted with dichloromethane. The organic phase is concentrated under reduced pressure. The evaporation residue is purified by silica-gel chromatography (preparative HPLC, lichrospher (Merck) RP18 12 μm 100 A, column: 25*250 mm). Elution: gradient of water, methanol+0.1% trifluoroacetic acid: 28/72 to 10/90.

$^1$H NMR (300 MHz, CDCl$_3$, δ in ppm): 1.13 (t, 3H, J=7.3 Hz); 2.01-2.11 (m, 3H); 2.23-2.34 (m, 1H); 2.58-2.98 (m, 2H); 4.32 (d, 1H, J=11.7 Hz); 4.52 (dd, 1H, J=5.6 Hz, J=7.6 Hz); 4.59-4.63 (m, 2H); 6.79-6.92 (m, 3H); 6.97 (d, 1H, J=3.5 Hz); 7.26-7.27 (m, 1H); 7.29-7.39 (m, 5H); 7.62 (d, 2H, J=8.5 Hz); 7.70 (d, 2H, J=8.5 Hz).

Mass (ES$^+$): 573 (M+1).

Appearance: viscous oil.

Compound 71

2-(2,3-dichloro-4-(3-hydroxy-3-(5-(4-(trifluoromethyl)phenyl)fur-2-yl)propyl)phenoxy)-2-methylpropanoic acid

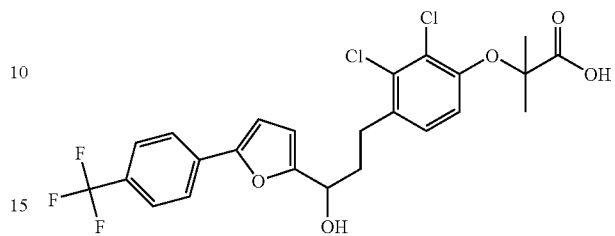

2-(2,3-Dichloro-4-(3-hydroxy-3-(5-(4-(trifluoromethyl) phenyl)fur-2-yl)propyl)-phenoxy)-2-methylpropanoic acid is prepared from 2-(2,3-dichloro-4-(3-oxo-3-(5-(4-(trifluoromethyl)phenyl)fur-2-yl)propyl)phenoxy)-2-methylpropanoic acid according to general procedure G. The evaporation residue is used "as is" for carrying out the next stage.

Compound 72

2-(2,3-dichloro-4-(3-methoxy-3-(5-(4-(trifluoromethyl)phenyl)fur-2-yl)propyl)phenoxy)-2-methylpropanoic acid

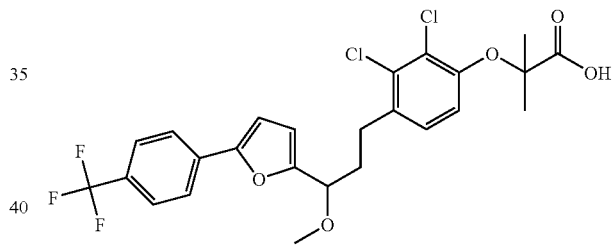

2-(2,3-Dichloro-4-(3-methoxy-3-(5-(4-(trifluoromethyl) phenyl)fur-2-yl)propyl)-phenoxy)-2-methylpropanoic acid is prepared from 2-(2,3-dichloro-4-(3-hydroxy-3-(5-(4-(trifluoromethyl)phenyl)fur-2-yl)propyl)phenoxy)-2-methyl propanoic acid using 2.1 equivalents of sodium hydride and 2.1 equivalents of iodomethane according to general procedure H.

The evaporation residue is purified by silica-gel chromatography (elution: cyclohexane/ethyl acetate: 9/1. Silica 40-63 μm.). The oil isolated is dissolved in ethanol in the presence of 2N sodium hydroxide (5 eq.). After stirring for 18 hours, the solvents are removed by evaporation under reduced pressure. The evaporation residue is acidified using dilute solution of hydrochloric acid and is then extracted with ethyl acetate. The organic phase is concentrated under reduced pressure.

$^1$H NMR (300 MHz, CDCl$_3$, δ in ppm): 1.63 (s, 6H); 2.11-2.32 (m, 2H); 2.75-2.97 (m, 2H); 3.34 (s, 3H); 4.25 (dd, 1H, J=5.8 Hz J=7.6 Hz); 6.42 (d, 1H, J=3.4 Hz); 6.73 (d, 1H, J=3.4 Hz); 6.93 (d, 1H, J=8.5 Hz); 7.05 (d, 1H, J=8.5 Hz); 7.62 (d, 2H, J=8.3 Hz); 7.75 (d, 2H, J=8.3 Hz).

Mass (ES$^-$): 529/531 (M−1).

Appearance: viscous oil.

Compound 73

2-(4-(3-hydroxy-3-(5-(4-(trifluoromethyl)phenyl)thien-2-yl)-propyl)-2,6-dimethylphenoxy)-2-methyl-propanoic acid

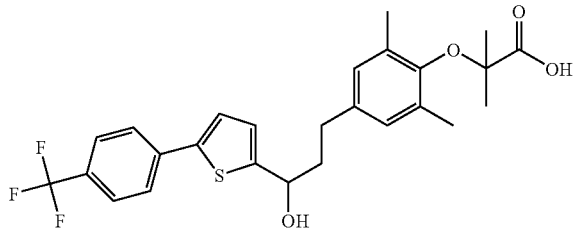

2-(4-(3-Hydroxy-3-(5-(4-(trifluoromethyl)phenyl)thien-2-yl)propyl)-2,6-dimethyl-phenoxy)-2-methylpropanoic acid is prepared from 2-(2,6-dimethyl-4-(3-oxo-3-(5-(4-(trifluoromethyl)phenyl)thien-2-yl)propyl)phenoxy)-2-methyl-propanoic acid according to general procedure G. The evaporation residue is used "as is" for carrying out the next stage.

$^1$H NMR (300 MHz, CDCl$_3$, δ in ppm): 1.51 (s, 6H); 2.07-2.28 (m, 8H); 2.56-2.76 (m, 2H); 4.90-4.95 (m, 1H); 6.84 (s, 2H); 6.97 (d, 1H, J=3.7 Hz); 7.25 (d, 1H, J=3.7 Hz); 7.61 (d, 2H, J=8.6 Hz); 7.66 (d, 2H, J=8.6 Hz).

Compound 74

2-(4-(3-methoxy-3-(5-(4-(trifluoromethyl)phenyl)thien-2-yl)propyl)-2,6-dimethylphenoxy)-2-methyl-propanoic acid

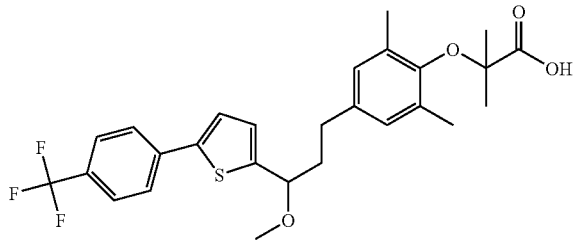

2-(4-(3-Methoxy-3-(5-(4-(trifluoromethyl)phenyl)thien-2-yl)propyl)-2,6-dimethylphenoxy)-2-methylpropanoic acid is prepared from 2-(4-(3-hydroxy-3-(5-(4-(trifluoromethyl)phenyl)thien-2-yl)propyl)-2,6-dimethylphenoxy)-2-methylpropanoic acid using 2.1 equivalents of sodium hydride and 2.1 equivalents of iodomethane according to general procedure H.

The evaporation residue is purified by silica-gel chromatography (elution: cyclohexane/ethyl acetate: 9/1. Silica 40-63 μm.). The oil isolated is dissolved in ethanol in the presence of 2N sodium hydroxide (5 eq.). After stirring for 18 hours, the solvents are removed by evaporation under reduced pressure. The evaporation residue is acidified using dilute solution of hydrochloric acid and is then extracted with ethyl acetate. The organic phase is concentrated under reduced pressure.

$^1$H NMR (300 MHz, MeOD, δ in ppm): 1.43 (s, 6H); 1.91-2.06 (m, 1H); 2.11-2.23 (m, 7H); 2.48-2.68 (m, 2H); 3.28 (s, 3H); 4.37 (t, 1H, J=6.7 Hz); 6.81 (s, 2H); 7.01 (d, 1H, J=3.8 Hz); 7.41 (d, 1H, J=3.8 Hz); 7.67 (d, 2H, J=8.2 Hz); 7.80 (d, 2H, J=8.2 Hz).

Mass (ES$^+$): 524 (M+NH$_4^+$), 530 (M+Na$^+$), 545 (M+K$^+$).
Appearance: viscous oil.

Compound 75 ethyl 2-(2,3-dichloro-4-(3-oxo-3-(5-(3-(trifluoromethyl)phenyl)thien-2-yl)-propyl)phenoxy)-2-methyl-propanoate

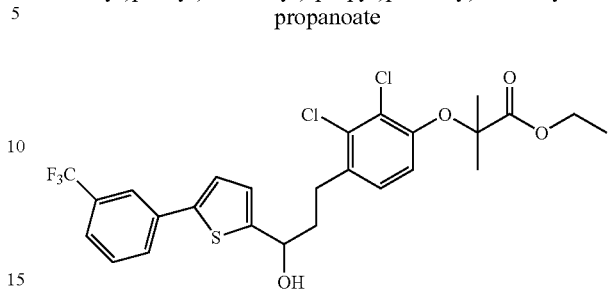

Ethyl 2-(2,3-dichloro-4-(3-oxo-3-(5-(3-(trifluoromethyl)phenyl)thien-2-yl)propyl)-phenoxy)-2-methylpropanoate is prepared from 3-(2,3-dichloro-4-hydroxy-phenyl)-1-(5-(3-(trifluoromethyl)phenyl)thien-2-yl)propan-1-one and ethyl bromo-isobutyrate according to general procedure D.

After stirring for 16 hours, the mixture is acidified with citric acid solution and extracted with ethyl acetate. The organic phase is washed with a saturated solution of ammonium chloride, dried over magnesium sulfate, filtered and then concentrated under reduced pressure. The evaporation residue is purified by silica-gel chromatography.

Elution: cyclohexane/ethyl acetate: 100/0 to 8/2.

$^1$H NMR (300 MHz, CDCl$_3$, δ in ppm): 1.27 (t, 3H, J=7.0 Hz); 1.61 (s, 6H); 3.18-3.24 (m, 4H); 4.25 (q, 2H, J=7.0 Hz); 6.77 (d, 1H, J=8.4 Hz); 7.11 (d, 1H, J=8.4 Hz); 7.38 (d, 1H, J=3.9 Hz); 7.56 (m, 1H); 7.63 (d, 1H, J=8.2 Hz); 7.68 (d, 1H, J=3.9 Hz); 7.82 (d, 1H, J=7.6 Hz); 7.88 (s, 1H).

Compound 76

2-(2,3-dichloro-4-(3-oxo-3-(5-(3-(trifluoromethyl)phenyl)thien-2-yl)propyl)phenoxy)-2-methylpropanoic acid

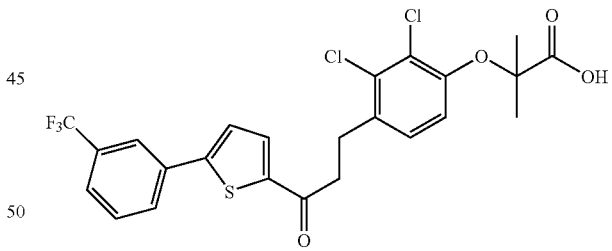

2-(2,3-Dichloro-4-(3-oxo-3-(5-(3-(trifluoromethyl)phenyl)thien-2-yl)propyl)-phenoxy)-2-methylpropanoic acid is prepared from ethyl 2-(2,3-dichloro-4-(3-oxo-3-(5-(3-(trifluoromethyl)phenyl)thien-2-yl)propyl)phenoxy)-2-methylpropanoate according to general procedure F using 10 equivalents of 2N sodium hydroxide solution.

After 16 hours at room temperature, the reaction mixture is concentrated under reduced pressure, acidified using dilute solution of hydrochloric acid then extracted with dichloromethane. The organic phase is dried over magnesium sulfate, filtered and then concentrated under reduced pressure. The evaporation residue is purified by silica-gel chromatography.

Elution: dichloromethane/methanol: 9/1. Silica 40-63 μm.

¹H NMR (300 MHz, CDCl₃, δ in ppm): 1.64 (s, 6H); 3.18-3.28 (m, 4H); 6.95 (d, 1H, J=8.4 Hz); 7.19 (d, 1H, J=8.4 Hz); 7.37 (d, 1H, J=3.9 Hz); 7.56 (m, 1H); 7.63 (d, 1H, J=7.6 Hz); 7.69 (d, 1H, J=3.9 Hz); 7.82 (d, 1H, J=7.6 Hz); 7.88 (s, 1H).

Compound 77 ethyl 2-(2,3-dichloro-4-(3-hydroxy-3-(5-(3-(trifluoromethyl)phenyl)thien-2-yl)-propyl)phenoxy)-2-methylpropanoate

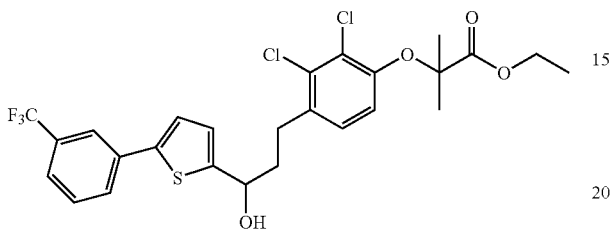

Ethyl 2-(2,3-dichloro-4-(3-hydroxy-3-(5-(3-(trifluoromethyl)phenyl)thien-2-yl)propyl)-phenoxy)-2-methylpropanoate is prepared from ethyl 2-(2,3-dichloro-4-(3-oxo-3-(5-(3-(trifluoromethyl)phenyl)thien-2-yl)propyl)phenoxy)-2-methylpropanoate according to general procedure G. The evaporation residue is used "as is" for carrying out the next stage.

¹H NMR (300 MHz, CDCl₃, δ in ppm): 1.28 (t, 3H, J=7.1 Hz); 1.62 (s, 6H); 2.14-2.22 (m, 2H); 2.81-2.97 (m, 2H); 4.27 (q, 2H, J=7.1 Hz); 4.95 (t, 1H, J=6.4 Hz); 6.78 (d, 1H, J=8.6 Hz); 7.00 (d, 1H, J=3.5 Hz); 7.05 (d, 1H, J=8.6 Hz); 7.24 (d, 1H, J=3.5 Hz); 7.47-7.55 (m, 2H); 7.75 (d, 1H, J=7.1 Hz); 7.82 (s, 1H).

Compound 78 ethyl 2-(2,3-dichloro-4-(3-methoxy-3-(5-(3-(trifluoromethyl)phenyl)thien-2-yl)propyl)phenoxy)-2-methylpropanoate

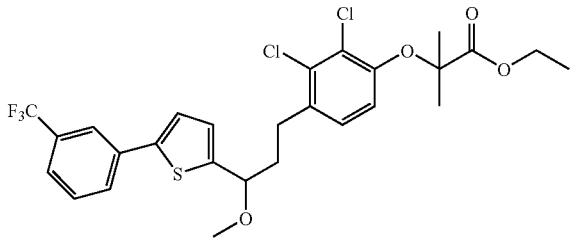

Ethyl 2-(2,3-dichloro-4-(3-methoxy-3-(5-(3-(trifluoromethyl)phenyl)thien-2-yl)propyl)-phenoxy)-2-methylpropanoate is prepared from ethyl 2-(2,3-dichloro-4-(3-hydroxy-3-(5-(3-(trifluoromethyl)phenyl)thien-2-yl)propyl)phenoxy)-2-methylpropanoate using 1.1 equivalents of sodium hydride and 1.1 equivalents of iodomethane according to general procedure H.

After stirring for 1 hour at room temperature, the reaction mixture is hydrolyzed and extracted with ethyl acetate. The organic phase is concentrated under reduced pressure and the evaporation residue is purified by silica-gel chromatography. Elution: cyclohexane/ethyl acetate: 9/1. Silica 40-63 μm.

¹H NMR (300 MHz, CDCl₃, δ in ppm): 1.28 (t, 3H, J=7.1 Hz); 1.61 (s, 6H); 2.02-2.23 (m, 2H); 2.71-2.94 (m, 2H); 4.25 (q, 2H, J=7.1 Hz); 3.32 (s, 3H); 4.32-4.36 (m, 1H); 6.73 (d, 1H, J=8.5 Hz); 6.96 (d, 1H, J=3.5 Hz); 7.01 (d, 1H, J=8.5 Hz); 7.24 (d, 1H, J=3.5 Hz); 7.48-7.50 (m, 2H); 7.74 (d, 1H, J=7.3 Hz); 7.81 (s, 1H).

Compound 79

2-(2,3-dichloro-4-(3-hydroxy-3-(5-(4-(trifluoromethoxy)phenyl)-thien-2-yl)propyl)phenoxy)-2-methylpropanoic acid

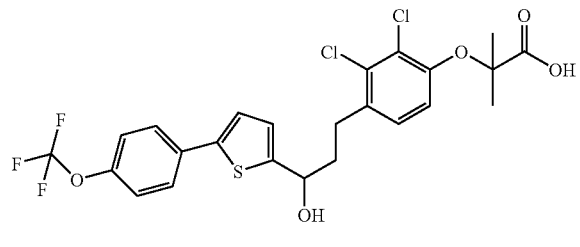

2-(2,3-Dichloro-4-(3-hydroxy-3-(5-(4-(trifluoromethoxy)phenyl)thien-2-yl)-propyl)phenoxy)-2-methylpropanoic acid is prepared from 2-(2,3-dichloro-4-(3-oxo-3-(5-(4-(trifluoromethoxy)phenyl)thien-2-yl)propyl)phenoxy)-2-methylpropanoic acid according to general procedure G. The evaporation residue is used "as is" for carrying out the next stage.

Compound 80

2-(2,3-dichloro-4-(3-methoxy-3-(5-(4-(trifluoromethoxy)phenyl)-thien-2-yl)propyl)phenoxy)-2-methylpropanoic acid

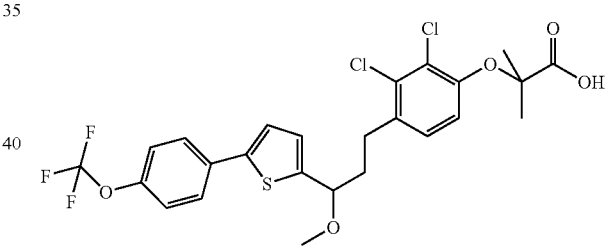

2-(2,3-Dichloro-4-(3-methoxy-3-(5-(4-(trifluoromethoxy)phenyl)thien-2-yl)-propyl)phenoxy)-2-methylpropanoic acid is prepared from 2-(2,3-dichloro-4-(3-hydroxy-3-(5-(4-(trifluoromethoxy)phenyl)thien-2-yl)propyl)phenoxy)-2-methylpropanoic acid using 2.1 equivalents of sodium hydride and 2.1 equivalents of iodomethane according to general procedure H.

The evaporation residue is purified by silica-gel chromatography (elution: cyclohexane/ethyl acetate: 9/1. Silica 40-63 μm.). The oil isolated is dissolved in ethanol in the presence of 2N sodium hydroxide (6 eq.). After stirring for 18 hours, the solvents are removed by evaporation under reduced pressure. The evaporation residue is acidified using dilute solution of hydrochloric acid and is then extracted with ethyl acetate. The organic phase is concentrated under reduced pressure.

¹H NMR (300 MHz, CDCl₃, δ in ppm): 1.60 (s, 6H); 1.98-2.29 (m, 2H); 2.72-2.97 (m, 2H); 3.32 (s, 3H); 4.35 (t, 1H, J=6.5 Hz); 6.89-6.97 (m, 2H); 7.01-7.08 (m, 1H); 7.16 (d, 1H, J=3.5 Hz); 7.22 (d, 2H, J=8.6 Hz); 7.59 (d, 2H, J=8.6 Hz).

Mass (ES⁺): 563/565 (M+1).

Appearance: viscous oil.

Example 5

In Vitro Evaluation of the PPAR-Activating Properties of the Compounds According to the Invention—Method 1

Principle

The activation of the PPARs was evaluated in vitro on a line of monkey kidney fibroblasts (COS-7) by measuring the transcriptional activity of chimeras constituted of the DNA binding domain of the Gal4 transcription factor of yeast and the ligand binding domain of the various PPARs. The compounds were tested at doses between $10^{-5}$ and 100 μm on the chimeras Gal4-PPARα, γ or δ, and the corresponding EC50 values were determined.

Protocol

Cell Culture

The COS-7 cells were obtained from the ATCC and were cultivated in DMEM medium supplemented with 10% (v/v) of fetal calf serum, 100 U/ml of penicillin (Gibco, Paisley, UK) and 2 mM of L-glutamine (Gibco, Paisley, UK). The cells were incubated at 37° C. in a humid atmosphere containing 5% $CO_2$.

Description of the Plasmids Used in Transfection

The plasmids Gal4(RE)_TkpGL3, pGal4-hPPARα, pGal4-hPPARγ, pGal4-hPPARδ and pGal4-φ are described in the literature (Raspe E et al., 1999). The constructs pGal4-hPPARα, pGal4-hPPARγ and pGal4-hPPARδ were obtained by cloning DNA fragments amplified by PCR corresponding to the DEF domains of the human nuclear receptors PPARα, PPARγ and PPARδ in the pGal4-φ vector.

Transfection

The COS-7 cells in suspension were transfected with 150 ng of DNA per well, with a pGal4-PPAR/Gal4(RE)_TkpGL3 ratio of 1/10, in the presence of 10% fetal calf serum. The cells were seeded in 96-well plates ($4 \times 10^4$ cells/well) and then incubated at 37° C. for 24 hours. Activation with the test compounds is carried out for 24 h at 37° C. in serum-free medium. At the end of the experiment, the cells were lysed and the luciferase activity was determined using the Steady-Lite™ HTS (Perkin Elmer) following the supplier's recommendations.

Results

Unexpectedly, the inventors demonstrated a significant, dose-dependent increase in luciferase activity in the cells transfected with the pGal4-hPPAR plasmids and treated with the compounds according to the invention. The experimental data are summarized in Table 1 below, which shows the EC50 measured for each PPAR isoform, as well as the maximum percentage response attained by each compound relative to the reference (phenofibric acid for PPARα, rosiglitazone for PPARγ and GW501516 for PPARδ).

The measured activities differ depending on the compound tested, and more or less selectivity with respect to the isoforms of PPAR was also observed among the compounds of the invention:

certain compounds according to the invention are selective with respect to a subtype of PPAR, other compounds according to the invention are activators of two or three subtypes simultaneously.

TABLE 1

| Compound No. | hPPARalpha | | hPPARgamma | | hPPARdelta | |
|---|---|---|---|---|---|---|
| | % max | $EC_{50}$ μM | % max | $EC_{50}$ μM | % max | $EC_{50}$ μM |
| 2 | 43 | 0.053 | 11 | 0.06 | 91 | 0.007 |
| 4 | 50 | 0.125 | 38 | ND | 107 | 0.034 |
| 9 | 54 | 0.006 | 41 | 0.28 | 84 | 0.019 |
| 11 | 39 | 0.288 | 55 | 1.17 | 105 | 0.003 |
| 13 | 20 | 0.977 | 58 | 0.49 | 1 | ND |
| 15 | 46 | 0.163 | 32 | 5.66 | 88 | 0.253 |
| 17 | 5 | 0.228 | 27 | 0.19 | 0 | ND |
| 19 | 47 | 0.001 | 27 | 0.18 | 85 | 0.015 |
| 21 | 50 | 0.017 | 63 | 0.08 | 97 | 0.008 |
| 23 | 48 | 0.000 | 49 | 0.40 | 95 | 0.016 |
| 27 | 47 | 1.314 | 30 | 2.82 | 77 | 0.589 |
| 29 | 56 | 0.002 | 65 | 1.27 | 88 | 0.037 |
| 32 | 52 | 0.008 | 67 | 0.21 | 75 | 0.036 |
| 34 | 61 | 0.060 | 37 | ND | 95 | 0.114 |
| 36 | 47 | 0.005 | 63 | ND | 85 | 0.009 |
| 44 | 54 | 0.016 | 46 | 0.10 | 109 | 0.027 |
| 46 | 58 | 0.011 | 30 | ND | 105 | 0.018 |
| 48 | 49 | 0.000 | 85 | 0.56 | 86 | 0.006 |
| 49 | 46 | 0.043 | 24 | 0.66 | 93 | 0.045 |
| 61 | 42 | 0.591 | 78 | 0.03 | 101 | 0.006 |
| 65 | 52 | 0.004 | 73 | ND | 79 | 0.109 |
| 69 | 61 | 0.033 | 15 | 3.53 | 90 | 0.292 |
| 70 | 47 | 0.227 | 56 | 0.97 | 67 | 0.216 |

Conclusion:

These results show that the compounds according to the invention bind and activate the hPPARα, hPPARγ, and/or hPPARδ receptors significantly. The activity of the compounds according to the invention varies depending on the chemical structure of the compound tested and according to the subtype of PPAR investigated.

Example 6

In Vitro Evaluation of the PPAR-Activating Properties of Compounds According to the Invention—Method 2

The principle, the cells and the plasmids used for example 5 were also employed in this example. Only the application of the transfection stage is slightly different. The details are presented below.

The adherent COS-7 cells are transfected with 40 μg of DNA per 225 $cm^2$ dish, with a pGal4-PPAR/Gal4(RE)_Tk-pGL3 ratio of 1/10, in the presence of 10% fetal calf serum. The cells are then detached and seeded in the absence of serum in 384-well plates ($2 \times 10^4$ cells/well) and incubated for 4 hours at 37° C. The compounds are then diluted in a 96-well plate and transferred to the 384-well plate. Activation with the test compounds is carried out for an additional 24 h at 37° C. in the presence of 1% of Ultroser™ lipid-free synthetic serum (Biosepra). These last 2 stages are automated using a Genesis Freedom 200™ station (Tecan). At the end of the experiment, the cells are lysed and the luciferase activity is determined using the Steady-Lite™ HTS (Perkin Elmer) following the supplier's recommendations.

Results

Unexpectedly, the inventors demonstrated a significant, dose-dependent increase in luciferase activity in the cells transfected with the pGal4-hPPAR plasmids and treated with the compounds according to the invention. The experimental data are summarized in Table 2 below, which shows the EC50 measured for each PPAR isoform, as well as the maximum percentage response attained by each compound relative to the reference (phenofibric acid for PPARα, rosiglitazone for PPARγ and GW501516 for PPARδ).

The measured activities differ depending on the compound tested, and more or less selectivity with respect to the PPAR isoforms is also observed among the compounds of the invention:

certain compounds according to the invention are selective with respect to a subtype of PPAR, other compounds according to the invention are activators of two or three subtypes simultaneously.

TABLE 2

| Compound No. | hPPARalpha | | hPPARgamma | | hPPARdelta | |
|---|---|---|---|---|---|---|
| | % max | $EC_{50}\mu M$ | % max | $EC_{50}\mu M$ | % max | $EC_{50}\mu M$ |
| 6 | 41 | 7.86 | 55 | 4.11 | 92 | 0.53 |
| 7 | 20 | 5.46 | 40 | 1.70 | 92 | 0.03 |
| 25 | 55 | 1.68 | 27 | 36.47 | 75 | 7.45 |
| 30 | 51 | 0.05 | 45 | 3.93 | 80 | 1.53 |
| 38 | 44 | 0.20 | 37 | 1.84 | 89 | 0.014 |
| 38 | 40 | 0.32 | 39 | 0.81 | 94 | 0.009 |
| 39 | 36 | 1.01 | 52 | 0.55 | 90 | 0.006 |
| 40 | 35 | 0.59 | 32 | 0.99 | 78.29 | 0.005 |
| 41 | 49 | 0.61 | 36 | 1.49 | 76 | 0.01 |
| 42 | 28 | 2.00 | 47 | 0.89 | 82.12 | 0.26 |
| 50 | 38 | 0.26 | 32 | 0.27 | 78 | 0.05 |
| 52 | 53 | 0.21 | 57 | 1.02 | 104 | 0.05 |
| 54 | 43 | 0.15 | 62 | 0.86 | 107 | 0.07 |
| 55 | 25 | 2.80 | 2 | ND | 34 | 4.71 |
| 57 | 44 | 1.00 | 39 | 1.52 | 88 | 0.35 |
| 59 | 47 | 0.00 | 57 | 0.23 | 107 | 0.03 |
| 63 | 46 | 4.21 | 44 | 7.91 | 97 | 0.18 |
| 67 | 45 | 0.01 | 37 | 4.82 | 75 | 0.36 |
| 72 | 59 | 0.27 | 70 | 0.16 | 97 | ND |

Conclusion:

These results show that the compounds according to the invention bind and activate the hPPARα, hPPARγ, and/or hPPARδ receptors significantly. The activity of the compounds according to the invention varies depending on the chemical structure of the compound tested and according to the subtype of PPAR investigated.

Example 7

In Vitro Evaluation of the PPARδ-Activating Properties of the Compounds According to the Invention by Measuring the Expression of Target Genes of PPARδ in Murine Myocytes Principle The stimulating effects of the compounds according to the invention on lipid and carbohydrate metabolism and on energy expenditure were evaluated by measuring the expression of pyruvate dehydrogenase kinase 4 (PDK4), carnitine palmitoyltransferase 1b (CPT1b), uncoupling protein 2 (UCP2) and uncoupling protein 3 (UCP3) by murine myocytes treated with the compounds according to the invention for 24 hours. It is established that regulation of the expression of these genes is directly controlled by PPARδ in this cell type. The more the expression of the genes is increased, the greater the stimulating action of the compound according to the invention on metabolism in the muscle cells.

Protocol

Differentiation of the C2C12 Cells to Myocytes

Cells from the murine cell line C2C12 (obtained from ECACC) are cultivated in DMEM medium (Gibco; 41965-039) with addition of 1% L-glutamine (Gibco; 25030), 1% of penicillin/streptomycin (VWR; BWSTL0022/100) and 10% decomplemented fetal calf serum (FCS. Gibco; 10270-106).

The cells are seeded on 24-well plates at a density of $50 \cdot 10^3$ cells/well. At confluence, the medium is replaced with a differentiating medium (basal medium with addition of 2% of horse serum (Gibco; 26050-088)), then incubated at 37° C. and 5% $CO_2$ for 4 days in order to differentiate them to myocytes.

Treatment

After 5 days of differentiation, the cells are put in a deprivation medium (basal medium without serum) for 6 hours. The cells are then treated with the compounds according to the invention in the deprivation medium. Compounds 2, 4, 7, 11, 39, 40, 46, 49 and 72 were in dose effect, corresponding to 1×, 10× and 100× their EC50 PPARδ. The compounds according to the invention were dissolved in dimethylsulfoxide (DMSO, Sigma; D5879). The cells were treated for 24 h at 37° C., 5% $CO_2$. The effect of the compounds according to the invention was compared with the effect of DMSO alone.

Extraction of the RNAs, Reverse Transcription and Quantitative PCR

After treatment, the total RNA is extracted from the cells using the NucleoSpine® 96 RNA kit (Macherey Nagel, Hoerdt, France) following the manufacturer's instructions.

1 μg of total RNA (quantified based on the UV spectrophotometer reading) was then reverse-transcribed to complementary DNA by reaction for 1 hour at 37° C. in a total volume of 30 μl containing buffer 1× (Invitrogen), 1.5 mM of DTT, 0.18 mM of dNTPs (Promega), 200 ng of pdN6 (Amersham), 30 U of RNase inhibitor (Promega) and 1 μl of MMLV-RT (Invitrogen).

The quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 μl of diluted reverse-transcription reaction mixtures with a hybridization temperature of 60° C. Primer pairs specific to the PDK4, CPT1b, UCP2 and UCP3 genes under investigation were used:

```
                                          (SEQ ID No. 11)
mPDK4: sense primer: 5'-TACTCCACTGCTCCAACACCTG-3'
and
                                          (SEQ ID No. 12)
antisense primer     5'-GTTCTTCGGTTCCCTGCTTG-3'

(SEQ ID No. 7)
mCPT1b: sense primer: 5'-GGACTGAGACTGTGCGTTCCTG-3'
and
                                          (SEQ ID No. 8)
antisense primer:    5'-AGTGCTTGGCGGATGTGGTT-3'

(SEQ ID No. 13)
mUCP2: sense primer: 5'-GTCGGAGATACCAGAGCACTGT
                         CG-3'
and
                                          (SEQ ID No. 14)
antisense primer:    5'-CACATCAACAGGGGAGGCGA-3'

(SEQ ID No. 15)
mUCP3: sense primer: 5'-GCACCGCCAGATGAGTTTTG-3'
and
                                          (SEQ ID No. 16)
antisense primer:    5'-GACGCTGGAGTGGTCCGCTC-3'
```

The amount of fluorescence emitted is directly proportional to the amount of complementary DNA present at the start of the reaction and amplified during PCR. For each target investigated, a range is produced by successive dilutions of a pool constituted of a few microliters of various reverse-transcription reaction mixtures. The relative expression levels of each target are thus determined using the efficacy curves obtained with the points in the range.

The levels of expression of the genes of interest were then normalized relative to the level of expression of the reference gene 36B4 (whose specific primers are: sense primer: 5'-CATGCTCAACATCTCCCCCTTCTCC-3' (SEQ ID No. 19) and antisense primer: 5'-GGGAAGGTGTAATCCGTCTCCACAG-3' (SEQ ID No. 20)). The induction factor, i.e. the ratio of the relative signal (induced by the compound according to the invention) to the mean of the relative values of the control group, was then calculated. The higher this factor, the greater the activating character of the compounds according to the invention with respect to gene expression. The final result is represented as the mean of the induction values in each experimental group.

Results

The inventors also demonstrated, on murine myocytes in vitro, that compounds 2, 4, 7, 11, 39, 40, 46, 48, 63 and 72 possess stimulating effects on the expression of genes involved in carbohydrate and lipid metabolism and in thermoregulation. The results obtained are presented in Table 3 below. These results show that the compounds according to the invention, starting from 1× EC50 PPARδ, induce a significant, dose-dependent increase in expression of PDK4, CPT1b, UCP2 and UCP3 in the myocytes.

TABLE 3

| Cpd | Dose | (µM) | PDK4 Induction | SD | t-Test | CPT1b Induction | SD | t-Test | UCP2 Induction | SD | t-Test | UCP3 Induction | SD | t-Test |
|---|---|---|---|---|---|---|---|---|---|---|---|---|---|---|
| 2 | 1x EC50 | 0.006 | 1.62 | 0.24 | *** | 1.81 | 0.40 | * | 3.46 | 0.34 | *** | 4.29 | 0.43 | *** |
|  | 10x EC50 | 0.06 | 2.11 | 0.02 | *** | 1.66 | 0.91 |  | 3.98 | 0.47 | *** | 4.62 | 1.31 | *** |
|  | 100x EC50 | 0.6 | 2.39 | 0.41 | *** | 2.97 | 0.62 | *** | 4.67 | 1.34 | *** | 6.95 | 1.82 | *** |
| 4 | 1x EC50 | 0.02 | 2.19 | 0.08 | *** | 1.78 | 0.34 | *** | 2.79 | 0.27 | *** | 2.45 | 0.25 | ** |
|  | 10x EC50 | 0.2 | 2.35 | 0.13 | *** | 1.93 | 0.27 | *** | 2.41 | 0.13 | *** | 2.34 | 0.36 | ** |
|  | 100x EC50 | 2 | 2.13 | 0.11 | *** | 1.98 | 0.38 | *** | 2.92 | 0.22 | *** | 2.37 | 0.36 | ** |
| 7 | 1x EC50 | 0.01 | 3.45 | 0.41 | *** | 1.71 | 0.34 | ** | 3.41 | 1.16 | *** | 4.30 | 0.32 | *** |
|  | 10x EC50 | 0.1 | 5.30 | 0.56 | *** | 2.14 | 0.41 | *** | 3.95 | 0.88 | *** | 5.09 | 1.32 | *** |
|  | 100x EC50 | 1 | 5.14 | 0.57 | *** | 2.50 | 0.62 | *** | 2.14 | 0.27 | *** | 5.24 | 1.45 | *** |
| 11 | 1x EC50 | 0.003 | 1.32 | 0.04 |  | 0.96 | 0.25 |  | 2.15 | 0.49 | *** | 1.45 | 0.53 |  |
|  | 10x EC50 | 0.03 | 2.85 | 0.42 | *** | 1.42 | 0.29 |  | 1.68 | 1.16 |  | 2.56 | 0.81 | *** |
|  | 100x EC50 | 0.3 | 4.58 | 0.47 | *** | 1.51 | 0.08 | * | 3.85 | 1.06 | *** | 4.96 | 1.02 | *** |
| 39 | 1x EC50 | 0.007 | 3.66 | 0.27 | *** | 2.46 | 0.85 | *** | 4.38 | 0.75 | *** | 3.39 | 0.82 | *** |
|  | 10x EC50 | 0.07 | 6.22 | 0.63 | *** | 2.16 | 0.39 | ** | 4.56 | 2.07 | *** | 3.85 | 0.87 | *** |
|  | 100x EC50 | 0.7 | 5.17 | 0.50 | *** | 3.81 | 0.21 | *** | 5.63 | 1.28 | *** | 5.24 | 0.63 | *** |
| 40 | 1x EC50 | 0.006 | 3.79 | 0.14 | *** | 1.94 | 0.55 | ** | 4.86 | 0.36 | *** | 4.12 | 0.41 | *** |
|  | 10x EC50 | 0.06 | 4.05 | 0.12 | *** | 2.13 | 0.31 | *** | 3.47 | 0.73 | *** | 2.97 | 0.74 | *** |
|  | 100x EC50 | 0.6 | 3.88 | 0.81 | *** | 1.91 | 0.77 | ** | 2.99 | 1.60 | ** | 2.72 | 0.39 | *** |
| 46 | 1x EC50 | 0.01 | 1.81 | 0.04 | *** | 2.03 | 0.36 | *** | 3.27 | 0.64 | *** | 3.38 | 0.92 | *** |
|  | 10x EC50 | 0.1 | 2.68 | 0.21 | *** | 2.63 | 0.59 | *** | 5.37 | 0.82 | *** | 5.60 | 0.36 | *** |
|  | 100x EC50 | 1 | 2.67 | 0.21 | *** | 2.91 | 0.40 | *** | 4.58 | 0.34 | *** | 5.61 | 1.63 | *** |
| 48 | 1x EC50 | 0.006 | 0.84 | 0.08 |  | 1.32 | 0.42 |  | 1.13 | 0.18 |  | 1.42 | 0.08 | * |
|  | 10x EC50 | 0.06 | 1.01 | 0.04 |  | 1.95 | 0.39 | *** | 2.04 | 0.33 | *** | 1.82 | 0.53 | ** |
|  | 100x EC50 | 0.6 | 1.78 | 0.16 | *** | 2.17 | 0.50 | *** | 4.64 | 0.18 | *** | 3.83 | 1.19 | *** |
| 63 | 1x EC50 | 0.06 | 1.86 | 0.14 | *** | 1.84 | 0.65 | ** | 3.36 | 0.41 | *** | 4.60 | 0.29 | *** |
|  | 10x EC50 | 0.60 | 2.04 | 0.21 | *** | 2.04 | 0.32 | *** | 4.44 | 0.47 | *** | 5.44 | 0.43 | *** |
|  | 100x EC50 | 1.6 | 2.63 | 0.86 | *** | 2.61 | 0.63 | *** | 4.23 | 0.44 | *** | 5.52 | 1.45 | *** |
| 72 | 1x EC50 | 0.01 | 4.01 | 0.30 | *** | 2.24 | 0.25 | *** | 3.09 | 0.87 | *** | 3.17 | 0.68 | *** |
|  | 10x EC50 | 0.1 | 5.05 | 0.20 | *** | 2.96 | 0.43 | *** | 4.25 | 0.97 | *** | 3.79 | 0.73 | *** |

TABLE 3-continued

| | | PDK4 | | | CPT1b | | | UCP2 | | | UCP3 | | |
|---|---|---|---|---|---|---|---|---|---|---|---|---|---|
| Cpd | Dose (µM) | Induction | SD | t-Test | Induction | SD | t-Test | Induction | SD | t-Test | Induction | SD | t-Test |
| 100x EC50 | 1 | 5.64 | 0.52 | *** | 3.67 | 0.64 | *** | 4.31 | 1.10 | *** | 4.48 | 0.25 | *** |

Conclusion

Unexpectedly, the experimental data presented show that the compounds according to the invention have a metabolic action in murine myocytes by activation of PPARδ.

Example 8

In Vivo Evaluation in the E2/E2 Mouse, of the Antilipemic and HDL-Cholesterol Synthesis Stimulating Properties of the Compounds According to the Invention by Lipid Assays and Measurement of the Expression of Genes Involved in Lipid and Carbohydrate Metabolism and Energy Dissipation Principle The antilipemic and HDL-cholesterol synthesis stimulating properties of the compounds according to the invention were evaluated in vivo by assay of the plasma lipids, analysis of the distribution of cholesterol and of triglycerides in the various plasma lipoprotein fractions and measurement of the expression of the target genes of the PPARs in the liver and skeletal muscle after treatment of dyslipidemic E2/E2 mice with compound 2.

The murine model used is the ApoE2/E2 type mouse, a transgenic mouse for the E2 isoform of human apolipoprotein E (Sullivan P M et al., 1998). In humans, this apolipoprotein, a constituent of the low and very low density lipoproteins (LDL-VLDL), occurs in three isoforms E2, E3 and E4. The E2 form has a mutation on an amino acid in position 158, which greatly weakens the affinity of this protein for the LDL receptor. The clearance of the VLDLs is accordingly almost zero. There is then accumulation of low-density lipoproteins and mixed hyperlipidemia called type III (high cholesterol and triglycerides).

PPARα regulates the expression of genes involved in the transport of lipids (apolipoproteins such as Apo AI, Apo AII and Apo CIII, membrane transporters such as FAT) or the catabolism of lipids (ACOX1, CPT-I or CPT-II, enzymes of the β-oxidation of fatty acids). Treatment with PPARα activators is therefore translated, in humans and in rodents, into a decrease in the circulating levels of triglycerides and of free fatty acids. Measurement of the plasma lipids and free fatty acids after treatment with the compounds according to the invention is therefore an indicator of the agonistic character of the PPARs and therefore of the antilipemic character of the compounds according to the invention.

The PPARα agonistic properties of the molecules according to the invention previously measured in vitro must be reflected at the hepatic level in a modulation of the expression of the target genes directly under the control of the PPARα receptor. The genes that were investigated in this experiment are the genes coding for PDK4 (pyruvate dehydrogenase kinase isoform 4, enzyme of carbohydrate metabolism), for AcoX1 (the AcoX1 present in the mouse corresponds to the gene of ACO in humans (acyl co-enzyme A oxidase, a key enzyme in the mechanism of the β-oxidation of fatty acids)) and for Apo CIII (an apolipoprotein involved in lipid metabolism).

Treatment with PPARδ activators is reflected, in humans and in rodents, in an increase in plasma HDL-cholesterol level.

Analysis of the distribution of cholesterol after treatment with the compounds according to the invention can therefore demonstrate the HDL-cholesterol synthesis stimulating character of the compounds according to the invention.

The PPARδ agonistic properties of the molecules according to the invention previously measured in vitro should also be reflected, at the level of the skeletal muscle, in overexpression of the target genes directly under the control of the PPARδ receptor. The genes that were investigated in this experiment are the genes coding for PDK4 (pyruvate dehydrogenase kinase isoform 4, enzyme of carbohydrate metabolism) and UCP2 (uncoupling protein 2, mitochondrial transporter involved in thermoregulation).

Measurement of the transcriptional activity of the target genes of the PPARs after treatment with the compounds according to the invention is therefore also an indicator of the antilipemic character of the compounds according to the invention.

Protocol

Treatment of the Animals

Apo E2/E2 transgenic mice were kept under a cycle of light and darkness of 12/12 hours at a constant temperature of 20±3° C. After acclimation for one week, the mice were weighed and put into groups of 6 animals selected so that the distribution of their body weights and of their plasma lipid levels determined for the first time before the experiment are uniform. The test compounds were suspended in carboxymethylcellulose (Sigma C4888) and administered by intragastric force feeding, at a rate of once per day for 13 days at the chosen dose. The animals had free access to water and to food (standard diet). At the end of the experiment, the animals were anesthetized after fasting for 4 hours, a blood sample was taken using anticoagulant (EDTA), then the mice were weighed and euthanased. The plasma was separated by centrifugation at 3000 rev/min for 20 minutes, and the samples were stored at +4° C.

Samples of liver and of skeletal muscle tissue were taken and frozen immediately in liquid nitrogen and then stored at −80° C. for later analyses.

Analysis of the Distribution of Cholesterol in the Plasma Lipoprotein Fractions

The various lipid fractions (VLDL, LDL, HDL) of the plasma were separated by gel filtration chromatography. The concentrations of cholesterol and of triglycerides were then measured in each fraction by enzyme assays (bioMérieux-Lyon-France) following the supplier's recommendations.

Measurement of Plasma Total Cholesterol

The plasma concentrations of total cholesterol were measured by enzyme assays (bioMérieux-Lyon-France) following the supplier's recommendations.

Measurement of HDL-Cholesterol

The low-density lipoproteins (VLDL and LDL) were precipitated with phosphotungstate. The precipitate was removed by centrifugation. The HDL-cholesterol present in the supernatant was quantified by enzyme assays (bioMérieux-Lyon-France) following the supplier's recommendations.

Analysis of Gene Expression by Quantitative RT-PCR

Hepatic Tissue

The total RNA was extracted from fragments of liver using the NucleoSpin® 96 RNA kit (Macherey Nagel, Hoerdt, France) following the manufacturer's instructions.

Skeletal Tissue

The total RNA was extracted from fragments of gastrocnemius skeletal muscle using the RNeasy® Fibrous Tissue kit (Qiagen) following the manufacturer's instructions.

1 µg of total RNA (quantified by spectrophotometry) was then reverse-transcribed to complementary DNA by reaction for 1 hour at 37° C. in a total volume of 30 µl containing buffer 1× (Invitrogen), 1.5 mM of DTT, 0.18 mM of dNTPs (Promega), 200 ng of pdN6 (Amersham), 30 U of RNase inhibitor (Promega) and 1 µl of MMLV-RT (Invitrogen).

The quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 µl of diluted reverse transcription reaction mixture with a hybridization temperature of 60° C. Primer pairs specific to the PDK4, AcoX1, ApoCIII and UCP2 genes under investigation were used:

```
                                      (SEQ ID No. 11)
mPDK4: sense primer:    5'-TACTCCACTGCTCCAACACC
                           TG-3'
and
                                      (SEQ ID No. 12)
antisense primer        5'-GTTCTTCGGTTCCCTGCTTG-3'

(SEQ ID No. 3)
mACOX1: sense primer:   5'-GAAGCCAGCGTTACGAGGTG-3'
and
                                      (SEQ ID No. 4)
antisense primer:       5'-TGGAGTTCTTGGGACGGGTG-3'

(SEQ ID No. 5)
mApoCIII: sense primer: 5'-CTCTTGGCTCTCCTGGCATC-3'
and
                                      (SEQ ID No. 6)
antisense primer        5'-GCATCCTGGACCGTCTTGGA-3'

(SEQ ID No. 13)
mUCP2: sense primer:    5'-GTCGGAGATACCAGAGCACTGT
and                        CG-3'

(SEQ ID No. 14)
antisense primer:       5'-CACATCAACAGGGGAGGCGA-3'
```

In both cases (hepatic tissue and skeletal muscle tissue), the amount of fluorescence emitted is directly proportional to the amount of complementary DNA present at the start of the reaction and amplified during PCR. For each target investigated, a range is produced by successive dilutions of a pool constituted of a few microliters of various reverse-transcription reaction mixtures. The relative expression levels of each target are thus determined using the efficacy curves obtained with the points in the range.

The levels of expression of the genes of interest were then normalized, in the hepatic tissue relative to the level of expression of the reference gene 36B4 (whose specific primers are: sense primer: 5'-CATGCTCAACATCTCCCCCT-TCTCC-3' (SEQ ID No. 19) and antisense primer: 5'-GG-GAAGGTGTAATCCGTCTCCACAG-3' (SEQ ID No. 20)), and in the skeletal muscle tissue relative to the level of expression of the reference gene 18S (whose specific primers are: sense primer: 5'-CGGACACGGACAGGATTGACAG-3' (SEQ ID No. 21) and antisense primer: 5'-AATCTCGGGTG-GCTGAACGC-3' (SEQ ID No. 22).

The induction factor, i.e. the ratio of the relative signal (induced by the compound according to the invention) to the mean of the relative values of the control group, was then calculated for each sample. The higher this factor, the greater the gene expression activating character of the compound. The final result is represented as the mean of the induction values in each experimental group.

Results

FIG. 1-1 compares the plasma total cholesterol level after 7 and 13 days of treatment with compound 2 at 50 mpk against the levels obtained with control animals. Unexpectedly, plasma total cholesterol levels were lowered significantly by the treatment starting from 7 days.

FIG. 1-2 compares the plasma HDL-cholesterol level after 7 and 13 days of treatment with compound 2 at 50 mpk against the levels obtained with control animals. Unexpectedly, plasma HDL-cholesterol levels were increased significantly by the treatment starting from 7 days.

FIG. 1-3 presents the distribution of cholesterol in the various plasma lipoprotein fractions of the E2/E2 mice, controls or treated for 13 days with compound 2 at 50 mpk. Unexpectedly, the plasma HDL-cholesterol level was increased by the treatment with compound 2, administered at a dose of 50 mpk. We also observe a significant decrease in plasma levels of LDL and VLDL by the treatment with compound 2, administered at a dose of 50 mpk.

FIG. 1-4 presents the distribution of triglycerides in the various plasma lipoprotein fractions of the E2/E2 mice, controls or treated for 13 days with compound 2 at 50 mpk. Unexpectedly, the level of triglycerides present in the VLDL was lowered by the treatment with compound 2, administered at a dose of 50 mpk.

Analysis of Gene Expression by Quantitative RT-PCR

The inventors also demonstrated in vivo that the compounds according to the invention are regulators of the expression of target genes of the PPARs. The results presented in FIGS. 1-5 to 1-9 show that compound 2, administered at 50 mpk for 13 days to E2/E2 mice, induces a significant increase in hepatic expression of the genes coding for PDK4 (FIG. 1-5), for AcoX1 (FIG. 1-6), a decrease in hepatic expression of the gene coding for ApoCIII (FIG. 1-7) as well as a significant increase of the genes coding for PDK4 (FIG. 1-8) and UCP2 (FIG. 1-9) in the skeletal muscle. These genes code for enzymes involved in lipid and carbohydrate metabolism as well as energy dissipation and the fact that their expression is modulated by the compounds according to the invention reinforces the notion that these compounds are of major importance within the sphere of metabolic pathologies.

Conclusion

The experimental data presented show that the compounds according to the invention stimulate in vivo the synthesis of HDL-cholesterol while having an antilipemic effect (lowering of the plasma levels of cholesterol and of triglycerides). Moreover, the experimental data presented show that the compounds according to the invention modulate the expression of genes regulated by the activation of the PPARs that code for enzymes involved in lipid and carbohydrate metabolism and in the dissipation of energy.

Example 9

In Vivo Evaluation, in the C57B16 Mouse, of the Antilipemic and HDL Cholesterol Synthesis Stimulating Properties of the Compounds According to the Invention Principle The effect of compound 2, administered at dose effect, is evaluated in vivo in the C57B16 mouse after 14 days of treatment by the oral route. At the end of the treatment, the antilipemic effect of compound 2 is evaluated by measuring the plasma levels of total cholesterol, of HDL-cholesterol, of triglycerides and of free fatty acids.

It was shown that treatment with PPARδ activators is reflected, in humans and in rodents, in an increase in plasma HDL-cholesterol level.

The PPARδ agonistic properties of the molecules according to the invention previously measured in vitro should be reflected at the level of the skeletal muscle in an overexpression of the target genes directly under the control of the PPARδ receptor: the genes that were investigated in this experiment are the genes coding for UCP2 (uncoupling protein 2, mitochondrial transporter involved in thermoregulation) and PDK4 (pyruvate dehydrogenase kinase isoform 4, enzyme of carbohydrate metabolism).

Measurement of the transcriptional activity of the target genes of the PPARs after treatment with the compounds according to the invention is therefore also an indicator of the antilipemic character of the compounds according to the invention.

Protocol

Treatment of the Animals

Female C57B16 mice were kept under a cycle of light and darkness of 12/12 hours at a constant temperature of 20±3° C. After acclimation for one week, the mice were weighed and put into groups of 6 animals selected so that the distribution of their body weight, of their plasma lipid levels and of total cholesterol determined for the first time before the experiment, is uniform. The test compounds were suspended in carboxymethylcellulose (Sigma C4888) and administered by intragastric force feeding, at a rate of once per day for 14 days at the chosen dose. The animals had free access to water and to food (standard diet). At the end of the experiment, the animals were anesthetized after fasting for 4 hours. A blood sample was taken using anticoagulant (EDTA), then the mice were weighed and euthanased. The plasma was separated by centrifugation at 3000 rev/min for 20 minutes, and the samples were stored at +4° C.

Samples of skeletal muscle tissue were taken and frozen immediately in liquid nitrogen and then stored at −80° C. for later analyses.

Measurement of Plasma Total Cholesterol and Triglycerides

Plasma concentrations of total cholesterol and of triglycerides were measured by enzyme assays (bioMérieux-Lyon-France) following the supplier's recommendations.

Measurement of HDL-Cholesterol

Low-density lipoproteins (VLDL and LDL) were precipitated with phosphotungstate. The precipitate was removed by centrifugation. The HDL-cholesterol present in the supernatant was quantified by enzyme assays (bioMérieux-Lyon-France) following the supplier's recommendations.

Measurement of Plasma Free Fatty Acids

Plasma concentrations of free fatty acids were measured by enzyme assays (WACO chemicals) following the supplier's recommendations.

Analysis of Gene Expression by Quantitative RT-PCR

Skeletal Tissue

Total RNA was extracted from fragments of gastrocnemius skeletal muscle using the RNeasy® Fibrous Tissue kit (Qiagen) following the manufacturer's instructions.

1 μg of total RNA (quantified on the basis of the spectrophotometer reading) was then reverse-transcribed to complementary DNA by reaction for 1 hour at 37° C. in a total volume of 30 μl containing buffer 1× (Invitrogen), 1.5 mM of DTT, 0.18 mM of dNTPs (Promega), 200 ng of pdN6 (Amersham), 30 U of RNase inhibitor (Promega) and 1 μl of MMLV-RT (Invitrogen).

Quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 μl of diluted reverse transcription reaction mixture with a hybridization temperature of 60° C. Primer pairs specific to the genes under investigation were used:

```
                                        (SEQ ID No. 11)
mPDK4: sense primer:  5'-TACTCCACTGCTCCAACACCTG-3'
and
                                        (SEQ ID No. 12)
antisense primer      5'-GTTCTTCGGTTCCCTGCTTG-3'

(SEQ ID No. 13)
mUCP2: sense primer:  5'-GTCGGAGATACCAGAGCACTGT
                         CG-3'
and
                                        (SEQ ID No. 14)
antisense primer:     5'-CACATCAACAGGGGAGGCGA-3'
```

The amount of fluorescence emitted is directly proportional to the amount of complementary DNA present at the start of the reaction and amplified during PCR. For each target investigated, a range is produced by successive dilutions of a pool constituted of a few microliters of various reverse transcription reaction mixtures. The relative expression levels of each target are thus determined using the efficacy curves obtained with the points in the range.

The levels of expression of the genes of interest were then normalized relative to the level of expression of the reference gene 18S (whose specific primers are:

```
                                        (SEQ ID No. 21)
sense primer:         5'-CGGACACGGACAGGATTGACAG-3'
and
                                        (SEQ ID No. 22))
antisense primer:     5'-AATCTCGGGTGGCTGAACGC-3'.
```

The induction factor, i.e. the ratio of the relative signal (induced by the compound according to the invention) to the mean of the relative values of the control group, was then calculated for each sample. The higher this factor, the greater the gene expression activating character of the compound. The final result is represented as the mean of the induction values in each experimental group.

Results

In general, the results obtained show that compound 2 improves the lipid profile of the C57B16 mice treated for 14 days.

FIG. 2-1 compares the plasma total cholesterol levels after 14 days of treatment with compound 2, administered at 1, 5, 10 and 50 mpk against the levels obtained with the control animals. Unexpectedly, the plasma total cholesterol levels were significantly increased at 5 and 50 mpk.

FIG. 2-2 compares the plasma HDL-cholesterol levels after 14 days of treatment with compound 2, administered at 1, 5, 10 and 50 mpk against the levels obtained with the control animals. Unexpectedly, the plasma HDL-cholesterol levels were significantly increased by the treatment in a dose-dependent manner starting from 1 mpk.

FIG. 2-3 compares the plasma triglyceride levels after 14 days of treatment with compound 2, administered at 1, 5, 10 and 50 mpk against the levels obtained with the control animals. Unexpectedly, the plasma triglyceride levels showed a dose-dependent decrease, with a significant effect at 50 mpk.

FIG. 2-4 compares the plasma levels of free fatty acids after 14 days of treatment with compound 2, administered at 1, 5, 10 and 50 mpk against the levels obtained with the control animals. Unexpectedly, the plasma levels of free fatty acids were lowered significantly starting from 10 mpk.

Analysis of Gene Expression by Quantitative RT-PCR

The inventors also demonstrated that the compounds according to the invention are, in vivo, regulators of the expression of target genes of the PPARs. The results presented in FIGS. 2-5 and 2-6 show that compound 2, administered at 50 mpk for 14 days to C57Bl6 mice, induces a significant increase in expression of the genes coding for PDK4 (FIG. 2-5) and UCP2 (FIG. 2-6) in skeletal muscle. These genes code for proteins involved in carbohydrate metabolism and the dissipation of energy and the fact that their expression is modulated by the compounds according to the invention reinforces the notion that these compounds are of major importance within the sphere of metabolic pathologies.

Conclusion

Unexpectedly, the experimental data show that the compounds according to the invention stimulate in vivo the synthesis of HDL-cholesterol while having an antilipemic effect (lowering the plasma triglyceride levels and of free fatty acids). Moreover, the experimental data show that the compounds according to the invention modulate the expression of genes regulated by the activation of the PPARs in the skeletal muscle, said genes coding for enzymes involved in carbohydrate metabolism and energy dissipation.

Example 10

In Vivo Evaluation, in the C57Bl6 Mouse, of the HDL Cholesterol Synthesis Stimulating Properties of the Compounds According to the Invention by Lipid Assays and Measurement of the Expression of Genes Involved in Lipid and Carbohydrate Metabolism and Energy Dissipation Principle The effect of the compounds according to the invention was evaluated in vivo in the C57Bl6 mouse after 14 days of treatment by the oral route. At the end of the treatment, the distribution of cholesterol in the various plasma lipoprotein fractions was determined. This was compared with the profile obtained in the control animals (not treated with the compounds according to the invention). The effect of the compounds according to the invention was evaluated in the C57Bl6 mouse by measuring the plasma levels of total cholesterol and of HDL-cholesterol after 14 days of treatment by the oral route. These levels were compared with those obtained with control animals (not treated with the compounds according to the invention). The measured difference provides evidence of the antilipemic effect of the compounds according to the invention.

It was shown that treatment with PPARδ activators is reflected, in humans and in rodents, in an increase in the plasma HDL-cholesterol level.

The PPARδ agonistic properties of the molecules according to the invention previously measured in vitro should be reflected at the level of the skeletal muscle in overexpression of the target genes directly under the control of the PPARδ receptor: the genes that were investigated in this experiment are the genes coding for PDK4 (enzyme of carbohydrate metabolism), CPT1b (enzyme of lipid metabolism), UCP2 and UCP3 (mitochondrial transporters involved in thermoregulation).

Measurement of the transcriptional activity of the target genes of the PPARs after treatment with the compounds according to the invention is therefore also an indicator of the antilipemic character of the compounds according to the invention.

Protocol

Treatment of the Animals

Female C57Bl6 mice were kept under a cycle of light and darkness of 12/12 hours at a constant temperature of 20±3° C. After acclimation for one week, the mice were weighed and put into groups of 6 animals selected so that the distribution of their body weight, of their plasma lipid levels and of total cholesterol determined for the first time before the experiment, is uniform. The test compounds were suspended in carboxymethylcellulose (Sigma C4888) and administered by intragastric force feeding, at a rate of once per day for 14 days at the chosen dose. The animals had free access to water and to food (standard diet). At the end of the experiment, the animals were anesthetized after fasting for 4 hours, a blood sample was taken using anticoagulant (EDTA), then the mice were weighed and euthanased. The plasma was separated by centrifugation at 3000 rev/min for 20 minutes, and the samples were stored at +4° C.

Samples of skeletal muscle tissue were taken and frozen immediately in liquid nitrogen and then stored at −80° C. for later analyses.

Measurement of Plasma Total Cholesterol

The plasma concentrations of total cholesterol were measured by enzyme assays (bioMérieux-Lyon-France) following the supplier's recommendations.

Measurement of HDL-Cholesterol

The low-density lipoproteins (VLDL and LDL) were precipitated with phosphotungstate. The precipitate was removed by centrifugation. The HDL-cholesterol present in the supernatant was quantified by enzyme assays (bioMérieux-Lyon-France) following the supplier's recommendations.

Analysis of the Distribution of Cholesterol in the Plasma Lipoprotein Fractions

The various lipid fractions (VLDL, LDL, HDL) of the plasma were separated by gel filtration chromatography. The concentrations of cholesterol were then measured in each fraction by enzyme assays (bioMérieux-Lyon-France) following the supplier's recommendations.

Analysis of Gene Expression by Quantitative RT-PCR

The total RNA was extracted from fragments of gastrocnemius skeletal muscle using the RNeasy® Fibrous Tissue kit (Qiagen) following the manufacturer's instructions.

1 µg of total RNA (quantified based on the spectrophotometer reading) was then reverse-transcribed to complementary DNA by reaction for 1 hour at 37° C. in a total volume of 30

μl containing buffer 1× (Invitrogen), 1.5 mM of DTT, 0.18 mM of dNTPs (Promega), 200 ng of pdN6 (Amersham), 30 U of RNase inhibitor (Promega) and 1 μl of MMLV-RT (Invitrogen).

The quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 μl of diluted reverse transcription reaction mixture with a hybridization temperature of 60° C. Primer pairs specific to the genes under investigation were used:

```
                                        (SEQ ID No. 11)
mPDK4: sense primer: 5'-TACTCCACTGCTCCAACACCTG-3'
and (SEQ ID No. 12)
antisense primer     5'-GTTCTTCGGTTCCCTGCTTG-3'

(SEQ ID No. 7)
mCPT1b: sense primer: 5'-GGACTGAGACTGTGCGTTCCTG-3'
and (SEQ ID No. 8)
antisense primer:    5'-AGTGCTTGGCGGATGTGGTT-3'

(SEQ ID No. 13)
mUCP2: sense primer: 5'-GTCGGAGATACCAGAGCACTGT
                        CG-3'
and (SEQ ID No. 14)
antisense primer:    5'-CACATCAACAGGGGAGGCGA-3'

(SEQ ID No. 15)
mUCP3: sense primer: 5'-GCACCGCCAGATGAGTTTTG-3'
and (SEQ ID No. 16)
antisense primer:    5'-GACGCTGGAGTGGTCCGCTC-3'
```

The amount of fluorescence emitted is directly proportional to the amount of complementary DNA present at the start of the reaction and amplified during PCR. For each target investigated, a range is produced by successive dilutions of a pool constituted of a few microliters of various reverse transcription reaction mixtures. The relative expression levels of each target are thus determined using the efficacy curves obtained with the points in the range.

The levels of expression of the genes of interest were then normalized relative to the level of expression of the reference gene 18S (whose specific primers are:

```
                                        (SEQ ID No. 21)
sense primer:        5'-CGGACACGGACAGGATTGACAG-3'
and (SEQ ID No. 22))
antisense primer:    5'-AATCTCGGGTGGCTGAACGC-3'.
```

The induction factor, i.e. the ratio of the relative signal (induced by the compound according to the invention) to the mean of the relative values of the control group, was then calculated for each sample. The higher this factor, the greater the gene expression activating character of the compound. The final result is represented as the mean of the induction values in each experimental group.

Results

In general, the results obtained show that compounds 4 and 7 according to the invention improve the lipid profile of the C57Bl6 mice treated for 14 days.

FIG. 3-1 compares the plasma total cholesterol level after 14 days of treatment with compounds 4 and 7 according to the invention, administered at 50 mpk against the levels obtained with the control animals. Unexpectedly, the plasma total cholesterol levels were significantly increased by the treatment with compounds 4 and 7 at 50 mpk.

FIG. 3-2 compares the plasma HDL-cholesterol level after 14 days of treatment with compounds 4 and 7 according to the invention, administered at 50 mpk against the levels obtained with the control animals. Unexpectedly, the plasma HDL-cholesterol levels were significantly increased by the treatment with compound 4 at 50 mpk. The treatment with compound 7 according to the invention at 50 mpk also induced a nonsignificant increase in the HDL-cholesterol level.

FIG. 3-3 presents the distribution of cholesterol in the plasma lipoprotein fractions of the C57Bl6 mice, controls or treated for 14 days with compounds 4 and 7 at 50 mpk. Unexpectedly, the plasma HDL-cholesterol level was increased by the treatments with compounds 4 and 7.

Analysis of Gene Expression by Quantitative RT-PCR

The inventors also demonstrated that the compounds according to the invention are, in vivo, regulators of the expression of target genes of the PPARs. The results presented in FIGS. 3-4 to 3-7 show that compounds 4 and 7 according to the invention, administered at 50 mpk for 14 days to C57Bl6 mice, induce a significant increase of the genes coding for PDK4 (FIG. 3-4), CPT1b (FIG. 3-5), UCP2 (FIG. 3-6) and UCP3 (FIG. 3-7) in skeletal muscle. These genes code for enzymes strongly involved in lipid and carbohydrate metabolism and the dissipation of energy, and the fact that their expression is modulated by the compounds according to the invention reinforces the notion that these compounds are potentially of major importance within the sphere of metabolic pathologies.

Conclusion

Unexpectedly, the experimental data presented show that the compounds according to the invention stimulate in vivo the synthesis of HDL-cholesterol. Moreover, the experimental data presented show that, in the skeletal muscle, the compounds according to the invention modulate the expression of genes regulated by the activation of the PPARs that code for enzymes strongly involved in carbohydrate metabolism and energy dissipation.

Example 11

In Vivo Evaluation, in the db/db Mouse, of the Antilipemic, Antidiabetic and PPAR-Activating Properties of the Compounds According to the Invention Principle The effect of the compounds according to the invention is evaluated in vivo in the db/db mouse by measuring the plasma triglycerides and insulinemia after 28 days of treatment with compound 2 by the oral route. These levels are compared with those obtained with control animals (not treated with the compound according to the invention). The measured difference provides evidence of the antilipemic effect and effect on insulin resistance of the compound according to the invention.

The efficacy of the compound according to the invention is also evaluated by measuring, in the hepatic and muscle tissues, the expression of genes involved in carbohydrate and lipid metabolism, and the dissipation of energy. The levels of expression of each gene are normalized relative to the level of expression of the reference genes 36B4 in the liver and 18S in the skeletal muscle. The induction factor, i.e. the ratio of the relative signal (induced by the compound according to the invention) to the mean of the relative values of the control group, is then calculated. The higher this factor, the greater the gene expression activating character of the compound. The final result is represented as the mean of the induction values in each experimental group.

Protocol

Treatment of the Animals

Female db/db mice were kept under a cycle of light and darkness of 12/12 hours at a constant temperature of 20±3° C. After acclimation for one week, the mice were weighed and put in groups of 8 animals selected so that the distribution of their body weight and of their plasma lipid levels, determined for the first time before the experiment, are uniform. The test compounds were suspended in carboxymethylcellulose (Sigma C4888) and administered by intragastric force feeding, at a rate of once per day for 28 days at the chosen dose. The animals had free access to water and to food (standard diet). The food intake and the weight gain are recorded throughout the experiment. At the end of the experiment, the animals were anesthetized after fasting for 4 hours, a blood sample was taken using anticoagulant (EDTA), then the mice were weighed and euthanased. The plasma was separated by centrifugation at 3000 rev/min for 20 minutes, and the samples were stored at +4° C.

Samples of hepatic and muscle tissues were taken and frozen immediately in liquid nitrogen and then stored at −80° C. for later analyses.

Measurement of Plasma Level of Triglycerides

The plasma concentrations of triglycerides were measured by enzyme assays (bioMérieux-Lyon-France) following the supplier's recommendations.

Measurement of Plasma Insulinemia

The murine insulin is assayed by the ELISA method (using the INSCR020 kit from the supplier Crystal chem). A mouse antiinsulin antibody is fixed on a microplate. The serum to be assayed for insulin is then deposited on this plate. A guinea pig antiinsulin antibody will recognize the insulin/mouse monoclonal antiinsulin antibody complex and attach to it. Finally a peroxidase-labeled anti-guinea pig antibody is added and attaches to the guinea pig antiinsulin antibody.

Colorimetric reaction is carried out by addition of the enzyme OPD (ortho phenyl diamine) to the substrate. The intensity of the coloration is proportional to the amount of insulin present in the sample.

Analysis of Gene Expression by Quantitative RT-PCR

Hepatic Tissue

The total RNA was extracted from fragments of liver using the NucleoSpin® 96 RNA kit (Macherey Nagel, Hoerdt, France) following the manufacturer's instructions.

Muscle Tissue

The total RNA was extracted from fragments of muscle using the RNeasy® Fibrous Tissue kit (Qiagen) following the manufacturer's instructions.

1 µg of total RNA (quantified by UV spectrophotometry) was then reverse-transcribed to complementary DNA by reaction for 1 hour at 37° C. in a total volume of 30 µl containing buffer 1× (Invitrogen), 1.5 mM of DTT, 0.18 mM of dNTPs (Promega), 200 ng of pdN6 (Amersham), 30 U of RNase inhibitor (Promega) and 1 µl of MMLV-RT (Invitrogen).

The quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 µL of diluted reverse-transcription reaction mixture with a hybridization temperature of 60° C. The primer pairs specific to the genes under investigation are as follows.

```
                                            (SEQ ID No. 11)
mPDK4: sense primer:  5'-TACTCCACTGCTCCAACACCTG-3'
and
                                            (SEQ ID No. 12)
antisense primer      5'-GTTCTTCGGTTCCCTGCTTG-3'

(SEQ ID No. 3)
mACOX1: sense primer: 5'-GAAGCCAGCGTTACGAGGTG-3'
and
                                            (SEQ ID No. 4)
antisense primer:     5'-TGGAGTTCTTGGGACGGGTG-3'

(SEQ ID No. 7)
mCPT1b: sense primer: 5'-GGACTGAGACTGTGCGTTCCTG-3'
and
                                            (SEQ ID No. 8)
antisense primer:     5'-AGTGCTTGGCGGATGTGGTT-3'

(SEQ ID No. 15)
mUCP3: sense primer:  5'-GCACCGCCAGATGAGTTTTG-3'
and
                                            (SEQ ID No. 16)
antisense primer:     5'-GACGCTGGAGTGGTCCGCTC-3'
```

The amount of fluorescence emitted is directly proportional to the amount of complementary DNA present at the start of the reaction and amplified during PCR. For each target investigated, a range is produced by successive dilutions of a pool constituted of a few microliters of various reverse-transcription reaction mixtures. The relative expression levels of each target are thus determined using the efficacy curves obtained with the points in the range.

The levels of expression of the genes of interest were then normalized, in the hepatic tissue relative to the level of expression of the reference gene 36B4 (whose specific primers are: sense primer: 5'-CATGCTCAACATCTCCCCCT-TCTCC-3' (SEQ ID No. 19) and antisense primer: 5'-GG-GAAGGTGTAATCCGTCTCCACAG-3' (SEQ ID No. 20)), and in the muscle tissue relative to the level of expression of the reference gene 18S (whose specific primers are: sense primer: 5'-CGGACACGGACAGGATTGACAG-3' (SEQ ID No. 21) and antisense primer: 5'-AATCTCGGGTGGCT-GAACGC-3' (SEQ ID No. 22)). The induction factor was calculated for each sample. The higher this factor, the greater the gene expression activating character of the compound. The final result is represented as the mean of the induction values in each experimental group.

Results

Measurement of Plasma Triglyceride Levels

FIG. 4-1 compares the plasma triglyceride levels after 28 days of treatment with compound 2, administered at 50 mpk, against the levels obtained for the control animals. Unexpectedly, the triglyceride level is lowered significantly by the treatment with the compound according to the invention.

Measurement of Insulinemia

FIG. 4-2 compares the plasma levels of insulin after 28 days of treatment with compound 2, administered at 50 mpk, against the levels obtained with the control animals. Unexpectedly, insulinemia is lowered significantly after 28 days of treatment of the animals with compound 2.

Analysis of Gene Expression by Quantitative RT-PCR

The inventors also demonstrated in vivo that the compounds according to the invention are regulators of the expression of target genes of the PPARs. The results presented in FIGS. 4-3 and 4-4 show that compound 2, administered at 50 mpk for 28 days in db/db mice, induces a significant increase in expression of the genes coding for PDK4 (FIG. 4-3) and for ACOX1 (FIG. 4-4) in the liver. These genes code for enzymes involved in lipid and carbohydrate metabolism, and are recognized as being target genes of PPARα in the liver. The fact that their expression is modulated by compound 2 reinforces the notion that this compound is of major importance in connection with metabolic pathologies. Furthermore, the inventors also demonstrated in vivo that compound 2 is a regulator of the expression of target genes of PPARδ in skeletal muscle. The results presented in FIGS. 4-5 to 4-7 show that compound 2 administered at 50 mpk for 28 days in db/db mice, induces a significant increase in expression of the genes coding for CPT1b (FIG. 4-5), PDK4 (FIG. 4-6) and UCP2 (FIG. 4-7) in the skeletal muscle.

These genes code for proteins involved in lipid and carbohydrate metabolism and thermoregulation, and are known to be target genes of PPARδ in the muscle. The fact that their expression is modulated by compound 2 reinforces the notion that this compound is of major importance in connection with metabolic pathologies.

Conclusion

Unexpectedly, the experimental data presented show that compound 2 possesses antilipemic and antidiabetic properties in the db/db mouse. Moreover, the experimental data show that the compounds according to the invention modulate the expression of genes regulated by the activation of the PPARs that code for enzymes involved in lipid and carbohydrate metabolism and thermoregulation.

Example 12

In Vitro Evaluation of the Metabolic Properties of the Compounds According to the Invention in a Murine Myocyte Model Principle The stimulating effects of the compounds according to the invention were evaluated by measuring the β-oxidation of fatty acids by murine myocytes pretreated with the compounds according to the invention for 24 hours. The more the induction of the β-oxidation of fatty acids is increased, the greater the stimulating action of the compound according to the invention on metabolism in the muscle cells.

The objective is to measure the amount of tritiated water formed during the mitochondrial oxidation of $^3$H-labeled fatty acids.

Protocol

Differentiation of the C2C12 Cells to Myocytes

The C2C12 murine cell line (obtained from ECACC) is cultivated in DMEM medium (Gibco; 41965-039) with addition of 1% L-glutamine (Gibco; 25030), 1% penicillin/streptomycin (VWR; BWSTL0022/100) and 10% decomplemented fetal calf serum (FCS. Gibco; 10270-106).

The cells are seeded on 48-well plates at a density of $25 \cdot 10^3$ cells/well. At confluence, the medium is replaced with a differentiating medium (basal medium with addition of 2% of horse serum (Gibco; 26050-088)), then incubated at 37° C. and 5% $CO_2$ for 4 days in order to differentiate them to myocytes.

Treatment

After 4 days of differentiation, the cells are treated with the compounds according to the invention added to the culture medium for differentiation. Compound 2 was tested by dose effect from 0.01 to 1 µM, and the others were tested at a dose of 1 µM. The compounds according to the invention are dissolved in dimethylsulfoxide (DMSO, Sigma; D5879). The cells are treated for 24 h at 37° C., 5% $CO_2$. The effect of the compounds according to the invention is compared with the effect of DMSO alone.

Measurement of β-Oxidation

After 24 hours of treatment, the culture medium is replaced with a DMEM medium 1 g/L glucose (Gibco; 21885-025) with addition of 1% L-glutamine (Gibco; 25030), 1% penicillin/streptomycin (VWR; BWSTL0022/100) and 1 mM L-carnitine (Alfa Aefar; A 17618). The cells are then incubated with tritiated palmitate/BSA complex (0.1 mM) at 37° C. in the presence of 5% $CO_2$. The reaction is stopped after 1, 2 and 3 hours and the proteins are precipitated with distribution of TCA 10%.

Firstly, tritium counting is performed on 100 µL of precipitated culture supernatant.

Secondly, 50 µL of precipitated supernatant is evaporated for 2 days, then the residual tritium is measured in order to evaluate the amount of tritiated palmitate not converted to water.

A standard range is prepared by successive dilutions of the tritiated palmitate/BSA complex in order to determine the amount of palmitate converted to water. For each time of the kinetics, 1 h, 2 h and 3 h, the amount in nanomoles of oxidized palmitate is calculated by linear regression. The areas under the curve are determined for each set of conditions and the results are normalized with DMSO.

The final result is represented as the mean of the induction values in each experimental group.

Results

The inventors also demonstrated in vitro, on myocytes, that the compounds according to the invention have stimulating effects on the β-oxidation of fatty acids. The results presented in FIG. 5 show that compound 2, in dose effect starting from 0.01 µM and compounds 4 and 11 according to the invention, at 1 µm, induce a significant increase in β-oxidation of fatty acids in murine myocytes.

Conclusion

Unexpectedly, the experimental data presented show that the compounds according to the invention have a metabolic action in the murine myocytes, inducing the catabolism of fatty acids.

Example 13

In Vitro Evaluation of the Reverse Cholesterol Transport-Activating Properties of the Compounds According to the Invention Principle The effect of the compounds according to the invention on reverse cholesterol transport was evaluated by measuring the expression of the ABCA1 gene (ATP-binding cassette, subfamily A, member 1; membrane transporter involved in the efflux of cholesterol) in human macrophages. The more the expression of ABCA1 is increased, the greater the stimulating action of the compound according to the invention on reverse cholesterol transport.

Protocol

Differentiation of the THP-1 Cells to Macrophages

The THP1 human monocyte line (obtained from ATCC) is cultivated in RPMI1640 medium with addition of 25 mM Hepes (Gibco; 42401-018), 1% glutamine (Gibco; 25030-24), 1% penicillin/streptomycin (Biochrom AG; A 2213) and 10% decomplemented fetal calf serum (FCS. Gibco; 26050-088).

The cells are seeded on 24-well plates (Primaria BD Falcon) at a density of 3·10⁵ cells/well and incubated at 37° C. and 5% $CO_2$ for 72 h in the presence of 30 ng/ml of phorbol 12-myristate 13-acetate (PMA) in order to differentiate them to macrophages.

Treatment

The differentiating medium is drawn off and replaced with the treatment medium (same composition as the culture medium but without fetal calf serum and with 1% of ultroser (Pall Life Science; P/N267051)).

The compounds according to the invention are dissolved in dimethylsulfoxide (DMSO, Fluka; 41640). Compound 2 was tested at a dose of 1 µM. The cells are treated for 24 h at 37° C., 5% CO2. The effect of the compounds according to the invention is compared with the effect of DMSO alone.

Extraction of the RNAs, Reverse Transcription and Quantitative PCR

After treatment, the total RNA is extracted from the cells using the NucleoSpin® 96 RNA kit (Macherey Nagel, Hoerdt, France) following the manufacturer's instructions.

1 µg of total RNA (quantified based on the spectrophotometer reading) was then reverse-transcribed to complementary DNA by reaction for 1 hour at 37° C. in a total volume of 30 µl containing buffer 1× (Invitrogen), 1.5 mM of DTT, 0.18 mM of dNTPs (Promega), 200 ng of pdN6 (Amersham), 30 U of RNase inhibitor (Promega) and 1 µl of MMLV-RT (Invitrogen).

The quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 µl of diluted reverse transcription reaction mixtures with a hybridization temperature of 60° C. Primer pairs specific to the gene under investigation were used:

```
                                          (SEQ ID No. 1)
hABCA1: sense primer:   5'-CTGAGGTTGCTGCTGTGGAAG-3'

(SEQ ID No. 2)
antisense primer:       5'-CATCTGAGAACAGGCGAGCC-3'
```

The amount of fluorescence emitted is directly proportional to the amount of complementary DNA present at the start of the reaction and amplified during PCR. For each target investigated, a range is produced by successive dilutions of a pool constituted of a few µl of different reverse transcription reaction mixtures. The relative expression levels of each target are thus determined using the efficacy curves obtained with the points in the range.

The levels of expression of the genes of interest were then normalized, relative to the level of expression of the reference gene 36B4 (whose specific primers are: sense primer: 5'-CATGCTCAACATCTCCCCCTTCTCC-3' (SEQ ID No. 19) and antisense primer: 5'-GGGAAGGTGTAATCCGTCTCCA-CAG-3' (SEQ ID No. 20)).

The induction factor, i.e. the ratio of the relative signal (induced by the compound according to the invention) to the mean of the relative values of the control group, was then calculated. The higher this factor, the greater the gene expression activating character of the compound. The final result is represented as the mean of the induction values in each experimental group.

Results

The inventors demonstrated that, in vitro in human macrophages, the compounds according to the invention have a stimulating action on reverse cholesterol transport. The results presented in FIG. 6-1 show that compound 2, at 1 µm, induces a significant increase in expression of the gene coding for ABCA1 in human macrophages. The results presented in FIG. 6-2 show that compounds 4 and 7 according to the invention, at 1 µm and 300 nM respectively, induce a significant increase in expression of the gene coding for ABCA1 in human macrophages.

Conclusion

Unexpectedly, the experimental data presented show that the compounds according to the invention stimulate reverse cholesterol transport.

Example 14

In Vitro Evaluation of the Antiinflammatory Properties of the Compounds According to the Invention in a Model of Human Monocytes Principle The antiinflammatory effects of the compounds according to the invention were evaluated by measuring the secretion and expression of macrophages chemoattractant protein (MCP1) and of matrix metalloproteinase 9 (MMP9) by monocytes treated with the compounds according to the invention for 24 hours and stimulated with PMA (phorbol 12-myristate 13-acetate, which causes an inflammatory response of the cells). The more the amount of MCP1 secreted is reduced, the greater the inhibitory action of the compounds according to the invention on the inflammatory reaction. Similarly, the more the expression of the genes coding for MCP1 and MMP9 is inhibited, the greater the antiinflammatory effect of the compounds according to the invention.

Protocol

Culture of the THP-1 Cells

The THP1 human monocyte line (obtained from ATCC) is cultivated in RPMI1640 medium with addition of 25 mM Hepes (Gibco; 42401-018), 1% glutamine (Gibco; 25030-24) 1% penicillin/streptomycin (Biochrom AG; A 2213) and 10% decomplemented fetal calf serum (FCS. Gibco; 10270-106).

Treatment

The cells are seeded on 24-well plates (Primaria BD Falcon) at a density of 8.70·10⁵ cells/well in the treatment medium (same composition as the culture medium but with 0.2% of decomplemented fetal calf serum) and in the presence of 5 ng/mL of phorbol 12-myristate 13-acetate (PMA) for inducing the inflammatory response.

The compounds according to the invention were tested at 0.1, 0.3 and/or at 1 µm, and dissolved in dimethylsulfoxide (DMSO, Fluka; 41640). The cells are treated for 24 h at 37° C., 5% $CO_2$. The effect of the compound according to the invention is compared with the effect of DMSO alone.

Measurement of MCP1 Secretion

The treatment medium is recovered and the concentration of MCP1 is measured using the ELISA kit "Human MCP1 Elisa set" (BD OptEIA; 555179) following the manufacturer's recommendations.

A human antiMCP1 monoclonal antibody is fixed on a plate, then the supernatants, containing the MCP1 secreted by the cells, are distributed. A biotinylated antiMCP1 antibody will then attach to the complex. A third antibody, conjugated and coupled to a peroxidase enzyme, makes it possible, in the presence of substrate, to initiate an enzymatic reaction, the result of which is a coloration that is proportional to the amount of MCP1 fixed, and can be measured by spectrophotometry. A range is produced starting from a known concentration point, making it possible to calculate the MCP1 concentration in each sample.

The induction factor, i.e. the ratio of the signal induced by the compound according to the invention to the signal of the control group, was then calculated. The lower this factor, the greater the inhibitory effect of the compound on MCP1 secretion. The final result is represented as the mean of the induction values of each experimental group.

Extraction of the RNAs, Reverse Transcription and Quantitative PCR

After treatment, the total RNA is extracted from the cells using the NucleoSpin® 96 RNA kit (Macherey Nagel, Hoerdt, France) following the manufacturer's instructions.

1 µg of total RNA (quantified based on the reading of the UV spectrophotometer) was then reverse-transcribed to complementary DNA by reaction for 1 hour at 37° C. in a total volume of 30 µl containing buffer 1× (Invitrogen), 1.5 mM of DTT, 0.18 mM of dNTPs (Promega), 200 ng of pdN6 (Amersham), 30 U of RNase inhibitor (Promega) and 1 µl of MMLV-RT (Invitrogen).

The quantitative PCR experiments were carried out using the MyiQ Single-Color Real-Time PCR Detection System (Biorad, Marnes-la-Coquette, France) and were performed using the iQ SYBR Green Supermix kit following the supplier's recommendations, in 96-well plates, on 5 µl of diluted reverse-transcription reaction mixture with a hybridization temperature of 60° C. Primer pairs specific to the MCP1 and MMP9 genes under investigation were used:

```
hMCP1:  sense primer:      5'-AGGAAGATCTCAGTGCAGAGG-3'   (SEQ ID No. 9)
and
        antisense primer:  5'-AGTCTTCGGAGTTTGGGTTTG-3'    (SEQ ID No. 10)

hMMP9:  sense primer:      5'-TGGCACCACCACAACATCAC-3'    (SEQ ID No. 17)
and
        antisense primer:  5'-ACCACAACTCGTCATCGTCG-3'    (SEQ ID No. 18)
```

The amount of fluorescence emitted is directly proportional to the amount of complementary DNA present at the start of the reaction and amplified during PCR. For each target investigated, a range is produced by successive dilutions of a pool constituted of a few microliters of various reverse-transcription reaction mixtures. The relative expression levels of each target are thus determined using the efficacy curves obtained with the points in the range.

The levels of expression of the genes of interest were then normalized, in the hepatic tissue relative to the level of expression of the reference gene 36B4 (whose specific primers are: sense primer: 5'-CATGCTCAACATCTCCCCCT-TCTCC-3' (SEQ ID No. 19) and antisense primer: 5'-GG-GAAGGTGTAATCCGTCTCCACAG-3' (SEQ ID No. 20)). The induction factor, i.e. the ratio of the relative signal (induced by the compound according to the invention) to the mean of the relative values of the control group, was then calculated. The lower this factor, the greater the inhibitory effect of the compound on gene expression. The final result is represented as the mean of the induction values in each experimental group.

Results

The inventors also demonstrated, on monocytes in vitro, that the compounds according to the invention have antiinflammatory effects. The results presented in FIG. 7-1 show that compounds 7 and 11 according to the invention, at 1 µm, induce a significant decrease in secretion of MCP1 in human monocytes. The results presented in FIGS. 7-2 and 7-3 show that compounds 7 and 11 according to the invention, at 1 µm, induce a significant decrease in expression of MCP1 and MMP9 in human monocytes. The results presented in FIG. 7-4 show that compound 2, at 0.1 and 0.3 µm, induces a significant decrease in expression of MCP1 in human monocytes.

Conclusion

Unexpectedly, the experimental data presented show that the compounds according to the invention have an antiinflammatory action in monocytes stimulated with PMA.

GENERAL CONCLUSION

The inventors have demonstrated that the compounds according to the invention have HDL-cholesterol synthesis stimulating properties, antilipemic properties (lowering the plasma triglyceride and free fatty acids levels) as well as antidiabetic properties. Moreover, the inventors demonstrated that the compounds according to the invention are regulators of the expression of genes coding for enzymes involved in lipid and carbohydrate metabolism and energy dissipation. These results, obtained in vivo, provide evidence of the therapeutic potential of the compounds according to the invention with respect to pathologies associated with metabolic syndrome, such as dyslipidemias, obesity, atherosclerosis etc.

Furthermore, the inventors have demonstrated the PPAR activating character in various cellular models, notably reflected in regulation of the expression of genes coding for enzymes involved in the metabolism of lipids and carbohydrates, and in thermoregulation, and in an increase in catabolism of the fatty acids, as well as antiinflammatory action.

REFERENCES de la Monte S M, et al., *Therapeutic rescue of neurodegeneration in experimental type 3 diabetes: Relevance to Alzheimer's disease*, J Alzheimers Dis, 2006, 10 (1), 89-109

Fox-Tucker J, *The Cardiovascular Market Outlook to 2010*, BUSINESS INSIGHTS REPORTS, 2005, 1-174

Gross B, et al., *Peroxisome Proliferator-Activated Receptor b/d: A novel target for the reduction of atherosclerosis*, DRUG DISCOVERY TODAY: THERAPEUTIC STRATEGIES, 2005, 2 (3), 237-243

International Atherosclerosis Society, *Harmonized Clinical. Guidelines on Prevention of Atherosclerotic Vascular Disease*, 2003, Kota B P, et al., *An overview on biological mechanisms of PPARs*, Pharmacol Res, 2005, 51 (2), 85-94

Lefebvre P, et al., *Sorting out the roles of PPARalpha in energy metabolism and vascular homeostasis*, J Clin Invest, 2006, 116 (3), 571-580

Lehrke M and Lazar M A, *The many faces of PPARgamma*, Cell, 2005, 123 (6), 993-9

Liu Y and Miller A, *Ligands to peroxisome proliferator-activated receptors as therapeutic options for metabolic syndrome*, DRUG DISCOVERY TODAY: THERAPEUTIC STRATEGIES, 2005, 2 (3), 165-169

Mensah M, *The Atlas of Heart Disease and Stroke*, 2004,

Polak, *Oral administration of the selective PPARd agonist GW0742 reduced clinical symptoms and reduces astroglial and microglial inflammatory activation in a model of EAE*, J Neuroimmunol, 2005, Raspe E, et al., *Modulation of rat liver apolipoprotein gene expression and serum lipid levels by tetradecylthioacetic acid (TTA) via PPARalpha activation*, J Lipid Res, 1999, 40 (11), 2099-110

The invention claimed is:

1. Compounds derived from substituted 3-phenyl-1-(phenylthienyl)propan-1-ones and 3-phenyl-1-(phenylfuranyl)propan-1-ones of general formula (I):

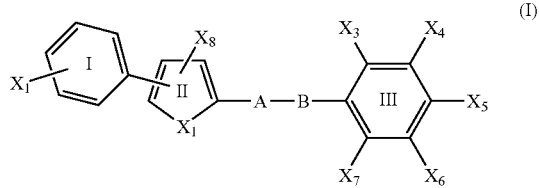

in which:
X1 represents a halogen, a R1, —SR1 or —OR1 group;
X2 represents a sulfur or oxygen atom;
X3 represents a halogen, a R3, —SR3 or —OR3 group;
X4 represents a halogen, a R4, —SR4 or —OR4 group;
X5 represents a R5, —SR5 or —OR5 group;
X6 represents a halogen, a R6, —SR6 or —OR6 group;
X7 represents a halogen, a R7, —SR7 or —OR7 group;
X8 represents a R8 group;
R1 representing a hydrogen or an alkyl group having 1 to 4 carbon atoms, said alkyl group being optionally halogenated;
R3, R4, R6, R7 and R8, which may be identical or different, selected from hydrogen or an alkyl group having 1 to 4 carbon atoms;
R5 representing an alkyl radical formed from a saturated linear carbon chain, having 1 to 4 carbon atoms, said carbon chain being:
 bound, by its end opposite to the phenyl group (III), to a substituent selected from —COOR12 and —CONR12R13, R12 and R13, which may be identical or different, representing a hydrogen or an alkyl group having 1 to 4 carbon atoms;
 unbranched or branched with at least one alkyl or alkenyl group having 1 to 4 carbon atoms, or substituted with a phenyl group;

A represents:
 (i) a carbonyl group (CO),
 (ii) an oxime group (C=N—O—H) or oxime ether group (C=N—O—R11), with R11 selected from a hydrogen atom, an alkyl group (linear or branched) having 1 to 7 carbon atoms, substituted or not with an aryl group, notably a phenyl group, said alkyl and aryl groups being optionally halogenated, or
 (iii) a —CR9R10 group, R9 representing a hydrogen atom and R10 representing an —OR11 group, R11 being selected from a hydrogen atom or an alkyl group (linear or branched) having 1 to 7 carbon atoms, said alkyl group being unsubstituted or substituted with a cycloalkyl group, notably cyclohexyl, an aryl group, notably phenyl or a heteroaryl group, notably pyridinyl, said alkyl, cycloalkyl, aryl or heteroaryl groups being optionally halogenated;
B represents:
 (i) an unsubstituted, saturated alkyl group having two carbon atoms ($CH_2$—$CH_2$), or
 (ii) an unsubstituted alkene group, having two carbon atoms (CH=CH),
their stereoisomers (diastereoisomers, enantiomers), pure or mixed, racemic mixtures, geometric isomers, tautomers, salts, hydrates, solvates, solid forms and mixtures thereof.

2. The compounds according to claim 1, characterized in that X5 represents an —OR5 group, with R5 representing an alkyl radical whose said carbon chain is bound to a —COOR12 substituent.

3. The compounds according to claim 1, characterized in that X5 is selected from the groups: —OC(CH$_3$)$_2$COOR12, —OCH(CH$_2$CH$_3$)COOR12, —O(CH$_2$)$_3$C(CH$_3$)$_2$COOR12, —OCH(C$_6$H$_5$)COOR12 and —OCH$_2$COOR12.

4. The compound according to claim 1, characterized in that A represents a carbonyl group C=O.

5. The compound according to claim 1, characterized in that A represents a —CHOR11 group, with R11 selected from a hydrogen atom, a methyl, ethyl, isopropyl, cyclohexylmethyl, benzyl, iodobenzyl and pyridinylmethyl group.

6. The compounds according to claim 1, characterized in that A represents a C=N—O—R11 group, with R11 selected from a hydrogen atom and a methyl group.

7. The compounds according to claim 1, characterized in that ring II is substituted with ring I in position $C_4$.

8. The compounds according to claim 1, characterized in that ring II is substituted with ring I in position $C_5$.

9. The compounds according to claim 1, characterized in that X1 is in the para position relative to the position of ring II.

10. The compounds according to claim 1, characterized in that X1 is selected from a trifluoromethyl group, a bromine atom, a methyloxy group, a methylthio group and a trifluoromethoxy group and a hydrogen atom.

11. The compounds according to claim 1, characterized in that at least one of the groups X3, X4, X6 and X7 represents a halogen atom.

12. The compounds according to claim 1, characterized in that X3 and X4 are identical and correspond to halogen atoms.

13. The compounds according to claim 1, characterized in that X3 and X4 are identical and correspond to chlorine or fluorine atoms.

14. The compounds according to claim 1, characterized in that at least one of the groups X3, X4, X6 and X7 represents a halogen atom, and the remaining group(s) among X3, X4, X6 and X7 represents a hydrogen atom or hydrogen atoms.

15. The compounds according to claim 1, characterized in that X4 and/or X6 represents an alkyl group.

16. The compounds according to claim 1, characterized in that X4 and X6 are two methyl groups, and X3, X7 are hydrogen atoms.

17. The compounds according to claim 1, characterized in that they are selected from:
- tert-butyl2-(2,3-dichloro-4-(3-oxo-3-(5-(4-(trifluoromethyl)phenyl)thien-2-yl)propyl)-phenoxy)-2-methylpropanoate;
- 2-(2,3-dichloro-4-(3-oxo-3-(5-(4-(trifluoromethyl)phenyl)thien-2-yl)-propyl)phenoxy)-2-methylpropanoic acid;
- tert-butyl 2-(2,3-dichloro-4-(3-hydroxy-3-(5-(4-(trifluoromethyl)phenyl)thien-2-yl)-propyl)phenoxy)-2-methylpropanoate;
- 2-(2,3-dichloro-4-(3-hydroxy-3-(5-(4-(trifluoromethyl)phenyl)thien-2-yl)propyl)phenoxy)-2-methylpropanoic acid;
- tert-butyl 2-(4-(3-(4-iodobenzyloxy)-3-(5-(4-(trifluoromethyl)phenyl)thien-2-yl)-propyl)-2,3-dichlorophenoxy)-2-methylpropanoate;
- 2-(4-(3-(4-iodobenzyloxy)-3-(5-(4-(trifluoromethyl)phenyl)thien-2-yl)-propyl)-2,3-dichlorophenoxy)-2-methylpropanoic acid;
- 2-(4-(3-(benzyloxy)-3-(5-(4-(trifluoromethyl)phenyl)thien-2-yl)propyl)-2,3-dichlorophenoxy)-2-methylpropanoic acid;
- tert-butyl 2-(2,3-dichloro-4-(3-oxo-3-(5-(4-(trifluoromethyl)phenyl)thien-2-yl)-propyl)-phenoxy)butanoate;
- 2-(2,3-dichloro-4-(3-oxo-3-(5-(4-(trifluoromethyl)phenyl)thien-2-yl)-propyl)phenoxy)butanoic acid;
- tert-butyl 2-(2,3-dichloro-4-(3-oxo-3-(4-(4-(trifluoromethyl)phenyl)thien-2-yl)propyl)-phenoxy)-2-methylpropanoate;
- 2-(2,3-dichloro-4-(3-oxo-3-(4-(4-(trifluoromethyl)phenyl)thien-2-yl)-propyl)phenoxy)-2-methylpropanoic acid;
- methyl 5-(2,3-dichloro-4-(3-oxo-3-(5-(4-(trifluoromethyl)phenyl)thien-2-yl)propyl)-phenoxy)-2,2-dimethylpentanoate;
- 5-(2,3-dichloro-4-(3-oxo-3-(5-(4-(trifluoromethyl)phenyl)thien-2-yl)propyl)phenoxy)-2,2-dimethylpentanoic acid;
- tert-butyl 2-(2,3-dichloro-4-(3-oxo-3-(5-(4-(trifluoromethyl)phenyl)thien-2-yl)propyl-phenoxy)acetate;
- 2-(2,3-dichloro-4-(3-oxo-3-(5-(4-(trifluoromethyl)phenyl)thien-2-yl)-propyl)phenoxy)acetic acid;
- ethyl 2-(2,3-dichloro-4-(3-oxo-3-(5-(4-(trifluoromethyl)phenyl)thien-2-yl)propyl)-phenoxy)-2-phenylacetate;
- 2-(2,3-dichloro-4-(3-oxo-3-(5-(4-(trifluoromethyl)phenyl)thien-2-yl)-propyl)phenoxy)-2-phenylacetic acid;
- tert-butyl 2-(2-chloro-4-(3-oxo-3-(5-(4-(trifluoromethyl)phenyl)thien-2-yl)propyl)-phenoxy)-2-methylpropanoate;
- 2-(2-chloro-4-(3-oxo-3-(5-(4-(trifluoromethyl)phenyl)thien-2-yl)-propyl)phenoxy)-2-methylpropanoic acid;
- tert-butyl 2-(3-chloro-4-(3-oxo-3-(5-(4-(trifluoromethyl)phenyl)thien-2-yl)propyl)-phenoxy)-2-methylpropanoate;
- 2-(3-chloro-4-(3-oxo-3-(5-(4-(trifluoromethyl)phenyl)thien-2-yl)-propyl)phenoxy)-2-methylpropanoic acid;
- tert-butyl 2-(2-fluoro-4-(3-oxo-3-(5-(4-(trifluoromethyl)phenyl)thien-2-yl)propyl)-phenoxy)-2-methylpropanoate;
- 2-(2-fluoro-4-(3-oxo-3-(5-(4-(trifluoromethyl)phenyl)thien-2-yl)propyl)-phenoxy)-2-methylpropanoic acid;
- tert-butyl 2-(2-fluoro-4-(3-oxo-3-(5-(4-(trifluoromethyl)phenyl)thien-2-yl)propyl)-phenoxy)acetate;
- 2-(2-fluoro-4-(3-oxo-3-(5-(4-(trifluoromethyl)phenyl)thien-2-yl)propyl)-phenoxy)acetic acid;
- 2-(2-fluoro-4-(3-hydroxy-3-(5-(4-(trifluoromethyl)phenyl)thien-2-yl)-propyl)phenoxy)acetic acid;
- 2-(4-(3-(benzyloxy)-3-(5-(4-(trifluoromethyl)phenyl)thien-2-yl)propyl)-2-fluorophenoxy)acetic acid;
- tert-butyl 2-(2-fluoro-4-(3-oxo-3-(5-(4-(trifluoromethyl)phenyl)thien-2-yl)propyl)-phenoxy)butanoate;
- 2-(2-fluoro-4-(3-oxo-3-(5-(4-(trifluoromethyl)phenyl)thien-2-yl)propyl)-phenoxy)butanoic acid;
- 2-(2-fluoro-4-(3-hydroxy-3-(5-(4-(trifluoromethyl)phenyl)thien-2-yl)-propyl)phenoxy)butanoic acid;
- tert-butyl 2-(2-bromo-4-(3-oxo-3-(5-(4-(trifluoromethyl)phenyl)thien-2-yl)propyl)-phenoxy)butanoate;
- 2-bromo-4-(3-oxo-3-(5-(4-(trifluoromethyl)phenyl)thien-2-yl)-propyl)phenoxy)butanoic acid;
- tert-butyl 2-(2-bromo-4-(3-oxo-3-(5-(4-(trifluoromethyl)phenyl)thien-2-yl)propyl)-phenoxy)acetate;
- 2-(2-bromo-4-(3-oxo-3-(5-(4-(trifluoromethyl)phenyl)thien-2-yl)-propyl)phenoxy)acetic acid;
- tert-butyl 2-(2-bromo-4-(3-oxo-3-(5-(4-(trifluoromethyl)phenyl)thien-2-yl)propyl)-phenoxy)-2-methylpropanoate;
- 2-(2-bromo-4-(3-oxo-3-(5-(4-(trifluoromethyl)phenyl)thien-2-yl)-propyl)phenoxy)-2-methylpropanoic acid;
- tert-butyl 2-(2,3-dichloro-4-(3-oxo-3-(5-(4-(trifluoromethyl)phenyl)fur-2-yl)propyl)-phenoxy)-2-methylpropanoate;
- 2-(2,3-dichloro-4-(3-oxo-3-(5-(4-(trifluoromethyl)phenyl)fur-2-yl)-propyl)phenoxy)-2-methylpropanoic acid;
- 2-(2,3-dichloro-4-(3-(pyridin-3-ylmethoxy)-3-(5-(4-(trifluoromethyl)-phenyl)thien-2-yl)propyl)phenoxy)-2-methylpropanoic acid;
- 2-(2,3-dichloro-4-(3-methoxy-3-(5-(4-(trifluoromethyl)phenyl)thien-2-yl)propyl)phenoxy)-2-methylpropanoic acid;

2-(2,3-dichloro-4-(3-ethoxy-3-(5-(4-(trifluoromethyl)phenyl)thien-2-yl)propyl)phenoxy)-2-methylpropanoic acid;
2-(2,3-dichloro-4-(3-(cyclohexylmethoxy)-3-(5-(4-(trifluoromethyl)-phenyl)thien-2-yl)propyl)phenoxy)-2-methylpropanoic acid;
tert-butyl 2-(2,3-dichloro-4-(3-oxo-3-(5-(4-(trifluoromethoxy)phenyl)thien-2-yl)-propyl)phenoxy)-2-methylpropanoate;
2-(2,3-dichloro-4-(3-oxo-3-(5-(4-(trifluoromethoxy)phenyl)thien-2-yl)-propyl)phenoxy)-2-methylpropanoate acid;
tert-butyl 2-(2,3-difluoro-4-(3-oxo-3-(5-(4-(trifluoromethyl)phenyl)thien-2-yl)propyl)-phenoxy)-2-methylpropanoate;
2-(2,3-difluoro-4-(3-oxo-3-(5-(4-(trifluoromethyl)phenyl)thien-2-yl)-propyl)phenoxy)-2-methylpropanoic acid;
tert-butyl 2-(2,6-dimethyl-4-(3-oxo-3-(5-(4-(trifluoromethyl)phenyl)thien-2-yl)propyl)-phenoxy)-2-methylpropanoate;
2-(2,6-dimethyl-4-(3-oxo-3-(5-(4-(trifluoromethyl)phenyl)thien-2-yl)-propyl)phenoxy)-2-methylpropanoic acid;
2-(2,3-dichloro-4-(3-(hydroxyimino)-3-(5-(4-(trifluoromethyl)phenyl)-thien-2-yl)propyl)phenoxy)-2-methylpropanoic acid;
2-(2,3-dichloro-4-(3-(methoxyimino)-3-(5-(4-(trifluoromethyl)phenyl)-thien-2-yl)propyl)phenoxy)-2-methylpropanoic acid;
tert-butyl 2-(4-(3-(5-(4-bromophenyl)thien-2-yl)-3-oxopropyl)-2,3-dichlorophenoxy)-2-methylpropanoate;
2-(4-(3-(5-(4-bromophenyl)thien-2-yl)-3-oxopropyl)-2,3-dichloro-phenoxy)-2-methylpropanoic acid;
tert-butyl 2-(2,3-dichloro-4-(3-(5-(4-(methylthio)phenyl)thien-2-yl)-3-oxopropyl)-phenoxy)-2-methylpropanoate;
2-(2,3-dichloro-4-(3-(5-(4-(methylthio)phenyl)thien-2-yl)-3-oxo-propyl)phenoxy)-2-methylpropanoic acid;
2-(2,3-dichloro-4-(3-isopropoxy-3-(5-(4-(trifluoromethyl)phenyl)thien-2-yl)propyl)phenoxy)-2-methylpropanoic acid;
tert-butyl 2-(2,3-dichloro-4-(3-oxo-3-(5-phenylthiophen-2-yl)propyl)phenoxy)-2-methylpropanoate;
2-(2,3-dichloro-4-(3-oxo-3-(5-phenylthien-2-yl)propyl)phenoxy)-2-methylpropanoic acid;
tert-butyl 2-methyl-2-(2-methyl-4-(3-oxo-3-(5-(4-(trifluoromethyl)phenyl)thiophen-2-yl)propyl)phenoxy)propanoate;
2-methyl-2-(2-methyl-4-(3-oxo-3-(5-(4-(trifluoromethyl)phenyl)-thiophen-2-yl)propyl)phenoxy)propanoic acid;
2-(2,3-dichloro-4-(3-hydroxy-3-(4-(4-(trifluoromethyl)phenyl)thien-2-yl)propyl)phenoxy)-2-methylpropanoic acid;
2-(4-(3-(benzyloxy)-3-(4-(4-(trifluoromethyl)phenyl)thien-2-yl)propyl)-2,3-dichlorophenoxy)-2-methylpropanoic acid;
2-(2,3-difluoro-4-(3-hydroxy-3-(5-(4-(trifluoromethyl)phenyl)thien-2-yl)propyl)phenoxy)-2-methylpropanoic acid;
2-(4-(3-(benzyloxy)-3-(5-(4-(trifluoromethyl)phenyl)thien-2-yl)propyl)-2,3-difluorophenoxy)-2-methylpropanoic acid;
tert-butyl 2-(4-(3-oxo-3-(5-(4-(trifluoromethyl)phenyl)thien-2-yl)propyl)phenoxy)-butanoate;
2-(4-(3-oxo-3-(5-(4-(trifluoromethyl)phenyl)thien-2-yl)propyl)-phenoxy)-butanoic acid;
tert-butyl 2-methyl-2-(4-(3-oxo-3-(5-(4-(trifluoromethyl)phenyl)thien-2-yl)propyl)-phenoxy)propanoate;
2-(4-(3-oxo-3-(5-(4-(trifluoromethyl)phenyl)thien-2-yl)propyl)-phenoxy)-2-methylpropanoic acid;
tert-butyl 2-(4-(3-oxo-3-(5-(4-(trifluoromethyl)phenyl)thien-2-yl)propyl)phenoxy)-acetate;
2-(4-(3-oxo-3-(5-(4-(trifluoromethyl)phenyl)thien-2-yl)propyl)-phenoxy)acetic acid;
2-(4-(3-(benzyloxy)-3-(5-(4-(trifluoromethyl)phenyl)thien-2-yl)propyl)-2-fluorophenoxy)butanoic acid;
2-(2,3-dichloro-4-(3-hydroxy-3-(5-(4-(trifluoromethyl)phenyl)furan-2-yl)propyl)phenoxy)-2-methylpropanoic acid;
2-(2,3-dichloro-4-(3-methoxy-3-(5-(4-(trifluoromethyl)phenyl)fur-2-yl)propyl)phenoxy)-2-methylpropanoic acid;
2-(4-(3-hydroxy-3-(5-(4-(trifluoromethyl)phenyl)thien-2-yl)propyl)-2,6-dimethylphenoxy)-2-methylpropanoic acid;
2-(4-(3-methoxy-3-(5-(4-(trifluoromethyl)phenyl)thien-2-yl)propyl)-2,6-dimethylphenoxy)-2-methylpropanoic acid;
ethyl 2-(2,3-dichloro-4-(3-oxo-3-(5-(3-(trifluoromethyl)phenyl)thien-2-yl)propyl)-phenoxy)-2-methylpropanoate;
2-(2,3-dichloro-4-(3-oxo-3-(5-(3-(trifluoromethyl)phenyl)thien-2-yl)-propyl)phenoxy)-2-methylpropanoic acid;
ethyl 2-(2,3-dichloro-4-(3-hydroxy-3-(5-(3-(trifluoromethyl)phenyl)thien-2-yl)-propyl)phenoxy)-2-methylpropanoate;
ethyl 2-(2,3-dichloro-4-(3-methoxy-3-(5-(3-(trifluoromethyl)phenyl)thien-2-yl)-propyl)phenoxy)-2-methylpropanoate;
2-(2,3-dichloro-4-(3-hydroxy-3-(5-(4-(trifluoromethoxy)phenyl)thien-2-yl)propyl)phenoxy)-2-methylpropanoic acid;
2-(2,3-dichloro-4-(3-methoxy-3-(5-(4-(trifluoromethoxy)phenyl)thien-2-yl)propyl)phenoxy)-2-methylpropanoic acid.

18. The compounds according to claim 1, as medicinal products.

19. A pharmaceutical composition comprising, in a pharmaceutically acceptable carrier, at least one compound as defined in claim 1, optionally in combination with one or more other therapeutic and/or cosmetic active principles.

20. A pharmaceutical composition comprising, in a pharmaceutically acceptable carrier, at least one compound as defined in claim 1, in combination with one or more compounds selected from the following list:
an antidiabetic,
insulin,
an antilipemic and/or cholesterol-lowering molecule,
an antihypertensive or hypotensive agent,
an antiplatelet agent,
an antiobesity agent,
an antiinflammatory agent,
an antioxidant,
an agent used in the treatment of heart failure,
an agent used for the treatment of coronary insufficiency,
an anticancer agent,
an antiasthmatic,
a corticoid used in the treatment of skin diseases
a vasodilator and/or an antiischemic agent.

21. The pharmaceutical composition according to claim 19, for treating the complications associated with metabolic syndrome, insulin resistance, dyslipidemias, atherosclerosis, cardiovascular diseases, obesity, hypertension, inflammatory diseases, cerebral ischemia, autoimmune diseases, neurodegenerative pathologies or cancers.

22. The pharmaceutical composition according to claim 19, for treating the cardiovascular risk factors connected with disturbances of lipid and/or carbohydrate metabolism.

23. The pharmaceutical composition according to claim 19, for the treatment of diabetes.

24. The pharmaceutical composition according to claim 19, for the treatment of dyslipidemias.

* * * * *